US011932650B2

(12) United States Patent
Movassaghi et al.

(10) Patent No.: US 11,932,650 B2
(45) Date of Patent: Mar. 19, 2024

(54) POTENT AGELASTATIN DERIVATIVES AS MODULATORS FOR CANCER INVASION AND METASTASIS

(71) Applicants: Massachusetts Institute of Technology, Cambridge, MA (US); Tufts Medical Center, Inc., Boston, MA (US)

(72) Inventors: Mohammad Movassaghi, Lincoln, MA (US); Alyssa H. Antropow, Boston, MA (US); Rachel J. Buchsbaum, Winchester, MA (US); Kun Xu, Dorchester, MA (US)

(73) Assignees: Massachusetts Institute of Technology, Cambridge, MA (US); Tufts Medical Center, Inc., Boston, MA (US)

( * ) Notice: Subject to any disclaimer, the term of this patent is extended or adjusted under 35 U.S.C. 154(b) by 472 days.

(21) Appl. No.: 16/612,468

(22) PCT Filed: May 11, 2018

(86) PCT No.: PCT/US2018/032327
§ 371 (c)(1),
(2) Date: Nov. 11, 2019

(87) PCT Pub. No.: WO2018/209239
PCT Pub. Date: Nov. 15, 2018

(65) Prior Publication Data
US 2020/0062771 A1   Feb. 27, 2020
US 2021/0053977 A9   Feb. 25, 2021

Related U.S. Application Data

(60) Provisional application No. 62/504,877, filed on May 11, 2017.

(51) Int. Cl.
C07D 487/14    (2006.01)
A61P 35/04     (2006.01)
C07D 498/22    (2006.01)

(52) U.S. Cl.
CPC ............ *C07D 487/14* (2013.01); *A61P 35/04* (2018.01); *C07D 498/22* (2013.01)

(58) Field of Classification Search
None
See application file for complete search history.

(56) References Cited

U.S. PATENT DOCUMENTS

| | | |
|---|---|---|
| 4,197,311 A | 4/1980 | Wepplo et al. |
| 4,816,397 A | 3/1989 | Boss et al. |
| 4,816,567 A | 3/1989 | Cabilly et al. |
| 4,906,562 A | 3/1990 | Hellström et al. |
| 4,935,495 A | 6/1990 | Hellström et al. |
| 4,940,726 A | 7/1990 | Pettit et al. |
| 4,946,778 A | 8/1990 | Ladner et al. |
| 4,996,237 A | 2/1991 | Pettit et al. |
| 5,225,539 A | 7/1993 | Winter et al. |
| 5,242,824 A | 9/1993 | Hellström et al. |
| 5,338,845 A | 8/1994 | Barrow et al. |
| 5,409,953 A | 4/1995 | Pettit et al. |
| 5,423,753 A | 6/1995 | Fowles et al. |
| 5,430,062 A | 7/1995 | Cushman et al. |
| 5,475,092 A | 12/1995 | Chari et al. |
| 5,504,074 A | 4/1996 | D'Amato et al. |
| 5,525,632 A | 6/1996 | Obsumi et al. |
| 5,545,806 A | 8/1996 | Lonberg et al. |
| 5,561,122 A | 10/1996 | Pettit |
| 5,569,786 A | 10/1996 | Pettit et al. |
| 5,569,825 A | 10/1996 | Lonberg et al. |
| 5,585,089 A | 12/1996 | Queen |
| 5,625,126 A | 4/1997 | Lonberg et al. |
| 5,633,425 A | 5/1997 | Lonberg et al. |
| 5,646,176 A | 7/1997 | Golik et al. |
| 5,661,016 A | 8/1997 | Lonberg et al. |
| 5,661,143 A | 8/1997 | D'Amato et al. |
| 5,674,906 A | 10/1997 | Hatanaka et al. |
| 5,731,353 A | 3/1998 | Ohsumi et al. |
| 5,821,337 A | 10/1998 | Carter et al. |
| 5,877,158 A | 3/1999 | Bosslet et al. |
| 5,886,025 A | 3/1999 | Pinney |

(Continued)

FOREIGN PATENT DOCUMENTS

CN   105198885 A   12/2015
CN   104447755 B   6/2016

(Continued)

OTHER PUBLICATIONS

Dorwald, F. A., Side Reactions in Organic Synthesis, 2005, Wiley: VCH, Weinheim, p. IX (Year: 2005).*
Antropow et al., "Synthesis and Evaluation of Agelastatin Derivatives as Potent Modulators for Cancer Invasion and Metastasis", Jul. 2017, The Journal of Organic Chemistry, 82(15), pp. 7720-7731. (DOI: 10.1021/acs.joc.7b01162) (Year: 2017).*
Invitation to Pay Additional Fees for PCT/US2018/032327, dated Jul. 23, 2018.
International Search Report and Written Opinion for PCT/US2018/032327, dated Sep. 21, 2018.
International Preliminary Report on Patentability for PCT/US2018/032327, dated Nov. 21, 2019.

(Continued)

*Primary Examiner* — Jeffrey S Lundgren
*Assistant Examiner* — Anthony Joseph Seitz
(74) *Attorney, Agent, or Firm* — Wolf, Greenfield & Sacks, P.C.

(57) ABSTRACT

The present disclosure relates to derivatized agelastatin compounds and methods for the treatment, prevention, or delay of cancer, comprising administering a therapeutically effect amount of the derivatized agelastatin compounds, a pharmaceutically acceptable salt thereof, or a composition thereof to a subject in need thereof. Methods for making the derivatized agelastatin compounds are also provided.

42 Claims, 20 Drawing Sheets
Specification includes a Sequence Listing.

(56) References Cited

U.S. PATENT DOCUMENTS

| | | |
|---|---|---|
| 5,892,069 A | 4/1999 | D'Amato et al. |
| 5,929,211 A | 7/1999 | Ashkenazi et al. |
| 5,985,837 A | 11/1999 | Ritter et al. |
| 6,054,297 A | 4/2000 | Carter et al. |
| 6,103,236 A | 8/2000 | Suzawa et al. |
| 6,147,076 A | 11/2000 | Danishefsky et al. |
| 6,150,407 A | 11/2000 | Tuséet al. |
| 6,162,810 A | 12/2000 | Carson et al. |
| 6,162,930 A | 12/2000 | Pinney et al. |
| 6,169,104 B1 | 1/2001 | Tuséet al. |
| 6,201,001 B1 | 3/2001 | Wang et al. |
| 6,214,345 B1 | 4/2001 | Firestone et al. |
| 6,232,327 B1 | 5/2001 | Nickel et al. |
| 6,262,094 B1 | 7/2001 | Hoefle et al. |
| 6,268,488 B1 | 7/2001 | Barbas, III et al. |
| 6,271,220 B1 | 8/2001 | Garst |
| 6,329,420 B1 | 12/2001 | Uckun et al. |
| 6,335,364 B1 | 1/2002 | Uckun et al. |
| 6,350,777 B2 | 2/2002 | Pinney et al. |
| 6,358,957 B1 | 3/2002 | Fukumoto et al. |
| 6,407,213 B1 | 6/2002 | Carter et al. |
| 6,423,753 B1 | 7/2002 | Dougherty |
| 6,433,012 B1 | 8/2002 | Tuséet al. |
| 6,528,676 B1 | 3/2003 | D'Amato et al. |
| 6,582,928 B1 | 6/2003 | Ashkenazi et al. |
| 6,620,976 B2 | 9/2003 | Sakanoue et al. |
| 6,639,055 B1 | 10/2003 | Carter et al. |
| 6,677,435 B2 | 1/2004 | Barbas, III et al. |
| 6,759,509 B1 | 7/2004 | King et al. |
| 6,815,530 B2 | 11/2004 | Ekwuribe et al. |
| 6,835,802 B2 | 12/2004 | Ekwuribe et al. |
| 6,855,689 B2 | 2/2005 | Firestone et al. |
| 6,858,580 B2 | 2/2005 | Ekwuribe et al. |
| 6,870,033 B1 | 3/2005 | Hsei et al. |
| 6,897,034 B2 | 5/2005 | Bebbington et al. |
| 7,018,809 B1 | 3/2006 | Carter |
| 7,030,082 B2 | 4/2006 | Soltero et al. |
| 7,087,840 B2 | 8/2006 | Herring et al. |
| 7,091,186 B2 | 8/2006 | Senter et al. |
| 7,115,573 B2 | 10/2006 | Pickford et al. |
| 7,119,162 B2 | 10/2006 | Ekwuribe et al. |
| 7,122,636 B1 | 10/2006 | Hsei et al. |
| 7,183,076 B2 | 2/2007 | Arathoon et al. |
| 7,214,663 B2 | 5/2007 | Bebbington et al. |
| 7,214,776 B2 | 5/2007 | Hsei et al. |
| 7,223,837 B2 | 5/2007 | de Groot et al. |
| 7,256,257 B2 | 8/2007 | Doronina et al. |
| 7,304,032 B2 | 12/2007 | Bebbington et al. |
| 7,319,139 B2 | 1/2008 | Brasalawsky et al. |
| 7,375,078 B2 | 5/2008 | Feng |
| 7,427,399 B2 | 9/2008 | Jakobovits et al. |
| 7,479,544 B2 | 1/2009 | Clark et al. |
| 7,494,646 B2 | 2/2009 | Jakobovits et al. |
| 7,507,405 B2 | 3/2009 | Hsei et al. |
| 7,521,541 B2 | 4/2009 | Eigenbrot et al. |
| 7,541,442 B2 | 6/2009 | Gudas et al. |
| 7,547,768 B2 | 6/2009 | Dowd et al. |
| 7,553,816 B2 | 6/2009 | Senter et al. |
| 7,585,834 B2 | 9/2009 | Wender et al. |
| 7,595,379 B2 | 9/2009 | Gudas et al. |
| 7,659,241 B2 | 2/2010 | Senter et al. |
| 7,662,936 B2 | 2/2010 | Kadkhodayan et al. |
| 7,691,962 B2 | 4/2010 | Boyd et al. |
| 7,696,313 B2 | 4/2010 | Pickford et al. |
| 7,705,045 B2 | 4/2010 | de Groot et al. |
| 7,714,016 B2 | 5/2010 | Gangwar et al. |
| 7,723,485 B2 | 5/2010 | Junutula et al. |
| 7,745,394 B2 | 6/2010 | Doronina et al. |
| 7,749,504 B2 | 7/2010 | Cairns et al. |
| 7,750,116 B1 | 7/2010 | Doronina et al. |
| 7,754,441 B2 | 7/2010 | de Sauvage et al. |
| 7,754,681 B2 | 7/2010 | Feng |
| 7,803,915 B2 | 9/2010 | Cairns et al. |
| 7,811,565 B2 | 10/2010 | Jakobovits et al. |
| 7,816,317 B2 | 10/2010 | Bebbington et al. |
| 7,829,531 B2 | 11/2010 | Senter et al. |
| 7,834,154 B2 | 11/2010 | Koch et al. |
| 7,842,789 B2 | 11/2010 | Hsei et al. |
| 7,846,893 B2 | 12/2010 | Sinko et al. |
| 7,851,437 B2 | 12/2010 | Senter et al. |
| 7,855,275 B2 | 12/2010 | Eigenbrot et al. |
| 7,858,759 B2 | 12/2010 | Brandt et al. |
| 7,888,536 B2 | 2/2011 | Davis et al. |
| 7,893,023 B2 | 2/2011 | Trouet et al. |
| 7,964,566 B2 | 6/2011 | Doronina et al. |
| 7,964,567 B2 | 6/2011 | Doronina et al. |
| 7,968,090 B2 | 6/2011 | Raitano et al. |
| 7,989,434 B2 | 8/2011 | Feng |
| 7,989,595 B2 | 8/2011 | Dennis et al. |
| 8,012,978 B2 | 9/2011 | Zhao et al. |
| 8,158,590 B2 | 4/2012 | Beusker et al. |
| 8,337,856 B2 | 12/2012 | Blättler et al. |
| 9,353,150 B2 | 5/2016 | Movassaghi et al. |
| 9,434,736 B2 | 9/2016 | Movassaghi et al. |
| 9,464,093 B2 | 10/2016 | Tun et al. |
| 9,962,383 B2 | 5/2018 | Movassaghi et al. |
| 10,220,099 B2 | 3/2019 | Movassaghi et al. |
| 10,640,508 B2 | 5/2020 | Movassaghi et al. |
| 10,918,627 B2 | 2/2021 | Movassaghi et al. |
| 10,918,735 B2 | 2/2021 | Movassaghi et al. |
| 2003/0096743 A1 | 5/2003 | Senter et al. |
| 2003/0130189 A1 | 7/2003 | Senter et al. |
| 2003/0149003 A1 | 8/2003 | Chaplin et al. |
| 2005/0143429 A1 | 6/2005 | Danishefsky et al. |
| 2008/0050310 A1 | 2/2008 | Ebens et al. |
| 2008/0267981 A1 | 10/2008 | Janda et al. |
| 2009/0068202 A1 | 3/2009 | Chen et al. |
| 2009/0203584 A1 | 8/2009 | Cuthbertson et al. |
| 2009/0280056 A1 | 11/2009 | Dennis et al. |
| 2010/0125065 A1 | 5/2010 | Moon et al. |
| 2010/0210543 A1 | 8/2010 | Rabuka et al. |
| 2010/0215669 A1 | 8/2010 | Chen et al. |
| 2011/0118480 A1 | 5/2011 | Vijayaraghavan et al. |
| 2011/0124844 A1 | 5/2011 | Davis et al. |
| 2011/0135667 A1 | 6/2011 | Chen et al. |
| 2011/0137017 A1 | 6/2011 | Eigenbrot et al. |
| 2011/0142859 A1 | 6/2011 | Ebens, Jr. et al. |
| 2011/0195021 A1 | 8/2011 | Deckert et al. |
| 2011/0195022 A1 | 8/2011 | Deckert et al. |
| 2011/0269972 A1 | 11/2011 | Loh et al. |
| 2012/0183566 A1 | 7/2012 | Barfield et al. |
| 2014/0187500 A1 | 7/2014 | Movassaghi et al. |
| 2015/0080405 A1 | 3/2015 | Movassaghi et al. |
| 2015/0274742 A1 | 10/2015 | Tun et al. |
| 2016/0354483 A1 | 12/2016 | Movassaghi et al. |
| 2017/0143708 A1 | 5/2017 | Movassaghi et al. |
| 2017/0333405 A1 | 11/2017 | Movassaghi et al. |
| 2017/0342077 A1 | 11/2017 | Movassaghi et al. |
| 2018/0360830 A1 | 12/2018 | Movassaghi et al. |
| 2019/0119286 A1 | 4/2019 | Movassaghi et al. |
| 2019/0255187 A1 | 8/2019 | Movassaghi et al. |
| 2020/0385407 A1 | 12/2020 | Movassaghi et al. |
| 2021/0329919 A9 | 10/2021 | Movassaghi et al. |

FOREIGN PATENT DOCUMENTS

| | | |
|---|---|---|
| EP | 0105360 A | 4/1984 |
| EP | 0217577 A | 4/1987 |
| EP | 0375562 A | 6/1990 |
| FR | 2438034 A1 | 4/1980 |
| WO | WO 88/003145 A2 | 5/1988 |
| WO | WO 92/016486 A1 | 10/1992 |
| WO | WO 94/014787 A1 | 7/1994 |
| WO | WO 95/004535 A1 | 2/1995 |
| WO | WO 98/039323 A1 | 9/1998 |
| WO | WO 99/002166 A1 | 1/1999 |
| WO | WO 99/002514 A2 | 1/1999 |
| WO | WO 99/034788 A1 | 7/1999 |
| WO | WO 99/035150 A1 | 7/1999 |
| WO | WO 99/035164 A1 | 7/1999 |
| WO | WO 99/048495 A1 | 9/1999 |
| WO | WO 99/051224 A1 | 10/1999 |
| WO | WO 99/051246 A1 | 10/1999 |
| WO | WO 2000/000514 A2 | 1/2000 |

(56) References Cited

FOREIGN PATENT DOCUMENTS

| | | |
|---|---|---|
| WO | WO 2000/006556 A1 | 2/2000 |
| WO | WO 2000/026229 A1 | 5/2000 |
| WO | WO 2000/035865 A2 | 6/2000 |
| WO | WO 2000/040529 A1 | 7/2000 |
| WO | WO 2000/041669 A2 | 7/2000 |
| WO | WO 2000/048590 A1 | 8/2000 |
| WO | WO 2000/073264 A1 | 12/2000 |
| WO | WO 2001/009103 A2 | 2/2001 |
| WO | WO 2001/012579 A2 | 2/2001 |
| WO | WO 2001/019794 A2 | 3/2001 |
| WO | WO 2001/022954 A2 | 4/2001 |
| WO | WO 2001/024763 A2 | 4/2001 |
| WO | WO 2001/030803 A1 | 5/2001 |
| WO | WO 2001/040268 A2 | 6/2001 |
| WO | WO 2001/040309 A2 | 6/2001 |
| WO | WO 2001/068654 A2 | 9/2001 |
| WO | WO 2001/081288 A1 | 11/2001 |
| WO | WO 2001/081355 A1 | 11/2001 |
| WO | WO 2001/082909 A2 | 11/2001 |
| WO | WO 2001/084929 A1 | 11/2001 |
| WO | WO 2001/092224 A2 | 12/2001 |
| WO | WO 2002/004434 A1 | 1/2002 |
| WO | WO 2002/006267 A2 | 1/2002 |
| WO | WO 2002/008213 A1 | 1/2002 |
| WO | WO 2002/012228 A1 | 2/2002 |
| WO | WO 2002/014329 A1 | 2/2002 |
| WO | WO 2002/022576 A2 | 3/2002 |
| WO | WO 2002/022626 A1 | 3/2002 |
| WO | WO 2002/042319 A2 | 5/2002 |
| WO | WO 2002/047604 A2 | 6/2002 |
| WO | WO 2002/050007 A2 | 6/2002 |
| WO | WO 2002/060872 A1 | 8/2002 |
| WO | WO 2002/088172 A2 | 11/2002 |
| WO | WO 2002/098883 A1 | 12/2002 |
| WO | WO 2003/026577 A2 | 4/2003 |
| WO | WO 2003/043583 A2 | 5/2003 |
| WO | WO 2003/068144 A2 | 8/2003 |
| WO | WO 2004/010957 A2 | 2/2004 |
| WO | WO 2004/013093 A2 | 2/2004 |
| WO | WO 2004/016801 A2 | 2/2004 |
| WO | WO 2004/032828 A2 | 4/2004 |
| WO | WO 2004/043344 A2 | 5/2004 |
| WO | WO 2004/043493 A1 | 5/2004 |
| WO | WO 2004/106343 A2 | 12/2004 |
| WO | WO 2005/001038 A2 | 1/2005 |
| WO | WO 2005/009369 A2 | 2/2005 |
| WO | WO 2005/037992 A2 | 4/2005 |
| WO | WO 2005/081711 A2 | 9/2005 |
| WO | WO 2005/082023 A2 | 9/2005 |
| WO | WO 2005/084390 A2 | 9/2005 |
| WO | WO 2006/055578 A2 | 5/2006 |
| WO | WO 2006/065533 A2 | 6/2006 |
| WO | WO 2006/086733 A2 | 8/2006 |
| WO | WO 2006/132670 A2 | 12/2006 |
| WO | WO 2007/008603 A1 | 1/2007 |
| WO | WO 2007/008848 A2 | 1/2007 |
| WO | WO 2007/011968 A2 | 1/2007 |
| WO | WO 2007/019232 A2 | 2/2007 |
| WO | WO 2007/024222 A1 | 3/2007 |
| WO | WO 2007/024536 A2 | 3/2007 |
| WO | WO 2007/030642 A2 | 3/2007 |
| WO | WO 2007/062138 A2 | 5/2007 |
| WO | WO 2007/089149 A2 | 8/2007 |
| WO | WO 2007/103288 A2 | 9/2007 |
| WO | WO 2007/137170 A2 | 11/2007 |
| WO | WO 2008/070593 A2 | 6/2008 |
| WO | WO 2008/078109 A2 | 7/2008 |
| WO | WO 2009/017394 A2 | 2/2009 |
| WO | WO 2009/048967 A1 | 4/2009 |
| WO | WO 2009/052431 A2 | 4/2009 |
| WO | WO 2009/080830 A1 | 7/2009 |
| WO | WO 2009/080831 A1 | 7/2009 |
| WO | WO 2009/080832 A1 | 7/2009 |
| WO | WO 2009/117531 A1 | 9/2009 |
| WO | WO 2009/134870 A1 | 11/2009 |
| WO | WO 2009/134952 A2 | 11/2009 |
| WO | WO 2009/134976 A1 | 11/2009 |
| WO | WO 2009/134977 A1 | 11/2009 |
| WO | WO 2009/135181 A2 | 11/2009 |
| WO | WO 2010/008726 A1 | 1/2010 |
| WO | WO 2010/025272 A1 | 3/2010 |
| WO | WO 2010/062171 A2 | 6/2010 |
| WO | WO 2010/081004 A1 | 7/2010 |
| WO | WO 2010/111018 A1 | 9/2010 |
| WO | WO 2010/126551 A1 | 11/2010 |
| WO | WO 2010/126552 A1 | 11/2010 |
| WO | WO 2010/128087 A2 | 11/2010 |
| WO | WO 2010/141566 A1 | 12/2010 |
| WO | WO 2011/038159 A2 | 3/2011 |
| WO | WO 2011/050180 A1 | 4/2011 |
| WO | WO 2011/091286 A1 | 7/2011 |
| WO | WO 2011/100398 A1 | 8/2011 |
| WO | WO 2011/100403 A1 | 8/2011 |
| WO | WO 2011/106528 A1 | 9/2011 |
| WO | WO 2011/112978 A1 | 9/2011 |
| WO | WO 2011/130613 A1 | 10/2011 |
| WO | WO 2011/133039 A2 | 10/2011 |
| WO | WO 2011/162933 A1 | 12/2011 |
| WO | WO 2012/019024 A2 | 2/2012 |
| WO | WO 2012/047724 A1 | 4/2012 |
| WO | WO 2012/054748 A2 | 4/2012 |
| WO | WO 2012/058592 A2 | 5/2012 |
| WO | WO 2012/061590 A1 | 5/2012 |
| WO | WO 2012/078688 A2 | 6/2012 |
| WO | WO 2012/112687 A1 | 8/2012 |
| WO | WO 2012/112708 A1 | 8/2012 |
| WO | WO 2012/128868 A2 | 9/2012 |
| WO | WO 2012/135517 A2 | 10/2012 |
| WO | WO 2012/135522 A2 | 10/2012 |
| WO | WO 2012/135740 A2 | 10/2012 |
| WO | WO 2012/138537 A2 | 10/2012 |
| WO | WO 2012/138749 A2 | 10/2012 |
| WO | WO 2012/145112 A2 | 10/2012 |
| WO | WO 2012/149412 A2 | 11/2012 |
| WO | WO 2012/177837 A2 | 12/2012 |
| WO | WO 2013/055990 A1 | 4/2013 |
| WO | WO 2013/055993 A1 | 4/2013 |
| WO | WO 2014/059314 A1 | 4/2014 |
| WO | WO 2014/089177 A2 | 6/2014 |

OTHER PUBLICATIONS

Invitation to Pay Additional Fees for PCT/US2020/026415, dated Jul. 1, 2020.
International Search Report and Written Opinion for PCT/US2020/026415, dated Sep. 7, 2020 (.
Aoyagi et al., Mild and Efficient One-Step Synthesis of Trithiocarbonates Using Minimum Amount of CS2. Synlett. 2006;636-638.
Delfourne, Marine natural products and other derivatives as potent indoleamine 2,3-dioxygenase inhibitors. Mini Rev Med Chem. 2012;12(10):988-996. doi:10.2174/138955712802762374.
Jabri et al., Enantioselective Total Synthesis of Plectosphaeroic Acid B and C. J. Org. Chem. Aug. 27, 2013;78(17):8766-8788. doi: 10.1021/jo4015479.
Olsson et al., Synthesis of Potent Cytotoxic Epidithiodiketopiperazines Designed for Derivatization. J Org Chem. Apr. 3, 2020;85(7):4648-4662. doi: 10.1021/acs.joc.9b03371. Epub Mar. 19, 2020. PMID: 32126173; PMCID: PMC7127967.
Ried et al, Uber Synthese und Reaktionen neuer vinyloger Chlorformamidine. Liebigs Ann Chem. 1986:389-394.
Shi et al., Synthesis and Reactions of 2-(Alkylthio )-4,4-dimenthyl-1,3-thiazole-5(4H)-thiones. Helvetica Chemica Acta. 1994;77:1903-1920.
Yu et al., A new epipolythiodioxopiperazine with antibacterial and cytotoxic activities from the endophytic fungus *Chaetomium* sp. M336. Nat Prod Res. 2018;32(6):689-694. doi:10.1080/14786419.2017.1338285.
International Search Report and Written Opinion for PCT/US2013/073062, dated May 20, 2014.
International Preliminary Report on Patentability for PCT/US2013/073062, dated Jun. 9, 2015.

(56) References Cited

OTHER PUBLICATIONS

International Search Report and Written Opinion for PCT/US2014/056263, dated Dec. 4, 2014.
International Preliminary Report on Patentability for PCT/US2014/056263, dated Mar. 22, 2016.
International Search Report and Written Opinion for PCT/US2017/032040, dated Aug. 11, 2017.
International Preliminary Report on Patentability for PCT/US2017/032040, dated Nov. 22, 2018.
International Search Report and Written Opinion for PCT/US2017/034327, dated Sep. 1, 2017.
International Preliminary Report on Patentability for PCT/US2017/034327, dated Dec. 6, 2018.
Adam, W et al., Photochemistry of the Azoalkanes 2,3-Diazabicyclo[2.2.1]hept-2-ene and Spiro[cyclopropane-1, 7-[2,3]diazabicyclo[2.2.1]hept-2-ene]: On the Questions of One-Bond vs. Two-Bond Cleavage during the Denitrogenation, Cyclization vs. Rearrangement of the 1,3-Diradicals, and Double Inversion, J. Org. Chem. 1985, 50, pp. 3303-3312.
Adams et al., Concise Total Synthesis of (+)-Luteoalbusins A and B. Organic Letters Aug. 2015;17(17):4268-4271. DOI: 10.1021/acs.orglett.5b02059.
Adjibade Y. et al., In Vitro Cytotoxicity of Polyindolenine Alkaloids on Rat Hepatoma Cell Lines. Structure Activity Relationships, Journal of Ethnopharmacology 1990, 29, pp. 127-136.
Aleksandrzak et al., Antimitotic activity of diaryl compounds with structural features resembling combretastatin A-4. Anticancer Drugs. Jul. 1998; 9(6):545-50.
Aliev et al., A concise approach to the epidithiodiketopiperazine (ETP) core. Tetrahedron Lett. 2006; 47(14):2387-2390.
Amador, T. A. et al., Antinociceptive Profile of Hodgkinsine, Planta Med 2000, 66, pp. 770-772.
Amir et al., Self-immolative dendrimers. Angew Chem Int Ed Engl. Sep. 29, 2003; 42(37):4494-9.
Amsberry et al., The lactonization of 2'-hydroxyhydrocinnamic acid amides: a potential prodrug for amines. J. Org. Chem. 1990; 55(23):5867-5877.
Andersen et al., Penicillium expansum: consistent production of patulin, chaetoglobosins, and other secondary metabolites in culture and their natural occurrence in fruit products. J Agric Food Chem. Apr. 21, 2004;52(8):2421-8.
Anderson et al., Studies on Total Synthesis of the Cytotoxic Marine Alkaloid Agelastatin A, J. Org. Chem., 63:7594-7595 (1998).
Andres et al., Combretatropones—hybrids of combretastatin and colchicine. Synthesis and biochemical evaluation Bioorganic. Med. Chem. Lett. 1993; 3(4):571-576.
Anet et al., Hodgkinsine, the Alkaloid of Hodgkinsonia Frutescens F. Muell, J. Chem. 1961, 14, pp. 173-174.
Anthon I, U. et al., Naturally Occurring Cyclotryptophans and Cyclotryptamines, Alkaloids: Chemical and Biological Perspectives, Pelletier, S. W., Ed.; Pergamon: London, 1999; vol. 13, pp. 163-236.
Bacher et al., D-24851, a novel synthetic microtubule inhibitor, exerts curative antitumoral activity in vivo, shows efficacy toward multidrug-resistant tumor cells, and lacks neurotoxicity. Cancer Res. Jan. 1, 2001; 61(1):392-9.
Bai et al., Interaction of dolastatin 10 with tubulin: induction of aggregation and binding and dissociation reactions. Molecular Pharmacology May 1995; 47(5):965-976.
Baldwin, J. E. et al., Azo Anions in Synthesis. Use of Trityl- and Diphenyl-4-Pyridylmenthylhydrazones for Reductive C—C Bond Formation, Tetrahedron 1986, vol. 42, No. 15, pp. 4235-4246.
Banwell et al., Synthesis, X-Ray Crystal Structure and Tubulin-Binding Properties of a Benzofuran Analogue of the Potent Cytotoxic Agent Combretastatin A4. Australian Journal of Chemistry 1999; 52(8):767-774.
Barrow et al., WIN 64821, a new competitive antagonist to substance P, isolated from an *aspergillus* species: structure determination and solution conformation. J. Org. Chem. 1993; 58(22):6016-6021.

Beck et al., Mild Aerobic Oxidative Palladium (II) Catalyzed C—H Bond Functionalization: Regioselective and Switchable C—H Alkenylation and Annulation of Pyrroles. J. Am. Chem. Soc. 2006; 128(8):2528-2529.
Bedford et al., Synthesis of water-soluble prodrugs of the cytotoxic agent Combretastatin A4. Bioorganic. Med. Chem. Lett. 1996; 6(2):157-160.
Behenna et al., Confirmation of the absolute configuration of (−)-aurantioclavine. Tetrahedron Letters Apr. 2011;52(17):2152-2154.
Belmar et al., Total Synthesis of (±)-Communesin F via a Cycloaddition with Indol-2-one. J. Am. Chem. Soc., 2012;134(41):16941-16943. DOI: 10.1021/ja307277w.
Belmar et al., Total Synthesis of (±)-isophellibiline and (±)-communesin F, and Design, Synthesis and Pharmacological Evaluation of Dihydro-β-erythroidine (DHβE) Analogs. Pennslyvania State University Dissertation 2012.
Benkovics et al., Oxaziridine-mediated oxyamination of indoles: an approach to 3-aminoindoles and enantiomerically enriched 3-aminopyrroloindolines. Angew Chem Int Ed Engl. Nov. 22, 2010;49(48):9153-7. doi: 10.1002/anie.201004635.
Beretz et al., Polyindolinic Alkaloids from Psychotria forsteriana. Potent Inhibitors of the Aggregation of Human Platelets, Planta Med. 1985, 51, pp. 300-303.
Bernardo et al., A Novel Redox Mechanism for the Glutathione-dependent Reversible Uptake of a Fungal Toxin in Cells. J Biol. Chem. 2003; 278(47):46549-46555.
Bertling et al., Candida albicans and its metabolite gliotoxin inhibit platelet function via interaction with thiols. Thromb Haemost. Aug. 2010;104(2):270-8.
Blokhin et al., Characterization of the interaction of the marine cyanobacterial natural product curacin A with the colchicine site of tubulin and initial structure-activity studies with analogues. Molecular Pharmacology Sep. 1995; 48(3):523-531.
Boger et al., Synthesis of the lower subunit of rhizoxin. J. Org. Chem. 1992; 57(8):2235-2244.
Boyer et al. Synthesis and Anticancer Activity of Epipolythiodiketopiperazine Alkaloids. Chem Sci. 2013;4(4):1646-1657. doi:10.1039/C3SC50174D.
Boyer et al., Concise Total Synthesis of (+)-Gliocladins B and C. Chem Sci. Jan. 1, 2012;3(6):1798-1803. Epub Mar. 30, 2012.
Brak et al., Total Synthesis of (−)-Aurantioclavine. Org. Lett., 2010;12(9):2004-2007. DOI: 10.1021/01100470g.
Brown et al., Investigation of various N-heterocyclic substituted piperazine versions of 5/7-{[2-(4-aryl-piperazin-1-yl)-ethyl]-propyl-amino}-5,6,7,8-tetrahydro-naphthalen-2-ol: effect on affinity and selectivity for dopamine D3 receptor. Bioorg Med Chem. Jun. 1, 2009;17(11):3923-33.
Bundgaard, (C) Means to enhance penetration: (1) Prodrugs as a means to improve the delivery of peptide drugs. Advanced Drug Delivery Reviei vs. 1992; 8(1):1-38.
Canham et al., Stereocontrolled enantioselective total synthesis of the [2+2] quadrigeminealkaloids, Tetrahedron 2015, 71, pp. 6424-6436.
Chaib et al., Anti-leukemia activity of chaetocin via death receptor-dependent apoptosis and dual modulation of the histone methyltransferase SUV39H1. Leukemia. Apr. 2012;26(4):662-74.
Chang et al., Heterocyclic Compounds. Part 15. NN'-Di-t-Butylthiadiaziridine 1, 1-Dioxide:Synthesis and Reactions, J. Chem. Soc., Perkin Trans. 1, 1977, pp. 1601-1605.
Chen et al., Ecology-based screen identifies new metabolites from a Cordyceps-colonizing fungus as cancer cell proliferation inhibitors and apoptosis inducers. Cell Prolif. Dec. 2009;42(6):838-47.
Cherblanc et al., On the Determination of the Stereochemistry of Semisynthetic Natural Product Analogues using Chiroptical Spectroscopy: Desulfurization of Epidithiodioxopiperazine Fungal Metabolites. Chem.—Eur. J. 2011; 17(42):11868-11875.
Choi et al., Agelastatin A (AgA), a Marine Sponge Derived Alkaloid, Inhibits Wnt/Beta-Catenin Signaling and Selectively Induces Apoptosis in Chronic Lymphocytic Leukemia Independently of p53, Blood (ASH Annual Meeting Abstracts), 118:Abstract1786, 2 pages (2011).

(56) References Cited

OTHER PUBLICATIONS

Chou et al., Therapeutic Cure against Human Tumor Xenografts inNude Mice by a Microtubule Stabilization Agent,Fludelone, via Parenteral or Oral Route. Cancer Res. 2005; 65(20):9445-9454.
Codelli et al., Enantioselective Total Synthesis of (−)-Acetylaranotin, a Dihydrooxepine Epidithiodiketopiperazine. J. Am. Chem. Soc. 2012; 134(4):1930-1933.
Coffen et al., A short synthesis of aromatic analogues of the aranotins. J. Org. Chem. Mar. 18, 1977:42(6):948-52.
Cogan et al., Asymmetric synthesis of chiral amines by highly diastereoselective 1,2-additions of organometallic reagents to N-tert-butanesulfinyl imines. Tetrahedron Jul. 1999;55(29):8883-8904.
Coleman et al., Antifungal activity of microbial secondary metabolites. PLoS One. 2011;6(9):e25321.
Collet et al., Catalytic C—H amination: recent progress and future directions, Chem. Commun. 2009:5061-5074.
Combeau et al., RPR112378 and RPR115781 : Two Representatives of a New Family of Microtubule Assembly Inhibitors. Molecular Pharmacology Mar. 2000; 57(3):553-563.
Cook et al., Epidithiodiketopiperazines Block the Interaction between Hypoxia-inducible Factor-1α (HIF-1α) and p300 by a Zinc Ejection Mechanism. J Biol. Chem. 2009; 284:26831-26838.
Cordell, G. A. et al., Bisindole Alkaloids, The Alkaloids: Chemistry and Physiology, Manske R. H. F., Rodrigo, R. G. A., Ed .; Academic Press: New York, 1981; vol. 20, pp. 3-295.
Coretese et al., Podophyllotoxin as a probe for the colchicine binding site of tubulin. J Biol Chem. Feb. 25, 1977;252(4):1134-40.
Corey, E. J. et al., Enantioselective Total Synthesis of Ecteinascidin 743, J. Am. Chem. Soc. 1996, 118, pp. 9202-9203.
Coste et al., Concise Total Synthesis of (+)-Bionectins A and C. Chem Sci. 2013;4(8):3191-3197. doi:10.1039/C3SC51150B.
Crawley et al., A Synthetic Approach to Nomofungin/Communesin B. Org. Lett., 2003, 5(18), pp. 3169-3171. DOI: 10.1021/o1034407v.
Crich et al., Expedient Synthesis of threo-β-Hydroxy-α-amino Acid Derivatives: Phenylalanine, Tyrosine, Histidine, and Tryptophan. J. Org. Chem. 2006; 71(18):7106-7109.
Crich, D. et al., Chemistry of the Hexahydropyrrolo[2,3-b]indoles: Configuration, Conformation, Reactivity, and Applications in Synthesis, Acc. Chem. Res. 2007, 40, pp. 151-161.
Cushman et al., Synthesis and evaluation of stilbene and dihydrostilbene derivatives as potential anticancer agents that inhibit tubulin polymerization. J. Med. Chem. 1991; 34(8):2579-2588.
Cushman et al., Synthesis of Analogs of 2-Methoxyestradiol with Enhanced Inhibitory Effects on Tubulin Polymerization and Cancer Cell Growth. J. Med. Chem. 1997; 40(15):2323-2334.
Dalsgaard, P. W. et al., Communesins G and H, New Alkaloids from the Psychrotolerant Fungus *Penicillium rivulum*, J. Nat. Prod. 2005, 68, pp. 258-261.
D'Ambrosia et al., Agelastatin A, a New Skeleton Cytotoxic Alkaloid of the Oroidin Family. Isolation from the Axinellid Sponge Agelas dendromorpha of the Coral Sea, J. Chem. Soc., Chem. Commun., pp. 1305-1306 (1993).
D'Ambrosio et al., The Active Centres of Agelastatin A, a Strongly Cytotoxic Alkaloid of the Coral Sea Axinellid Sponge Agelas dendromorpha, as Determined by Comparative Bioassays with Semisynthetic Derivatives, Helv. Chim. Acta, 79:727-735(1996).
Davis, F. A. et al., Adventures in Sulfur-Nitrogen Chemistry, J. Org. Chem. 2006, 71, pp. 8993-9003.
Davis, F. A. et al., Asymmetric synthesis of amino acids using sulfinimines (thiooxime S-oxides), Chem. Soc. Rev. 1998, 27, pp. 13-18.
De Groot et al., Cascade-release dendrimers liberate all end groups upon a single triggering event in the dendritic core. Angew Chem Int Ed Engl. Sep. 29, 2003; 42(37):4490-4.
De Groot et al., Design, Synthesis, and Biological Evaluation of a Dual Tumor-specific Motive Containing Integrin-targeted Plasmin-cleavable Doxorubicin Prodrug. Molecular Cancer Therapeutics 2002; 1(11):901-911.
De Groot et al., Synthesis and Biological Evaluation of Novel Prodrugs of Anthracyclines for Selective Activation by the Tumor-Associated Protease Plasmin. J. Med. Chem. 1999; 42(25):5277-5283.
De Loera, D. et al., Efficient Aziridine Synthesis in Metastable Crystalline Phases by Photoinduced Denitrogenation of Crystalline Triazolines, Org. Lett. 2012, vol. 14, No. 15, pp. 3874-3877.
De Loera, D. et al., Photoinduced and Thermal Denitrogenation of Bulky Triazoline Crystals: Insights into Solid-to-Solid Transformation, J. Am. Chem. Soc. 2013, 135, pp. 6626-6632.
Delorbe et al., Enantioselective Total Synthesis of (+)-Gliocladine C: Convergent Construction of Cyclotryptamine-Fused Polyoxopiperazines and a General Approach for Preparing Epidithiodioxopiperazines from Trioxopiperazine Precursors. J Am Chem Soc. Apr. 7, 2011;133(17):6549-52.
DeLorbe et al., General Approach for Preparing Epidithiodioxopiperazines from Trioxopiperazine Precursors: Enantioselective Total Syntheses of (+)- and (−)-Gliocladine C, (+)-Leptosin D, (+)-T988C, (+)-Bionectin A, and (+)-Gliocladin A. J. Am. Chem. Soc. 2013; 135(10):4117-4128.
Denmark et al., Palladium-Catalyzed Cross-Coupling Reactions of 2-Indolyldimethylsilanols with Substituted Aryl Halides. Org. Lett. 2004; 6(20):3649-3652.
Depew et al., Total Synthesis of 5-N-Acetylardeemin and Amauromine: Practical Routes to Potential MDR Reversal Agents. J. Am. Chem. Soc.1999; 121(51):11953-11963.
DePorter, S. M. et al., N-Nosyl oxaziridines as terminal oxidants in copper(II)-catalyzed olefinoxyaminations, Tetrahedron 2010, 51, pp. 5223-5225.
Dong et al., Nematicidal epipolysulfanyldioxopiperazines from Gliocladium roseum. J Nat Prod. Oct. 2005;68(10):1510-3.
Dorr et al., Antitumor activity of combretastatin-A4 phosphate, a natural product tubulin inhibitor. Invest. New Drugs Jun. 1996; 14(2):131-137.
Du Bois, Rhodium-Catalyzed C—H Amination. An Enabling Method for Chemical Synthesis, Org. Process Res. Dev. 2011, 15, pp. 758-762.
Dubey et al., Direct organocatalytic coupling of carboxylated piperazine-2,5-diones with indoles through conjugate addition of carbon nucleophiles to indolenine intermediates. Tetrahedron Lett. 2010;51(4):609-612. doi:10.1016/j.tetlet.2009.11.068.
Dubowchik et al., Monomethoxytrityl (MMT) as a versatile amino protecting group for complex prodrugs of anticancer compounds sensitive to strong acids, bases and nucleophiles. Tetrahedron Letters 1997; 38(30):5257-60.
Dubs et al., Eine neue Methode zur Herstellung gemischter Disulfide. Vorläufige Mitteilung Helv. Chim. Acta 1976; 59(4):1307-1311.
Ducki et al., Potent antimitotic and cell growth inhibitory properties of substituted chalcones. Bioorg Med Chem Lett. May 5, 1998; 8(9):1051-6.
Engel, P. S. et al., Thermolysis of Free-Radical Initiators: tert-Butylazocumene and Its 1,3- and 1,4-Bisazo and 1,3,5-Trisazo Analogues, J. Am. Chem. Soc. 2001, 123, pp. 3706-3715.
Engel, P. S., Mechanism of the Thermal and Photochemical Decomposition of Azoalkanes, Chemical Reviews Apr. 1980, vol. 80, No. 2, 52 pages.
Engel, P. S., Photochemistry of Aliphatic Azo Compounds in Solution, Accounts of Chemical Research 1973, vol. 6, pp. 275-281.
Espino, C. G. et al., A Rh-Catalyzed C—H Insertion Reaction for the Oxidative Conversion ofCarbamates to Oxazolidinones, Angew. Chem. Int. Ed. 2001, 40:3, pp. 598-600.
Espino, C. G. et al., Expanding the Scope of C—H Amination through Catalyst Design, J. Am. Chem. Soc. 2004, 126, pp. 15378-15379.
Eto et al., Conformation of aromatic rings in isolable atropisomers of 2-arylindoline derivatives and kinetic evidences for π-π interaction. Tetrahedron Lett. Jan. 23, 2010;66(4):898-903.
Fan, Y.-Q. et al., Alkaloids with Cardiovascular Effects from the Marine-Derived Fungus *Penicilliumexpansum* Y32, Mar. Drugs 2015, 13, pp. 6489-6504.
Fang, C.-L. et al., Dimerization of a 3-Substituted Oxindole at C-3 and Its Application to the Synthesis of (±)-Folicanthine, J. Am. Chem. Soc. 1994, 116, pp. 9480-9486.

(56) References Cited

OTHER PUBLICATIONS

Fink et al., Mercaptoacyl Dipeptides as Orally Active Dual Inhibitors of Angiotensin-Converting Enzyme and Neutral Endopeptidase. J. Med. Chem. 1996; 39(16):3158-3168.
Fiori, K. W. et al., A mechanistic analysis of the Rh-catalyzed intramolecular C—H amination reaction, Tetrahedron 2009, 65, pp. 3042-3051.
Fiori, K. W. et al., Catalytic Intermolecular Amination of C—H Bonds: Method Development and Mechanistic Insights, J. Am. Chem. Soc. 2007, 129, pp. 562-568.
Firouzabadi et al., Bispyridinesilver permanganate[Ag(C5H5N)2]MnO4: an efficient oxidizing reagent for organic substrates. Tetrahedron Lett. 1982; 23(17): 1847-1850.
Flynn et al., The synthesis and tubulin binding activity of thiophene-based analogues of combretastatin A-4. Bioorg Med Chem Lett. Sep. 3, 2001; 11(17):2341-3.
Foo, K. et al., Total Synthesis-Guided Structure Elucidation of (+)-Psychotetramine, Angew. Chem. Int. Ed. Engl. 2011, 50(12), pp. 2716-2719.
Fotsis et al., The endogenous oestrogen metabolite 2-methoxyoestradiol inhibits angiogenesis and suppresses tumour growth. Nature. Mar. 17, 1994; 368(6468):237-9.
Frisch et al., Synthesis of Short Polyoxyethylene-Based Heterobifunctional Cross-Linking Reagents. Application to the Coupling of Peptides to Liposomes. Bioconjugate Chem., 1996, 7(2), pp. 180-186.
Fuchs, J. R. et al., Total Synthesis of (+)-Peroporamidine, J. Am. Chem. Soc. 2004, 126, pp. 5068-5069.
Fukuyama et al., A total synthesis of gliotoxin. J. Am. Chem. Soc. 1976; 98(21):6723-6724.
Furst, L. et al., Total Synthesis of (+)-Gliocladin C Enabled by Visible-Light Photoredox Catalysis, Angew. Chem. Int. Ed. 2011, 50, pp. 9655-9659.
Gardiner et al., The epipolythiodioxopiperazine (ETP) class of fungal toxins: distribution, mode of action, functions and biosynthesis. Microbiology. Apr. 2005; 151(Pt 4):1021-32.
Gardner et al., Understanding C—H bond oxidations: H. and H-transfer in the oxidation of toluene by permanganate. Science. Sep. 29, 1995; 269(5232):1849-51.
Gastpar et al., Methoxy-Substituted 3-Formyl-2-phenylindoles Inhibit Tubulin Polymerization. J. Med. Chem. 1998; 41(25):4965-4972.
Gerwick et al., Structure of Curacin A, a Novel Antimitotic, Antiproliferative and Brine Shrimp Toxic Natural Product from the Marine Cyanobacterium *Lyngbya majuscula*. J. Org. Chem. 1994; 59(6):1243-1245.
Getahun et al., Synthesis of alkoxy-substituted diaryl compounds and correlation of ring separation with inhibition of tubulin polymerization: differential enhancement of inhibitory effects under suboptimal polymerization reaction conditions. J. Med. Chem. 1992; 35(6):1058-1067.
Gilow et al., Sulfenylation of some pyrroles and indoles. J Heterocyclic Chem. 1991, 28(4):1025-1034.
Golitz et al., A New Method for the Introduction of Trifluoromethyl Groups, Angew. Chem. Int. Ed. Engl. 1977, 16, No. 12, pp. 854-855.
Govek et al., Total Synthesis of (+)-asperazine, Tetrahedron 2007, 63, pp. 8499-8513.
Greene et al., Greene's Protective Groups in Organic Synthesis, Fifth Edition, Wiley, New York, NY 2014, Chapter 7, Protection for the Amino Group, 299 pages (Parts 1 & 2).
Greiner et al., Identification of a specific inhibitor of the histone methyltransferase SU(VAR)3-9. Nat Chem Biol. Aug. 2005;1(3):143-5.
Gueritte-Voegelein, F. et al., Alkaloids From Psychotria Oleoides with Activity on Growth Hormone Release, J. Nat. Prod. 1992, 55, pp. 923-930.
Gwaltney et al., Novel sulfonate derivatives: potent antimitotic agents. Bioorg Med Chem Lett. Jul. 9, 2001; 11(13):1671-3.
Hadimani et al., Synthesis, in vitro, and in vivo evaluation of phosphate ester derivatives of combretastatin A-4. Bioorg. Med. Chem. Lett. 2003; 13(9):1505-1508.
Hale et al., Enantiospecific Formal Total Synthesis of the Tumor and GSK-3b Inhibiting Alkaloid, (−)-Agelastatin A, Org. Lett., 5(16):2927-2930 (2003).
Hall, E. S. et al., Biogenetic-Type Synthesis of the Calycanthaceous Alkaloids, Tetrahedron 1967, 23, pp. 4131-4141.
Hamada et al., Selective removal of electron-accepting p-toluene- and naphthalenesulfonyl protecting groups for amino function via photoinduced donor acceptor ion pairs with electron-donating aromatics. J. Am. Chem. Soc. 1986; 108(1):140-145.
Hammonds et al., Studies to show that with podophyllotoxin the early replicative stages of herpes simplex virus type 1 depend upon functional cytoplasmic microtubules. J Med Microbiol. Sep. 1996; 45(3):167-72.
Han et al., Synthesis and Anticancer Activity of All Known (−)-Agelastatin Alkaloids, The Journal of Organic Chemistry, 78, p. 11970-11984 (2013).
Han, S.-J. et al., A Diastereodivergent Synthetic Strategy for the Syntheses of Communesin F and Peroporamidine, Org. Lett. 2014, 16, pp. 3316-3319.
Han, S.-J. et al., Evolution of a Unified, Sterodivergent Approach to the Synthesis of Communesin F and Peroporamidine, J. Org. Chem. 2015, 80, pp. 528-547.
Hansen et al., A stereoselective synthetic approach to (2S,3R)-N-(1′,1′-dimethyl-2′,3′-epoxypropyl)-3-hydroxytryptophan, a component of cyclomarin A. Tetrahedron: Asymmetry 2006; 17(1):15-21.
Hatanaka et al., Novel B-ring modified combretastatin analogues: syntheses and antineoplastic activity. Bioorg Med Chem Lett. Dec. 1, 1998; 8(23):3371-4.
Hay et al., A 2-nitroimidazole carbate prodrug of 5-amino-1-(chloromethyl)-3-[(5,6,7-trimethoxyindol-2-yl)carbonyl]-1,2-dihydro-3H-benz[e]indole (amino-seco-CBI-TMI) for use with ADEPT and GDEPT. Bioorg. Med. Chem. Lett. 1999; 9:2237-2242.
Hayashi, H. et al., New Insecticidal Compounds, Communesins C, D and E, from Penicillium expansum Link MK-57, Biosci. Biotechnol. Biochem. 2004, 68, pp. 753-756.
He et al., Total Syntheses of (−)-Asperlicin and (−)-Asperlicin C. J Am Chem Soc. Jun. 11, 1998;120(25):6417-8.
Hegedus, L. S. et al., Palladium-Catalyzed Reactions in the Synthesis of 3- and 4-Substituted Indoles. 3. Total Synthesis of(±)-Aurantioclavine, J. Org. Chem. 1987, 52, pp. 3319-3322.
Hendrickson, J. B. et al., Total Synthesis of the Calycanthaceous Alkaloids. Chimonanthine, R. Proc. Chem. Soc. 1962, pp. 383-384.
Hendrickson, J.B. et al., Total Synthesis of the Calycanthaceous Alkaloids, Tetrahedron 1964, vol. 20, pp. 565-579.
Herscheid et al., Biosynthesis of gliotoxin. Synthesis of sulfur-bridged dioxopiperazines from N-hydroxyamino acids. J. Org. Chem. 1980; 45(10):1885-1888.
Herzon, S. B. et al., Enantioselective Synthesis of Stephacidin B, J. Am. Chem. Soc. 2005, 127, pp. 5342-5344.
Higuchi et al., First Total Synthesis of Hinckdentine A. Org Lett. 2009;11(1):197-9.
Higuchi et al., Preparation of 2,2-disubstituted 1,2-dihydro-3H-indol-3-ones via oxidation of 2-substituted indoles and Mannich-type reaction. Tetrahedron Lett. Feb. 6, 2010;66(6):1236-43.
Hino et al., Synthesis of 3,6-diethoxycarbonyl-3,6-epipolythia-2,5-piperazinedione derivatives. Tetrahedron Lett. 1971; 12(33):3127-3129.
Hino, T. et al., Chemistry and Reactions of Cyclic Tautomers of Tryptamines and Tryptophans, The Alkaloids: Chemistry and Pharmacology, Brossi, A., Ed.; Academic Press: New York, 1989; vol. 34, pp. 1-75.
Hino, T. et al., Oxidative Dimerization of Nb-Methoxycarbonyltryptamines by Dye-Sensitized Photooxygenation in Formic Acid. Synthesis of (±)-Folicanthine and (±)-Chimonanthine, Tetrahedron Letters 1978, 49, pp. 4913-4916.
Hino, T. et al., Total Synthesis of (±)-Folicanthine, Tetrahedron Letters 1963, 25, pp. 1757-1760.
Hoffmann, S. et al., A Powerful Brönsted Acid Catalyst for the Organocatalytic Asymmetric Transfer Hydrogenation of Imines, Angew. Chem. Int. Ed. 2005, 44, pp. 7424-7427.
Hoijemberg, P. A. et al., Photolysis of an asymmetrically substituted diazene in solution and in the crystalline state, Photochem. Photobiol. Sci. 2009, 8, pp. 961-969.

(56) References Cited

OTHER PUBLICATIONS

Holwell et al., Anti-vascular effects of vinflunine in the MAC 15A transplantable adenocarcinoma model. Br. J. Cancer., 2001; 84:290-295.
Hossain, T. Md et al., Synthesis of Bisbicyclo[1.1.1]pentyldiazene. The Smallest Brigehead Diazene, J. Org. Chem. 2001, 66, pp. 6282-6285.
Hsieh et al., Structure-activity and crystallographic analysis of benzophenone derivatives—the potential anticancer agents. Bioorg Med Chem Lett. 2002; 13(1):101-105.
Huang et al., Diketopiperazines from Marine Organisms. Chem. Biodiv. 2010; 7(12):2809-2829.
Huard, K. et al., N-Tosyloxycarbamates as Reagents in Rhodium-Catalyzed C—H Amination Reactions, Chem. Eur. J. 2008, 14, pp. 6222-6230.
Ikeda, H. et al., Evidence for Significant Through-Space and Through-Bond Electronic Coupling in the 1,4-Diphenylcyclohexane-1,4-diyl Radical Cation Gained by Absorption Spectroscopy and OFT Calculations, Chem. Eur. J. 2007, 13, DD. 9207-9215.
Isham et al., Chaetocin: a promising new antimyeloma agent with in vitro and in vivo activity mediated via imposition of oxidative stress. Blood. Mar. 15, 2007;109(6):2579-88.
Isham et al., The anticancer effects of chaetocin are independent of programmed cell death and hypoxia, and are associated with inhibition of endothelial cell proliferation. Br J Cancer. Jan. 17, 2012;106(2):314-23.
Ishikawa, H. et al., Dimerization of indole derivatives with hypervalent iodines(III): a new entry for the concise total synthesis of rac- and meso-chimonanthines, Tetrahedron Lett. 2002, 43, pp. 5637-5639.
Iwasa et al., Total Synthesis of (+)-Chaetocin and its Analogues: Their Histone Methyltransferase G9a Inhibitory Activity. J. Am. Chem. Soc. 2010; 132(12):4078-4079.
Iwasa, et al., Epipolythiodiketopiperazine Alkaloids: Total Syntheses and Biological Activities. Isr. J Chem. 2011; 51(3-4):420-433.
Jadulco, R. C., Isolation and Structure Elucidation of Bioactive Secondary Metabolites from Marine Sponges and Sponge-derived Fungi, 2002, 88 pages.
Jadulco, R. et al., New Communesin Derivatives from the Fungus *Penicillium* sp. Derived from theMediterranean Sponge *Axinella verrucosa*, J. Nat. Prod. 2004, 67, pp. 78-81.
Jamison, C. R. et al., Enantioselective Synthesis of Polypyrroloindolines by Controlled Oligomerization, Nat. Chem. 2017, doi: 10.1038/nchem.2825, 1 page.
Janik et al., Synthesis and antimicrobtubule activity of combretatropone derivatives. Bioorg. Med. Chem. Lett. 2002; 10:1895-1903.
Jannic, V. et al., Pyrrolidinoindoline alkaloids from Psychotria oleoides and Psychotria lyciiflora. J Nat Prod. Jun. 1999;62(6):838-43.
Jiang et al., Disulfide- and Multisulfide-Containing Metabolites from Marine Organisms. Chem. Rev. 2012; 112(4):2179-2207.
Jiang et al., Epipolythiodioxopiperazines from fungi: chemistry and bioactivities. Mini Rev Med Chem. Aug. 2011;11(9):728-45.
Jiang et al., Synthesis and biological evaluation of 2-styrylquinazolin-4(3H)-ones, a new class of antimitotic anticancer agents which inhibit tubulin polymerization. J. Med. Chem. 1990; 33(6):1721-1728.
Jordan et al., Fungal epipolythiodioxopiperazine toxins have therapeutic potential and roles in disease. Trends Pharmacol. Sci. 8, 144-149.
Jouanneau et al., Derivatization of agelastatin A leading to bioactive analogs and a trifunctional probe, Bioorganic & Medicinal Chemistry Letters, 26, p. 2092-2097 (2016).
Kakeya, et al., Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid. Chem. Pharm. Bull. 1984 32(2):692-698.
Kaneko et al., New hydrazone derivatives of Adriamycin and their immunoconjugates—a correlation between acid stability and cytotoxicity. Bioconjugate Chem. 1991; 2(3):133-141.
Kanoh et al., (−)-Phenylahistin arrests cells in mitosis by inhibiting tubulin polymerization. J Antibiot (Tokyo). Feb. 1999; 52(2):134-41.
Karaman et al., Preparation and properties of quaternary ammonium and phosphonium permanganates. J. Org. Chem. 1984; 49(23):4509-4516.
Kerzaon et al., Structural investigation and elucidation of new communesins from a marine-derived Penicillium expansum Link by liquid chromatography/electrospray ionization mass spectrometry. Rapid Commun Mass Spectrom. Dec. 2009;23(24):3928-38. doi: 10.1002/rcm.4330.
Kieffer, M. E. et al., Copper-Catalyzed Diastereoselective Arylation of Tryptophan Derivatives: Total Synthesis of (+)-Naseseazines A and B, J. Am. Chem. Soc. 2013, 135(15), pp. 5557-5560.
Kim et al., Alkylthiolation of allylic sulfides. [2,3] Sigmatropic rearrangement of thiosulfonium ions. J. Org. Chem. 1979; 44(12):1897-1904.
Kim et al., Biogenetically inspired syntheses of alkaloid natural products. Chem Soc Rev. Nov. 2009;38(11):3035-50. doi: 10.1039/b819925f. Epub Sep. 23, 2009.
Kim et al., Concise Total Synthesis and Stereochemical Revision of (+)-Naseseazines A and B: Regioselective Arylative Dimerization of Diketopiperazine Alkaloids. J. Am. Chem. Soc. 2011;133(38):14940-14943.
Kim et al., General approach to epipolythiodiketopiperazine alkaloids: total synthesis of (+)-chaetocins A and C and (+)-12,12'-dideoxychetracin A. J Am Chem Soc. Oct. 20, 2010;132(41):14376-8. doi: 10.1021/ja106869s.
Kim et al., Total synthesis of (+)-11, 11 '-dideoxyverticillin A, Science. 2009;324(5924):238-41.
Kim, H. et al., Transition-Metal-Mediated Direct C—H Amination of Hydrocarbons with Amine Reactants: The Most Desirable but Challenging C—N Bond-Formation Approach, ACS Catal. 2016, 6, pp. 2341-2351.
Kim, J. et al., Biogenetically-Inspired Total Synthesis of Epidithiodiketopiperazines, Acc. Chem. Res. 2015, 48, pp. 1159-1171.
King et al., Facile synthesis of maleimide bifuntional linkers, Tetrahedron Lett. 2002; 43:1987-1990.
Kingsbury et al., A novel peptide delivery system involving peptidase activated prodrugs as antimicrobial agents. Synthesis and biological activity of peptidyl derivatives of 5-fluorouracil. J. Med. Chem. 1984; 27:1447-1451.
Kingston et al., The Chemistry of Taxol, a Clinically Useful Anticancer Agent. J. Nat. Prod. 1990; 53(1):1-12.
Kishi et al., Total synthesis of dehydrogliotoxin. J. Am. Chem. Soc. 1973; 95(19):6492-6493.
Kitir, B. et al., Total synthesis and structural validation of cyclodepsipeptides solonamide A and B, Tetrahedron 2014, 70, pp. 7721-7732.
Kobayashi et al., Synthetic study on an antitumor antibiotic rhizoxin by using an enzymatic process on prochiral β-substituted glutarates. Pure Appl. Chem. 1992; 64(8):1121-1124.
Kodanko, J. J. et al., Enantioselective Total Syntheses of the Cyclotryptamine Alkaloids Hodgkinsine and Hodgkinsine B, Angew. Chem. Int. Ed. 2003, 42, pp. 2528-2531.
Kodanko, J. J. et al., Synthesis of All Low-energy Stereoisomers of the Tris(pyrrolidinoindoline) Alkaloid Hodgkinsine and Preliminary Assessment of Their Antinociceptive Activity, J. Org. Chem. 2007, 72, pp. 7909-7914.
Kosower, E. M., Monosubstituted Diazenes (Diimides). Suprising Intermediates, Accounts ofChemical Research 1971, vol. 1, No. 6, pp. 193-198.
Kricheldorf, H.R. Synthese von Isothiocyanatocarbonsäurechloriden aus Lactamen. Angew. Chem. 1975; 87(14):517.
Krishnan, S. et al., Pd-Catalyzed Enantioselective Aerobic Oxidation of Secondary Alcohols:Applications to the Total Synthesis of Alkaloids, J. Am. Chem. Soc. 2008, 130, pp. 13745-13754.
Kroutil et al., First preparative biocatalytic hydrolysis and S-methylation of cyclic trithiocarbonates. Tetrahedron 2002; 58(13):2589-2592.
Ksander et al., Chemie der α-Aminonitrile 1. Mitteilung Einleitung und Wege zu Uroporphyrinogen-octanitrilen. Helv Chim Acta. Jul. 8, 1987;70(4):1115-72.

(56) References Cited

OTHER PUBLICATIONS

Kung et al., Small molecule blockade of transcriptional coactivation of the hypoxia-inducible factor pathway. Cancer Cell. Jul. 2004;6(1):33-43.

Kurokawa, T. et al., Synthesis of 1,3-Diamines Through Rhodium-Catalyzed C—H Insertion, Angew. Chem. Int. Ed. 2009, 48, pp. 2777-2779.

Laguzza et al., New antitumor monoclonal antibody-vinca conjugates LY203725 and related compounds: design, preparation, and representative in vivo activity. J. Med. Chem. 1989; 32(3):548-555.

Langer, R., New methods of drug delivery, Science Sep. 28, 1990: vol. 249, Issue 4976, pp. 1527-1533.

Lathrop et al., Radical-mediated dimerization and oxidation reactions for the synthesis of complex alkaloids. Chimia (Aarau). 2012;66(6):389-93. doi: 10.2533/chimia.2012.389.

Lathrop, S. P. et al., Application of diazene-directed fragment assembly to the total synthesis and stereochemical assignment of (+)-desmethyl-meso-chimonanthine and related heterodimeric alkaloids, Chem. Sci. 2014, 5, DD. 333-340.

Lavielle et al., New .alpha.-amino phosphonic acid derivatives of vinblastine: chemistry and antitumor activity. J. Med. Chem. 1991; 34(7):1998-2003.

Lawrence et al., The interaction of chalcones with tubulin. Anticancer Drug Des. Apr. 2000; 15(2):135-41.

Lebsack, A. D. et al., Enantioselective Total Synthesis of Quadrigemine C and Psycholeine, J. Am. Chem. Soc. 2002, 124, pp. 9008-9009.

Lee et al., Antihepatoma activity of chaetocin due to deregulated splicing of hypoxia-inducible factor 1α pre-mRNA in mice and in vitro. Hepatology. Jan. 2011;53(1):171-80.

Leoni et al., Indanocine, a microtubule-binding indanone and a selective inducer of apoptosis in multidrug-resistant cancer cells. J Natl Cancer Inst. Feb. 2, 2000;92(3):217-24.

Li et al., An integrated approach to the discovery of potent agelastatin A analogues for brain tumors: chemical synthesis and biological, physicochemical and CNS pharmacokinetic analyses, Med. Chem. Commun., 4, p. 1093-1098 (2013).

Li et al., Cytotoxic metabolites from the antarctic psychrophilic fungus *Oidiodendron truncatum*. J Nat Prod. May 25, 2012;75(5):920-7. doi: 10.1021/np3000443. Epub May 14, 2012.

Li et al., General Approach for the Synthesis of Ajmaline/Sarpagine Indole Alkaloids: Enantiospecific Total Synthesis of (+)-Ajmaline, Alkaloid G, and Norsuaveoline via the Asymmetric Pictet-Spengler Reaction. J Am Chem Soc. Jul. 16, 1999;121(30):6998-7010.

Li et al., Ligand-based targeted therapy: a novel strategy for hepatocellular carcinoma. Int J Nanomedicine. Oct. 31, 2016;11:5645-5669. eCollection 2016.

Li et al., Pharmacokinetics of Agelastatin A in the central nervous system. Med. Chem. Commun. 2012;3:233-237.

Liang et al., Organocatalytic stereoselective conjugate addition of 3-substituted oxindoles with in situ generated ortho-quinone methides. Tetrahedron Lett. May 2, 2018;59(18):1742-7.

Libot, F. et al., Biomimetic Transformation of Hodgkinsine, a Pyrrolidinoindoline Alkaloids, Heterocycles 1988, 27, pp. 2381-2386.

Libot, F. et al., Rubiacees D'Oceanie: Alcalo'ldes de Psychotria Oleoides de Nouvelle—Caledonie et de Calycodendron Milnei du Vanuatu (Nouvelles-Hebrides), Journal of Natural Products 1987, vol. 50, No. 3, pp. 468-473.

Lim, Y.-K. et al., Novel Route to Azobenzenes via Pd-Catalyzed Coupling Reactions of Aryl Hydrazides with Aryl Halides, Followed by Direct Oxidations, Org. Lett. 2003, vol. 5, No. 7, pp. 979-982.

Lin et al., Antimitotic natural products combretastatin A-4 and combretastatin A-2: studies on the mechanism of their inhibition of the binding of colchicine to tubulin. Biochemistry 1989; 28(17):6984-6991.

Lin, H.-C. et al., Elucidation of the Concise Biosynthetic Pathway of the Communesin Indole Alkaloids, Angew. Chem. Int. Ed. 2015, 54, pp. 3004-3007.

Lin, H.-C. et al., P450-Mediated Coupling of Indole Fragments To Forge Communesin and Unnatural Isomers, J. Am. Chem. Soc. 2016, 138, pp. 4002-4005.

Lindovska, P. et al., Concise Synthesis of (−)-Hodgkinsine, (−)-Calycosidine, (−)-Hodgkinsine B, (−)-Quadrigemine C, and (−)-Psycholeine via Convergent and Directed Modular Assembly of Cyclotryptamines, https://www.ncbi.nlm.nih.qov/m/pubmed/29058431, 2017, 7 paqes.

Link, J. T. et al., Stereocontrolled Total Syntheses of meso-Chimonanthine and meso-Calycanthine via a Novel Samarium Mediated Reductive Dialkylation, J. Am. Chem. Soc. 1996, 118, pp. 8166-8167.

Little, R. D. et al., Total Synthesis of the Marine Natural Product il9(12l-Capnellene. Reversal of Regiochemistry in the Intramolecular 1,3-Diyl Trapping Reaction, J. Am. Chem. Soc. 1983, 105, pp. 928-932.

Little, Diyl Trapping and Electroreductive Cyclization Reactions, Chem. Rev. 1996, 96, pp. 93-114.

Liu et al., Verticillin A overcomes apoptosis resistance in human colon carcinoma through DNA methylation-dependent upregulation of BNIP3. Cancer Res. Nov. 1, 2011;71(21):6807-16.

Liu, P. et al., Total Synthesis of the Polycyclic Fungal Metabolite (±)-Communesin F, Angew. Chem. Int. Ed. 2010, 49:2000-2003.

Loach, R. P. et al., Concise Total Synthesis of (+)-Asperazine, (+)-Pestalazine A, and (+)-iso-Pestalazine A. Structure Revision of (+)-Pestalazine A, J. Am. Chem. Soc. 2016, 138(3), pp. 1057-1064.

Mahboobi et al., Synthetic 2-Aroylindole Derivatives as a New Class of Potent Tubulin-Inhibitory, Antimitotic Agents. J. Med. Chem. 2001; 44(26):4535-4553.

Mannila et al., Combretastatin Analogs via Hydration of Stilbene Derivatives. Liebigs. Ann. Chem. 1993; 1993(9):1037-1039.

March, Advanced Organic Chemistry, Third Edition: John Wiley & Sons, inc. New York, NY, Chapter 1, Localized Chemical Bonding n pp. 16-18.

Mascitti, V. et al., Total Synthesis of (±)-Pentacycloanammoxic Acid, J. Am. Chem. Soc. 2004, 126, pp. 15664-15665.

Mason et al., Agelastatin A: a novel inhibitor of osteopontin-mediated adhesion, invasion, and colony formation, Mol. Cancer Ther., 7:548-558 (2008).

Matano et al., Synthesis and Charge-Carrier Transport Properties of Poly(phosphole P-alkanesulfonylimide)s, Org. Lett., 2013, 15 (4), pp. 932-935.

Matsuda, Y. et al., Total Synthesis and Structure Reinvestigation of So-Called Isochimonanthine, Heterocycles 2005, 65, pp. 1031-1033.

May, J. A. et al., Biomimetic approach to communesin B (a.k.a. nomofungin), Tetrahedron Letters 2003, 44, pp. 1203-1205.

May, J. A. et al., The structural and synthetic implications of the biosynthesis of the calycanthaceous alkaloids, the communesins, and nomofungin, Tetrahedron 2006, 62, pp. 5262-5271.

Medarde et al., Synthesis and antineoplastic activity of combretastatin analogues: Heterocombretastatins. Eur. J. Med. Chem., 1998; 33(1)71-77.

Medarde et al., Synthesis and pharmacological activity of combretastatin analogues. Naphthylcombretastatins and related compounds. Bioorganic. Med. Chem. Lett. 1995; 5(3):229-232.

Medarde et al., Synthesis and pharmacological activity of diarylindole derivatives. Cytotoxic agents based on combretastatins. Bioorg Med Chem Lett. Aug. 1, 1999; 9(16):2303-2308.

Medina et al., Novel antineoplastic agents with efficacy against multidrug resistant tumor cells. Bioorg Med Chem Lett. Oct. 6, 1998; 8(19):2653-6.

Michaelis, D. J. et al., Oxaziridine-mediated enantioselective aminohydroxylation of styrenes catalyzed by copper(II) bis(oxazoline) complexes, Tetrahedron 2009, 65, pp. 5118-5124.

Miknis et al., Total synthesis of (.+−.)-aspirochlorine. J. Am. Chem. Soc. 1993; 115(2):536-547.

Miller et al., Specific Inhibition of Viral Ribonucleic Acid Replication by Gliotoxin. Science Jan. 26, 1968; 159(3813):431-432.

Moody et al., Dirhodium(II) tetraacetate catalysed reactions of diazo thioamides: isolation and cycloaddition of anhydro-4-hydroxy-

(56) References Cited

OTHER PUBLICATIONS 1,3-thiazolium hydroxides (thioisomünchnones), an approach to analogues of dehydrogliotoxin. Org. Biomol. Chem. 2003;1(15):2716-2722.
Morton, D. et al., Chiral non-racemic sulfinimines: versatile reagents for asymmetric synthesis, Tetrahedron 2006, 62, pp. 8869-8905.
Movassaghi et al., Total Synthesis of All (−)-Agelastatin Alkaloids Asymmetric Synthesis Ii: More Methods and Applications. 2013;391-396. DOI: 10.1002/9783527652235.ch49.
Movassaghi et al., Total synthesis of all (−)-agelastatin alkaloids. Chem. Sci. 2010;1:561-66.
Movassaghi, M. et al., Concise Total Synthesis of (−)-Calycanthine, (+)-Chimonanthine, and(+)-Folicanthine, Angew. Chem. Int. Ed. 2007, 46, pp. 3725-3728.
Movassaghi, M. et al., Concise Total Synthesis of (+)-WIN 64821 and (−)-Ditryptophenaline, Angew. Chem. Int. Ed. 2008, 47, pp. 1485-1487.
Movassaghi, M. et al., Directed Heterodimerization: Stereocontrolled Assembly via Solvent-Caged Unsymmetrical Diazene Fragmentation, J. Am. Chem. Soc. 2011, 133, pp. 13002-13005.
Mu et al., Synthesis, anticancer activity, and inhibition of tubulin polymerization by conformationally restricted analogues of lavendustin A. J Med Chem. Apr. 24, 2003; 46(9):1670-82.
Müllbacher et al., Structural relationship of epipolythiodioxopiperazines and their immunomodulating activity. Molec. Immunol. Feb. 1986; 23(2):231-235.
Myers et al., A Concise, Stereocontrolled Synthesis of (−)-Saframycin A by the Directed Condensation of α-Amino Aldehyde Precursors. J Am Chem Soc. Nov. 5, 1999;121(46):10828-29.
Nakada et al., The first total synthesis of the antitumor macrolide, rhizoxin. Tetrahedron Lett., 1993; 34(6):1039-1042.
Nakagawa, M. et al., Oxidative Dimerization of Nb-Acyltryptophans Total Synthesis and Absolute Configuration of Ditryptophenaline, Tetrahedron Letters 1981, vol. 22, No. 52, pp. 5323-5326.
Nam, Combretastatin A-4 analogues as antimitotic antitumor agents. Curr Med Chem. Sep. 2003; 10(17):1697-722.
Nam et al., Synthesis and anti-tumor activity of novel combretastatins: combretocyclopentenones and related analogues. Bioorg Med Chem Lett. 2002; 12(15):1955-1958.
Nascimento, R. R. G. et al., New Alkaloids from *Margaritopsis carrascoana* (Rubiaceae), J. Braz. Chem. Soc. 2015, vol. 26, No. 6, pp. 1152-1159.
Nelsen, S. F. et al., Azocumene. I. Preparation and Decomposition of Azocumene. Unsymmetrical Coupling Products of the Cumyl Radical, Journal of the American Chemical Society, Jan. 5, 1966, 88:1, pp. 137-143.
Nelson, H. M. et al., Chiral Anion Phase Transfer of Aryldiazonium Cations: An Enantioselective Synthesis of C3-Diazenated Pyrroloindolines, Angew. Chem. Int. Ed. 2014, 53, pp. 5600-5603.
Neuman, R. C. et al., cis-Diazenes. Viscosity Effects, One-Bond Scission, and Cis-Trans Isomerization, J. Org. Chem. 1990, 55, pp. 2682-2688.
Nguyen-Hai et al., Combretoxazolones: synthesis, cytotoxicity and antitumor activity. Bioorg. Med. Chem. Lett. 2001; 11(23):3073-3076.
Nicolaou et al., A Practical Sulfenylation of 2,5-Diketopiperazines. Angew. Chem. Int. Ed. 2012; 51(3):728-732.
Nicolaou et al., Synthesis of epothilones A and B in solid and solution phase. Nature. May 15, 1997;387(6630):268-72.
Nicolaou et al., Total Synthesis of Epicoccin G. J. Am. Chem. Soc. 2011; 133(21):8150-8153.
Nielsen et al., Glycolamide Esters as Biolabile Prodrugs of Carboxylic Acid Agents: Synthesis, Stability, Bioconversion, and Physicochemical Properties. J. Pharma. Sciences. 1988; 77(4):285-298.
Nishida et al., Fungal metabolite gliotoxin targets flavocytochrome b558 in the activation of the human neutrophil NADPH oxidase. Infect Immun. Jan. 2005; 73(1):235-44.
Numata, A. et al., Communesins, Cytotoxic Metabolites of a Fungus Isolated from a Marine Alga, Tetrahedron Lett. 1993, 34, pp. 2355-2358.
Oguri et al., Amino Acids and Peptides. XXIX. A New Efficient Asymmetric Synthesis of α-Amino Acid Derivatives with Recycle of a Chiral Reagent-Asymmetric Alkylation of a Chiral Schiff Base from Glycine. Chem. Pharm. Bull. 1978; 26(3):803-808.
Ohme, R. et al., Preparation of Azo Compounds from N,N'-Dialkylsulfamides, Angew. Chem. Internat. Edit. 1965, vol. 4, No. 5, p. 433.
Ohsumi et al., Novel Combretastatin Analogues Effective against Murine Solid Tumors: Design and Structure—Activity Relationships. J. Med. Chem. 1998; 41(16):3022-3032.
Ohsumi et al., Syntheses and antitumor activity of cis-restricted combretastatins: 5-membered heterocyclic analogues. Bioorg Med Chem Lett. Nov. 17, 1998; 8(22):3153-8.
Okoth et al., End-labeled amino terminated monotelechelic glycopolymers generated by ROMP and Cu(I)-catalyzed azide-alkyne cycloaddition, Beilstein J. Org. Chem. 2013, 9, 608-612.
Ottenheijm et al., Approaches to analogs of dehydrogliotoxin. 6. An efficient synthesis of a gliotoxin analog with anti-reverse transcriptase activity. J. Org. Chem. 1976: 41(21):3433-3438.
Overman et al., Construction of Epidithiodioxopiperazines by Directed Oxidation of Hydroxyproline-Derived Dioxopiperazines. Org. Lett. 2007; 9(25):5267-5270.
Overman, L. E. et al., Direct Stereo- and Enantiocontrolled Synthesis of Vicinal Stereogenic Quaternary Carbon Centers. Total Synthesis of meso- and (−)-Chimonanthine and (+)-Calycanthine, J. Am. Chem. Soc. 1999, 121, pp. 7702-7703.
Overman, L. E. et al., Enantioselective Construction of Vicinal Stereogenic Quaternary Centers by Dialkylation: Practical Total Syntheses of(+)- and meso-Chimonanthine, Angew. Chem. Int. Ed. 2000, vol. 39, No. 1):213-215.
Overman, L. E. et al., Enantioselective synthesis of (−)-idiospermuline, Tetrahedron 2003, 59:6905-6919.
Overman, L. E. et al., Enantioselective Total Synthesis of (+)-Gliocladin C, Org. Lett. 2007, 9(2):339-341.
Overman, L. E. et al., Enantioselective Total Synthesis of the Cyclotryptamine Alkaloid Idiospermuline, Angew. Chem. Int. Ed. 2003, 42, pp. 2525-2528.
Owellen et al., Inhibition of tubulin-microtubule polymerization by drugs of the Vinca alkaloid class. Cancer Res. Apr. 1976; 36(4):1499-502.
Pahl et al., The immunosuppressive fungal metabolite gliotoxin specifically inhibits transcription factor NF-kappaB. J Exp Med. Apr. 1, 1996; 183(4): 1829-1840.
Patel et al., Straightforward access to protected syn alpha-amino-beta-hydroxy acid derivatives. Angew Chem Int Ed Engl. 2008; 47(22):4224-7.
Patron et al., Origin and distribution of epipolythiodioxopiperazine (ETP) gene clusters in filamentous ascomycetes. BMC Evolutionary Biology 2007; 7:174.
Perez-Balado, C. et al., Expedient Total Synthesis of WIN 64745 and WIN 64821, Org. Lett. 2008, vol. 10, No. 17, pp. 3701-3704.
Perez-Balado, C. et al., Stereocontrolled and Versatile Total Synthesis of Bispyrrolidinoindoline Diketopiperazine Alkaloids: Structural Revision of the Fungal Isolate (+)- Asperdimin, Chem. Eur. J. 2009, 15, pp. 9928-9937.
Pettit et al., Antineoplastic agents 365. Dolastatin 10 SAR probes. Anticancer Drug Des. Jun. 1998; 13(4):243-77.
Pettit et al., Antineoplastic Agents, 122. Constituents of Combretum caffrum. J. Nat. Prod. 1987; 50(3):386-391.
Pettit et al., Antineoplastic agents. 113. Synthesis of natural (−)-combretastatin. J. Org. Chem. 1985; 50(18):3404-3406.
Pettit et al., Antineoplastic agents. 257. Isolation and structure of spongistatin 1. J. Org. Chem. 1993; 58(6):1302-1304.
Pettit et al., Antineoplastic Agents. 291. Isolation and Synthesis of Combretastatins A-4, A-5, and A-6. J. Med. Chem. 1995; 38(10):1666-1672.
Pettit et al., Antineoplastic Agents. 443. Synthesis of the Cancer Cell Growth Inhibitor Hydroxyphenstatin and Its Sodium Diphosphate Prodrug. J. Med. Chem. 2000; 43(14):2731-2737.

(56) References Cited

OTHER PUBLICATIONS

Pettit et al., Antineoplastic agents. 487. Synthesis and biological evaluation of the antineoplastic agent 3,4-methylenedioxy-5,4'-dimethoxy-3'-amino-Z-stilbene and derived amino acid amides. J Med Chem. Feb. 13, 2003; 46(4):525-31.
Pettit et al., cation salts, combretastatin A-3, diphosphate, prodrugs. Anti-Cancer Drug Design 2000: 15(6):397-403.
Pettit et al., Isolation and structure of combretastatin. Canadian Journal of Chemistry, 1982, 60(11): 1374-137.
Pettit et al., The isolation and structure of a remarkable marine animal antineoplastic constituent: dolastatin 10. J. Am. Chem. Soc. 1987; 109(22):6883-6885.
Pinney et al., A new anti-tubulin agent containing the benzo[b]thiophene ring system. Bioorg Med Chem Lett. Apr. 19, 1999; 9(8):1081-6.
Pinney et al., Synthesis and biological evaluation of aryl azide derivatives of combretastatin A-4 as molecular probes for tubulin. Bioorg Med Chem. Oct. 2000; 8(10):2417-25.
Poisel et al., Syntheseversuche in der Reihe der 3.6-Epidithio-2.5-dioxo-piperazin-Antibiotika Gliotoxin, Sporidesmin, Aranotin und Chaetocin, II. Chem. Ber., 1971; 104(6):1714-1721.
Polaske et al., Enantioselective organocatalytic α-sulfenylation of substituted diketopiperazines. Tetrahedron: Asym. 2009; 20(23):2742-2750.
Porter, N. A. et al., Diazenyl Radicals: A 15N CIDNP and Radical Trapping Study of Unsymmetric Diazenes, Journal of the American Chemical Society Feb. 1, 1978, 100:3:920-925.
Porter, N. A. et al., Photolysis of Unsymmetric Azo Compounds. Cis Azo Compound Intermediates, Journal of the American Chemical Society Jun. 27, 1973, 95:13:4361-4367.
PUBCHEM CID 161244 deposited on Mar. 27, 2005, pp. 1-15.
PUBCHEM CID 18624123 deposited on Dec. 4, 2007, pp. 1-12.
PUBCHEM CID 69829071 deposited on Dec. 1, 2012, pp. 1-12.
Rao et al., Radical mediated enantioselective construction of C-1 to C-9 segment of rhizoxin. Tetrahedron Lett. 1992; 33(27):3907-3910.
Rao et al., Studies directed towards the total synthesis of rhizoxin: Stereoselective synthesis of C-12 to C-18 segment. Tetrahedron Lett. 1993; 34(4):707-710.
Rasolonjanahary, R. et al., Psycholeine, a natural alkaloid extracted from Psychotria oleoides, acts as a weak antagonist of somatostatin, European Journal of Pharmacology 1995, 285, pp. 19-23.
Rezanka et al., Pharmacologically Active Sulfur-Containing Compounds. Anti-Infect. Agents Med. Chem., 2006; 5(2):187-224.
Rightsel et al., Antiviral Activity of Gliotoxin and Gliotoxin Acetate. Nature. Dec. 26, 1964;204:1333-4.
Robak, M. T. et al., Synthesis and Applications of tert-Butanesulfinamide, Chem. Rev. 2010, 110, pp. 3600-3740 (Parts 1 & 2).
Robinson, R. et al., Calcycanthine and Calycanthidine, Chem. Ind. 1954, 27, pp. 783-784.
Rodrigues et al., Synthesis and beta-lactamase-mediated activation of a cephalosporin-taxol prodrug. Chem Biol. Apr. 1995; 2(4):223-7.
Roizen, J. L. et al., Metal Catalyzed Nitrogen-Atom Transfer methods for the Oxidation of Aliphatic C—H Bonds, Accounts of Chemical Research, Jan. 10, 2012, vol. 45, No. 6, pp. 911-922.
Roizen, J. L. et al., Selective Intermolecular Amination of C—H Bonds at Tertiary Carbon Centers, Angew. Chem. Int. Ed. 2013, 52, pp. 11343-11346.
Ross et al., The Chemistry of Methyl Vinyl Ketone. II. Reactions with Esters, β-Keto Esters, Malonic Ester, Amines, Tar Bases, and Inorganic Salts. J. Org. Chem. 1964; 29(8):2346-2350.
Rowland et al., Antitumor properties of vindesine-monoclonal antibody conjugates. Cancer Immunol. Immunother. Feb. 1985; 19(1):1-7.
Ruff et al., Thiolation of symmetrical and unsymmetrical diketopiperazines. Org. Biomol. Chem. 2012; 10(5):935-940.
Saad, H.-E. A. et al., Biological Activities of Pyrrolidinoindoline Alkaloids from Calycodendron milnei, Planta Med. 1995, 61, pp. 313-316.
Sala et al., Tetrabutylammonium permanganate: an efficient oxidant for organic substrates. J. Chem. Soc., Chem. Commun. 1978; 253-254.
Salayova et al., Stereoselective synthesis of 1-methoxyspiroindoline phytoalexins and their amino analogues. Tetrahedron: Asymmetry. Sep. 15, 2014;24(16-17):1221-33.
Schammel, A. W. et al., Exploration of the interrupted Fischer indolization reaction, Tetrahedron 2010, 66, pp. 4687-4695.
Schiff et al., Promotion of microtubule assembly in vitro by taxol. Nature 1979; 277:665-667.
Schmidt. M.A. et al., New Strategies for the Synthesis of Hexahydropyrroloindole Alkaloids Inspired by Biosynthetic Hypotheses, Synlett 2008, 3, pp. 0313-0324.
Schumacher et al., Potent Antitumor Activity of 2-Methoxyestradiol in Human Pancreatic Cancer Cell Lines. Clin. Cancer Res. 1999; 5(3):493-499.
Scott et al., Reaction Pathways in the Photochemical Conversion of Diphenylamines to Carbazoles, J. Am. Chem. Soc. 1964, 86, pp. 302-303.
Senanayake, C.H. et al., Enantiopure Sulfoxides and Sulfinamides: Recent Developments in Their Stereoselective Synthesis and Applications to Asymmetric Synthesis, Aldrichim. Acta 2005, 38, pp. 93-104.
Seo, J. H. et al., Synthetic Studies on Perophoramidine and the Communesins: Construction of the Vicinal Quaternary Stereocenters, J. Org. Chem. 2006, 71, pp. 8891-8900.
Sevier et al., Formation and transfer of disulphide bonds in living cells. Nat Rev Mol Cell Biol. Nov. 2002;3(11):836-47.
Shamis et al., Bioactivation of Self-Immolative Dendritic Prodrugs by Catalytic Antibody 38C2, J. Am. Chem. Soc. 2004; 126 (6):1726-1731.
Shan et al., Selective, covalent modification of β-tubulin residue Cys-239 by T138067, an antitumor agent with in vivo efficacy against multidrug-resistant tumors. Proc. Nat. Acad. Sci. USA May 11, 1999; 96(10):5686-5691.
Shi et al., Distinct reactivity differences of metal oxo and its corresponding hydroxo moieties in oxidations: implications from a manganese(IV) complex having dihydroxide ligand. Angew Chem Int Ed Engl. Aug. 1, 2011; 50(32):7321-4.
Shin et al., Transition-Metal-Catalyzed C—N Bond Forming Reactions Using Organic Azides as the Nitrogen Source: A Journey for the Mild and Versatile C—H Amination. Acc. Chem. Res. 2015;48:1040-1052.
Shirai et al., Asymmetric synthesis of antimitotic combretadioxolane with potent antitumor activity against multi-drug resistant cells. Bioorg Med Chem Lett. Aug. 4, 1998; 8(15):1997-2000.
Shirai et al., Synthesis and nti-tubulin activity of aza-combretastatins. Bioorganic. Med. Chem. Lett. 1994; 4(5):699-704.
Shiraki et al., The synthesis and stereospecific solid-state photodecarbonylation of hexasubstituted mesa- and d,/-ketones. Photochem. Photobiol. Sci. 2011;10:1480-1487.
Shiraki, S. et al., Solid-state photochemistry of crystalline pyrazolines: reliable generation and reactivity control of 1,3-biradicals and their potential for the green chemistry sysnthesis of substitutedcyclopropanes, Photochem. Photobiol. Sci. 2012, 11, pp. 1929-1937.
Singh et al., Antineoplastic agents. 166. Isolation, structure, and synthesis of combretastatin C-1. J. Org. Chem. 1989; 54(17):4105-4114.
Singh et al., Recent trends in targeted anticancer prodrug and conjugate design. Curr Med Chem. 2008;15(18):1802-26.
Soledade et al., Minor phytotoxins from the blackleg fungus *Phoma lingam*. Phytochem. 1990; 29(3):777-782.
Solladie-Cavallo et al., A Four-Step Diastereoselective Synthesis of D-erythro-Sphingosine by an Enantioselective Aldol Reaction Using a Titanium Enolate Derived from a Chiral Iminoglycinate. J. Org. Chem. 1994; 59(11):3240-3242.
Solladie-Cavallo et al., A four-step synthesis of erythro-m-chloro-3-hydroxytyrosine ethyl ester enantiomerically pure. Tetrahedron Lett., 1998; 39(15):2191-2194.

(56) References Cited

OTHER PUBLICATIONS

Solladie-Cavallo et al., Diastereoselective monoalkylation of lithium and potassium enolates of a chiral imine of ethyl glycinate: the role of added salts. Organometallics. 1993; 12(9):3743-3747.
Solladie-Cavallo et al., Enantioselective synthesis of optically pure natural S(+) or unnatural R(−) DABA. Tetrahedron Lett. 1989;30(44):6011-6014.
Somei et al., Preparations of melatonin and 1-hydroxymelatonin, and its novel nucleophilicdimerization to (±)-3a,3a'-bispyrrolo[2,3-b]indoles. Heterocycles. 1999;51(6):1237-1242.
Somei, M. et al., A novel reductive amino-cyclization method and its application for the total syntheses of (±)-aurantio-clavine and (±)-lophocerine, Heterocycles 2007, 7 4, pp. 943-950.
Speth et al., Gliotoxin as putative virulence factor and immunotherapeutic target in a cell culture model of cerebral aspergillosis. Mol Immunol. Sep. 2011;48(15-16):2122-9.
Springer et al., The structure of ditryptophenaline—a new metabolite of aspergillusflavus. Tetrahedron Lett. 1977: 18(28):2403-2406.
Steininger, Synthesis of 5-Chloromethyl-2,dinitrotetrahydrofuran. Angew. Chem. Internat. Edit. 1965;4(5):433.
Stephens, D. E. et al., Straightforward Access to Hexahydropyrrolo[2,3-b]indole Core by aRegioselective C3-Azo Coupling Reaction of Arenediazonium Compounds with Tryptamines, Eur. J. Org. Chem. 2014, pp. 3662-3670.
Steven, A. et al., Total Synthesis of Complex Cyclotryptamine Alkaloids: Stereocontrolled Construction of Quaternary Carbon Stereocenters, Angew. Chem. Int. Ed. 2007, 46, pp. 5488-5508.
Still et al., Rapid chromatographic technique for preparative separations with moderate resolution J. Org. Chem. 1978, 43, 2923.
Stork, the stereospecific synthesis of reserpine. Pure Appl Chem. 1989;61(3):439-42.
Storm et al., Effect of small changes in orientation on reaction rate. J. Am. Chem. Soc. 1972; 94(16):5815-5825.
Stout et al., Potent Fluorinated Agelastatin Analogues for Chronic Lymphocytic Leukemia: Design, Synthesis, and Pharmacokinetic Studies, J. Med. Chem., 57, p. 5085-5093 (2014).
Strassner et al., Mechanism of Permanganate Oxidation of Alkanes: Hydrogen Abstraction and Oxygen Rebound J. Am. Chem. Soc. 2000; 122(32):7821-7822.
Stueber et al, Carbonates, Thiocarbonates, and the Corresponding Monoalkyl Derivatives. 1. Their Preparation and Isotropic 13C NMR Chemical Shifts. Inorg. Chem. 2001; 40(8):1902-1911.
Suetsugu, S. et al., Asymmetric Synthesis of (−)-Aurantioclavine via Palladium-CatalyzedIntramolecular Allylic Amination, Org. Lett. 2014, 16, pp. 996-999.
Sugiyama et al., Syntheses of four unusual amino acids, constituents of cyclomarin A. Tetrahedron Lett. 2002: 43(19):3489-2492.
Sumiyoshi, T. et al., Laser Flash Photolysis of Azocumenes. Direct Observation of StepwiseDecomposition, Bull. Chem. Soc. Jpn. 1987, 60, pp. 77-81.
Sun et al., Construction of 3-oxyindoles via hypervalent iodine mediated tandem cyclization-acctoxylation of o-acyl anilines. Chem Commun. 2010;46(36):6834-6.
Sun et al., Enabling ScFvs as multi-drug carriers: A dendritic approach, Bioorganic & Medicinal Chemistry Letters 2003; 11:1761-1768.
Sun et al., Syntheses of Dendritic Linkers Containing Chlorambucil Residues for the Preparation of Antibody-Multidrug Immunoconjugates, Bioorganic & Medicinal Chemistry Letters 2002; 12:2213-2215.
Szalai et al., Geometric disassembly of dendrimers: dendritic amplification. J Am Chem Soc. Dec. 24, 2003;125(51):15688-9.
Tadano et al., Bio-Inspired Dimerization Reaction of Tryptophan Derivatives in Aqueous AcidicMedia: Three-Step Syntheses of (+)-WIN 64821, (−)-Ditryptophenaline, and (+)-Naseseazine B. Angew. Chem. Int. Ed. 2013;52:7990-7994.
Tahir et al., Secreted Caveolin-1 Stimulates Cell Survival/Clonal Growth and Contributes to Metastasis in Androgen-insensitive Prostate Cancer. Cancer Res. 2001; 61(10):3882-3885.
Takahashi et al., Inhibition of histone H3K9 methyltransferases by gliotoxin and related epipolythiodioxopiperazines. J Antibiot (Tokyo). May 2012;65(5):263-5.
Teng et al., Unnatural enantiomer of chaetocin shows strong apoptosis-inducing activity through caspase-8/caspase-3 activation. Bioorg. Med. Chem. Lett. 2010; 20(17):5085-5088.
Teniou et al., (+)(1R,2R,5R) 2-Hydroxy-3-pinanone as Chiral Auxiliary in Erythro-selective Aldol Reactions. Asian J Chem. 2006; 18:2487-2490.
Tibodeau et al., the anticancer agent chaetocin is a competitive substrate and inhibitor of thioredoxin reductase. Antioxid Redox Signal. May 2009; 11(5):1097-106.
Tilvi et al., Agelastatin E, Agelastatin F, and Benzosceptrin C from the Marine Sponge Agelas dendromorpha, J. Nat. Prod., 73, p. 720-723 (2010).
Timberlake et al., Thiadiaziridine 1, 1-Dioxides: Synthesis and Chemistry. J. Org. Chem. 1981;46:2082-2089.
Toki et al., Protease-Mediated Fragmentation of p-Amidobenzyl Ethers: A New Strategy for the Activation of Anticancer Prodrugs. J. Org. Chem. 2002; 67(6):1866-1872.
Trail et al., Cure of xenografted human carcinomas by BR96-doxorubicin immunoconjugates. Science Jul. 9, 1993; 261(5118):212-215.
Trail et al., Effect of Linker Variation on the Stability, Potency, and Efficacy of Carcinoma-reactive BR64-Doxornbicin Immunoconjugates. Cancer Research 1997; 57:100-105.
Traunecker et al., Bispecific single chain molecules (Janusins) target cytotoxic lymphocytes on HIV infected cells. EMBO J. Dec. 1991; 10(12): 3655-3659.
Trost, B. M. et al., Recent Advances on the Total Syntheses of Communesin Alkaloids andPerophoramidine, Chem. Eur. J. 2015, 21:16318-16343.
Trown, P.W, Antiviral activity of N, N'-dimethyl-epidithiapiperazinedione, a synthetic compound related to the gliotoxins, LL-S88alpha and beta, chetomin and the sporidesmins. Biochem Biophys Res Commun. Nov. 8, 1968;33(3):402-7.
Tsuji, T. et al., Diazenes. VI. Alkyldizenes, Journal of the American Chemical Society 1971, 93(8), pp. 1992-1999.
Uckun et al., Structure-based design of a novel synthetic spiroketal pyran as a pharmacophore for the marine natural product spongistatin 1. Bioorg Med Chem Lett. Mar. 20, 2000; 10(6):541-5.
Uraguchi, D. et al., Catalytic Asymmetric Oxidation of N-Sulfonyl I mines with HydrogenPeroxide-Trichloroacetonitrile System, J. Am. Chem. Soc. 2013, 135, pp. 8161-8164.
Usami et al., Gliocladins A-C and Glioperazine ; Cytotoxic Dioxo- or Trioxopiperazine Metabolites from a *Gliocladium* Sp. Separated from a Sea Hare. Heterocycles 2004; 63(5):2004:1123-1129.
Verbitski, S. M. et al., Isolation, Structure Determination, and Biological Activity of a Novel Alkaloid, Perophoramidine, from the Philippine Ascidian Perophora namei, J. Org. Chem. 2002, 67, pp. 7124-7126.
Verdier-Pinard et al., A Steroid Derivative with Paclitaxel-Like Effects on Tubulin Polymerization. Molecular Pharmacology Mar. 2000: 57(3):568-575.
Verdier-Pinard et al., Biosynthesis of radiolabeled curacin A and its rapid and apparently irreversible binding to the colchicine site of tubulin. Arch Biochem Biophys. Oct. 1, 1999; 370(1):51-8.
Verotta, L. et al., Pyrrolidinoindoline Alkaloids from Psychotria colorata, J. Nat. Prod. 1998, 61, pp. 392-396.
Verotta, L. et al., Synthesis and Antinociceptive Activity of Chimonanthines and Pyrrolidinoindoline-Type Alkaloids, Bioorganic & Medicinal Chemistry 2002, 10, pp. 2133-2142.
Vingushin et al., Gliotoxin is a dual inhibitor of farnesyltransferase and geranylgeranyltransferase I with antitumor activity against breast cancer in vivo. Med Oncol. 2004;21(1):21-30.
Walker, A High Yielding Synthesis of N-Alkyl Maleimides Using a Novel Modification of the Mitsunobu Reaction. J. Org. Chem., 1995; 60(16):5352-5355.
Wang et al., Potent, Orally Active Heterocycle-Based Combretastatin A-4 Analogues: Synthesis, Structure-Activity Relationship, Pharmacokinetics, and In Vivo Antitumor Activity Evaluation. J. Med. Chem. 2002; 45(8):1697-1711.

(56) References Cited

OTHER PUBLICATIONS

Wang et al., Synthesis of B-ring homologated estradiol analogues that modulate tubulin polymerization and microtubule stability. J Med Chem. Jun. 15, 2000; 43(12):2419-29.
Wantanabe et al., Reaction of 1-Acyl and Aroyl-2-hydroxy-3,3-dimethylindolines with Arylamines Catalyzed by BF3•Etherate. Formation of Dihydroindolo[1,2-c]quinazoline. Heterocycles. 2007;71(2):343-59.
Waring et al., Gliotoxin and related epipolythiodioxopiperazines. Gen Pharmacol. Dec. 1996;27(8):1311-6.
Waring et al., The chemistry and biology of the immunomodulating agent gliotoxin and related epipolythiodioxopiperazines. Med Res Rev. Oct.-Dec. 1988;8(4):499-524.
Wen et al., Synthesis of a fully protected (2S,3R)-N-(1',1'-dimethyl-2'-propenyl)-3-hydroxytryptophan from tryptophan. Tetrahedron Lett. 2002: 43(30):5291-5294.
Wen et al., Total Synthesis of Cyclomarin C. Org. Lett. 2004; 6(16):2721-2724.
Wender, P. A. et al., Practical Synthesis of Prostratin, OPP, and Their Analogs, Adjuvant Leads Against Latent HIV, Science May 8, 2008, 320(5876), pp. 649-652.
Wenkert et al., Five-membered aromatic heterocycles as dienophiles in Diels-Alder reactions. Furan, pyrrole, and indole. J. Am. Chem. Soc. 1988; 110(21):7188-7194.
White, K. L. et al., Concise Total Syntheses of (+)-Haplocidine and (+)-Haplocine Via Late-StageOxidation of ( +)-Fendleridine Derivatives, J. Am. Chem. Soc. 2016, 138(35), pp. 11383-11389.
Wigley, L. J. et al., Natural and directed biosynthesis of communesin alkaloids, Phytochemistry 2006, 67, pp. 561-569.
Williams et al., Divergent, generalized synthesis of unsymmetrically substituted 2,5-piperazinediones. J. Am. Chem. Soc. 1985; 107(11):3246-3253.
Williams et al., Syntheses of the fungal metabolites (.+-.)-gliovictin and (.+-.)-hyalodendrin. J. Org. Chem. 1980; 45(13):2625-2631.
Williamson, K. S. et al., Iron Catalyzed Asymmetric Oxyamination of Olefins, J. Am. Chem. Soc. 2012, 134, pp. 12370-12373.
Williamson, K. S. et al., Iron-Catalyzed Aminohydroxylation of Olefins, J. Am. Chem. Soc. 2010, 132, pp. 4570-4571.
Woods et al., The interaction with tubulin of a series of stilbenes based on combretastatin A-4. Br J Cancer. Apr. 1995; 71(4):705-11.
Woodward, R. B. et al., Calycanthine: The Structure of the Alkaloid and its Degradation Product, Calycanine, Proc. Chem. Soc. 1960: 76-78.
Wu-Wong et al., Identification and Characterization of A-105972, an Antineoplastic Agent. Cancer Res. 2001; 61:1486-1492.
Xie, W. et al., Highly Enantioselective Bromocyclization of Tryptamines and Its Application in theSynthesis of(−)-Chimonanthine, Angew. Chem. Int. Ed. 2013, 52, pp. 12924-12927.
Xu, J.-B. et al., Studies on the Alkaloids of the Calycanthaceae and Their Syntheses, Molecules 2015, 20, pp. 6715-6738.
Xu, L. et al., Iridium(III)-Catalyzed Regioselective C7-Amination of N-Pivaloylindoles with Sulfonoazides, J. Org. Chem. 2016, 81, pp. 10476-10483.

Xu, Z. et al., Total Synthesis of Clavicipitic Acid and Aurantioclavine: Stereochemistry of Clavicipitic Acid Revisited, J. Org. Chem. 2010, 75, pp. 7626-7635.
Yamada, F. et al., A Total and Practical Synthesis of Ergot Alkaloid, (±)-Aurantioclavine, Chem. Pharm. Bull. 1985, 33, pp. 2162-2163.
Yamada, K. et al., Concise Synthesis of (±)-Aurantioclavine through a Base-Promoted Pictet-Spengler Reaction, Eur. J. Org. Chem. 2009, pp. 5752-5759.
Yanagihara et al., Leptosins isolated from marine fungus *leptoshaeria* species inhibit DNA topoisomerases I and/or II and induce apoptosis by inactivation of Akt/protein kinase B. Cancer Sci. Nov. 2005;96(11):816-24.
Yang, J. et al., Total Synthesis of (±)-Communesin F, J. Am. Chem. Soc. 2007, 129, pp. 13794-13795.
Yano et al., Chetomin induces degradation of XIAP and enhances TRAIL sensitivity in urogenital cancer cells. Int J Oncol. Feb. 2011;38(2):365-74.
Yu et al., A General Strategy for the Synthesis of Vincamajine-Related Indole Alkaloids: Stereocontrolled Total Synthesis of (+)-Dehydrovoachalotine, (−)-Vincamajinine, and (−)-11-Methoxy-17-epivincamajine as Well as the Related Quebrachidine Diol, Vincamajine Diol, and Vincarinol1. J Org Chem. Apr. 19, 2005;70(10):3963-79.
Yu et al., Stereocontrolled Total Synthesis of (−)-Vincamajinine and (−)-11-Methoxy-17-epivincamajine. J Am Chem Soc. Jan. 21, 2004;126(5):1358-9.
Zalatan, D. N. et al., Metal-Catalyzed Oxidations of C—H to C—N Bonds, Top. Curr. Chem. 2010, 292, pp. 347-378.
Zalatan, D. N. et al., Understanding the Differential Performance of Rh2(esp)2 as a Catalyst for C—H Amination, J. Am. Chem. Soc. 2009, 131, pp. 7558-7559.
Zhang et al., Microtubule effects of welwistatin, a cyanobacterial indolinone that circumvents multiple drug resistance. Molecular Pharmacology Feb. 1996; 49(2):288-294.
Zheng et al., Bionectins A-C, Epidithiodioxopiperazines with Anti-MRSA Activity, from Bionectra byssicola F120, J. Nat. Prod., 2006, 69 (12), pp. 1816-1819.
Zhou, P. et al., Recent advances in asymmetric reactions using sulfinimines (N-sulfinyl imines), Tetrahedron 2004, 60, pp. 8003-8030.
Zhu et al., Aptamer-Drug Conjugates. Bioconjug Chem. Nov. 18, 2015;26(11):2186-97. doi: 10.1021/acs.bioconjchem.5b00291. Epub Jul. 14, 2015.
Zuo, Z. et al., Enantioselective Total Syntheses of Communesins A and B, Angew. Chem. Int. Ed. 2011, 50, pp. 12008-12011.
Zuo, Z. et al., Total Synthesis and Absolute Stereochemical Assignment of (−)-Communesin F, J. Am. Chem. Soc. 2010, 132, pp. 13226-13228.
International Preliminary Report on Patentability for PCT/US2020/026415, dated Dec. 16, 2021.
Mcmahon, VEGF receptor signaling in tumor angiogenesis. Oncologist. 2000;5 Suppl 1:3-10. doi: 10.1634/theoncologist.5-suppl_1-3. PMID: 10804084.
Pinedo et al., Translational Research: the role of VEGF in tumor angiogenesis. Oncologist. Jan. 2000;5:1-2.

* cited by examiner (−)-agelastatin A (1)

(−)-agelastatin B (2)

(−)-agelastatin C (3)

(−)-agelastatin D (4)

(−)-agelastatin E (5)

(−)-agelastatin F (6)

A. Serial mouse weights

B. Final tumor weights

Lung metastases in AgA-treated mice after mixed cell xenograft co-implantation (SUM1315 / Tiam1deficient mammary fibroblast xenograft)

Lung metastases in AgE-treated mice after mixed cell xenograft co-implantation
(SUM1315 / Tiam1deficient mammary fibroblast xenograft)

SEQUENCE LISTING

```
<160> NUMBER OF SEQ ID NOS: 4

<210> SEQ ID NO 1
<211> LENGTH: 20
<212> TYPE: DNA
<213> ORGANISM: artificial sequence
<220> FEATURE:
<223> OTHER INFORMATION: GAPDH sense

<400> SEQUENCE: 1
ctgcaccacc aactgcttag                                              20

<210> SEQ ID NO 2
<211> LENGTH: 20
<212> TYPE: DNA
<213> ORGANISM: artificial sequence
<220> FEATURE:
<223> OTHER INFORMATION: GAPDH antisense

<400> SEQUENCE: 2
ttcagctcag ggatgacctt                                              20

<210> SEQ ID NO 3
<211> LENGTH: 20
<212> TYPE: DNA
<213> ORGANISM: artificial sequence
<220> FEATURE:
<223> OTHER INFORMATION: OPN sense

<400> SEQUENCE: 3
gacctcagaa gatgcactat                                              20

<210> SEQ ID NO 4
<211> LENGTH: 20
<212> TYPE: DNA
<213> ORGANISM: artificial sequence
<220> FEATURE:
<223> OTHER INFORMATION: OPN antisense

<400> SEQUENCE: 4
gacctcagaa gatgcactat                                              20
```

POTENT AGELASTATIN DERIVATIVES AS MODULATORS FOR CANCER INVASION AND METASTASIS

CROSS REFERENCE TO RELATED APPLICATIONS

This application is a national stage filing under 35 U.S.C. § 371 of International Patent Application No. PCT/US2018/032327, filed May 11, 2018, which claims priority under 35 U.S.C. § 119(e) to U.S. Provisional Application No. 62/504,877, filed May 11, 2017, the contents of each of which are incorporated herein by reference in their entireties.

STATEMENT REGARDING FEDERALLY SPONSORED RESEARCH

This invention was made with government support under GM074825 awarded by the National Institutes of Health, and W81XWH-11-1-0814 awarded by the U.S Army Research Office. The government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Sep. 23, 2023, is named M123770095US01-SUBSEQ-WWZ and is 1,306 bytes in size.

FIELD OF DISCLOSURE

The present disclosure relates to potent agelastatin derivatives as modulators for cancer invasion and metastasis.

BACKGROUND

The agelastatin alkaloids' have been of interest to the scientific community for many years due to their interesting molecular structure as well as potent biological activities.[2] A general strategy for the total synthesis of all known agelastatins (FIG. 1) has been previously reported, enabling the comprehensive, comparative anticancer study of these naturally occurring alkaloids along with many synthetic derivatives.[3-5] Recent work in this area has offered new synthetic strategies[6] as well as biological study of the natural alkaloids and synthetic derivatives.[7]

AgA (1, FIG. 1) has been shown to inhibit vitamin D-induced transcription of osteopontin (OPN) in mammary fibroblasts at concentrations well below the cytotoxic range.[9] In this context, OPN transcription and secretion is induced by down-regulation of the Rac GTPase exchange factor Tiam1.[11] Down-regulation of fibroblast Tiam1 and up-regulation of fibroblast OPN in the tumor microenvironment are associated with increased invasiveness in human breast cancers.[9]

A method of 3D co-culture was developed which enables assessment of the effects of mammary fibroblasts on associated breast cancer cells.[9] This led to the discovery that the mammary fibroblast Tiam1-OPN pathway modulates breast cancer invasion and metastasis through regulating epithelial-mesenchymal transition (EMT) and cancer stem cell populations in associated breast cancer cells.[9,12] The concentrations of AgA (1) in the aforementioned assays (75-100 nM) are far below cytotoxic range in cell culture. However, direct dosing of mice with AgA (1) at the previously published in vivo dose used in one to four day studies[1c,2b,d] (2.5 mg/kg/day) led to toxicity in the animals within three to four weeks that precluded further dosing.[13]

There is a need to provide compounds with improved safety profiles which can provide a useful alternative to known agelastatin compounds.

SUMMARY

The present disclosure provides compounds that are effective in treating, preventing, and/or delaying cancer (e.g., breast cancer).

The present disclosure provides compounds and compositions useful in the treatment of cancer (e.g., breast cancer). In various embodiments, a compound is provided having the structure of Formula (I):

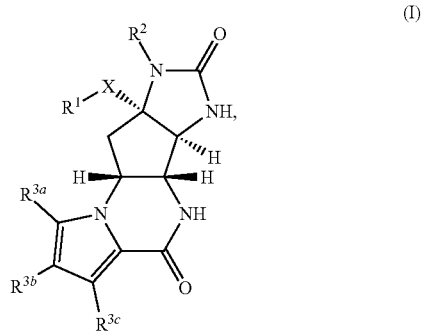

or a pharmaceutically acceptable salt, tautomer, or stereoisomer thereof, wherein:

X is —O—, —S—, or —N($R^6$)—;

$R^1$ is H, $C_{1-10}$ alkyl, $C_{2-10}$ alkenyl, or $C_{2-8}$ alkynyl, optionally substituted with one or more $R^4$;

or alternatively, X and combine to form —$N_3$.

$R^2$ is $C_{1-10}$ alkyl, $C_{2-10}$ alkenyl, or $C_{2-8}$ alkynyl, optionally substituted with one or more $R^5$, wherein up to 3 —$CH_2$— units of $R^2$ are optionally replaced by an —O—, —S—, or —$NR^6$—, provided that no adjacent —$CH_2$— is replaced;

or alternatively, $R^1$ and $R^2$ taken together with the atoms to which they are attached form a $C_{5-10}$ heterocycloalkyl, $C_{5-10}$ heterocycloalkenyl, or $C_{5-10}$ heterocycloalkynyl ring, optionally substituted with one or more $R^4$;

$R^{3a}$, $R^{3b}$, and $R^{3c}$ are each independently H or halogen;

$R^4$ is halogen, —$C_{1-5}$ alkyl, oxo, —OH, —$OR^6$, —$N_3$, —$N(R^6)_2$, —NH(C=O)$R^6$, —NH(C=O)$OR^6$, —NH(C=O)N($R^6$)$_2$, —(C=O)$R^6$, heteroaryl,

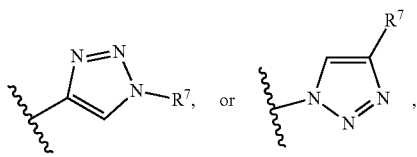

and two adjacent R⁴ groups may take the form

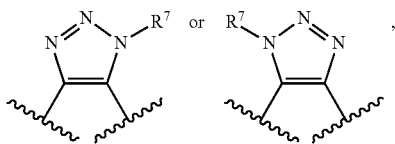

wherein the C=C double bond of the triazole is part of R¹;
R⁵ is halogen, oxo, —OH, —OR⁶, —N₃, —N(R⁶)₂,

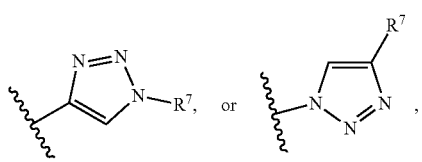

and two adjacent R⁵ groups may take the form

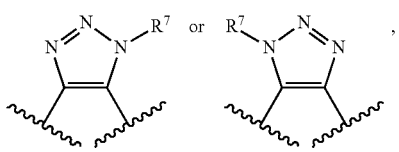

wherein the C=C double bond of the triazole is part of R²;
and
R⁶ is independently H, —C₁₋₅ alkyl, —C₂₋₅ alkenyl, —C₁₋₅ alkynyl, —C₁₋₅ alkyl-SiMe₃, aryl, or heteroaryl;
R⁷ is selected from the group consisting of hydrogen, optionally substituted aliphatic, optionally substituted heteroaliphatic, optionally substituted aryl, optionally substituted heteroaryl, optionally substituted acyl, resin, protein, reporter molecule, and label molecule;
wherein, R⁷ is optionally joined to the core by a linker L, wherein the linker L is selected from the group consisting of optionally substituted alkylene, optionally substituted alkenylene, optionally substituted alkynylene, optionally substituted heteroalkylene, optionally substituted heteroalkenylene, optionally substituted heteroalkynylene, optionally substituted arylene, optionally substituted heteroarylene, and optionally substituted acylene, with the proviso that the compound is not agelastatin A, agelastatin B, agelastatin E,

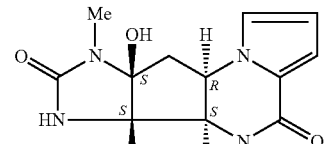

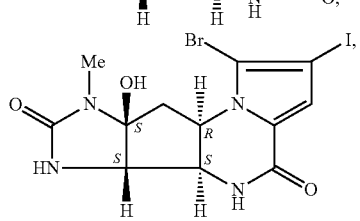

-continued

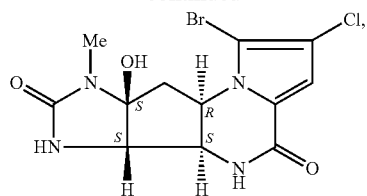

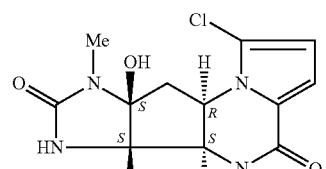

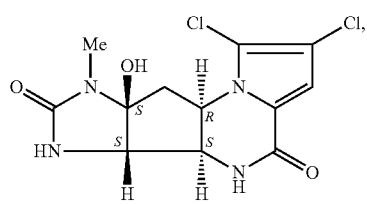

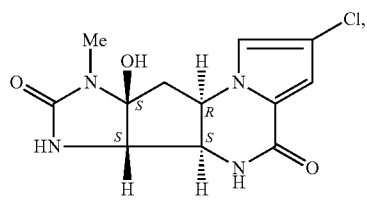

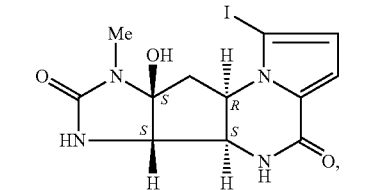

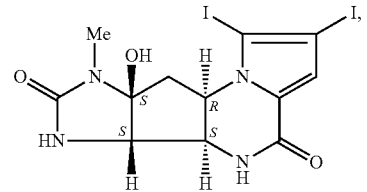

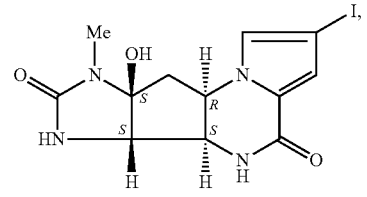

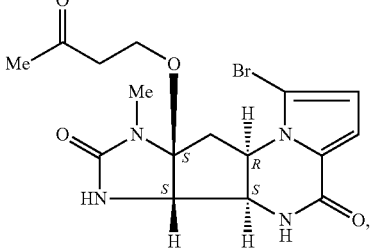

-continued
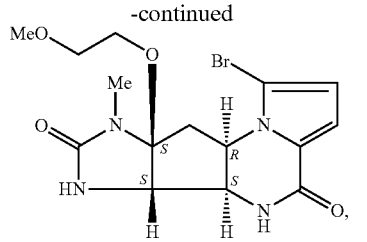
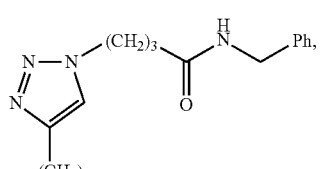
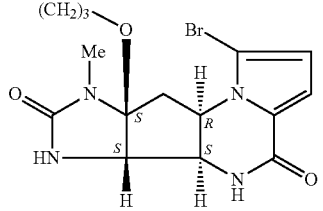
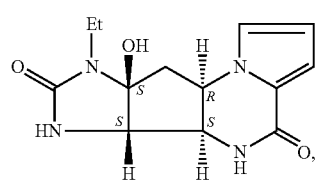
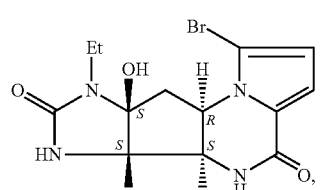
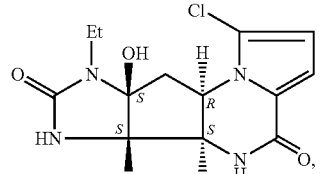
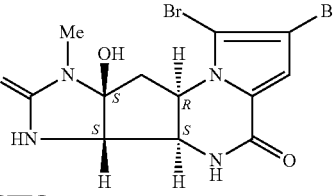
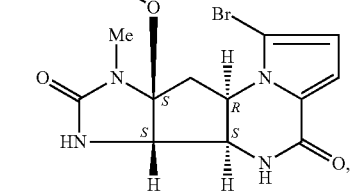
-continued
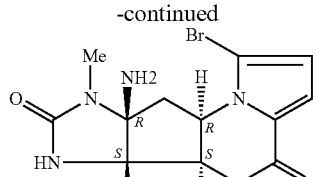
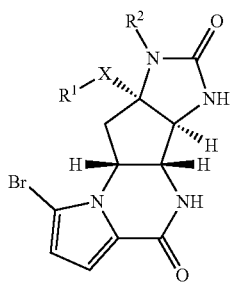
In some embodiments, the compound is a compound of Formula (Ia):
$$\text{(Ia)}$$
or a pharmaceutically acceptable salt, tautomer, or stereoisomer thereof, wherein R$^1$, R$^2$, and X are as described above.
In some embodiments, the compound is a compound of Formula (Ib):

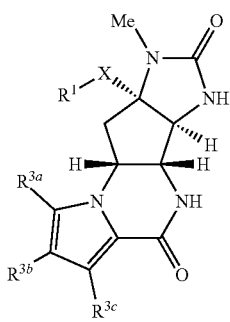

(Ib)

or a pharmaceutically acceptable salt, tautomer, or stereoisomer thereof, wherein X, $R^1$, and $R^{3a-3c}$ are as defined above.

In some embodiments, the compound is a compound of Formula (Ic):

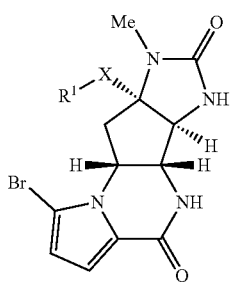

(Ic)

or a pharmaceutically acceptable salt, tautomer, or stereoisomer thereof, wherein X and $R^1$ are as described above.

In some embodiments, the compound is a compound of Formula (Id):

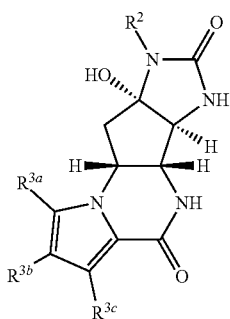

(Id)

or a pharmaceutically acceptable salt, tautomer, or stereoisomer thereof, wherein $R^2$ and $R^{3a-3c}$ are as defined above.

In some embodiments, the compound is a compound of Formula (Ie):

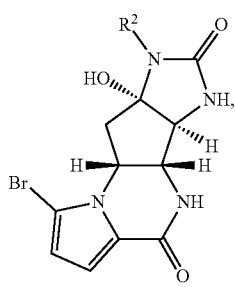

(Ie)

or a pharmaceutically acceptable salt, tautomer, or stereoisomer thereof, wherein $R^2$ is as defined above.

In some embodiments of Formula (I)-(Ic), $R^1$ is $C_{1-10}$ alkyl, $C_{2-10}$ alkenyl, or $C_{2-8}$ alkynyl, optionally substituted with one or more $R^4$, or alternatively, X and $R^1$ are combined to form $-N_3$.

In some embodiments of the present disclosure, compounds of Formula (I)-(Ic) are provided, wherein X is —O— or —S—. In certain embodiments, X is —O—.

In some embodiments of Formula (I), (Ia), (Id), or (Ie), $R^2$ is $C_{1-10}$ alkyl, optionally substituted with one or more $R^5$, wherein up to 3 —$CH_2$— units of $R^2$ are optionally replaced by an —O—, —S—, or —$NR^6$—, provided that no adjacent —$CH_2$— is replaced. In some embodiments, up to 3 —$CH_2$— units of $R^2$ are optionally replaced by an O. In other embodiments, $R^2$ is methyl.

In some embodiments, compounds of Formula (I), (Ib), and (Id) are provided, wherein $R^{3a}$ is Br or Cl, $R^{3b}$ is H, and $R^{3c}$ is H. In other embodiments, $R^{3a}$ is Br, $R^{3b}$ is H, and $R^{3c}$ is H. In some embodiments, $R^{3a}$ is Br or Cl, $R^{3b}$ is Br or Cl, and $R^{3c}$ is H. In other embodiments, $R^{3a}$ is Br, $R^{3b}$ is Br, and $R^{3c}$ is H.

In various embodiments of the present disclosure, a compound of Formula (I) is provided having a structure selected from:

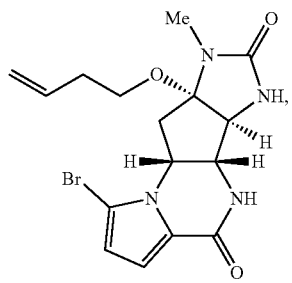

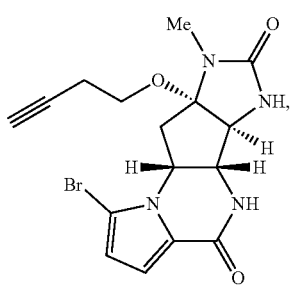

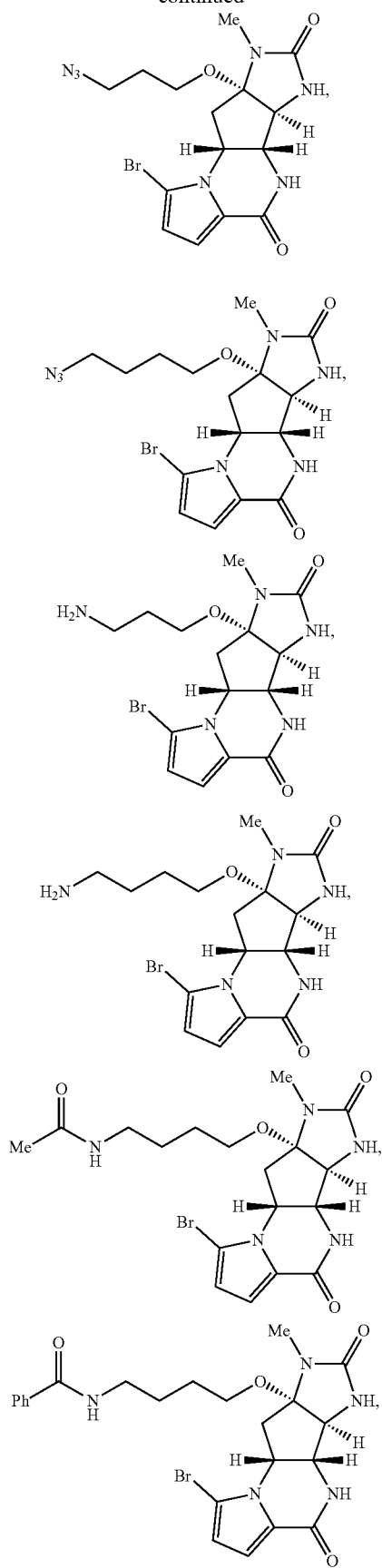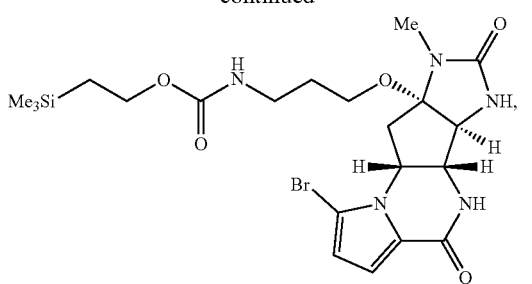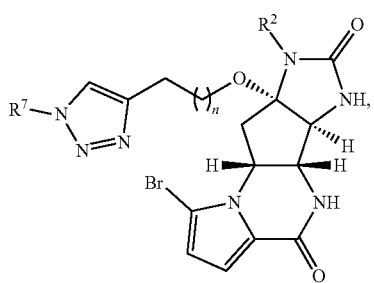
or a pharmaceutically acceptable salt, tautomer, or stereoisomer thereof.
In various embodiments of the present disclosure, a compound of Formula (I) is provided having a structure selected from:

-continued

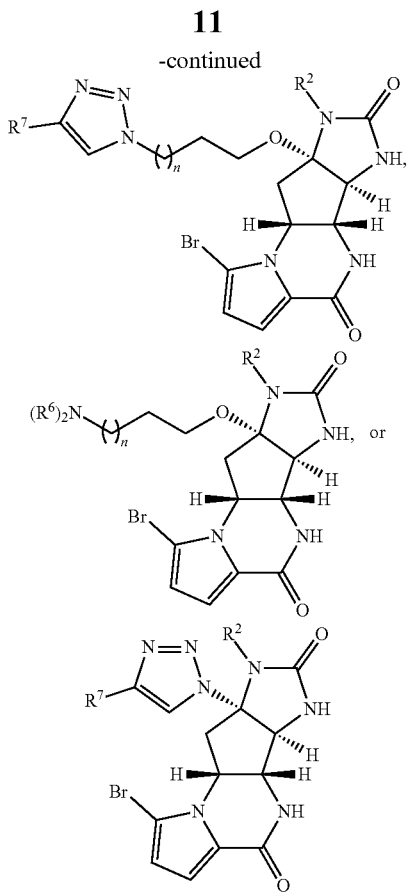

wherein R² is H or Me.

In some embodiments of the present disclosure, the compound of Formula (I) is:

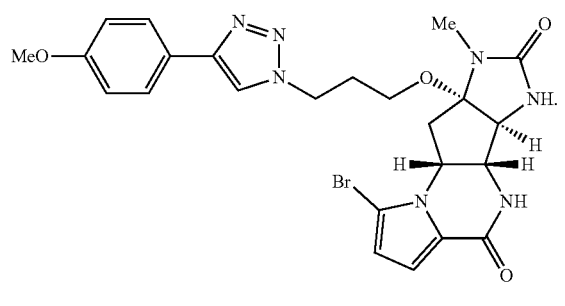 [SMILES: COc1ccc(-c2cn(CCCO[C@@]34C[C@@H]5[C@@H](NC(=O)c6ccc(Br)n65)[C@@H]3NC(=O)N4C)nn2)cc1]

In some embodiments of the present disclosure, the compound of Formula (I) is selected from:

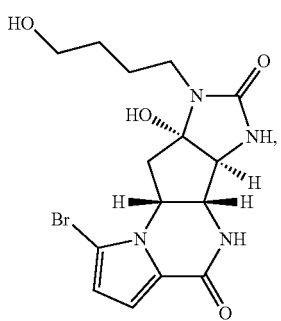

-continued

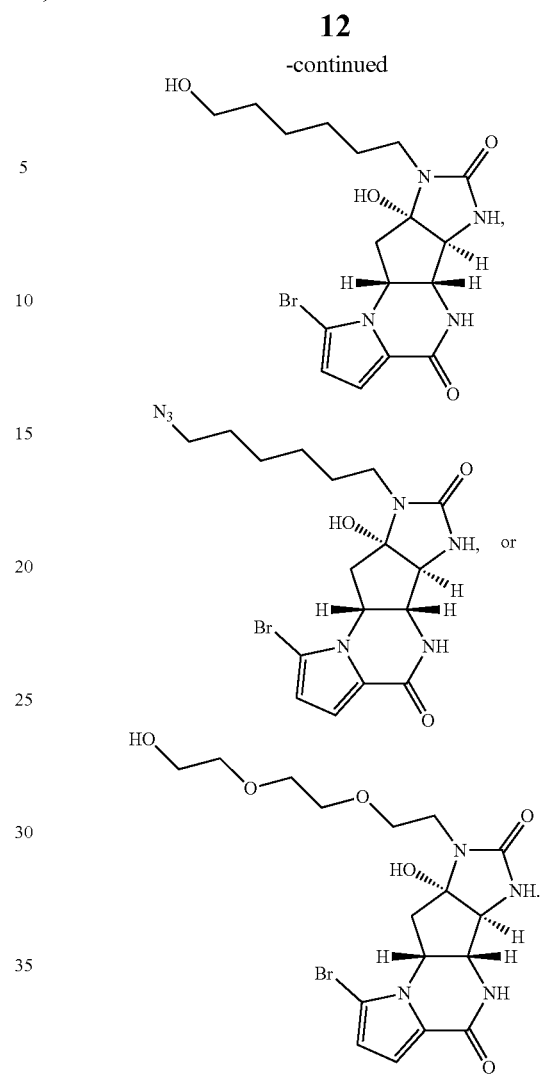

In some embodiments, the compound of Formula (I) is:

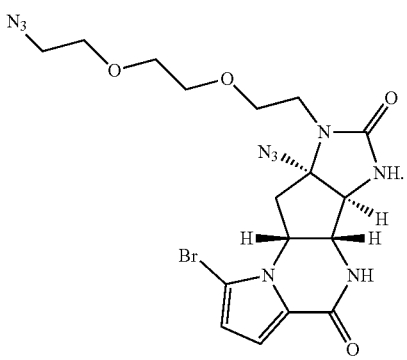 [SMILES: [N-]=[N+]=NCCOCCOCCN1C(=O)N[C@H]2[C@@H]3NC(=O)c4ccc(Br)n4[C@@H]3C[C@]21N=[N+]=[N-]]

In various embodiments of the present disclosure, a pharmaceutical composition is provided comprising any of the compounds of Formula (I)-(Ie) disclosed herein and a pharmaceutically acceptable excipient.

The present disclosure also provides a method for the treatment, prevention, or delay of cancer, comprising administering a therapeutically effect amount of a compound of Formula (I)-(Ie), a pharmaceutically acceptable salt thereof, or a composition thereof to a subject in need thereof.

In some embodiments, the cancer is prevented or delayed. In some embodiments, the cancer is recurrent cancer at the primary site, metastatic cancer, or recurrent metastatic cancer.

In some embodiments, the cancer is breast cancer, lung cancer, colorectal cancer, stomach cancer, ovarian cancer, papillary thyroid carcinoma, melanoma, prostate cancer, esophageal cancer, liver cancer, bladder cancer, renal cancer, head and neck cancers, salivary gland cancer, endometrial cancer, cervical cancer, pancreatic cancer, sarcoma, glioblastoma and glioma, or pleural mesothelioma.

In certain embodiments, the cancer is breast cancer. In specific embodiments, the breast cancer is metastatic breast cancer or recurrent metastatic breast cancer.

In some embodiments, the cancer is characterized by a tumor microenvironment exhibiting down regulation of fibroblast Tiam1 and upregulation of fibroblast OPN. In other embodiments, the cancer is characterized by a tumor microenvironment exhibiting upregulation of fibroblast OPN.

In some embodiments, the administering of a compound of Formula (I)-(Ie) is before surgery and/or radiotherapy and/or systemic medical therapy. In other embodiments, the administering is after surgery and/or radiotherapy and/or systemic medical therapy. In still other embodiments, the administering is concurrent with systemic medical therapy. In related embodiments, systemic medical therapy includes chemotherapies, hormonal therapies, targeted biologic therapies, and/or immunotherapies.

In various embodiments, treatment with compounds of the present disclosure results in inhibition of induced transcription of osteopontin (OPN) in fibroblasts, inflammatory cells, and immune cells of the tumor microenvironment. In some embodiments, the inhibition occurs at or below the cytotoxic range determined for the cancer cells being treated. In some embodiments, the inhibition results in interference with cancer cell adhesion, cancer cell invasion, and cancer stem cell populations.

In some embodiments, the transcription is of splice variants of OPN. In certain embodiments, the spice variants are osteopontin-a, osteopontin-b, or osteopontin-c.

In certain embodiments, the fibroblasts are mammary fibroblasts.

In some embodiments of the present disclosure, the method further comprising coadministration to the subject one of the following:

an antitumor agent selected from the group consisting of paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethilenethiophosphoramide, trimethylolomelamine, bullatacin, bullatacinone, camptothecin, bryostatin, callystatin, cryptophycin 1, cryptophycin 8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, detorbicin, 6-diazo-5-oxo-L-norleucine, ADRIAMYCIN, epirubicin, esorubicin, idarubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone, aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, epothilone, etoglucid, lentinan, lonidamine, maytansine, ansamitocine, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, schizophyllan, spirogermanium, tenuazonic acid, triaziquone, roridine A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxantrone, vincristine, vinorelbine, novantrone, teniposide, edatrexate, daunomycin, aminopterin, xeloda, ibandronate, irinotecan, topoisomerase inhibitor, difluoromethylornithine (DMFO), retinoic acid, capecitabine, and pharmacologically acceptable salts or derivatives thereof;

an anti-metabolite agent selected from the group consisting of, 5-fluorouracil, 5-fluorouracil prodrugs (e.g., capecitabine), 5-fluorodeoxyuridine monophosphate, cytarabine, 5-azacytidine, gemcitabine, mercaptopurine, thioguanine, azathioprine, adenosine, pentostatin, erythrohydroxynonyladenine, cladribine and pharmacologically acceptable salts or derivatives thereof;

an anti-estrogen agent selected from the group consisting of selective estrogen receptor modulators, pure receptor antagonists, aromatase inhibitors, and anti-gonadotropins and pharmacologically acceptable salts or derivatives thereof; wherein the selective estrogen receptor modulator (SERM) is selected from the group consisting of anordrin, bazedoxifene, broparestrol, clomifene, cyclofenil, lasofoxifene, ormeloxifene, ospemifene, raloxifene, tamoxifen citrate, toremifene citrate, and pharmacologically acceptable salts or derivatives thereof;

the pure receptor antagonist is selected from the group consisting of fulvestrant, brilanestrant, elacestrant, and pharmacologically acceptable salts or derivatives thereof;

the aromatase inhibitor is selected from the group consisting of anastrozole, letrozole, vorozole, exemestane, formestane and pharmacologically acceptable salts or derivatives thereof;

the anti-gonadotropin is selected from the group consisting of triptorelin, leuprolide acetate, and pharmacologically acceptable salts or derivatives thereof;

a tyrosine kinase inhibitor selected from the group consisting of trastuzumab, pertuzumab, imatinib, gefitinib, erlotinib, sunitinib, adavosertib, lapatinib and pharmacologically acceptable salts or derivatives thereof; and an immune checkpoint inhibitor selected from the group consisting of ipilimumab, pembrolizumab, nivolumab, avelumab, durvalumab, atezolizumab and pharmacologically acceptable salts or derivatives thereof.

In various embodiments, the present disclosure provides a method of making a compound of claim 1, comprising addition of a nucleophile to an iminium intermediate of Formula (II).

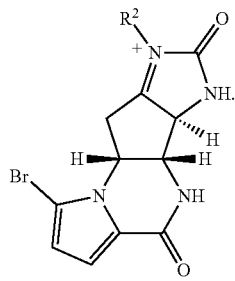
(II)

In various embodiments, the nucleophile added to Formula (II) is $R^1$—XH, wherein X is —O—, —S—, or —N($R^4$)—.

In various embodiments, the present disclosure provides a method of making a compound of Formula (I), comprising acid-promoted cyclization of a compound of Formula (III) to afford a compound of Formula (Id):

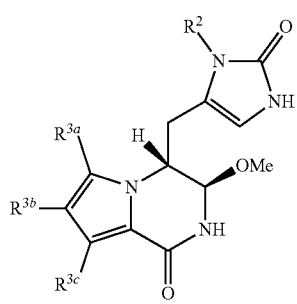
(III)

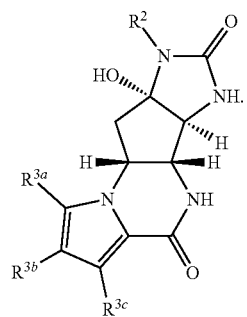
(Id)

In various embodiments, the acid used to promote the acid-promoted cyclization is methanesulfonic acid, p-toluenesulfonic acid, sulfuric acid, hydrochloric acid, trifluoroacetic acid, trifluoromethanesulfonic acid, and nitric acid.

In various embodiments, the present disclosure provides a method of making compound (III), comprising copper-mediated coupling between a compound of Formula (IV) and a compound of Formula (V):

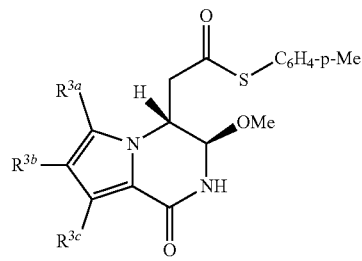
(IV)

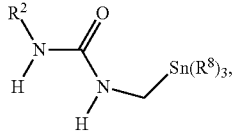
(V)

wherein $R^8$ is alkyl or cycloalkyl.

In various embodiments, the copper-mediated coupling is carried out with copper (I)-thiophene-2-carboxylate (CuTC) or copper(I) diphenylphosphinate (CuDPP).

In some embodiments, the copper-mediated coupling further comprises treatment with an acid.

DETAILED DESCRIPTION

Described herein is the synthesis of new agelastatin alkaloid derivatives and their anticancer evaluation in the context of the breast cancer microenvironment. A variety of N1-alkyl and C5-ether agelastatin derivatives were accessed via a convergent imidazolone synthesis from a common thioester along with appropriately substituted components (e.g., urea and alcohol). These agelastatin derivatives were evaluated in a variety of ways, including in a three-dimensional co-culture assay for determining the effects of mammary fibroblasts on associated breast cancer cells. It was discovered that agelastatin alkaloids are potent modulators for cancer invasion and metastasis at non-cytotoxic doses. Herein the increased potency of (−)-agelastatin E as compared to (−)-agelastatin A is described, in addition to identification of new agelastatin derivatives with activity that is equivalent to (−)-agelastatin E. The chemistry described here provides a platform for the rapid synthesis and facile derivitization of agelastatin with excellent potency (e.g., 50-100 nM) as modulators for cancer invasion and metastasis.

Figure 1:
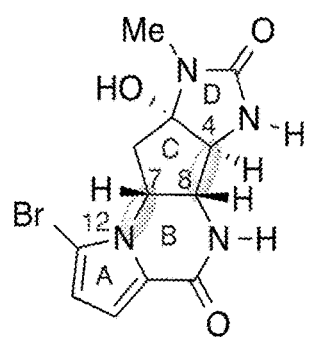
FIG. 1 shows the structures of (−)-agelastatins A-F (1-6).
Figure 1:
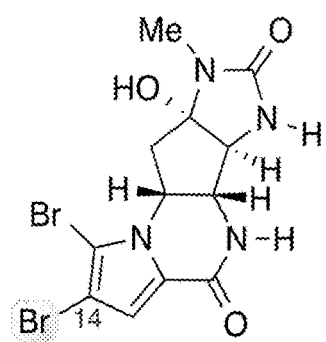
Figure 1:
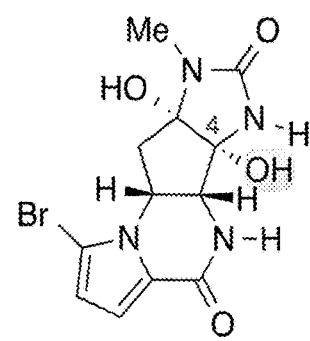
Figure 1:
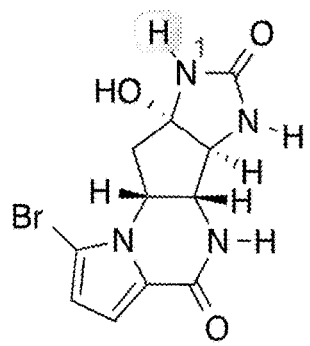
Figure 1:
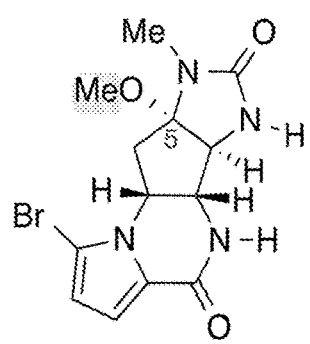
Figure 1:
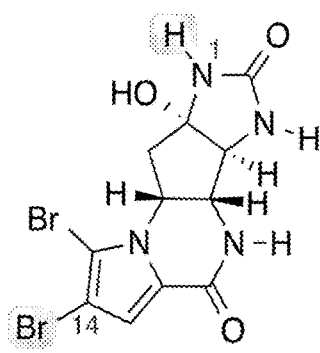

Developing a method for the direct conversion of a common thioester intermediate to the corresponding imidazolone that served as a nucleophile in a biogenetically inspired cyclization event to secure the CD-ring portion of these alkaloids was important to the synthesis of agelastatin derivatives. In addition to streamlining the synthesis of all known agelastatin alkaloids, this strategy provides the foundation for access to various derivatives.[3,8] Late-stage diversification allows for agelastatin derivatives with variations (for example at the N1- and C5-positions) on the agelastatin core. The synthesis of agelastatins derivatives is described herein, including their evaluation along with natural agelastatins in a three-dimensional (3D) co-culture assay probing their impact on fibroblasts in the tumor microenvironment, 9-10 and the discovery of the increased potency of (−)-agelastatin E (5, AgE. FIG. 1) and distinct new derivatives as compared to (−)-agelastatin A (1, AgA, FIG. 1) as modulators for cancer invasion and metastasis.

As used above, and throughout this disclosure, the following terms, unless otherwise indicated, shall be understood to have the following meanings. If a term is missing, the conventional term as known to one skilled in the art controls.

As used herein, the terms "including," "containing," and "comprising" are used in their open, non-limiting sense.

The indefinite articles "a" and "an," as used herein, unless clearly indicated to the contrary, should be understood to mean "at least one" The phrase "and/or," as used herein, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B), in another embodiment, to B only (optionally including elements other than A); in yet another embodiment, to both A and B (optionally including other elements), etc.

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in claims, shall have its ordinary meaning as used in the field of patent law.

As used herein, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A. and at least one, optionally including more than one, B (and optionally including other elements); etc.

To provide a more concise description, some of the quantitative expressions given herein are not qualified with the term "about" It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions.

Concentrations that are given as percentages refer to mass ratios, unless indicated differently.

A "patient" is a mammal, e.g., a human, mouse, rat, guinea pig, dog, cat, horse, cow, pig, or non-human primate, such as a monkey, chimpanzee, baboon or rhesus. "Patient" includes both human and animals.

The terms "effective amount" or "therapeutically effective amount" when used in connection with a compound refer to a sufficient amount of the compound to provide the desired biological result. That result can be reduction and/or alleviation of the signs, symptoms, or causes of a disease, or any other desired alteration of a biological system. For example, an "effective amount" for therapeutic use is the amount of the composition comprising a compound as disclosed herein required to provide a clinically significant decrease in a disease. An appropriate "effective amount" in any individual case may be determined by one of ordinary skill in the art using routine experimentation. Thus, the expression "effective amount" generally refers to the quantity for which the active substance has therapeutic effects. In the present case the active substance is the inhibitor of the inflammasome.

As used herein, the terms "treat" or "treatment" are synonymous with the term "prevent" and are meant to indicate a postponement of development of diseases, preventing the development of diseases, and/or reducing severity of such symptoms that will or are expected to develop. Thus, these terms include ameliorating existing disease symptoms, preventing additional symptoms, ameliorating or preventing the underlying causes of symptoms, inhibiting the disorder or disease, e.g., arresting the development of the disorder or disease, relieving the disorder or disease, causing regression of the disorder or disease, relieving a condition caused by the disease or disorder, or stopping or alleviating the symptoms of the disease or disorder.

The term "disorder" is used in this disclosure to mean, and is used interchangeably with, the terms disease, condition, or illness, unless otherwise indicated.

"Adjuvant setting" refers to a clinical setting in which an individual has had a history of cancer, and generally (but not necessarily) been responsive to therapy, which includes, but is not limited to, surgery (e.g., surgery resection), radiotherapy, and chemotherapy. However, because of their history of cancer, these individuals are considered at risk of development of the disease. Treatment or administration in the "adjuvant setting" (also referred to herein as adjuvant therapy) refers to a prior or subsequent mode of treatment. The degree of risk (e.g., when an individual in the adjuvant setting is considered as "high risk" or "low risk") depends upon several factors, most usually the extent of disease when first treated. In some embodiments, "adjuvant therapy" herein refers to therapy given after definitive surgery, after which no evidence of residual disease can be detected, so as to reduce the risk of disease recurrence, either local or metastatic. The goal of adjuvant therapy is to prevent or delay recurrence of the cancer, and therefore to reduce the chance of cancer-related death.

"Neoadjuvant setting" refers to a clinical setting in which the method is carried out before the primary/definitive therapy.

As used herein, "delaying" the development of cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of subjects. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer progression that may be initially undetectable and includes occurrence, recurrence, and onset.

As used herein, by "combination therapy" is meant that a first agent be administered in conjunction with another agent. "In conjunction with" refers to administration of one treatment modality in addition to another treatment modality, such as administration of an primary cancer therapy (e.g., anti-tumor agent) described herein in addition to administration of the other agent to the same individual. As such, "in conjunction with" refers to administration of one treatment modality before, during, or after delivery of the other treatment modality to the individual. Such combinations are considered to be part of a single treatment regimen.

By using the terms "pharmaceutically acceptable" or "pharmacologically acceptable" it is intended to mean a material which is not biologically, or otherwise, undesirable—the material may be administered to an individual without causing any substantially undesirable biological effects or interacting in a deleterious manner with any of the components of the composition in which it is contained.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject. Excipients should be selected on the basis of compatibility and the release profile properties of the desired dosage form. Exemplary carrier materials include, e.g., binders, suspending agents, disintegration agents, filling agents, surfactants, solubilizers, stabilizers, lubricants, wetting agents, diluents, spray-dried dispersions, and the like.

The term "pharmaceutically compatible carrier materials" may comprise, e.g., acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, and the like. See, e.g., Hoover, John E, *Remington's Pharmaceutical Sciences*, Mack Publishing Co., Easton, Pa. 1975.

As used herein, the term "subject" encompasses mammals and non-mammals. Examples of mammals include, but are not limited to, any member of the class Mammalia: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like Examples of non-mammals include, but are not limited to, birds, fish and the like. In one embodiment of the present disclosure, the mammal is a human.

The present disclosure also includes "prodrugs" of compounds. The term "prodrug" means a compound which is convertible in vivo by metabolic means (e.g., by hydrolysis) to a disclosed compound or active ingredient. Prodrugs can be prepared by techniques known to one skilled in the art. These techniques generally modify appropriate functional, e.g., a hydroxy, amino, carboxylic, etc., groups in a given compound. These modified functional groups, however, regenerate original functional groups by routine manipulation or in vivo. Examples of prodrugs include, but are not limited to esters (e.g., acetate, formate, and benzoate derivatives), carbamates (e.g., N,N-dimethylaminocarbonyl) of hydroxy or amino functional groups in compounds of the present disclosure, amides (e.g., trifluoroacetylamino, acetylamino, and the like), and the like. Since prodrugs are known to enhance numerous desirable qualities of pharmaceuticals (e.g., solubility, bioavailability, manufacturing, transport, pharmacodynamics, etc.), the compounds of the present disclosure may be delivered in prodrug form. Prodrugs, for instance, may be bioavailable by oral administration even when the parent drug is not. Thus, the present disclosure is intended to cover prodrugs of the presently claimed compounds, methods of delivering the same, and compositions containing the same. Generally speaking, prodrugs are derivatives of per se drugs that after administration undergo conversion or metabolism to the physiologically active species. The conversion may be spontaneous, such as hydrolysis in the physiological environment, or may be enzyme-catalyzed. Prodrugs include compounds that can be oxidized, reduced, aminated, deaminated, hydroxylated, dehydroxylated, hydrolyzed, esterified, alkylated, dealkylated, acylated, deacylated, phosphorylated, and/or dephosphorylated to produce the active compound.

The terms "administered", "administration", or "administering" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body, including an animal, in need of treatment by bringing such individual in contact with, or otherwise exposing such individual to, such compound.

As used herein, "alkyl" means a straight chain or branched saturated chain having from 1 to 10 carbon atoms. Representative saturated alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl and the like, and longer alkyl groups, such as heptyl, and octyl and the like. An alkyl group can be unsubstituted or substituted. Alkyl groups containing three or more carbon atoms may be straight, or branched. As used herein, "lower alkyl" means an alkyl having from 1 to 6 carbon atoms.

As used herein, an "alkenyl" includes an unbranched or branched hydrocarbon chain containing 2-10 carbon atoms. The "alkenyl" group contains at least one double bond. The double bond of an alkenyl group can be unconjugated or conjugated to another unsaturated group. Examples of alkenyl groups include, but are not limited to, ethylenyl, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl and the like. An alkenyl group can be unsubstituted or substituted. Alkenyl, as defined herein, may also be branched or straight.

As used herein, "alkynyl" includes an unbranched or branched unsaturated hydrocarbon chain containing 2-10 carbon atoms. The "alkynyl" group contains at least one triple bond. The triple bond of an alkynyl group can be unconjugated or conjugated to another unsaturated group. Examples of alkynyl groups include, but are not limited to, ethynyl, propynyl, butynyl, pentynyl, hexynyl, methylpropynyl, 4-methyl-1-butynyl, 4-propyl-2-pentynyl, 4-butyl-2-hexynyl and the like. An alkynyl group can be unsubstituted or substituted.

The term "hydroxyl" or "hydroxy" means an OH group:

The term "alkoxy" as used herein refers to a straight or branched chain saturated hydrocarbon containing 1-12 carbon atoms containing a terminal "O" in the chain, i.e., —O(alkyl). Examples of alkoxy groups include, without limitation, methoxy, ethoxy, propoxy, butoxy, t-butoxy, or pentoxy groups.

It should also be noted that any carbon as well as heteroatom with unsatisfied valences in the text, schemes, examples and Tables herein is assumed to have the sufficient number of hydrogen atom(s) to satisfy the valences.

As used herein, references to hydrogen may also refer to a deuterium substitution if desired. The term "deuterium" as used herein means a stable isotope of hydrogen having odd numbers of protons and neutrons.

The term "halo" or "halogen" refers to fluorine, chlorine, bromine, or iodine.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amino" as used herein means a substituent containing at least one nitrogen atom. Specifically, $NH_2$, —NH(alkyl) or alkylamino, —N(alkyl)$_2$ or dialkylamino, amide, carboxamide, urea, and sulfamide substituents are included in the term "amino".

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic or polycyclic aromatic radical of 5 to 18 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. The substituents can themselves be optionally substituted. Examples include, but are not limited to, benzothiophene, furyl, thienyl, pyrrolyl, pyridyl, pyrazinyl, pyrazolyl, pyridazinyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, benzoimidazolyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[ 2,1-b][1,3,4]thiadiazolyl, thieno[2,3-b]pyrrolyl, 3-H-indolyl, and derivatives thereof. Furthermore when containing two fused rings the heteroaryl groups herein defined may have an unsaturated or partially saturated ring fused with a fully saturated ring.

As used herein, the term "cycloalkyl" refers to a saturated or partially saturated, monocyclic, fused or spiro polycyclic, carbocycle having from 3 to 18 carbon atoms per ring. The cycloalkyl ring or carbocycle may be optionally substituted by one or more substituents, e.g., 1 to 5 substituents, at any point of attachment. The substituents can themselves be optionally substituted. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, bicyclo[2.2.2]octenyl, decahydronaphthalenyl, octahydro-1H-indenyl, cyclopentenyl, cyclohexenyl, cyclohexa-1,4-dienyl, cyclohexa-1,3-dienyl, 1,2,3,4-tetrahydronaphthalenyl, octahydropentalenyl, 3a,4,5,6,7,7a-hexahydro-1H-indenyl, 1,2,3,3a-tetrahydropentalenyl, bicyclo[3.1.0]hexanyl, bicyclo[2.1.0]pentanyl, spiro[3.3]heptanyl, bicyclo[2.2.1]heptanyl, bicyclo[2.2.1]hept-2-enyl, bicyclo[2.2.2]octanyl, 6-methylbicyclo[3.1.1]heptanyl, 2,6,6-trimethylbicyclo[3.1.1]heptanyl, and derivatives thereof.

As used herein, the term "cycloalkenyl" refers to a partially saturated, monocyclic, fused or spiro polycyclic, carbocycle having from 3 to 18 carbon atoms per ring and contains at least one double bond. The cycloalkenyl ring may be optionally substituted by one or more substituents, e.g., 1 to 5 substituents, at any point of attachment. The substituents can themselves be optionally substituted.

As used herein, the term "heterocycloalkyl" or "heterocyclyl" refers to a saturated or partially unsaturated and non-aromatic monocyclic, or fused or spiro, polycyclic, ring structure of 4- to- 18 atoms containing carbon and heteroatoms taken from oxygen, nitrogen, or sulfur and wherein there is not delocalized n-electrons (aromaticity) shared among the ring carbon or heteroatoms. The heterocycloalkyl or heterocyclyl ring structure may be substituted by one or more substituents. The substituents can themselves be optionally substituted. Examples of heterocycloalkyl or heterocyclyl rings include, but are not limited to, oxetanyl, azetidinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, homotropanyl, dihydrothiophen-2(3H)-onyl, tetrahydrothiophene 1,1-dioxide, 2,5-dihydro-1H-pyrrolyl, imidazolidin-2-one, pyrrolidin-2-one, dihydrofuran-2(3H)-one, 1,3-dioxolan-2-one, isothiazolidine 1,1-dioxide, 4,5-dihydro-1H-imidazolyl, 4,5-dihydrooxazolyl, oxiranyl, pyrazolidinyl, 4H-1,4-thiazinyl, thiomorpholinyl, 1,2,3,4-tetrahydropyridinyl, 1,2,3,4-tetrahydropyrazinyl, 1,3-oxazinan-2-one, tetrahydro-2H-thiopyran 1,1-dioxide, 7-oxabicyclo [2.2.1]heptanyl, 1,2-thiazepane 1,1-dioxide, octahydro-2H-quinolizinyl, 1,3-diazabicyclo[2.2.2]octanyl, 2,3-dihydrobenzo[b][1,4]dioxine, 3-azabicyclo[3.2.1]octanyl, 8-azaspiro[4.5]decane, 8-oxa-3-azabicyclo[3.2.1]octanyl, 2-azabicyclo[2.2.1]heptane, 2,8-diazaspiro[5.5]undecanyl, 2-azaspiro[5.5]undecanyl, 3-azaspiro[5.5]undecanyl, decahydroisoquinolinyl, 1-oxa-8-azaspiro[4.5]decanyl, 8-azabicyclo[3.2.1]octanyl, 1,4'-bipiperidinyl, azepanyl, 8-oxa-3-azabicyclo[3.2.1]octanyl, 3,4-dihydro-2H-benzo[b][1,4]oxazinyl, 5,6,7,8-tetrahydroimidazo[1,2-a]pyridinyl, 1,4-diazepanyl, phenoxathiinyl, benzo[d][1,3]dioxolyl, 2,3-dihydrobenzofuranyl, 2,3-dihydrobenzo[b][1,4]dioxinyl, 4-(piperidin-4-yl)morpholinyl, 3-azaspiro[5.5]undecanyl, decahydroquinolinyl, piperazin-2-one, 1-(pyrrolidin-2-ylmethyl)pyrrolidinyl, 1,3'-bipyrrolidinyl, and 6,7,8,9-tetrahydro-1H,5H-pyrazolo[1,2-a][1.0.2]diazepinyl.

Numerical ranges, as used herein, are intended to include sequential integers. For example, a range expressed as "from 0 to 5" would include 0, 1, 2, 3, 4 and 5.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, oxo, -halogen, $C_1$-$C_6$ alkyl, $C_1$-$C_6$ alkoxy, $C_1$-$C_6$ haloalkyl, $C_1$-$C_6$ haloalkoxy, —$OC_1$-$C_6$ alkenyl. —$OC_1$-$C_6$ alkynyl, —$C_1$-$C_6$ alkenyl, —$C_1$-$C_6$ alkynyl, —OH, CN (cyano), —$CH_2CN$, —OP(O)(OH)$_2$, —C(O)OH, —OC(O)$C_1$-$C_6$ alkyl, —C(O)$C_1$-$C_6$ alkyl, —C(O)—$C_0$-$C_6$ alkylenyl-cycloalkyl. —C(O)—$C_0$-$C_6$ alkylenyl-heterocycloalkyl, —C(O)—$C_0$-$C_6$ alkylenyl-aryl, —C(O)—$C_0$-$C_6$ alkylenyl-heteroaryl, —OC(O)$OC_1$-$C_6$ alkyl, $NH_2$, NH($C_1$-$C_6$ alkyl), N($C_1$-$C_6$ alkyl)$_2$, —C(O)$NH_2$, —C(O)NH($C_1$-$C_6$ alkyl), —C(O)N($C_1$-$C_6$ alkyl)$_2$, —C(O)NH cycloalkyl, —C(O)N($C_1$-$C_6$ alkyl)cycloalkyl, —C(O)NHheterocycloalkyl, —C(O)N($C_1$-$C_6$ alkyl)heterocycloalkyl, —C(O)NHaryl, —C(O)N($C_1$-$C_6$ alkyl)aryl, —C(O)NHheteroaryl, —C(O)N($C_1$-$C_6$ alkyl)heteroaryl, —S(O)$_2$—$C_1$-$C_6$ alkyl, —S(O)$_2$—$C_1$-$C_6$ haloalkyl, —S(O)$_2$— cycloalkyl, —S(O)$_2$-heterocycloalkyl, —S(O)$_2$— aryl, —S(O)$_2$-heteroaryl-$C_0$-$C_6$ alkylenyl-S(O)$_2NH_2$, —S(O)$_2$NH$C_1$-$C_6$ alkyl, —S(O)$_2$N($C_1$-$C_6$ alkyl)$_2$, —S(O)$_2$NHcycloalkyl, —S(O)$_2$NHheterocycloalkyl, —S(O)$_2$NHaryl, —S(O)$_2$NHhetereoaryl, —NHS(O)$_2C_1$-$C_6$ alkyl, —N($C_1$-$C_6$ alkyl)S(O)$_2$($C_1$-$C_6$ alkyl), —NHS(O)$_2$aryl, —N($C_1$-$C_6$ alkyl)S(O)$_2$ aryl, —NHS(O)$_2$ heteroaryl, —N($C_1$-$C_6$ alkyl) S(O)$_2$ heteroaryl, —NHS(O)$_2$ cycloalkyl, —N($C_1$-$C_6$ alkyl) S(O)$_2$ cycloalkyl, —NHS(O)$_2$ heterocycloalkyl, —N($C_1$-$C_6$ alkyl)S(O)$_2$ heterocycloalkyl, —N($C_1$-$C_6$ alkyl)S(O)$_2$ aryl, —$C_0$-$C_6$ alkylenyl-aryl, —$C_0$-$C_6$ alkylenyl-heteroaryl, —$C_0$-$C_6$ alkylenyl-cycloalkyl, —$C_0$-$C_6$ alkylenyl-heterocycloalkyl, —O-aryl, —NH-aryl, and N($C_1$-$C_6$ alkyl)aryl. The substituents can themselves be optionally substituted. When a multifunctional moiety is shown, the point of attachment to the core is indicated by a line, e.g., (cycloalkyloxy)alkyl- refers to alkyl being the point of attachment to the core while cycloalkyl is attached to alkyl via the oxy group. "Optionally substituted" also refers to "substituted" or "unsubstituted", with the meanings described above.

The term "oxa" as used herein refers to an "—O—" group.

The term "oxo" as used herein refers to an "=O" group.

The term "solvate" refers to a complex of variable stoichiometry formed by a solute and solvent. Such solvents for the purpose of the present disclosure may not interfere with the biological activity of the solute. Examples of suitable solvents include, but are not limited to, water, methanol, ethanol, and acetic acid. Solvates wherein water is the solvent molecule are typically referred to as hydrates. Hydrates include compositions containing stoichiometric amounts of water, as well as compositions containing variable amounts of water.

The term "salt(s)", as employed herein, denotes acidic salts formed with inorganic and/or organic acids, as well as basic salts formed with inorganic and/or organic bases. In addition, when a compound of the Formula contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula may be formed, for example, by reacting a compound of Formula with an amount of acid or base, such as an equivalent amount, in a medium such as one in which the salt precipitates or in an aqueous medium followed by lyophilization.

In another embodiment of the present disclosure, the compounds of Formula (I) are enantiomers. In some embodiments the compounds are the (S)-enantiomer. In other embodiments the compounds are the (R)-enantiomer.

In yet other embodiments, the compounds of Formula (I) may be (+) or (−) enantiomers.

It should be understood that all isomeric forms are included within the present disclosure, including mixtures thereof. If the compound contains a double bond, the substituent may be in the E or Z configuration. If the compound contains a disubstituted cycloalkyl, the cycloalkyl substituent may have a cis- or trans-configuration. All tautomeric forms are also intended to be included.

Compounds of the various Formulae, and salts, solvates, esters and prodrugs thereof, may exist in their tautomeric form (for example, as an amide or imino ether). All such tautomeric forms are contemplated herein as part of the present disclosure.

The compounds of the various Formulae may contain asymmetric or chiral centers, and, therefore, exist in different stereoisomeric forms. It is intended that all stereoisomeric forms of the compounds of the various Formulae as well as mixtures thereof, including racemic mixtures, form part of the present disclosure. In addition, the present disclosure embraces all geometric and positional isomers. For example, if a compound of the various Formulae incorporates a double bond or a fused ring, both the cis- and trans-forms, as well as mixtures, are embraced within the scope of the present disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the various Formulae may be atropisomers (e.g., substituted biaryls) and are considered as part of the present disclosure. Enantiomers can also be separated by use of a chiral HPLC column.

It is also possible that the compounds of the present disclosure may exist in different tautomeric forms, and all such forms are embraced within the scope of the present disclosure. Also, for example, all keto-enol and imine-enamine forms of the compounds are included in the present disclosure.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of the present disclosure, as are positional isomers (such as, for example, 4-pyridyl and 3-pyridyl). (For example, if a compound of the various Formulae incorporates a double bond or a fused ring, both the cis- and trans-forms, as well as mixtures, are embraced within the scope of the present disclosure. Also, for example, all keto-enol and imine-enamine forms of the compounds are included in the present disclosure.) Individual stereoisomers of the compounds of the present disclosure may, for example, be substantially free of other isomers, or may be admixed, for example, as racemates or with all other, or other selected, stereoisomers. The chiral centers of the present disclosure can have the S or R configuration as defined by the IUPAC 1974 Recommendations.

The present disclosure also embraces isotopically-labelled compounds of the present disclosure which are identical to those recited herein, but for the fact that one or more atoms are replaced by an atom having an atomic mass or mass number different from the atomic mass or mass number usually found in nature. Examples of isotopes that can be incorporated into compounds of the present disclosure include isotopes of hydrogen, carbon, nitrogen, oxygen, phosphorus, fluorine and chlorine, such as $^2$H (or D), $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of the various Formulae (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of the various Formulae can generally be prepared by following procedures analogous to those disclosed in the Schemes and/or in the Examples herein below, by substituting an appropriate isotopically labelled reagent for a non-isotopically labelled reagent.

In some embodiments, the compound comprises at least one deuterium atom. For example, one or more hydrogen atoms in a compound of the present disclosure can be replaced or substituted by deuterium. In some embodiments, the compound comprises two or more deuterium atoms. In some embodiments, the compound comprises 1, 2, 3, 4, 5, 6, 7, 8, 9, 10, 11 or 12 deuterium atoms.

The compounds of the present disclosure may form salts which are also within the scope of the present disclosure. Reference to a compound of the Formula herein is understood to include reference to salts thereof, unless otherwise indicated.

The present disclosure is directed to compounds as described herein and pharmaceutically acceptable salts, enantiomers, hydrates, solvates, prodrugs, isomers, or tautomers thereof, and pharmaceutical compositions comprising one or more compounds as described herein, or pharmaceutically acceptable salts, enantiomers, hydrates, solvates, prodrugs, isomers, or tautomers thereof.

Compounds

The present disclosure provides compounds having the structure of Formula (I):

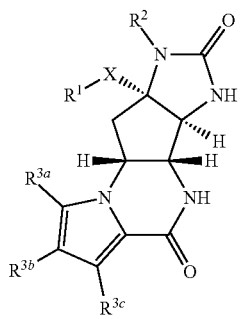

or a pharmaceutically acceptable salt, tautomer, or stereoisomer thereof, wherein: X is —O—, —S—, or —N($R^6$)—; $R^1$ is H, $C_{1-10}$ alkyl, $C_{2-10}$ alkenyl, or $C_{2-8}$ alkynyl, optionally substituted with one or more $R^4$; or alternatively, X and combine to form —$N_3$; $R^2$ is $C_{1-10}$ alkyl, $C_{2-10}$ alkenyl, or $C_{2-8}$ alkynyl, optionally substituted with one or more $R^5$, wherein up to 3 —$CH_2$— units of $R^2$ are optionally replaced by an —O—, —S—, or —$NR^6$—, provided that no adjacent —$CH_2$— is replaced; or alternatively, $R^1$ and $R^2$ taken together with the atoms to which they are attached form a $C_{5-10}$ heterocycloalkyl, $C_{5-10}$ heterocycloalkenyl, or $C_{5-10}$ heterocycloalkynyl ring, optionally substituted with one or more $R^4$; $R^{3a}$, $R^{3b}$, and $R^{3c}$ are each independently H or halogen; $R^4$ is halogen, —$C_{1-5}$ alkyl, oxo, —OH, —$OR^6$, —$N_3$, —N($R^6$)$_2$, —NH(C=O)$R^6$, —NH(C=O)O$R^6$, —NH(C=O)N($R^6$)$_2$, —(C=O)$R^6$, heteroaryl,

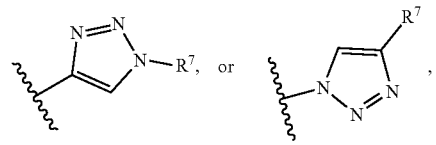

and two adjacent $R^4$ groups may take the form

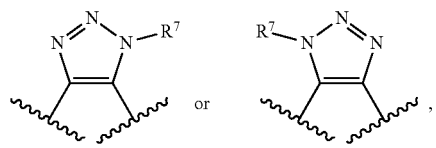

wherein the C=C double bond of the triazole is part of $R^1$; $R^5$ is halogen, oxo, —OH, —$OR^6$, —$N_3$, —N($R^6$)$_2$,

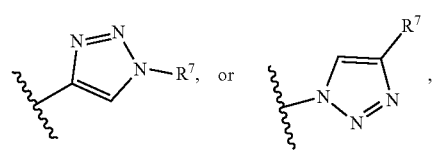

and two adjacent R⁵ groups may take the form

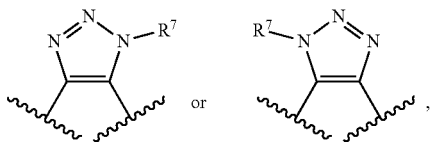

or wherein the C═C double bond of the triazole is part of R²; and R⁶ is independently H, —C$_{1-5}$ alkyl, —C$_{2-5}$ alkenyl, —C$_{1-5}$ alkynyl, —C$_{1-5}$ alkyl-SiMe$_3$, aryl, or heteroaryl; R⁷ is selected from the group consisting of hydrogen, optionally substituted aliphatic, optionally substituted heteroaliphatic, optionally substituted aryl, optionally substituted heteroaryl, optionally substituted acyl, resin, protein, reporter molecule, and label molecule, wherein. R⁷ is optionally joined to the core by a linker L, wherein the linker L is selected from the group consisting of optionally substituted alkylene, optionally substituted alkenylene, optionally substituted alkynylene, optionally substituted heteroalkylene, optionally substituted heteroalkenylene, optionally substituted heteroalkynylene, optionally substituted arylene, optionally substituted heteroarylene, and optionally substituted acylene. In some embodiments, the compound of Formula (I) is not is not agelastatin A, agelastatin B, agelastatin E,

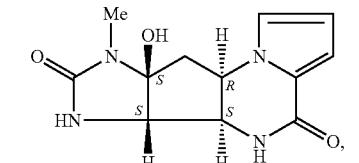

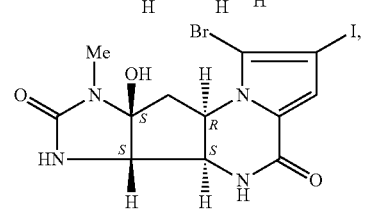

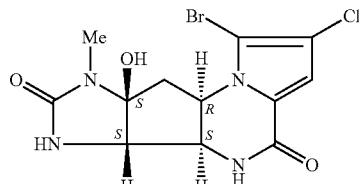

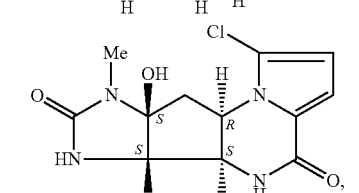

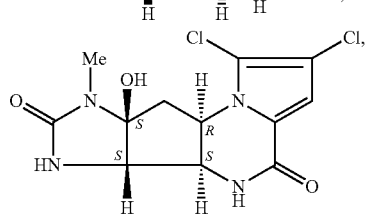

-continued

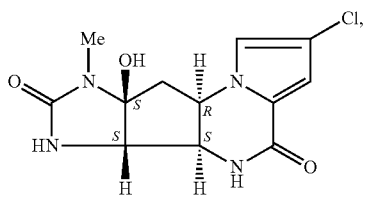

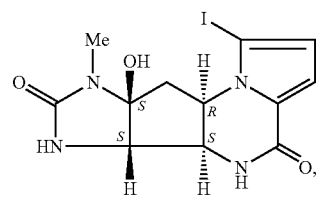

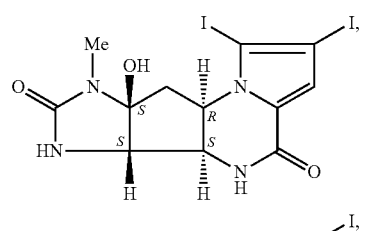

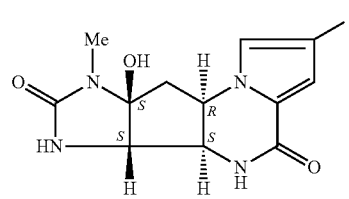

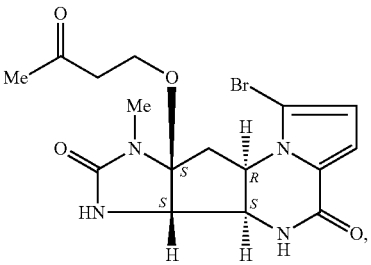

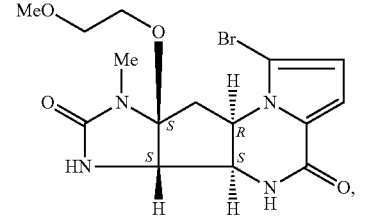

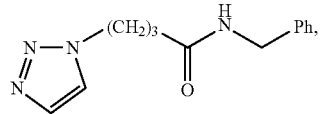

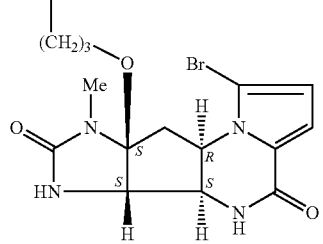

-continued

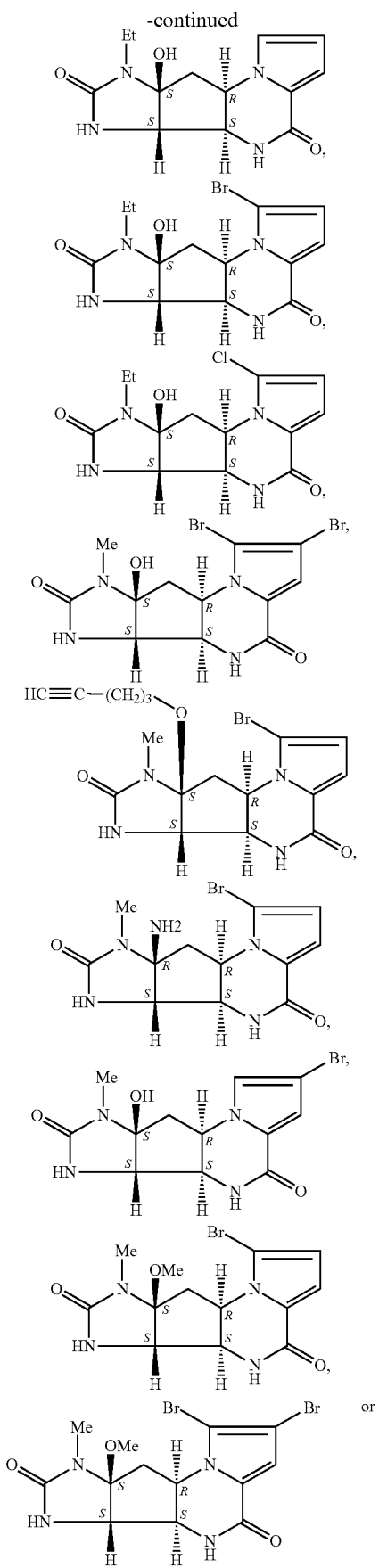

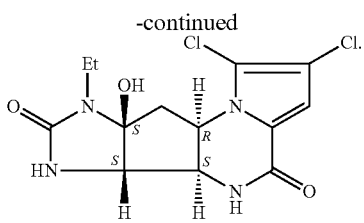

In some embodiments, X is —O—. In some embodiments, X is —S—. In some embodiments, X is —N(R$^6$)—. In some embodiments, R$^1$ is H. In some embodiments, R$^1$ is C$_{1-10}$ alkyl. In some embodiments, R$^1$ is C$_{2-10}$ alkenyl. In some embodiments, R$^1$ is C$_{2-8}$ alkynyl. In some embodiments, R$^1$ is optionally substituted with one or more R$^4$, where R$^4$ is halogen, —C$_{1-5}$ alkyl, oxo, —OH, —OR$^6$, —N$_3$, —N(R$^6$)$_2$, —NH(C=O)OR$^6$, —NH(C=O)OR$^6$, —NH(C=O)N(R$^6$)$_2$, —(C=O)R$^6$, or heteroaryl. In some embodiments, X and R$^1$ combine to form —N$_3$. In some embodiments, R$^2$ is C$_{1-10}$ alkyl. In some embodiments, R$^2$ is C$_{2-10}$ alkenyl. In some embodiments, R$^5$ is C$_{2-8}$ alkynyl. In some embodiments, R$^2$ is optionally substituted with one or more R$^5$, where R$^5$ is halogen. In some embodiments, R$^2$ is optionally substituted with one or more R$^5$, where R$^5$ is oxo. In some embodiments, R$^2$ is optionally substituted with one or more R$^5$, where R$^5$ is —OH. In some embodiments, R$^2$ is optionally substituted with one or more R$^5$, where R$^5$ is halogen. In some embodiments, R$^2$ is optionally substituted with one or more R$^5$, where R$^5$ is —OR$^6$. In some embodiments, R$^2$ is optionally substituted with one or more R$^5$, where R$^5$ is —N$_3$. In some embodiments, R$^2$ is optionally substituted with one or more RR, where R$^5$ is —N(R$^6$)$_2$. In some embodiments, up to 3 —CH$_2$— units of R$^2$ are optionally replaced by an —O—, —S—, or —NR$^6$—, provided that no adjacent —CH$_2$— is replaced. In some embodiments, each R$^6$ is independently H, —C$_{1-5}$ alkyl, —C$_{2-5}$ alkenyl, —C$_{1-5}$ alkynyl, —C$_{1-5}$ alkyl-SiMe$_3$, aryl, or heteroaryl.

In some embodiments, the present disclosure provides a compound of Formula (Ia):

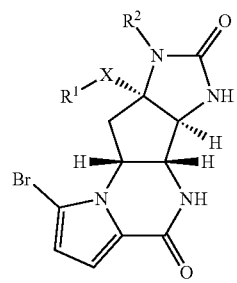

or a pharmaceutically acceptable salt, tautomer, or stereoisomer thereof. In some embodiments, X is —O—. In some embodiments, X is —S—. In some embodiments, X is —N(R$^6$)—. In some embodiments, R$^1$ is H. In some embodiments, R$^1$ is C$_{1-10}$ alkyl. In some embodiments, R$^1$ is C$_{2-10}$ alkenyl. In some embodiments, R$^1$ is C$_{2-8}$ alkynyl. In some embodiments, R$^1$ is optionally substituted with one or more R$^4$, where R$^4$ is halogen. —C$_{1-5}$ alkyl, oxo, —OH, —OR$^6$, —N$_3$, —N(R$^6$)$_2$, —NH(C=O)R$^6$, —NH(C=O)OR$^6$, —NH(C=O)N(R$^6$)$_2$, —(C=O)R$^6$, or heteroaryl. In some embodiments, X and R$^1$ combine to form —N$_3$. In some embodiments, R$^2$ is C$_{1-10}$ alkyl. In some embodiments, R$^2$ is C$_{2-10}$ alkenyl. In some embodiments, R$^2$ is C$_{2-8}$ alkynyl. In some embodiments, R² is optionally substituted with one or more R⁵, where R⁵ is halogen. In some embodiments, R² is optionally substituted with one or more R⁵, where R⁵ is oxo. In some embodiments, R² is optionally substituted with one or more R⁵, where R⁵ is —OH. In some embodiments, R² is optionally substituted with one or more R⁵, where R⁵ is halogen. In some embodiments, R² is optionally substituted with one or more R⁵, where R⁵ is —OR⁶. In some embodiments, R² is optionally substituted with one or more R⁵, where R⁵ is —N₃. In some embodiments, R² is optionally substituted with one or more R⁵, where R⁵ is —N(R⁶)₂. In some embodiments, up to 3 —CH₂— units of R² are optionally replaced by an —O—, —S—, or —NR⁶—, provided that no adjacent —CH₂— is replaced. In some embodiments, each R⁶ is independently H, —C₁₋₅ alkyl, —C₂₋₅ alkenyl, —C₁₋₅ alkynyl, —C₁₋₅ alkyl-SiMe₃, aryl, or heteroaryl. R³ᵃ, R³ᵇ, and R³ᶜ are each independently H or halogen (i.e., iodo, bromo, chloro, fluro). Thus in some embodiments, R³ᵃ, R³ᵇ, and R³ᶜ are each H. In some embodiments, R³ᵃ, R³ᵇ, and R³ᶜ are each halogen. In some embodiments, R³ᵃ, R³ᵇ, and R³ᶜ are a combination of H and halogen. In some embodiments, R³ᵃ is bromo and R³ᵇ and R³ᶜ are H. In some embodiments, R³ᵃ and R³ᵇ are each bromo and R³ᶜ is H. In some embodiments, R³ᵃ and R³ᵇ are each H and R³ᶜ is bromo. In some embodiments, R³ᵃ and R³ᶜ are each H and R³ᵇ is bromo. In some embodiments, R³ᵃ and R³ᶜ are each bromo and R³ᵇ is H. In some embodiments, R³ᵃ is H and R³ᵇ and R³ᶜ are each bromo. In some embodiments, R³ᵃ, R³ᵇ, and R³ᶜ are each bromo. In any of the preceding embodiments for R³ᵃ, R³ᵇ, and R³ᶜ, any bromo or H may be independently replaced with a fluroro, iodo, or chloro moiety allowing for all possible permutations.

In some embodiments, the present disclosure provides a compound of Formula (Ib):

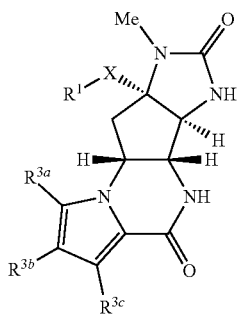

or a pharmaceutically acceptable salt, tautomer, or stereoisomer thereof. In some embodiments, X is —O—. In some embodiments, X is —S—. In some embodiments, X is —N(R⁶)—. In some embodiments, R¹ is H. In some embodiments, R¹ is C₁₋₁₀ alkyl. In some embodiments, R¹ is C₂₋₁₀ alkenyl. In some embodiments, R¹ is C₂₋₈ alkynyl. In some embodiments, R¹ is optionally substituted with one or more R⁴, where R⁴ is halogen, —C₁₋₅ alkyl, oxo, —OH, —OR⁶, —N₃, —N(R⁶)₂, —NH(C=O)R⁶, —NH(C=O)OR⁶, —NH(C=O)N(R⁶)₂, —(C=O)R⁶, or heteroaryl. In some embodiments, X and R¹ combine to form —N₃. R³ᵃ, R³ᵇ, and R³ᶜ are each independently H or halogen (i.e., iodo, bromo, chloro, fluro). Thus in some embodiments, R³ᵃ, R³ᵇ, and R³ᶜ are each H. In some embodiments, R³ᵃ, R³ᵇ, and R³ᶜ are each halogen. In some embodiments, R³ᵃ, R³ᵇ, and R³ᶜ are a combination of H and halogen. In some embodiments, R³ᵃ, is bromo and R³ᵇ and R³ᶜ are H. In some embodiments, R³ᵃ and R³ᵇ are each bromo and R³ᶜ is H. In some embodiments, R³ᵃ and R³ᵇ are each H and R³ᶜ is bromo. In some embodiments, R³ᵃ and R³ᶜ are each H and R³ᵇ is bromo. In some embodiments, R³ᵃ and R³ᶜ are each bromo and R³ᵇ is H. In some embodiments, R³ᵃ is H and R³ᵇ and R³ᶜ are each bromo. In some embodiments, R³ᵃ, R³ᵇ, and R³ᶜ are each bromo. In any of the preceding embodiments for R³ᵃ, R³ᵇ, and R³ᶜ, any bromo or H may be independently replaced with a fluroro, iodo, or chloro moiety allowing for all possible permutations.

In some embodiments, the present disclosure provides a compound of Formula (Ic):

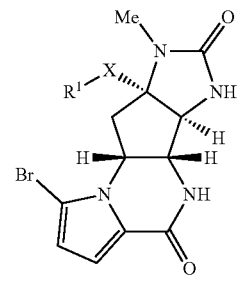

or a pharmaceutically acceptable salt, tautomer, or stereoisomer thereof. In some embodiments, X is —O—. In some embodiments, X is —S—. In some embodiments, X is —N(R⁶)—. In some embodiments, R¹ is H. In some embodiments, R¹ is C₁₋₁₀ alkyl. In some embodiments, R¹ is C₂₋₁₀ alkenyl. In some embodiments, R¹ is C₂₋₈ alkynyl. In some embodiments, R¹ is optionally substituted with one or more R⁴, where R⁴ is halogen, —C₁₋₅ alkyl, oxo, —OH, —OR⁶, —N₃, —N(R⁶)₂, —NH(C=O)R⁶, —NH(C=O)OR⁶, —NH(C=O)N(R⁶)₂, —(C=O)R⁶, or heteroaryl. In some embodiments, X and R¹ combine to form —N₃.

In some embodiments, the present disclosure provides a compound of Formula (Id):

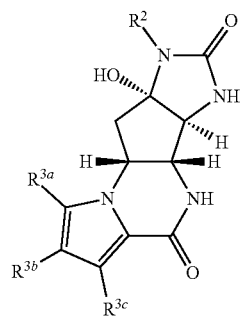

or a pharmaceutically acceptable salt, tautomer, or stereoisomer thereof. In some embodiments, R² is C₁₋₁₀ alkyl. In some embodiments, R² is C₂₋₁₀ alkenyl. In some embodiments, R² is C₂₋₈ alkynyl. In some embodiments, R² is optionally substituted with one or more R⁵, where R⁵ is halogen. In some embodiments, R² is optionally substituted with one or more R⁵, where R⁵ is oxo. In some embodiments, R² is optionally substituted with one or more R⁵, where R⁵ is —OH. In some embodiments, R² is optionally substituted with one or more R⁵, where R⁵ is halogen. In some embodiments, R² is optionally substituted with one or more R⁵, where R⁵ is —OR⁶. In some embodiments, R² is optionally substituted with one or more R⁵, where R⁵ is —N₃. In some embodiments, R² is optionally substituted with one or more $R^5$, where $R^5$ is —$N(R^6)_2$. In some embodiments, up to 3 —$CH_2$— units of $R^2$ are optionally replaced by an —O—, —S—, or —$NR^6$—, provided that no adjacent —$CH_2$— is replaced. In some embodiments, each $R^6$ is independently H, —$C_{1-5}$ alkyl, —$C_{2-5}$ alkenyl, —$C_{1-5}$ alkynyl, —$C_{1-5}$ alkyl-SiMe$_3$, aryl, or heteroaryl. $R^{3a}$, $R^{3b}$, and $R^{3c}$ are each independently H or halogen (i.e., iodo, bromo, chloro, fluro). Thus in some embodiments, $R^{3a}$, $R^{3b}$, and $R^{3c}$ are each H. In some embodiments, $R^{3a}$, $R^{3b}$, and $R^{3c}$ are each halogen. In some embodiments, $R^{3a}$, $R^{3b}$, and $R^{3c}$ are a combination of H and halogen. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In any of the preceding embodiments for $R^{3a}$, $R^{3b}$, and $R^{3c}$, any bromo or H may be independently replaced with a fluroro, iodo, or chloro moiety allowing for all possible permutations.

In some embodiments, the present disclosure provides a compound of Formula (Ie):

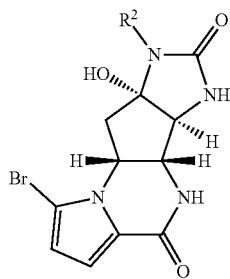

or a pharmaceutically acceptable salt, tautomer, or stereoisomer thereof. In some embodiments, $R^2$ is $C_{1-10}$ alkyl. In some embodiments, $R^2$ is $C_{2-10}$ alkenyl. In some embodiments, $R^2$ is $C_{2-8}$ alkynyl. In some embodiments, $R^2$ is optionally substituted with one or more $R^5$, where $R^5$ is halogen. In some embodiments, $R^2$ is optionally substituted with one or more $R^5$, where $R^5$ is oxo. In some embodiments, $R^2$ is optionally substituted with one or more $R^5$, where $R^5$ is —OH. In some embodiments, $R^2$ is optionally substituted with one or more $R^5$, where $R^5$ is halogen. In some embodiments, $R^2$ is optionally substituted with one or more $R^5$, where $R^5$ is —$OR^6$. In some embodiments, $R^2$ is optionally substituted with one or more $R^5$, where $R^5$ is —$N_3$. In some embodiments, $R^2$ is optionally substituted with one or more $R^5$, where $R^5$ is —$N(R^6)_2$. In some embodiments, up to 3 —$CH_2$— units of $R^2$ are optionally replaced by an —O—, —S— or —$NR^6$—, provided that no adjacent —$CH_2$— is replaced. In some embodiments, each $R^6$ is independently H, —$C_{1-5}$ alkyl, —$C_{2-5}$ alkenyl, —$C_{1-5}$ alkynyl, —$C_{1-5}$ alkyl-SiMe$_3$, aryl, or heteroaryl.

In some embodiments, $R^2$ is $C_{1-10}$ alkyl, optionally substituted with one or more $R^5$, wherein up to 3 —$CH_2$— units of $R^2$ are optionally replaced by an —O—. —S—, or —$NR^6$—, provided that no adjacent —$CH_2$— is replaced. In some embodiments, $R^2$ is $C_{1-10}$ alkyl, substituted with one or more $R^5$, wherein up to 3 —$CH_2$— units of $R^2$ are optionally replaced by an —O—, —S—, or —$NR^6$—, provided that no adjacent —$CH_2$— is replaced. In some embodiments, $R^2$ is $C_{1-10}$ alkyl, wherein up to 3 —$CH_2$— units of $R^2$ are optionally replaced by an —O—, —S—, or —$NR^6$—, provided that no adjacent —$CH_2$— is replaced. In some embodiments, $R^2$ is $C_{1-10}$ alkyl, optionally substituted with one or more $R^5$, wherein no —$CH_2$— units of $R^2$ are optionally replaced by an —O—, —S—, or —$NR^6$. In some embodiments, $R^2$ is $C_{1-10}$ alkyl, substituted with one or more $R^5$, wherein no —$CH_2$— units of $R^2$ are optionally replaced by an —O—, —S—, or —$NR^6$—. In some embodiments, $R^2$ is an unsubstituted $C_{1-10}$ alkyl, wherein no 3 —$CH_2$— units of $R^2$ are optionally replaced by an —O—, —S—, or —$NR^6$. In some embodiments, up to 3 —$CH_2$— units of $R^2$ are optionally replaced by an O.

In some embodiments, $R^2$ is methyl.

In some embodiments, $R^1$ is $C_{1-10}$ alkyl, $C_{2-10}$ alkenyl, or $C_{2-8}$ alkynyl, optionally substituted with one or more $R^4$, or alternatively, X and $R^1$ are combined to form —$N_3$. In some embodiments, $R^1$ is substituted with one or more $R^4$. In some embodiments, $R^1$ is not substituted with one or more $R^4$. In some embodiments, $R^1$ is optionally substituted with one or more $R^4$. In some embodiments, X and $R^1$ are combined to form —$N_3$.

In some embodiments, X is —O— or —S—. In some embodiments, X is —O—.

In some embodiments, $R^{3a}$ is Br or Cl, $R^{3b}$ is H, and $R^{3c}$ is H. In some embodiments, $R^{3a}$ is Br, $R^{3b}$ is H, and $R^{3c}$ is H. In some embodiments, $R^{3a}$ is Br or Cl, $R^{3b}$ is Br or Cl, and $R^{3c}$ is H. In some embodiments, $R^{3a}$ is Br, $R^{3b}$ is Br, and $R^{3c}$ is H.

In certain embodiments, the present disclosure provides for a compound, and pharmaceutically acceptable salts, solvates, hydrates, isomers, and tautomers thereof, selected from the group consisting of

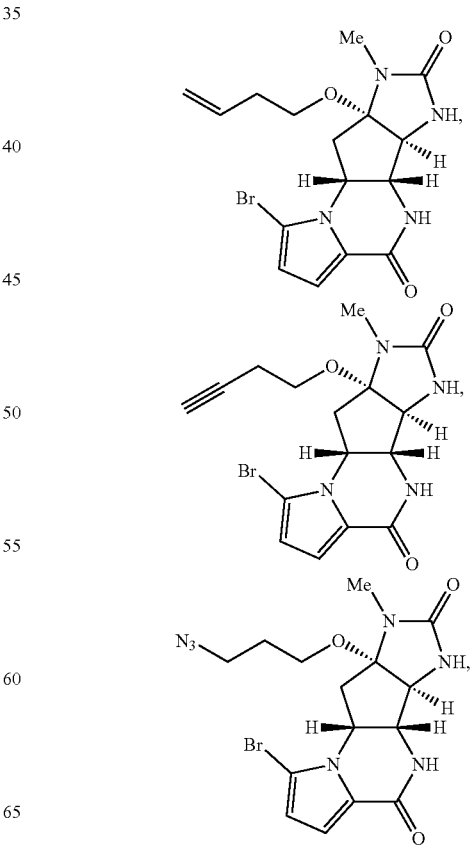

37
-continued
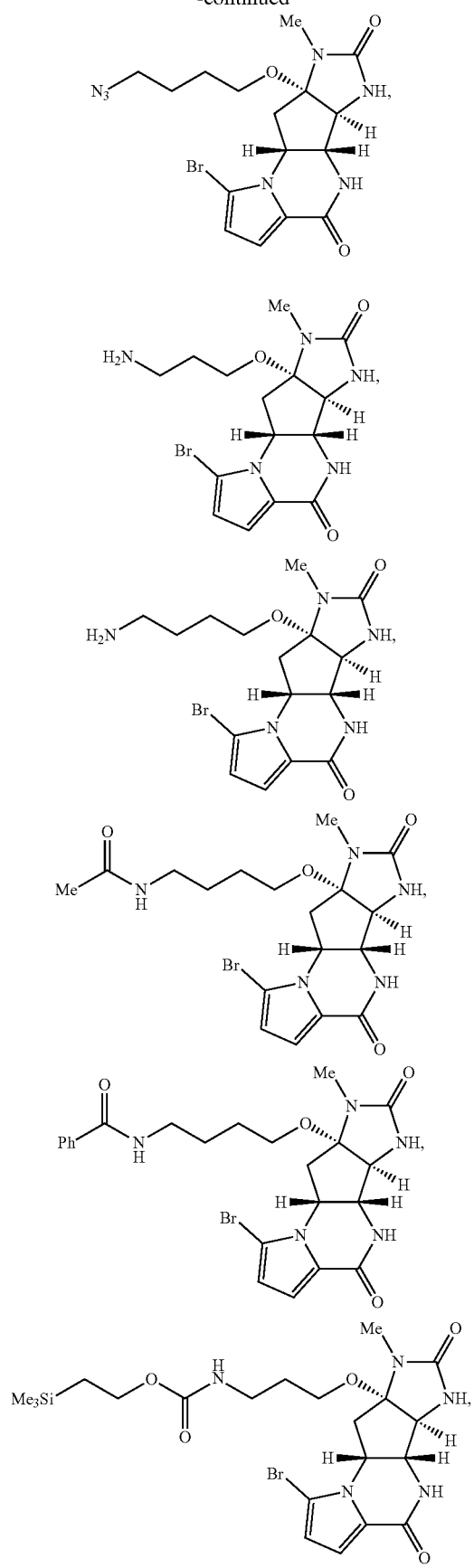
38
-continued
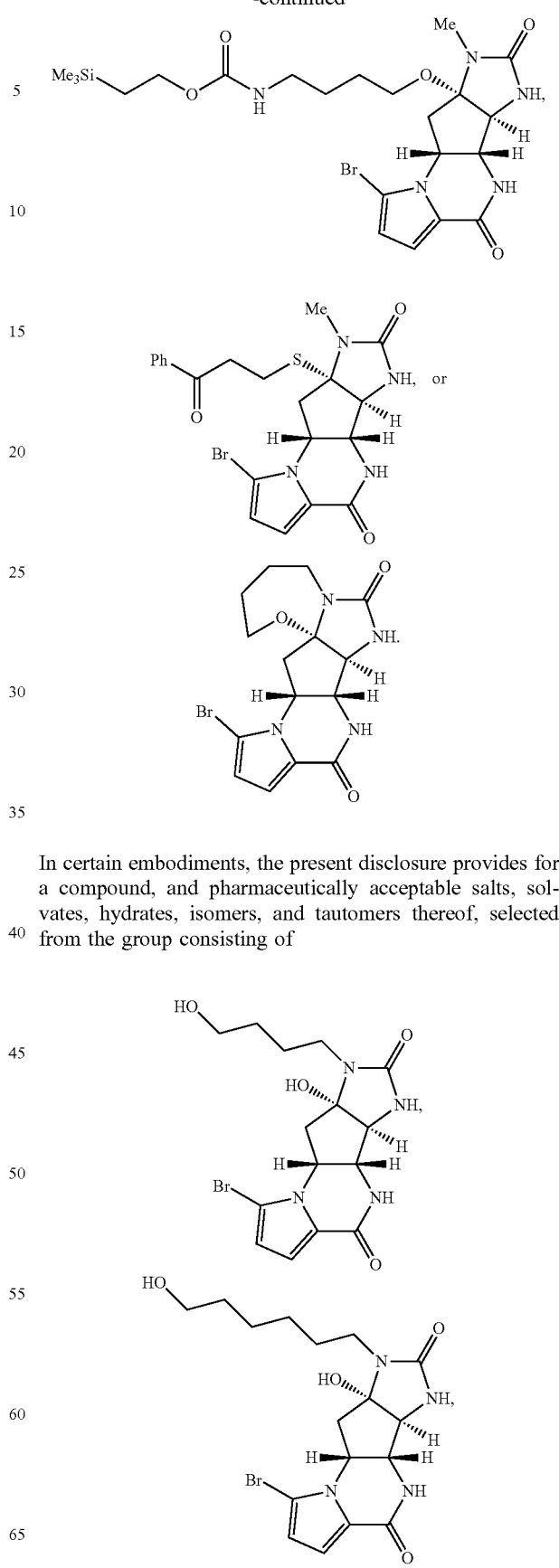
In certain embodiments, the present disclosure provides for a compound, and pharmaceutically acceptable salts, solvates, hydrates, isomers, and tautomers thereof, selected from the group consisting of -continued

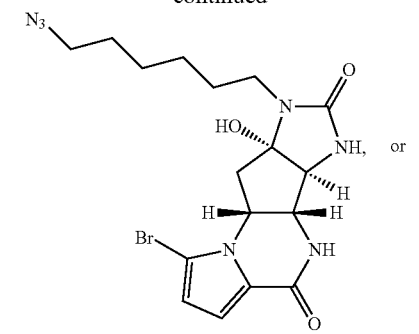

or

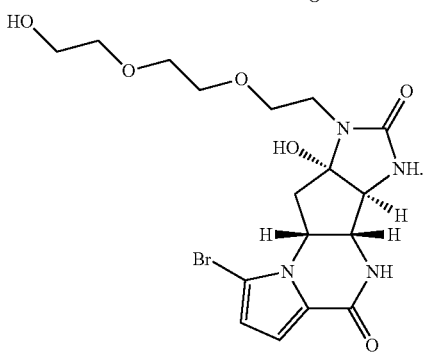

In certain embodiments, the present disclosure provides for a compound, and pharmaceutically acceptable salts, solvates, hydrates, isomers, and tautomers thereof, where the compound is

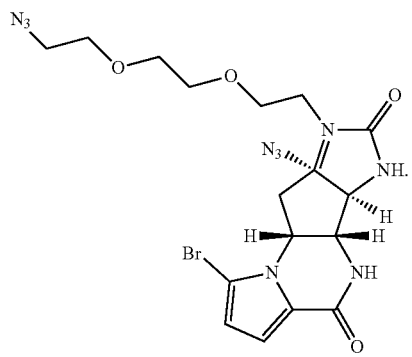

In certain embodiments, the present disclosure provides for a compound, and pharmaceutically acceptable salts, solvates, hydrates, isomers, and tautomers thereof, where the compound is

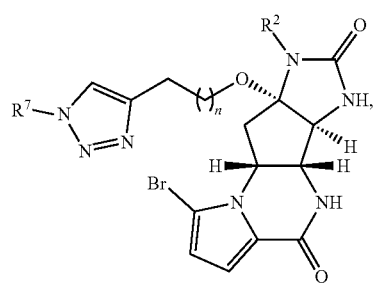

-continued

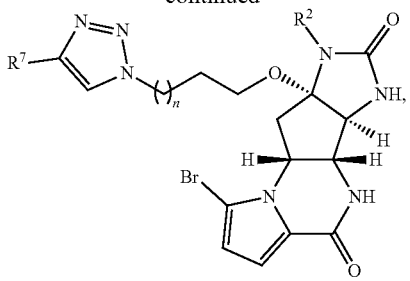

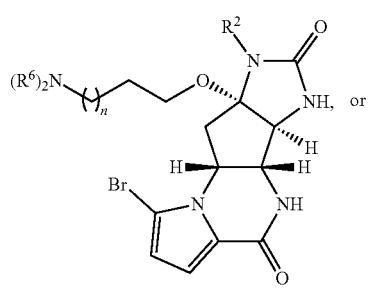

or

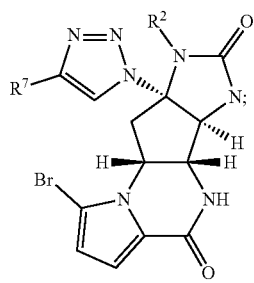

wherein $R^2$ is H or Me; $R^7$ is selected from the group consisting of hydrogen, optionally substituted aliphatic, optionally substituted heteroaliphatic, optionally substituted aryl, optionally substituted heteroaryl, optionally substituted acyl, resin, protein, reporter molecule, and label molecule; wherein, R7 is optionally joined to the core by a linker L, wherein the linker L is selected from the group consisting of optionally substituted alkylene, optionally substituted alkenylene, optionally substituted alkynylene, optionally substituted heteroalkylene, optionally substituted heteroalkenylene, optionally substituted heteroalkynylene, optionally substituted arylene, optionally substituted heteroarylene, and optionally substituted acylene. In some embodiments, $R^2$ is H. In other embodiments. $R^2$ is Me. In certain embodiments, the present disclosure provides for a compound, and pharmaceutically acceptable salts, solvates, hydrates, isomers, and tautomers thereof, where the compound is

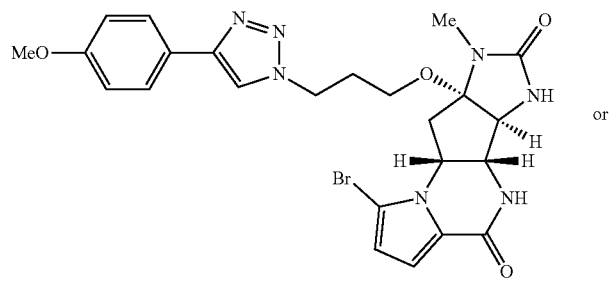
or
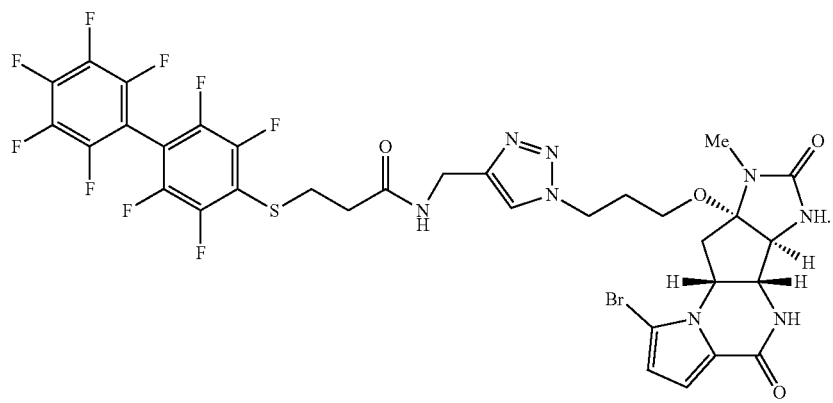
In specific embodiments, the compound of Formula (I) is
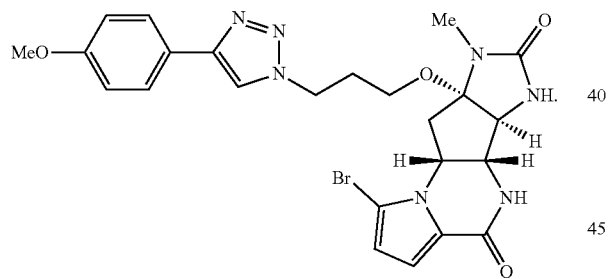
In certain embodiments, the present disclosure provides for a compound, and pharmaceutically acceptable salts, solvates, hydrates, isomers, and tautomers thereof, where the compound is
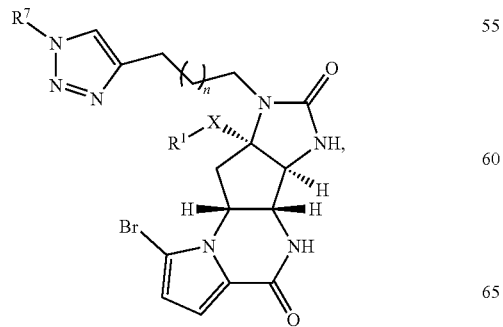
-continued
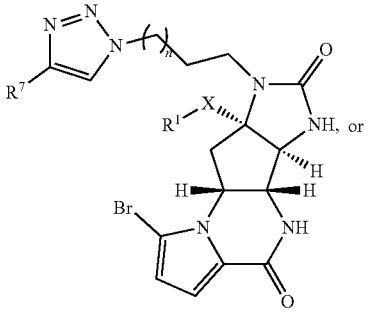
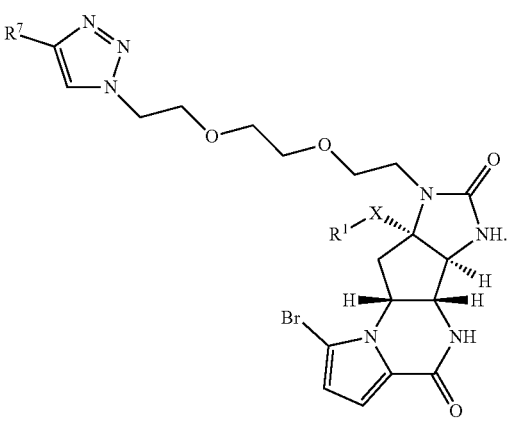

In specific embodiments, the compound of Formula (I) is

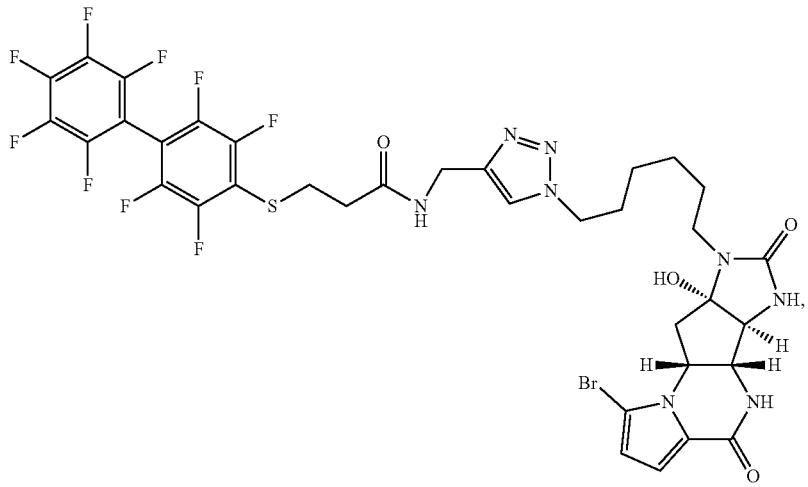

wherein X, $R^1$, $R^7$, and n are as defined above.

In various embodiments, the present disclosure also provides for internal triazole compounds of Formula (I). As an example meant only for illustrative purposes, by internal triazole compounds of Formula (I), triazoles of this type may have a general structure such as the following examples:

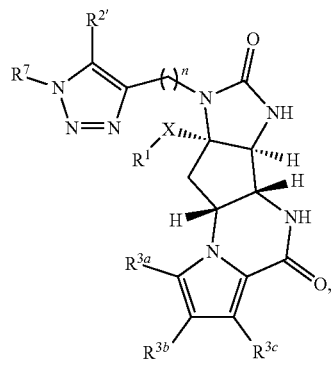

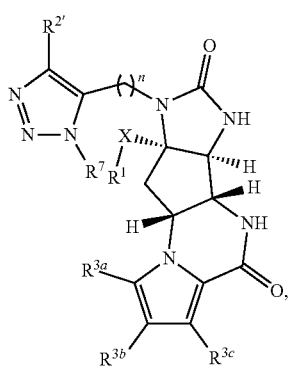

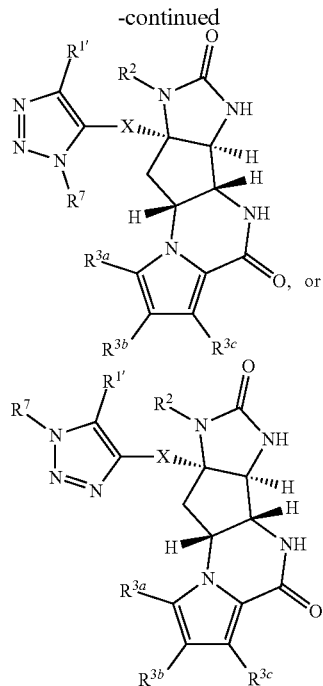

where $R^{1'}$ and $R^{2'}$ represent the rest of the $R^1$ or $R^2$ moiety.

In some embodiments, X is —O—, $R^1$ is H, $R^2$ is $C_{1-10}$ alkyl and $R^{3a}$, $R^{3b}$, and $R^{3c}$ are each independently H or halogen. For example, $R^2$ may be methyl, ethyl, propyl, butyl, pentyl, hexyl, heptyl, octyl, nonyl, decyl, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are each H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In any of the preceding embodiments for $R^{3a}$, $R^{3b}$, and $R^{3c}$, any bromo or H may be independently replaced with a fluroro, iodo, or chloro moiety allowing for all possible permutations. In some embodiments, $R^2$ is substituted with one or more $R^5$. For example, in some embodiments, $R^2$ is substituted with halogen, oxo, —OH, —$OR^6$, —$N_3$, or —$N(R^6)_2$. In some embodiments, up to 3 —$CH_2$— units of $R^2$ are replaced by an —O—, —S—, or —$NR^6$—, provided that no adjacent —$CH_2$— is replaced.

In some embodiments, X is —O—, $R^1$ is H, $R^2$ is $C_{2-10}$ alkenyl and $R^{3a}$, $R^{3b}$, and $R^{3c}$ are each independently H or halogen. For example, $R^2$ may be ethylene, propylene, butylene, pentylene, hexylene, heptylene, octylene, nonylene, decylene, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In any of the preceding embodiments for $R^{3a}$, $R^{3b}$, and $R^{3c}$, any bromo or H may be independently replaced with a fluoro, iodo, or chloro moiety allowing for all possible permutations. In some embodiments, $R^2$ is substituted with one or more $R^5$. For example, in some embodiments, $R^2$ is substituted with halogen, oxo, —OH, —$OR^6$, —$N_3$, or —$N(R^6)_2$. In some embodiments, up to 3 —$CH_2$— units of $R^2$ are replaced by an —O—, —S—, or —$NR^6$—, provided that no adjacent —$CH_2$— is replaced.

In some embodiments, X is —O—, $R^1$ is H, $R^2$ is $C_{2-10}$ alkynyl and $R^{3a}$, $R^{3b}$, and $R^{3c}$ are each independently H or halogen. For example, $R^2$ may be acetylenyl, propylyne, butylyne, pentylyne, hexylyne, heptylyne, octylyne, nonylyne, decylyne, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In any of the preceding embodiments for $R^{3a}$, $R^{3b}$, and $R^{3c}$, any bromo or H may be independently replaced with a fluoro, iodo, or chloro moiety allowing for all possible permutations. In some embodiments, $R^2$ is substituted with one or more $R^5$. For example, in some embodiments, $R^2$ is substituted with halogen, oxo, —OH, —$OR^6$, —$N_3$, or —$N(R^6)_2$. In some embodiments, up to 3 —$CH_2$— units of $R^2$ are replaced by an —O—, —S—, or —$NR^6$—, provided that no adjacent —$CH_2$— is replaced.

In some embodiments, X is —O—, $R^1$ is $C_{1-10}$ alkyl, $R^2$ is $C_{1-10}$ alkyl and $R^{3a}$, $R^{3b}$, and $R^{3c}$ are each independently H or halogen. For example, $R^1$ may be methyl, ethyl, propyl, butyl, pentyl, hexyl, heptyl, octyl, nonyl, decyl, and all isomers and branched derivatives thereof. For example, $R^2$ may be methyl, ethyl, propyl, butyl, pentyl, hexyl, heptyl, octyl, nonyl, decyl, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3b}$ are each H and $R^{3c}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —$OR^6$, —$N_3$, or —$N(R^6)_2$. In some embodiments, up to 3 —$CH_2$— units of $R^2$ are replaced by an —O—, —S—, or —$NR^6$—, provided that no adjacent —$CH_2$— is replaced. In some embodiments, $R^1$ is substituted with one or more $R^4$ moieties. For example, in some embodiments, $R^1$ is substituted with halogen, —$C_{1-5}$ alkyl, oxo, —OH, —$OR^6$, —$N_3$, —$N(R^6)_2$, —$NH(C=O)R^6$, —$NH(C=O)OR^6$, —$NH(C=O)N(R^6)_2$, —$(C=O)R^6$, or heteroaryl.

In some embodiments, X is —O—, $R^1$ is $C_{1-10}$ alkyl, $R^2$ is $C_{2-10}$ alkenyl and $R^{3a}$, $R^{3b}$, and $R^{3c}$ are each independently H or halogen. For example, $R^1$ may be methyl, ethyl, propyl, butyl, pentyl, hexyl, heptyl, octyl, nonyl, decyl, and all isomers and branched derivatives thereof. For example, $R^2$ may be ethylene, propylene, butylene, pentylene, hexylene, heptylene, octylene, nonylene, decylene, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —$OR^6$, —$N_3$, or —$N(R^6)_2$. In some embodiments, up to 3 —$CH_2$— units of $R^2$ are replaced by an —O—, —S—, or —$NR^6$—, provided that no adjacent —$CH_2$— is replaced. In some embodiments, $R^1$ is substituted with one or more $R^4$ moieties. For example, in some embodiments. $R^1$ is substituted with halogen, —$C_{1-5}$ alkyl, oxo, —OH, —$OR^6$, —$N_3$, —$N(R^6)_2$, —$NH(C=O)R^6$, —$NH(C=O)OR^6$, —$NH(C=O)N(R^6)_2$, —$(C=O)R^6$, or heteroaryl.

In some embodiments, X is —O—, $R^1$ is $C_{1-10}$ alkyl, $R^2$ is $C_{2-10}$ alkynyl and $R^{3a}$, $R^{3b}$, and $R^{3c}$ are each independently H or halogen. For example, $R^1$ may be methyl, ethyl, propyl, butyl, pentyl, hexyl, heptyl, octyl, nonyl, decyl, and all isomers and branched derivatives thereof. For example, $R^2$ may be acetylenyl, propylyne, butylyne, pentylyne, hexylyne, heptylyne, octylyne, nonylyne, decylyne, and all isomers and branched derivatives thereof. In some embodiments, $R^{3a}$ $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —$OR^6$, —$N_3$, or —$N(R^6)_2$. In some embodiments, up to 3 —$CH_2$— units of $R^2$ are replaced by an —O—, —S—, or —$NR^6$—, provided that no adjacent —$CH_2$— is replaced. In some embodiments, $R^1$ is substituted with one or more $R^4$ moieties. For example, in some embodiments, $R^1$ is substituted with halogen, —$C_{1-5}$ alkyl, oxo, —OH, —$OR^6$, —$N_3$, —$N(R^6)_2$, —$NH(C=O)R^6$, —$NH(C=O)OR^6$, —$NH(C=O)N(R^6)_2$, —$(C=O)R^6$, or heteroaryl.

In some embodiments, X is —O—, $R^1$ is $C_{1-10}$ alkenyl. $R^2$ is $C_{1-10}$ alkyl and $R^{3a}$, $R^{3b}$, and $R^{3c}$ are each independently H or halogen. For example, $R^1$ may be ethylene, propylene, butylene, pentylene, hexylene, heptylene, octylene, nonylene, decylene, and all isomers and branched derivatives thereof. For example, $R^2$ may be methyl, ethyl, propyl, butyl, pentyl, hexyl, heptyl, octyl, nonyl, decyl, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —$OR^6$, —$N_3$, or —$N(R^6)_2$. In some embodiments, up to 3 —$CH_2$— units of $R^2$ are replaced by an —O—, —S—, or —$NR^6$—, provided that no adjacent —$CH_2$— is replaced. In some embodiments, $R^1$ is substituted with one or more $R^4$ moieties. For example, in some embodiments, $R^1$ is substituted with halogen, —$C_{1-5}$ alkyl, oxo, —OH, —$OR^6$, —$N_3$, —$N(R^6)_2$, —NH(C=O)$R^6$, —NH(C=O)$OR^6$, —NH(C=O)$N(R^6)_2$, —(C=O)$R^6$, or heteroaryl.

In some embodiments, X is —O—, $R^1$ is $C_{2-10}$ alkenyl, $R^2$ is $C_{2-10}$ alkenyl and $R^{3a}$, $R^{3b}$, and $R^{3c}$ are each independently H or halogen. For example, $R^1$ may be ethylene, propylene, butylene, pentylene, hexylene, heptylene, octylene, nonylene, decylene, and all isomers and branched derivatives thereof. For example, $R^2$ may be ethylene, propylene, butylene, pentylene, hexylene, heptylene, octylene, nonylene, decylene, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —$OR^6$, —$N_3$, or —$N(R^6)_2$. In some embodiments, up to 3 —$CH_2$— units of $R^2$ are replaced by an —O—, —S—, or —$NR^6$—, provided that no adjacent —$CH_2$— is replaced. In some embodiments, $R^1$ is substituted with one or more $R^4$ moieties. For example, in some embodiments, $R^1$ is substituted with halogen, —$C_{1-5}$ alkyl, oxo, —OH, —$OR^6$, —$N_3$, —$N(R^6)_2$, —NH(C=O)$R^6$, —NH(C=O)$OR^6$, —NH(C=O)$N(R^6)_2$, —(C=O)$R^6$, or heteroaryl.

In some embodiments, X is —O—, $R^1$ is $C_{2-10}$ alkenyl, $R^2$ is $C_{2-10}$ alkynyl and $R^{3a}$, $R^{3b}$, and $R^{3c}$ are each independently H or halogen. For example, $R^1$ may be ethylene, propylene, butylene, pentylene, hexylene, heptylene, octylene, nonylene, decylene, and all isomers and branched derivatives thereof. For example, $R^2$ may be acetylenyl, propylyne, butylyne, pentylyne, hexylyne, heptylyne, octylyne, nonylyne, decylyne, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —$OR^6$, —$N_3$, or —$N(R^6)_2$. In some embodiments, up to 3 —$CH_2$— units of $R^2$ are replaced by an —O—, —S—, or —$NR^6$—, provided that no adjacent —$CH_2$— is replaced. In some embodiments, $R^1$ is substituted with one or more $R^4$ moieties. For example, in some embodiments, $R^1$ is substituted with halogen, —$C_{1-5}$ alkyl, oxo, —OH, —$OR^6$, —$N_3$, —$N(R^6)_2$, —NH(C=O)$R^6$, —NH(C=O)$OR^6$, —NH(C=O)$N(R^6)_2$, —(C=O)$R^6$, or heteroaryl.

In some embodiments, X is —O—, $R^1$ is $C_{2-10}$ alkynyl, $R^2$ is $C_{1-10}$ alkyl and $R^{3a}$, $R^{3b}$, and $R^{3c}$ are each independently H or halogen. For example, $R^1$ may be acetylynyl, propylyne, butylyne, pentylyne, hexylyne, heptylyne, octylyne, nonylyne, decylyne, and all isomers and branched derivatives thereof. For example, $R^2$ may be methyl, ethyl, propyl, butyl, pentyl, hexyl, heptyl, octyl, nonyl, decyl, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments. $R^2$ is substituted with halogen, oxo, —OH, —$OR^6$, —$N_3$, or —$N(R^6)_2$. In some embodiments, up to 3 —$CH_2$— units of $R^2$ are replaced by an —O—, —S—, or —$NR^6$—, provided that no adjacent —$CH_2$— is replaced. In some embodiments, $R^1$ is substituted with one or more $R^4$ moieties. For example, in some embodiments, $R^1$ is substituted with halogen, —$C_{1-5}$ alkyl, oxo, —OH, —$OR^6$, —$N_3$, —$N(R^6)_2$, —NH(C=O)$R^6$, —NH(C=O)$OR^6$, —NH(C=O)$N(R^6)_2$, —(C=O)$R^6$, or heteroaryl.

In some embodiments, X is —O—, $R^1$ is $C_{2-10}$ alkynyl, $R^2$ is $C_{2-10}$ alkenyl and $R^{3a}$, $R^{3b}$, and $R^{3c}$ are each independently H or halogen. For example, $R^1$ may be ethylene, propylene, butylene, pentylene, hexylene, heptylene, octylene, nonylene, decylene, and all isomers and branched derivatives thereof. For example, $R^2$ may be ethylene, propylene, butylene, pentylene, hexylene, heptylene, octylene, nonylene, decylene, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —$OR^6$, —$N_3$, or —$N(R^6)_2$. In some embodiments, up to 3 —$CH_2$— units of $R^2$ are replaced by an —O—. —S—, or —$NR^6$—, provided that no adjacent —$CH_2$— is replaced. In some embodiments, $R^1$ is substituted with one or more $R^4$ moieties. For example, in some embodiments, $R^1$ is substituted with halogen, —$C_{1-5}$ alkyl, oxo, —OH, —$OR^6$, —$N_3$, —$N(R^6)_2$, —NH(C=O)$R^6$, —NH(C=O)$OR^6$, —NH(C=O)$N(R^6)_2$, —(C=O)$R^6$, or heteroaryl.

In some embodiments, X is —O—, $R^1$ is $C_{2-10}$ alkynyl, $R^2$ is $C_{2-10}$ alkynyl and $R^{3a}$, $R^{3b}$, and $R^{3c}$ are each independently H or halogen. For example, $R^1$ may be ethylene, propylene, butylene, pentylene, hexylene, heptylene, octylene, nonylene, decylene, and all isomers and branched derivatives thereof. For example, $R^2$ may be acetylenyl, propylyne, butylyne, pentylyne, hexylyne, heptylyne, octylyne, nonylyne, decylyne, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —$OR^6$, —$N_3$, or —$N(R^6)_2$. In some embodiments, up to 3 —$CH_2$— units of $R^2$ are replaced by an —O—, —S—, or —$NR^6$—, provided that no adjacent —$CH_2$— is replaced. In some embodiments, $R^1$ is substituted with one or more $R^4$ moieties. For example, in some embodiments, $R^1$ is substituted with halogen, —$C_{1-5}$ alkyl, oxo, —OH, —$OR^6$, —$N_3$, —$N(R^6)_2$, —NH(C=O)$R^6$, —NH(C=O)$OR^6$, —NH(C=O)N($R^6$)$_2$, —(C=O)$R^6$, or heteroaryl.

In some embodiments, X is —S—, $R^1$ is H, $R^2$ is $C_{1-10}$ alkyl and $R^{3a}$, $R^{3b}$, and $R^{3c}$ are each independently H or halogen. For example, $R^2$ may be methyl, ethyl, propyl, butyl, pentyl, hexyl, heptyl, octyl, nonyl, decyl, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In any of the preceding embodiments for $R^{3a}$, $R^{3b}$, and $R^{3c}$, any bromo or H may be independently replaced with a fluoro, iodo, or chloro moiety allowing for all possible permutations. In some embodiments, $R^2$ is substituted with one or more $R^5$. For example, in some embodiments, $R^2$ is substituted with halogen, oxo, —OH, —$OR^6$, —$N_3$, or —$N(R^6)_2$. In some embodiments, up to 3 —$CH_2$— units of $R^2$ are replaced by an —O—, —S—, or —$NR^6$—, provided that no adjacent —$CH_2$— is replaced.

In some embodiments, X is —S—, $R^1$ is H, $R^2$ is $C_{2-10}$ alkenyl and $R^{3a}$, $R^{3b}$, and $R^{3c}$ are each independently H or halogen. For example, $R^2$ may be ethylene, propylene, butylene, pentylene, hexylene, heptylene, octylene, nonylene, decylene, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In any of the preceding embodiments for $R^{3a}$, $R^{3b}$, and $R^{3c}$, any bromo or H may be independently replaced with a fluoro, iodo, or chloro moiety allowing for all possible permutations. In some embodiments, $R^2$ is substituted with one or more $R^5$. For example, in some embodiments, $R^2$ is substituted with halogen, oxo, —OH, —$OR^6$, —$N_3$, or —$N(R^6)_2$. In some embodiments, up to 3 —$CH_2$— units of $R^2$ are replaced by an —O—, —S—, or —$NR^6$—, provided that no adjacent —$CH_2$— is replaced.

In some embodiments, X is —S—, $R^1$ is H, $R^2$ is $C_{2-10}$ alkynyl and $R^{3a}$, $R^{3b}$, and $R^{3c}$ are each independently H or halogen. For example, $R^2$ may be acetylenyl, propylyne, butylyne, pentylyne, hexylyne, heptylyne, octylyne, nonylyne, decylyne, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In any of the preceding embodiments for $R^{3a}$, $R^{3b}$, and $R^{3c}$, any bromo or H may be independently replaced with a fluoro, iodo, or chloro moiety allowing for all possible permutations. In some embodiments, $R^2$ is substituted with one or more $R^5$. For example, in some embodiments, $R^2$ is substituted with halogen, oxo, —OH, —$OR^6$, —$N_3$, or —$N(R^6)_2$. In some embodiments, up to 3 —$CH_2$— units of $R^2$ are replaced by an —O—, —S—, or —$NR^6$—, provided that no adjacent —$CH_2$— is replaced.

In some embodiments, X is —S—, $R^1$ is $C_{1-10}$ alkyl, $R^2$ is $C_{1-10}$ alkyl and $R^{3a}$, $R^{3b}$, and $R^{3c}$ are each independently H or halogen. For example, $R^1$ may be methyl, ethyl, propyl, butyl, pentyl, hexyl, heptyl, octyl, nonyl, decyl, and all isomers and branched derivatives thereof. For example, $R^2$ may be methyl, ethyl, propyl, butyl, pentyl, hexyl, heptyl, octyl, nonyl, decyl, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —$OR^6$, —$N_3$, or —$N(R^6)_2$. In some embodiments, up to 3 —$CH_2$— units of $R^2$ are replaced by an —O—, —S—, or —$NR^6$—, provided that no adjacent —$CH_2$— is replaced. In some embodiments, $R^1$ is substituted with one or more $R^4$ moieties. For example, in some embodiments, $R^1$ is substituted with halogen, —$C_{1-5}$ alkyl, oxo, —OH, —$OR^6$, —$N_3$, —$N(R^6)_2$, —NH(C=O)$R^6$, —NH(C=O)$OR^6$, —NH(C=O)N($R^6$)$_2$, —(C=O)$R^6$, or heteroaryl.

In some embodiments, X is —S—, $R^1$ is $C_{1-10}$ alkyl, $R^2$ is $C_{2-10}$ alkenyl and $R^{3a}$, $R^{3b}$, and $R^{3c}$ are each independently H or halogen. For example, $R^1$ may be methyl, ethyl, propyl, butyl, pentyl, hexyl, heptyl, octyl, nonyl, decyl, and all isomers and branched derivatives thereof. For example, $R^2$ may be ethylene, propylene, butylene, pentylene, hexylene, heptylene, octylene, nonylene, decylene, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —$OR^6$, —$N_3$, or —$N(R^6)_2$. In some embodiments, up to 3 —$CH_2$— units of $R^2$ are replaced by an —O—, —S—, or —$NR^6$—, provided that no adjacent —$CH_2$— is replaced. In some embodiments, $R^1$ is substituted with one or more $R^4$ moieties. For example, in some embodiments, $R^1$ is substituted with halogen, —$C_{1-5}$ alkyl, oxo, —OH, —$OR^6$, —$N_3$, —$N(R^6)_2$, —NH(C=O)$R^6$, —NH(C=O)$OR^6$, —NH(C=O)$N(R^6)_2$, —(C=O)$R^6$, or heteroaryl.

In some embodiments, X is —S—, $R^1$ is $C_{1-10}$ alkyl, $R^2$ is $C_{2-10}$ alkynyl and $R^{3a}$, $R^{3b}$, and $R^{3c}$ are each independently H or halogen. For example, $R^1$ may be methyl, ethyl, propyl, butyl, pentyl, hexyl, heptyl, octyl, nonyl, decyl, and all isomers and branched derivatives thereof. For example, $R^2$ may be acetylenyl, propylyne, butylyne, pentylyne, hexylyne, heptylyne, octylyne, nonylyne, decylyne, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments. $R^2$ is substituted with halogen, oxo, —OH, —$OR^6$, —$N_3$, or —$N(R^6)_2$. In some embodiments, up to 3 —$CH_2$— units of $R^2$ are replaced by an —O—. —S—, or —$NR^6$—, provided that no adjacent —$CH_2$— is replaced. In some embodiments, $R^1$ is substituted with one or more $R^4$ moieties. For example, in some embodiments, $R^1$ is substituted with halogen, —$C_{1-5}$ alkyl, oxo, —OH, —$OR^6$, —$N_3$, —$N(R^6)_2$, —NH(C=O)$R^6$, —NH(C=O)$OR^6$, —NH(C=O)$N(R^6)_2$, —(C=O)$R^6$, or heteroaryl.

In some embodiments, X is —S—, $R^1$ is $C_{1-10}$ alkenyl, $R^2$ is $C_{1-10}$ alkyl and $R^{3a}$, $R^{3b}$, and $R^{3c}$ are each independently H or halogen. For example, $R^1$ may be ethylene, propylene, butylene, pentylene, hexylene, heptylene, octylene, nonylene, decylene, and all isomers and branched derivatives thereof. For example, $R^2$ may be methyl, ethyl, propyl, butyl, pentyl, hexyl, heptyl, octyl, nonyl, decyl, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —$OR^6$, —$N_3$, or —$N(R^6)_2$. In some embodiments, up to 3 —$CH_2$— units of $R^2$ are replaced by an —O—, —S—, or —$NR^6$—, provided that no adjacent —$CH_2$— is replaced. In some embodiments, $R^1$ is substituted with one or more $R^4$ moieties. For example, in some embodiments, $R^1$ is substituted with halogen, —$C_{1-5}$ alkyl, oxo, —OH, —$OR^6$, —$N_3$, —$N(R^6)_2$, —NH(C=O)$R^6$, —NH(C=O)$OR^6$, —NH(C=O)$N(R^6)_2$, —(C=O)$R^6$, or heteroaryl.

In some embodiments, X is —S—, $R^1$ is $C_{2-10}$ alkenyl, $R^2$ is $C_{2-10}$ alkenyl and $R^{3a}$, $R^{3b}$, and $R^{3c}$ are each independently H or halogen. For example, $R^1$ may be ethylene, propylene, butylene, pentylene, hexylene, heptylene, octylene, nonylene, decylene, and all isomers and branched derivatives thereof. For example, $R^2$ may be ethylene, propylene, butylene, pentylene, hexylene, heptylene, octylene, nonylene, decylene, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —$OR^6$, —$N_3$, or —$N(R^6)_2$. In some embodiments, up to 3 —$CH_2$— units of $R^2$ are replaced by an —O—, —S—, or —$NR^6$—, provided that no adjacent —$CH_2$— is replaced. In some embodiments, $R^1$ is substituted with one or more $R^4$ moieties. For example, in some embodiments, $R^1$ is substituted with halogen, —$C_{1-5}$ alkyl, oxo, —OH, —$OR^6$, —$N_3$, —$N(R^6)_2$, —NH(C=O)R, —NH(C=O)$OR^6$, —NH(C=O)$N(R^6)_2$, —(C=O)$R^6$, or heteroaryl.

In some embodiments, X is —S—, $R^1$ is $C_{2-10}$ alkynyl, $R^2$ is $C_{1-10}$ alkyl and $R^{3a}$, $R^{3b}$, and $R^{3c}$ are each independently H or halogen. For example, $R^1$ may be acetylynyl, propylyne, butylyne, pentylyne, hexylyne, heptylyne, octylyne, nonylyne, decylyne, and all isomers and branched derivatives thereof. For example, $R^2$ may be methyl, ethyl, propyl, butyl, pentyl, hexyl, heptyl, octyl, nonyl, decyl, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —OR$^6$, —N$_3$, or —N(R$^6$)$_2$. In some embodiments, up to 3 —CH$_2$— units of $R^2$ are replaced by an —O—, —S—, or —NR$^6$—, provided that no adjacent —CH$_2$— is replaced. In some embodiments, $R^1$ is substituted with one or more $R^4$ moieties. For example, in some embodiments. $R^1$ is substituted with halogen, —C$_{1-5}$ alkyl, oxo. —OH, —OR$^6$, —N$_3$, —N(R$^6$)$_2$, —NH(C=O)R$^6$, —NH(C=O)OR$^6$, —NH(C=O)N(R$^6$)$_2$, —(C=O)R$^6$, or heteroaryl.

In some embodiments, X is —S—, $R^1$ is C$_{2-10}$ alkynyl, $R^2$ is C$_{2-10}$ alkenyl and $R^{3a}$, $R^{3b}$, and $R^{3c}$ are each independently H or halogen. For example, $R^1$ may be ethylene, propylene, butylene, pentylene, hexylene, heptylene, octylene, nonylene, decylene, and all isomers and branched derivatives thereof. For example, $R^2$ may be ethylene, propylene, butylene, pentylene, hexylene, heptylene, octylene, nonylene, decylene, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —OR$^6$, —N$_3$, or —N(R$^6$)$_2$. In some embodiments, up to 3 —CH$_2$— units of $R^2$ are replaced by an —O—, —S—, or —NR$^6$—, provided that no adjacent —CH$_2$— is replaced. In some embodiments, $R^1$ is substituted with one or more $R^4$ moieties. For example, in some embodiments, $R^2$ is substituted with halogen, —C$_{1-5}$ alkyl, oxo, —OH, —OR$^6$, —N$_3$, —N(R$^6$)$_2$, —NH(C=O)R$^6$, —NH(C=O)OR$^6$, —NH(C=O)N(R$^6$)$_2$, —(C=O)R$^6$, or heteroaryl.

In some embodiments, X is —S—, $R^1$ is C$_{2-10}$ alkynyl, $R^2$ is C$_{2-10}$ alkynyl and $R^{3s}$, $R^{3b}$, and $R^{3c}$ are each independently H or halogen. For example, $R^1$ may be ethylene, propylene, butylene, pentylene, hexylene, heptylene, octylene, nonylene, decylene, and all isomers and branched derivatives thereof. For example, $R^2$ may be acetylenyl, propylyne, butylyne, pentylyne, hexylyne, heptylyne, octylyne, nonylyne, decylyne, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments. $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —OR$^6$, —N$_3$, or —N(R$^6$)$_2$. In some embodiments, up to 3 —CH$_2$— units of $R^2$ are replaced by an —O—, —S—, or —NR$^6$—, provided that no adjacent —CH$_2$— is replaced. In some embodiments, $R^1$ is substituted with one or more $R^4$ moieties. For example, in some embodiments, $R^1$ is substituted with halogen, —C$_{1-5}$ alkyl, oxo, —OH, —OR$^6$, —N$_3$, —N(R$^6$)$_2$, —NH(C=O)R$^6$, —NH(C=O)OR$^6$, —NH(C=O)N(R$^6$)$_2$, —(C=O)R$^6$, or heteroaryl.

In some embodiments, X is —N(R$^6$)—, $R^1$ is H, $R^2$ is C$_{1-10}$ alkyl and $R^{3a}$R$^{3b}$, and $R^{3c}$ are each independently H or halogen. For example, $R^2$ may be methyl, ethyl, propyl, butyl, pentyl, hexyl, heptyl, octyl, nonyl, decyl, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In any of the preceding embodiments for $R^{3a}$, $R^{3b}$, and $R^{3c}$, any bromo or H may be independently replaced with a fluoro, iodo, or chloro moiety allowing for all possible permutations. In some embodiments, $R^2$ is substituted with one or more $R^5$. For example, in some embodiments, $R^2$ is substituted with halogen, oxo, —OH, —OR$^6$, —N$_3$, or —N(R$^6$)$_2$. In some embodiments, up to 3 —CH$_2$— units of $R^2$ are replaced by an —O—, —S—, or —NR$^6$—, provided that no adjacent —CH$_2$— is replaced. Each $R^6$ may independently be H, —C$_{1-5}$ alkyl, —C$_{2-5}$ alkenyl, —C$_{1-5}$ alkynyl, —C$_{1-5}$ alkyl-SiMe$_3$, aryl, or heteroaryl.

In some embodiments, X is —N(R$^6$)—, $R^1$ is H, $R^2$ is C$_{2-10}$ alkenyl and $R^{3a}$, $R^{3b}$, and $R^{3c}$ are each independently H or halogen. For example, $R^2$ may be ethylene, propylene, butylene, pentylene, hexylene, heptylene, octylene, nonylene, decylene, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In any of the preceding embodiments for $R^{3a}$, $R^{3b}$, and $R^{3c}$, any bromo or H may be independently replaced with a fluoro, iodo, or chloro moiety allowing for all possible permutations. In some embodiments, $R^2$ is substituted with one or more $R^5$. For example, in some embodiments, $R^2$ is substituted with halogen, oxo, —OH, —OR$^6$, —N$_3$, or —N(R$^6$)$_2$. In some embodiments, up to 3 —CH$_2$— units of $R^2$ are replaced by an —O—, —S—, or —NR$^6$—, provided that no adjacent —CH$_2$— is replaced. Each $R^6$ may independently be H, —C$_{1-5}$ alkyl, —C$_{2-5}$ alkenyl, —C$_{1-5}$ alkynyl, —C$_{1-5}$ alkyl-SiMe$_3$, aryl, or heteroaryl.

In some embodiments, X is —N(R$^6$)—, $R^1$ is H, $R^2$ is C$_{2-10}$ alkynyl and $R^{3a}$, $R^{3b}$, and $R^{3c}$ are each independently H or halogen. For example, $R^2$ may be acetylenyl, propylyne, butylyne, pentylyne, hexylyne, heptylyne, octylyne, nonylyne, decylyne, and all isomers and branched derivatives thereof. In some embodiments, $R^{3a}$, $R^{3b}$, and $R^{3c}$ are each H. In some embodiments. $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In any of the preceding embodiments for $R^{3a}$, $R^{3b}$, and $R^{3c}$, any bromo or H may be independently replaced with a fluoro, iodo, or chloro moiety allowing for all possible permutations. In some embodiments, $R^2$ is substituted with one or more $R^5$. For example, in some embodiments, $R^2$ is substituted with halogen, oxo, —OH, —OR$^6$, —N$_3$, or —N(R$^6$)$_2$. In some embodiments, up to 3 —CH$_2$— units of $R^2$ are replaced by an —O—, —S—, or —NR$^6$—, provided that no adjacent —CH$_2$— is replaced. Each $R^6$ may independently be H, —C$_{1-5}$ alkyl, —C$_{2-5}$ alkenyl, —C$_{1-5}$ alkynyl, —C$_{1-5}$ alkyl-SiMe$_3$, aryl, or heteroaryl.

In some embodiments, X is —N(R$^6$)—, $R^1$ is C$_{1-10}$ alkyl, $R^2$ is C$_{1-10}$ alkyl and $R^{3a}$, $R^{3b}$, and $R^{3c}$ are each independently H or halogen. For example, $R^1$ may be methyl, ethyl, propyl, butyl, pentyl, hexyl, heptyl, octyl, nonyl, decyl, and all isomers and branched derivatives thereof. For example, $R^2$ may be methyl, ethyl, propyl, butyl, pentyl, hexyl, heptyl, octyl, nonyl, decyl, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —OR$^6$, —N$_3$, or —N(R$^6$)$_2$. In some embodiments, up to 3 —CH$_2$— units of $R^2$ are replaced by an —O—, —S—, or —NR$^6$—, provided that no adjacent —CH$_2$— is replaced. In some embodiments, $R^1$ is substituted with one or more $R^4$ moieties. For example, in some embodiments, $R^1$ is substituted with halogen, —C$_{1-5}$ alkyl, oxo, —OH, —OR$^6$, —N$_3$, —N(R$^6$)$_2$, —NH(C=O)R$^6$, —NH(C=O)OR$^6$, —NH(C=O)N(R$^6$)$_2$, —(C=O)R$^6$, or heteroaryl. Each $R^6$ may independently be H, —C$_{1-5}$ alkyl. —C$_{2-5}$ alkenyl. —C$_{1-5}$ alkynyl, —C$_{1-5}$ alkyl-SiMe$_3$, aryl, or heteroaryl.

In some embodiments, X is —N(R$^6$)—, $R^1$ is C$_{1-10}$ alkyl, $R^2$ is C$_{2-10}$ alkenyl and $R^{3a}$, $R^{3b}$, and $R^{3c}$ are each independently H or halogen. For example, $R^1$ may be methyl, ethyl, propyl, butyl, pentyl, hexyl, heptyl, octyl, nonyl, decyl, and all isomers and branched derivatives thereof. For example, $R^2$ may be ethylene, propylene, butylene, pentylene, hexylene, heptylene, octylene, nonylene, decylene, and all isomers and branched derivatives thereof. In some embodiments, $R^{3a}$, $R^{3b}$, and $R^{3c}$ are each H. In some embodiments, $R^3$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —OR$^6$, —N$_3$, or —N(R$^6$)$_2$. In some embodiments, up to 3 —CH$_2$— units of $R^2$ are replaced by an —O—, —S—, or —NR$^6$—, provided that no adjacent —CH$_2$— is replaced. In some embodiments, $R^1$ is substituted with one or more $R^4$ moieties. For example, in some embodiments, $R^1$ is substituted with halogen, —C$_{1-5}$ alkyl, oxo, —OH, —OR$^6$, —N$_3$, —N(R$^6$)$_2$, —NH(C=O)R$^6$, —NH(C=O)OR$^6$, —NH(C=O)N(R$^6$)$_2$, —(C=O)R$^6$, or heteroaryl. Each $R^6$ may independently be H, —C$_{1-5}$ alkyl, —C$_{2-5}$ alkenyl. —C$_{1-5}$ alkynyl, —C$_{1-5}$ alkyl-SiMe$_3$, aryl, or heteroaryl.

In some embodiments, X is —N(R$^6$)—, $R^1$ is C$_{1-10}$ alkyl, $R^2$ is C$_{2-10}$ alkynyl and $R^{3a}$, $R^{3b}$ and $R^{3c}$ are each independently H or halogen. For example, $R^1$ may be methyl, ethyl, propyl, butyl, pentyl, hexyl, heptyl, octyl, nonyl, decyl, and all isomers and branched derivatives thereof. For example, $R^2$ may be acetylenyl, propylyne, butylyne, pentylyne, hexylyne, heptylyne, octylyne, nonylyne, decylyne, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3b}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments. $R^2$ is substituted with halogen, oxo, —OH, —OR$^6$, —N$_3$, or —N(R$^6$)$_2$. In some embodiments, up to 3 —CH$_2$— units of $R^2$ are replaced by an —O—, —S—, or —NR$^6$—, provided that no adjacent —CH$_2$— is replaced. In some embodiments, $R^1$ is substituted with one or more $R^4$ moieties. For example, in some embodiments, $R^1$ is substituted with halogen. —C$_{1-5}$ alkyl, oxo, —OH, —OR$^6$, —N$_3$, —N(R$^6$)$_2$, —NH(C=O)R$^6$, —NH(C=O)OR$^6$, —NH(C=O)N(R$^6$)$_2$, —(C=O)R$^6$, or heteroaryl. Each $R^6$ may independently be H, —C$_{1-5}$ alkyl, —C$_{2-5}$ alkenyl, —C$_{1-5}$ alkynyl, —C$_{1-5}$ alkyl-SiMe$_3$, aryl, or heteroaryl.

In some embodiments, X is —N(R$^6$)—, $R^1$ is C$_{1-10}$ alkenyl, $R^2$ is C$_{1-10}$ alkyl and $R^{3a}$, $R^{3b}$, and $R^{3c}$ are each independently H or halogen. For example, $R^1$ may be ethylene, propylene, butylene, pentylene, hexylene, heptylene, octylene, nonylene, decylene, and all isomers and branched derivatives thereof. For example, $R^2$ may be methyl, ethyl, propyl, butyl, pentyl, hexyl, heptyl, octyl, nonyl, decyl, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —OR$^6$, —N$_3$, or —N(R$^6$)$_2$. In some embodiments, up to 3 —CH$_2$— units of $R^2$ are replaced by an —O—. —S—, or —NR$^6$—, provided that no adjacent —CH$_2$— is replaced. In some embodiments, $R^1$ is substituted with one or more $R^4$ moieties. For example, in some embodiments. $R^1$ is substituted with halogen, —C$_{1-5}$ alkyl, oxo, —OH, —OR$^6$, —N$_3$, —N(R$^6$)$_2$, —NH(C=O)R$^6$, —NH(C=O)OR$^6$, —NH(C=O)N(R$^6$)$_2$, —(C=O)R$^6$, or heteroaryl. Each $R^6$ may independently be H, —C$_{1-5}$ alkyl. —C$_{2-5}$ alkenyl, —C$_{1-5}$ alkynyl, —C$_{1-5}$ alkyl-SiMe$_3$, aryl, or heteroaryl.

In some embodiments, X is —N(R$^6$)—, $R^1$ is C$_{2-10}$ alkenyl, $R^2$ is C$_{2-10}$ alkenyl and $R^{3a}$, $R^{3b}$, and $R^{3c}$ are each independently H or halogen. For example, $R^1$ may be ethylene, propylene, butylene, pentylene, hexylene, heptylene, octylene, nonylene, decylene, and all isomers and branched derivatives thereof. For example, $R^2$ may be ethylene, propylene, butylene, pentylene, hexylene, heptylene, octylene, nonylene, decylene, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —OR$^6$, —N$_3$, or —N(R$^6$)$_2$. In some embodiments, up to 3 —CH$_2$— units of $R^2$ are replaced by an —O—. —S—, or —NR$^6$—, provided that no adjacent —CH$_2$— is replaced. In some embodiments, $R^1$ is substituted with one or more $R^4$ moieties. For example, in some embodiments, $R^1$ is substituted with halogen, —C$_{1-5}$ alkyl, oxo, —OH, —OR$^6$, —N$_3$, —N(R$^6$)$_2$, —NH(C=O)R$^6$, —NH(C=O)OR$^6$, —NH(C=O)N(R$^6$)$_2$, —(C=O)R$^6$, or heteroaryl. Each $R^6$ may independently be H, —C$_{1-5}$ alkyl, —C$_{2-2}$ alkenyl, —C$_{1-5}$ alkynyl, —C$_{1-5}$ alkyl-SiMe$_3$, aryl, or heteroaryl.

In some embodiments, X is —N(R$^6$)—, $R^1$ is $C_{2-10}$ alkenyl, $R^2$ is $C_{2-10}$ alkynyl and $R^{3a}$, $R^{3b}$, and $R^{3c}$ are each independently H or halogen. For example, $R^1$ may be ethylene, propylene, butylene, pentylene, hexylene, heptylene, octylene, nonylene, decylene, and all isomers and branched derivatives thereof. For example, $R^2$ may be acetylenyl, propylyne, butylyne, pentylyne, hexylyne, heptylyne, octylyne, nonylyne, decylyne, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —OR$^6$, —N$_3$, or —N(R$^6$)$_2$. In some embodiments, up to 3 —CH$_2$— units of $R^2$ are replaced by an —O—. —S—, or —NR$^6$—, provided that no adjacent —CH$_2$— is replaced. In some embodiments, $R^1$ is substituted with one or more $R^4$ moieties. For example, in some embodiments, $R^1$ is substituted with halogen, —C$_{1-5}$ alkyl, oxo, —OH, —OR$^6$, —N$_3$, —N(R$^6$)$_2$, —NH(C=O)R$^6$, —NH(C=O)OR$^6$, —NH(C=O)N(R$^6$)$_2$, —(C=O)R$^6$, or heteroaryl. Each $R^6$ may independently be H, —C$_{1-5}$ alkyl. —C$_{2-8}$ alkenyl, —C$_{1-5}$ alkynyl, —C$_{1-5}$ alkyl-SiMe$_3$, aryl, or heteroaryl.

In some embodiments, X is —N(R$^6$)—, $R^1$ is $C_{2-10}$ alkynyl, $R^2$ is $C_{1-10}$ alkyl and $R^{3a}$, $R^{3b}$, and $R^{3c}$ are each independently H or halogen. For example, $R^1$ may be acetylynyl, propylyne, butylyne, pentylyne, hexylyne, heptylyne, octylyne, nonylyne, decylyne, and all isomers and branched derivatives thereof. For example, $R^2$ may be methyl, ethyl, propyl, butyl, pentyl, hexyl, heptyl, octyl, nonyl, decyl, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —OR$^6$, —N$_3$, or —N(R$^6$)$_2$. In some embodiments, up to 3 —CH$_2$— units of $R^2$ are replaced by an —O—, —S—, or —NR$^6$—, provided that no adjacent —CH$_2$— is replaced. In some embodiments, $R^1$ is substituted with one or more $R^4$ moieties. For example, in some embodiments, $R^1$ is substituted with halogen, —C$_{1-5}$ alkyl, oxo, —OH, —OR$^6$, —N$_3$, —N(R$^6$)$_2$, —NH(C=O)R$^6$, —NH(C=O)OR$^6$, —NH(C=O)N(R$^6$)$_2$. —(C=O)R$^6$, or heteroaryl. Each $R^6$ may independently be H, —C$_{1-5}$ alkyl, —C$_{2-5}$ alkenyl, —C$_{1-5}$ alkynyl. —C$_{1-5}$ alkyl-SiMe$_3$, aryl, or heteroaryl.

In some embodiments, X is —N(R$^6$)—, $R^1$ is $C_{2-10}$ alkynyl, $R^2$ is $C_{2-10}$ alkenyl and $R^{3a}$, $R^{3b}$, and $R^{3c}$ are each independently H or halogen. For example, $R^1$ may be ethylene, propylene, butylene, pentylene, hexylene, heptylene, octylene, nonylene, decylene, and all isomers and branched derivatives thereof. For example, $R^2$ may be ethylene, propylene, butylene, pentylene, hexylene, heptylene, octylene, nonylene, decylene, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —OR$^6$, —N$_3$, or —N(R$^6$)$_2$. In some embodiments, up to 3 —CH$_2$— units of $R^2$ are replaced by an —O—. —S—, or —NR$^6$—, provided that no adjacent —CH$_2$— is replaced. In some embodiments, $R^1$ is substituted with one or more $R^4$ moieties. For example, in some embodiments, $R^1$ is substituted with halogen, —C$_{1-5}$ alkyl, oxo, —OH, —OR$^6$, —N$_3$, —N(R$^6$)$_2$, —NH(C=O)R$^6$, —NH(C=O)OR$^6$, —NH(C=O)N(R$^6$)$_2$, —(C=O)R$^6$, or heteroaryl. Each $R^6$ may independently be H, —C$_{1-5}$ alkyl, —C$_{1-5}$ alkenyl, —C$_{1-5}$ alkynyl. —C$_{1-5}$ alkyl-SiMe$_3$, aryl, or heteroaryl.

In some embodiments, X is —N(R$^6$)—, $R^1$ is $C_{2-10}$ alkynyl, $R^2$ is $C_{2-10}$ to alkynyl and $R^{3a}$, $R^{3b}$, and $R^{3c}$ are each independently H or halogen. For example, $R^1$ may be ethylene, propylene, butylene, pentylene, hexylene, heptylene, octylene, nonylene, decylene, and all isomers and branched derivatives thereof. For example, $R^2$ may be acetylenyl, propylyne, butylyne, pentylyne, hexylyne, heptylyne, octylyne, nonylyne, decylyne, and all isomers and branched derivatives thereof. In some embodiments, $R^{3a}$, $R^{3b}$, and $R^{3c}$ are each H. In some embodiments, $R^{3a}$ is bromo and $R^{3b}$ and $R^{3c}$ are H. In some embodiments, $R^{3a}$ and $R^{3b}$ are each bromo and $R^{3c}$ is H. In some embodiments, $R^{3a}$ and $R^{3b}$ are each H and $R^{3c}$ is bromo. In some embodiments, $R^{3a}$ and $R^{3c}$ are each H and $R^{3b}$ is bromo. In some embodiments, $R^{3a}$ and $R^{3c}$ are each bromo and $R^{3b}$ is H. In some embodiments, $R^{3a}$ is H and $R^{3b}$ and $R^{3c}$ are each bromo. In some embodiments, $R^{3a}$, $R^{3b}$, and $R^{3c}$ are each bromo. In some embodiments, $R^2$ is substituted with one or more $R^5$. For example, in some embodiments, $R^2$ is substituted with halogen, oxo, —OH, —OR$^6$, —N$_3$, or —N(R$^6$)$_2$. In some embodiments, up to 3 —CH$_2$— units of $R^2$ are replaced by an —O—. —S—, or —NR$^6$—, provided that no adjacent —CH$_2$— is replaced. In some embodiments, $R^1$ is substituted with one or more $R^4$ moieties. For example, in some embodiments, $R^1$ is substituted with halogen, —C$_{1-5}$ alkyl, oxo, —OH, —OR$^6$, —N$_3$, —N(R$^6$)$_2$, —NH(C=O)R$^6$, —N(C=O)OR$^6$, —NH(C=O)N(R$^6$)$_2$, —(C=O)R$^6$, or heteroaryl. Each $R^6$ may independently be H, —$C_{1-5}$ alkyl. —$C_{2-8}$ alkenyl, —$C_{1-5}$ alkynyl, —$C_{1-5}$ alkyl-SiMe$_3$, aryl, or heteroaryl.

Unless otherwise stated, structures depicted herein are also meant to include compounds which differ only in the presence of one or more isotopically enriched atoms. For example, compounds having the present structure except for the replacement of a hydrogen atom by deuterium or tritium, or the replacement of a carbon atom by $^{13}$C or $^{14}$C, or the replacement of a nitrogen atom by $^{15}$N, or the replacement of an oxygen atom with $^{17}$O or $^{18}$O are within the scope of the present disclosure. Such isotopically labeled compounds are useful as research or diagnostic tools.

Methods of Treatment

The disclosed compounds (e.g., compounds of Formula I-Ie (i.e., compounds of Formula I, Ia, Ib, Ic, Id, and Ie), and their pharmaceutically acceptable salts have activity as pharmaceuticals, as discussed herein.

The present disclosure provides a method of treatment or prevention of a disease, disorder or condition including the step of administering an effective amount of a compound of the present disclosure, and pharmaceutically acceptable salts, prodrugs, solvates, hydrates, isomers, and tautomers thereof to thereby treat or prevent the disease, disorder or condition in a subject in need thereof.

The present disclosure provides a compound of the present disclosure, and pharmaceutically acceptable salts, prodrugs, solvates, hydrates, isomers, and tautomers thereof, or the pharmaceutical composition of the present disclosure for use in the treatment or prevention of a disease, disorder or condition in a subject in need thereof.

The present disclosure provides for use of a compound of the present disclosure, and pharmaceutically acceptable salts, prodrugs, solvates, hydrates, isomers, and tautomers thereof, for the treatment or prevention of a disease, disorder or condition in a subject in need thereof.

The present disclosure provides for use of a compound of the present disclosure, and pharmaceutically acceptable salts, prodrugs, solvates, hydrates, isomers, and tautomers thereof, in the manufacture of a medicament for the treatment or prevention of a disease, disorder or condition.

It was surprisingly discovered AgE (5) is more potent than AgA (1) in blocking the effects of fibroblast OPN on the invasiveness, migration potential, and cancer stem cell populations in associated cancer cells. As will be appreciated by a skilled artisan, this has wide ranging applications. For example, because AgE (5) and AgA (1) both block the effects of fibroblast OPN on the invasiveness, migration potential, and cancer stein cell populations in associated cancer cells, such as breast cancer, this implies that natural and derivatized agelastatin compounds are useful at treating, preventing, and/or delaying a variety of cancers associated with OPN overexpression. Thus, in some embodiments, the present disclosure provides a method for the treatment, prevention, or delay of cancer, comprising administering a therapeutically effective amount of a compound of the present disclosure, a pharmaceutically acceptable salt thereof, or a composition thereof to a subject in need thereof.

In one embodiment, the disease, disorder or condition is a cancer, tumor or other malignancy. As used herein, cancers tumors and malignancies, refer to diseases, disorders or conditions, or to cells or tissues associated with the diseases, disorders or conditions, characterized by aberrant or abnormal cell proliferation, differentiation and/or migration often accompanied by an aberrant or abnormal molecular phenotype that includes one or more genetic mutations or other genetic changes associated with oncogenesis, expression of tumor markers, loss of tumor suppressor expression or activity and/or aberrant or abnormal cell surface marker expression. In general embodiments, cancers, tumors and malignancies may include sarcomas, lymphomas, leukemias, solid tumors, blastomas, gliomas, carcinomas, melanomas and metastatic cancers, although without limitation thereto. A more comprehensive listing of cancers tumors and malignancies may be found at the National Cancer Institutes website http://www.cancer.gov/cancertopics/types/alphalist, which is hereby incorporated by reference in its entirety.

The cancer may be any cancer associated with OPN overexpression. For example, in some embodiments, the cancer is breast cancer, lung cancer, colorectal cancer, stomach cancer, ovarian cancer, papillary thyroid carcinoma, melanoma, prostate cancer, esophageal cancer, liver cancer, bladder cancer, renal cancer, head and neck cancers, salivary gland cancer, endometrial cancer, cervical cancer, pancreatic cancer, sarcoma, glioblastoma and glioma, or pleural mesothelioma. In some embodiments, the cancer is breast cancer. A skilled artisan will appreciate that a variety of breast cancers may be linked to OPN overexpression. In some embodiments, the breast cancer is selected from the group consisting of ductal carcinoma in situ (DCIS), invasive ductal carcinoma (IDC), tubular carcinoma, medullary carcinoma, mucinous carcinoma, papillary carcinoma, cribriform carcinoma, invasive lobular carcinoma (ILC), inflammatory breast cancer, lobular carcinoma in situ (LCIS), luminal A, luminal B, triple-negative/basal-like, and HER2-enriched, normal-like breast cancer. In some embodiments, the breast cancer is metastatic breast cancer or recurrent metastatic breast cancer.

In some embodiments, the cancer (e.g., breast cancer) is recurrent cancer at the primary site, metastatic cancer, or recurrent metastatic cancer. In some embodiments, the cancer (e.g., breast cancer) is prevented or delayed. In some embodiments, the cancer (e.g., breast cancer) is prevented. In some embodiments, the cancer (e.g., breast cancer) is delayed.

In some embodiments, the compounds of the present disclosure are administered before surgery and/or radiotherapy and/or systemic medical therapy. In some embodiments, the compounds of the present disclosure are administered before surgery. In some embodiments, the compounds of the present disclosure are administered before radiotherapy. In some embodiments, the compounds of the present disclosure are administered before systemic medical therapy. In various embodiments, systemic medical therapy includes chemotherapies, hormonal therapies, targeted biologic therapies, and/or immunotherapies.

Systemic therapies of the present disclosure are treatments that can spread throughout the body to treat cancer cells wherever they may be located. As noted, such drugs can be chemotherapies, hormonal therapies, targeted drugs, and/or immunotherapies. In various embodiments, systemic therapies reach cells throughout the body by traveling through the bloodstream.

In some embodiments, the compounds of the present disclosure are administered after surgery and/or radiotherapy and/or systemic medical therapy. In some embodiments, the compounds of the present disclosure are administered after surgery. In some embodiments, the compounds of the present disclosure are administered after radiotherapy. In some embodiments, the compounds of the present disclosure are administered after systemic medical therapy. In various embodiments, systemic medical therapy includes chemotherapies, hormonal therapies, targeted biologic therapies, and/or immunotherapies.

In some embodiments, the compounds of the present disclosure are administered concurrently with radiotherapy and/or systemic medical therapy. In some embodiments, the compounds of the present disclosure are administered concurrently with radiotherapy. In some embodiments, the compounds of the present disclosure are administered concurrently with systemic medical treatment. In various embodiments, systemic medical therapy includes chemotherapies, hormonal therapies, targeted biologic therapies, and/or immunotherapies.

In some embodiments, the compounds of the present disclosure are administered before and after surgery and/or radiotherapy and/or systemic medical therapy. In some embodiments, the compounds of the present disclosure are administered before and after surgery. In some embodiments, the compounds of the present disclosure are administered before and after radiotherapy. In some embodiments, the compounds of the present disclosure are administered before and after systemic medical therapy. In various embodiments, systemic medical therapy includes chemotherapies, hormonal therapies, targeted biologic therapies, and/or immunotherapies.

In some embodiments, the treatment results in inhibition of induced transcription of osteopontin (OPN) in fibroblasts, inflammatory cells, and immune cells of the tumor microenvironment. In some embodiments, the treatment results in inhibition of induced transcription of osteopontin (OPN) in fibroblasts. In some embodiments, the treatment results in inhibition of induced transcription of osteopontin (OPN) in inflammatory cells. In some embodiments, the treatment results in inhibition of induced transcription of osteopontin (OPN) in immune cells of the tumor microenvironment. In some embodiments, the fibroblasts are mammary fibroblasts. In some embodiments, the cancer is characterized by a tumor microenvironment exhibiting down regulation of fibroblast Tiam1 and upregulation of fibroblast OPN. In other embodiments, the cancer is characterized by a tumor microenvironment exhibiting upregulation of fibroblast OPN.

Osteopontin transcription can be stimulated by multiple factors, including but not limited to, stimulation by vitamin D. Without being bound by any particular theory, it has been discovered that agelastatin A can inhibit the induction of osteopontin transcription by cancer cell secreted factors as well as vitamin D. Thus, in various embodiments, such inhibition by agelastatin A can occur in any tissue, e.g., breast tissue. Multiple cell types in the tumor stroma, including macrophages and lymphocytes, also secrete osteopontin. Since agelastatin A can block metastasis of breast cancer cells to lung in vivo, which is a complex process involving various tumor microenvironments, it is understood that in various embodiments, agelastatin A can inhibit osteopontin transcription in macrophages and lymphocytes as well as fibroblasts.

In some embodiments, the inhibition occurs at or below the cytotoxic range determined for the cancer cells being treated. In some embodiments, the inhibition occurs at the cytotoxic range determined for the cancer cells being treated. In other embodiments, the inhibition occurs below the cytotoxic range determined for the cancer cells being treated. In some embodiments, the transcription is of splice variants of OPN. In some embodiments, the spice variants are osteopontin-a, osteopontin-b, or osteopontin-c. In some embodiments, the inhibition results in interference with cancer cell adhesion, cancer cell invasion, and cancer stem cell populations.

For the above-mentioned therapeutic uses the dosage administered will, of course, vary with the compound employed, the mode of administration, the treatment desired and the disorder indicated. For example, the daily dosage of the compound of the present disclosure, if inhaled, may be in the range from about 0.05 micrograms per kilogram body weight (µg/kg) to about 100 micrograms per kilogram body weight (µg/kg). Alternatively, if the compound is administered orally, then the daily dosage of the compound of the present disclosure may be in the range from about 0.01 micrograms per kilogram body weight (µg/kg) to about 100 milligrams per kilogram body weight (mg/kg).

Pharmaceutical Compositions

The disclosed compounds (e.g., compounds of Formula I-Ie), and pharmaceutically acceptable salts, tautomers, prodrugs or stereoisomers thereof may be used on their own but will generally be administered in the form of a pharmaceutical composition in which the disclosed compound/salt (e.g., compounds of Formula I-Ie and salts thereof) (active ingredient) is in association with a pharmaceutically acceptable adjuvant, diluent and; or carrier. Thus in some embodiments, the present disclosure provides a pharmaceutical composition comprising compounds of Formula I-Ie and a pharmaceutically acceptable adjuvant, diluent, carrier and/or excipient. In some embodiments, the present disclosure provides a pharmaceutical composition comprising compounds of Formula I-Ie and a pharmaceutically acceptable adjuvant. In some embodiments, the present disclosure provides a pharmaceutical composition comprising compounds of Formula I-Ie and a pharmaceutically acceptable diluent. In some embodiments, the present disclosure provides a pharmaceutical composition comprising compounds of Formula I-Ie and a pharmaceutically acceptable carrier. In some embodiments, the present disclosure provides a pharmaceutical composition comprising compounds of Formula I-Ie and a pharmaceutically acceptable excipient. Conventional procedures for the selection and preparation of suitable pharmaceutical formulations are described in, for example, "Pharmaceuticals—The Science of Dosage Form Designs", M. E. Aulton, Churchill Livingstone, 1988, which is hereby incorporated by reference in its entirety.

Depending on the mode of administration, the pharmaceutical composition will comprise from about 0.05 to about 99% w (percent by weight), more particularly from about 0.05 to about 80% w, still more particularly from about 0.10 to about 70% w, and even more particularly from about 0.10 to about 50% w, of active ingredient, all percentages by weight being based on total composition.

The present disclosure also provides a pharmaceutical composition comprising a disclosed compound (e.g., compound of Formula I-Ie), or a pharmaceutically acceptable salt thereof as hereinbefore defined, in association with a pharmaceutically acceptable adjuvant, diluent, carrier, and/or excipient.

The present disclosure further provides a process for the preparation of a pharmaceutical composition of the present disclosure which comprises mixing a disclosed compound (e.g., compound of Formula I-Ie), or a pharmaceutically acceptable salt thereof as hereinbefore defined with a pharmaceutically acceptable adjuvant, diluent, carrier, and/or excipient.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); or by rectal administration in the form of suppositories.

Dry powder formulations and pressurized HFA aerosols of the compounds of the present disclosure (including pharmaceutically acceptable salts) may be administered by oral or nasal inhalation. For inhalation, the compound is desirably finely divided. The finely divided compound preferably has a mass median diameter of less than 10 micrometres (pun), and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the present disclosure may also be administered by means of a dry powder inhaler. The inhaler may be a single or a multi dose inhaler, and may be a breath actuated dry powder inhaler.

One possibility is to mix the finely divided compound of the present disclosure with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatin capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

Another possibility is to process the compound as an amorphous dispersion in a polymer matrix such as hydroxypropyl methylcellulose (HPMC) or hydroxypropyl methylcellulose acetate succinate (HPMCAS). As the name suggests, spray-dried dispersions (SDDs) are obtained by dissolving drug and polymer in an organic solvent, atomizing the resulting solution into droplets, and evaporation to dried solid particles. SDDs are usually amenable for use a variety of final oral dosage forms, including capsules and tablets.

For oral administration the compound of the present disclosure may be admixed with an adjuvant or a carrier, for example, lactose, saccharose, sorbitol, mannitol; a starch, for example, potato starch, corn starch or amylopectin; a cellulose derivative; a binder, for example, gelatin or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatin, talcum and titanium dioxide. Alternatively, the tablet may be coated with a suitable polymer dissolved in a readily volatile organic solvent.

Suitable excipients include, but are not limited to, polymers, absorption enhancers, solubility enhancing agents, dissolution rate enhancing agents, bioadhesive agents, and controlled release agents. More particularly, suitable excipients include cellulose ethers, acrylic acid polymers, and bile salts. Other suitable excipients are described in detail in the Handbook of Pharmaceutical Excipients, published jointly by the American Pharmaceutical Association and The Pharmaceutical Society of Great Britain, the Pharmaceutical Press, 1986, which is incorporated by reference herein. Such excipients are commercially available and/or can be prepared by techniques known in the art.

For the preparation of soft gelatin capsules, the compound of the present disclosure may be admixed with, for example, a vegetable oil or polyethylene glycol. Hard gelatin capsules may contain granules of the compound using either the above-mentioned excipients for tablets. Also liquid or semisolid formulations of the compound of the present disclosure may be filled into hard gelatin capsules.

Liquid preparations for oral application may be in the form of syrups or suspensions, for example, solutions containing the compound of the present disclosure, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

Combination Therapy

The compounds of the present disclosure (that is, compounds of Formula I-Ie, and pharmaceutically acceptable salts thereof) may also be administered in conjunction with other compounds used for the treatment of the above conditions.

The present disclosure therefore further relates to combination therapies wherein a compound of the present disclosure or a pharmaceutical composition or formulation comprising a compound of the present disclosure is administered concurrently or sequentially or as a combined preparation with another therapeutic agent or agents, for the treatment of one or more of the conditions listed.

In some embodiments, the present disclosure provides a method for the treatment, prevention, or delay of cancer, comprising administering a therapeutically effect amount of a compound of the present disclosure, a pharmaceutically acceptable salt thereof, or a composition thereof to a subject in need thereof comprising coadministration to the subject of an additional therapeutic agent selected from the group consisting of antitumor agents, anti-metabolites, anti-estrogens, aromatase inhibitors, estrogen receptor antagonists, targeted therapies, tyrosine kinase inhibitors, and immune checkpoint inhibitors.

In some embodiments, the present disclosure provides a method for the treatment, prevention, or delay of cancer, comprising administering a therapeutically effect amount of a compound of the present disclosure, a pharmaceutically acceptable salt thereof, or a composition thereof to a subject in need thereof comprising coadministrating an antitumor agent. A variety of antitumor agents can be used in the context of the present disclosure and will be readily apparent to a skilled artisan, including, but not limited to paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethilenethiophosphoramide, trimethylolomelamine, bullatacin, bullatacinone, camptothecin, bryostatin, callystatin, cryptophycin 1, cryptophycin 8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, detorbicin, 6-diazo-5-oxo-L-norleucine, ADRIAMYCIN, epirubicin, esorubicin, idarubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone, aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, epothilone, etoglucid, lentinan, lonidamine, maytansine, ansamitocine, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, schizophyllan, spirogermanium, tenuazonic acid, triaziquone, roridine A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxantrone, vincristine, vinorelbine, novantrone, teniposide, edatrexate, daunomycin, aminopterin, xeloda, ibandronate, irinotecan, topoisomerase inhibitor, difluoromethylornithine (DMFO), retinoic acid, capecitabine, and pharmacologically acceptable salts or derivatives thereof.

In some embodiments, the present disclosure provides a method for the treatment, prevention, or delay of cancer, comprising administering a therapeutically effect amount of a compound of the present disclosure, a pharmaceutically acceptable salt thereof, or a composition thereof to a subject in need thereof comprising coadministrating an anti-metabolite agent. A variety of anti-metabolite agents can be used in the context of the present disclosure and will be readily apparent to a skilled artisan, including, but not limited to methotrexate, 5-fluorouracil, 5-fluorouracil prodrugs (e.g., capecitabine), 5-fluorodeoxyuridine monophosphate, cytarabine, 5-azacytidine, gemcitabine, mercaptopurine, thioguanine, azathioprine, adenosine, pentostatin, erythrohydroxynonyladenine, and cladribine.

In some embodiments, the present disclosure provides a method for the treatment, prevention, or delay of cancer, comprising administering a therapeutically effect amount of a compound of the present disclosure, a pharmaceutically acceptable salt thereof, or a composition thereof to a subject in need thereof comprising coadministrating of an anti-estrogen agent selected from the group consisting of selective estrogen receptor modulators, pure receptor antagonists, aromatase inhibitors, and anti-gonadotropins and pharmacologically acceptable salts or derivatives thereof.

In various embodiments, the anti-estrogen agent is a selective estrogen receptor modulator (SERM). A variety of SERMs can be used in the context of the present disclosure and will be readily apparent to a skilled artisan, including, but not limited to anordrin, bazedoxifene, broparestrol, clomifene, cyclofenil, lasofoxifene, ormeloxifene, ospemifene, raloxifene, tamoxifen citrate, toremifene citrate, and pharmacologically acceptable salts or derivatives thereof.

In various embodiments, the anti-estrogen agent is a pure receptor antagonist, A variety of pure receptor agonists can be used in the context of the present disclosure and will be readily apparent to a skilled artisan, including, but not limited to fulvestrant, brilanestrant, elacestrant, and pharmacologically acceptable salts or derivatives thereof.

In various embodiments, the anti-estrogen agent is an aromatase inhibitor. A variety of aromatase inhibitors can be used in the context of the present disclosure and will be readily apparent to a skilled artisan, including, but not limited to anastrozole, letrozole, vorozole, exemestane, formestane and pharmacologically acceptable salts or derivatives thereof.

In various embodiments, the anti-estrogen agent is an anti-gonadotropin. A variety of anti-gonadotropins can be used in the context of the present disclosure and will be readily apparent to a skilled artisan, including, but not limited to triptorelin, leuprolide acetate, and pharmacologically acceptable salts or derivatives thereof.

In some embodiments, the present disclosure provides a method for the treatment, prevention, or delay of cancer, comprising administering a therapeutically effect amount of a compound of the present disclosure, a pharmaceutically acceptable salt thereof, or a composition thereof to a subject in need thereof comprising coadministrating an tyrosine kinase inhibitor. A variety of tyrosine kinase inhibitors can be used in the context of the present disclosure and will be readily apparent to a skilled artisan, including, but not limited to trastuzumab, pertuzumab, imatinib, gefitinib, erlotinib, sunitinib, adavosertib, and lapatinib.

In some embodiments, the present disclosure provides a method for the treatment, prevention, or delay of cancer, comprising administering a therapeutically effect amount of a compound of the present disclosure, a pharmaceutically acceptable salt thereof, or a composition thereof to a subject in need thereof comprising coadministrating an immune checkpoint inhibitor. A variety of immune checkpoint inhibitors can be used in the context of the present disclosure and will be readily apparent to a skilled artisan, including, but not limited to ipilimumab, pembrolizumab, nivolumab, avelumab, durvalumab, and atezolizumab Methods of Synthesizing the Compounds The compounds of the present disclosure can be made according to the following methods. A skilled artisan will understand that such methods can be implemented in any of numerous ways. While a certain order may be implied, the methods may be arranged according to any suitable sequence. Embodiments, ordered in a manner different from those explicitly described are encompassed by the present disclosure.

In various embodiments, the present disclosure provides a method of making a compound of claim 1, comprising addition of a nucleophile to an iminium intermediate of Formula (II):

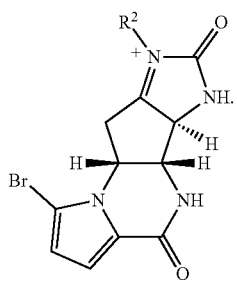

(II)

In various embodiments, the nucleophile added to Formula (II) is R¹—XH, wherein X is —O—, —S—, or —N(R⁴)—. In some embodiments, X is —O—. In other embodiments, X is —S—. In still other embodiments, X is —N(R⁴)—. In some embodiments, the nucleophile is the reaction solvent. In other embodiments, the nucleophile is used as a volume fraction ranging from about 1:1 to about 1:200 with reaction solvent, e.g., about 1:1, about 1:10, about 1:20, about 1:30, about 1:40, about 1:50, about 1:60, about 1:70, about 1:80, about 1:90, about 1:100, about 1:110, about 1:120, about 1:130, about 1:140, about 1:150, about 1:160, about 1:170, about 1:180, about 1:190, or about 1:200, including all ranges and subvalues therebetween. In other embodiments, the nucleophile is used in from about 1 equivalent (eq.) to about 50 equivalents compared to the reagents, e.g.; about 1 eq., about 5 eq., about 10 eq., about 15 eq., about 20 eq., about 25 eq., about 30 eq, about 35 eq, about 40 eq, about 45 eq, or about 50 eq., including all ranges and subvalues therebetween.

In various embodiments, the present disclosure provides a method of making a compound of Formula (I), comprising acid-promoted cyclization of a compound of Formula (II) to afford a compound of Formula (Id):

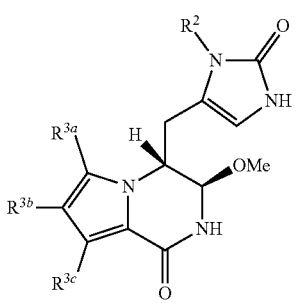

(III)

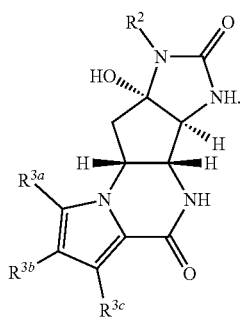

(Id)

In various embodiments, the acid used to promote the acid-promoted cyclization is methanesulfonic acid, p-toluenesulfonic acid, sulfuric acid, hydrochloric acid, trifluoroacetic acid, trifluoromethanesulfonic acid, and nitric acid. In some embodiments, the acid is trifluoroacetic acid. In other embodiments, the acid is methanesulfonic acid. In still other embodiments, the acid is hydrochloric acid. In yet other embodiments, the acid is trifluoromethanesulfonic acid.

In various embodiments, the present disclosure provides a method of making compound (III), comprising copper-mediated coupling between a compound of Formula (IV) and a compound of Formula (V):

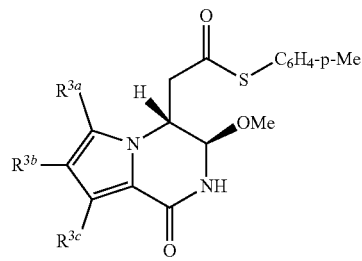

(IV)

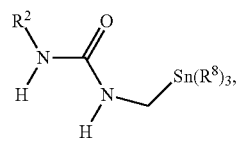

(V)

wherein $R^8$ is alkyl or cycloalkyl. In some embodiments, $R^8$ is alkyl. In other embodiments, $R^8$ is cycloalkyl. In specific embodiments, the alkyl is n-butyl. In other specific embodiments, the cycloalkyl is cyclohexyl.

In various embodiments, the copper-mediated coupling is carried out with copper (I)-thiophene-2-carboxylate (CuTC) or copper(I) diphenylphosphinate (CuDPP). In specific embodiments, the copper-mediated coupling is carried out with CuTC.

In some embodiments, the copper-mediated coupling further comprises treatment with an acid.

The compounds of the present disclosure (e.g., compound of Formula I-Ie), or a pharmaceutically acceptable salt, enantiomer, hydrate, solvate, prodrug, isomer, or tautomer thereof, may be prepared as described herein and modified by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999, which is hereby incorporated by reference in its entirety). These groups are removed at a convenient stage of the compound synthesis using methods that are readily apparent to those skilled in the art. The selection processes, as well as the reaction conditions and order of their execution, shall be consistent with the preparation of disclosed compounds (e.g., compounds of Formula I-Ie).

Those skilled in the art will recognize if a stereocenter exists in the compounds of Formula I-Ie. Accordingly, the present disclosure includes both possible stereoisomers (unless specified in the synthesis) and includes not only racemic compounds but the individual enantiomers and/or diastereomers as well. When a compound is desired as a single

69 enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994), which is hereby incorporated by reference in its entirety.

The compounds described herein may be made from commercially available starting materials or synthesized using known organic, inorganic, and/or enzymatic processes.

EXAMPLES

The following examples are provided to illustrate the present disclosure, and should not be construed as limiting thereof. In these examples, all parts and percentages are by weight, unless otherwise noted. Abbreviations in the examples are noted below.

Figure 2:
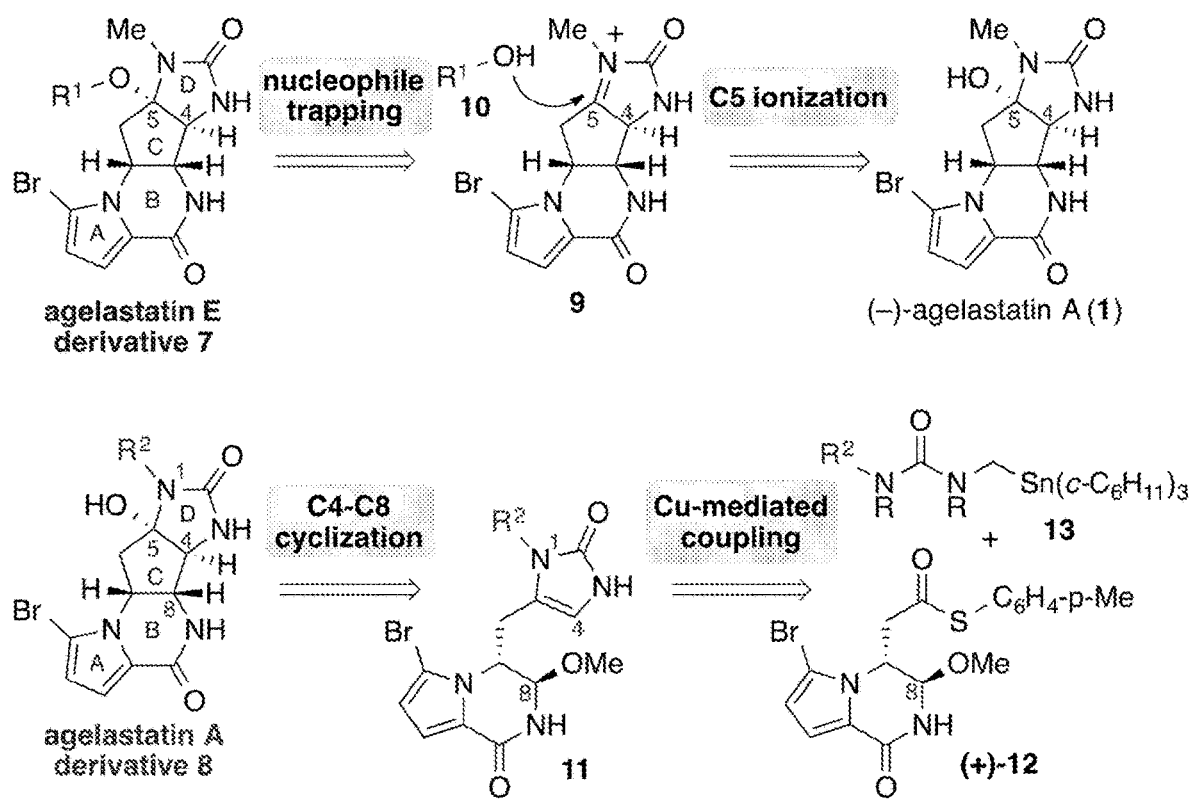
FIG. 2 shows a retrosynthetic analysis of agelastatin alkaloid derivatives.

Abbreviations
HPLC high performance liquid chromatography
mL milliliter
mmol millimole
MeOH methanol
NMR nuclear magnetic resonance
THF tetrahydrofuran
TLC thin layer chromatography Example 1: Synthesis and Biological Examination of New Agelastatin a and E Derivatives Results and Discussion In addition to studying other natural members of the agelastatin alkaloid family, the examination of new agelastatin derivatives in a 3D co-culture assay modeling the breast cancer microenvironment was desired.[9] Prompted by preliminary biological data (vide infra), it was of particular interest to examine derivatives which were accessible via late-stage modifications in the synthesis of agelastatins.[3] As illustrated in FIG. 2, the AgE derivative series 7 includes C5-ether variants that were envisioned to be prepared by nucleophilic trapping of iminium ion 9.[3a] Complementarily, the AgA derivative series 8 (FIG. 2) includes N1-substituted analogs that were planned to be accessed via application of imidazolone D-ring synthesis methodology. Starting with the common thioester (+)-12 and urea derivative 13, rapid access to N-substituted pre-agelastatin 11 as the substrate for C-ring cyclization reaction was envisioned.[3]

Numerous agelastatin alkaloid derivatives were prepared (Table 1) through application of the synthesis of pre-agelastatin 11, which is subject to C-ring cyclization followed by C5-substitution. Under optimal conditions (vide infra), C5-ionization of AgA (1) followed by nucleophilic trapping afforded the C5-substituted AgE derivative series 7 (Table 1, entries 1-11). A versatile imidazolone synthesis methodology using a common thioester (+)-12 allowed introduction of the N1-substituent in pre-agelastatin 11, which after cyclization afforded the desired N1-substituted AgA derivative series 8 (Table 1, entries 12-16). These new derivatives offer diverse functional groups enabling further derivatization with potential for future studies concerning agelastatin alkaloids. Importantly, the synthesis of agelastatin derivatives 7 and 8 (vide infra) was informed and guided by concurrent biological studies of these alkaloids and their derivatives. Specifically, the biological evaluation of AgA

70

(1) and AgE (5) disclosed herein has been critical to the design and synthesis of agelastatin derivatives including those illustrated in Table 1.

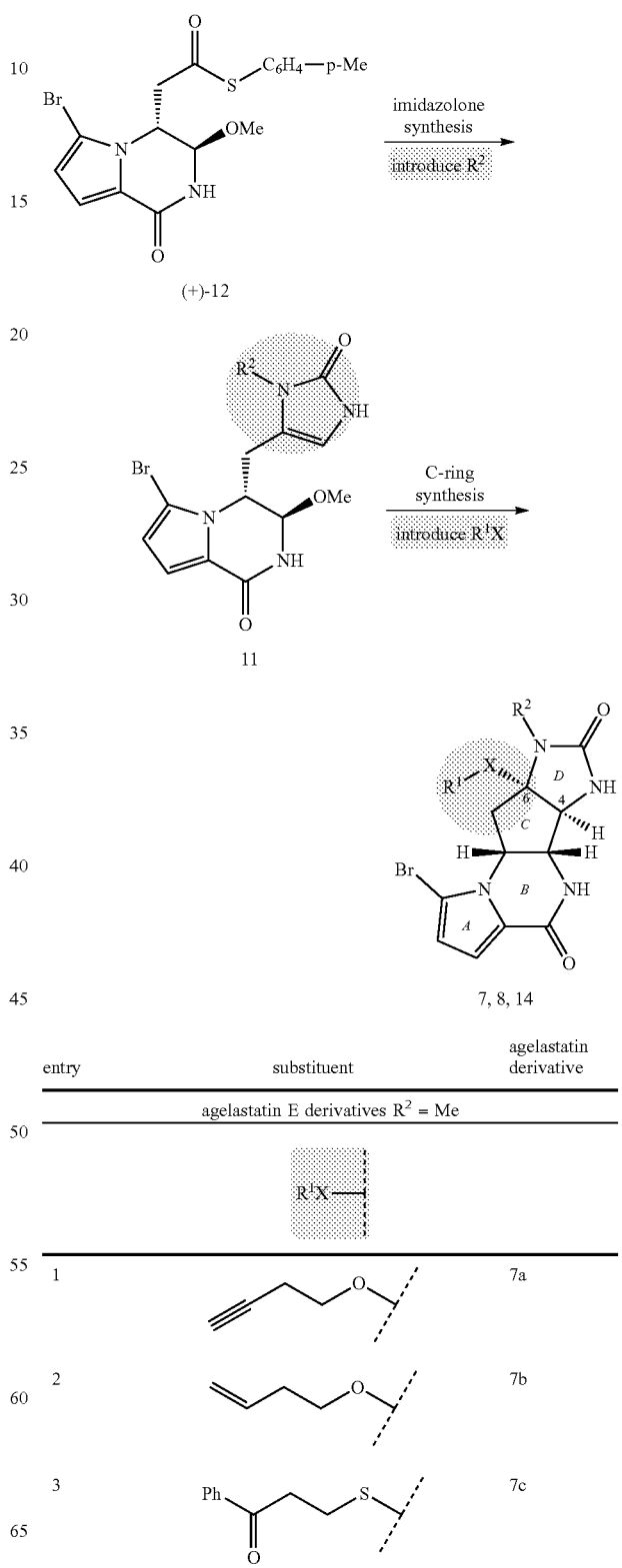

TABLE 1

TABLE 1-continued

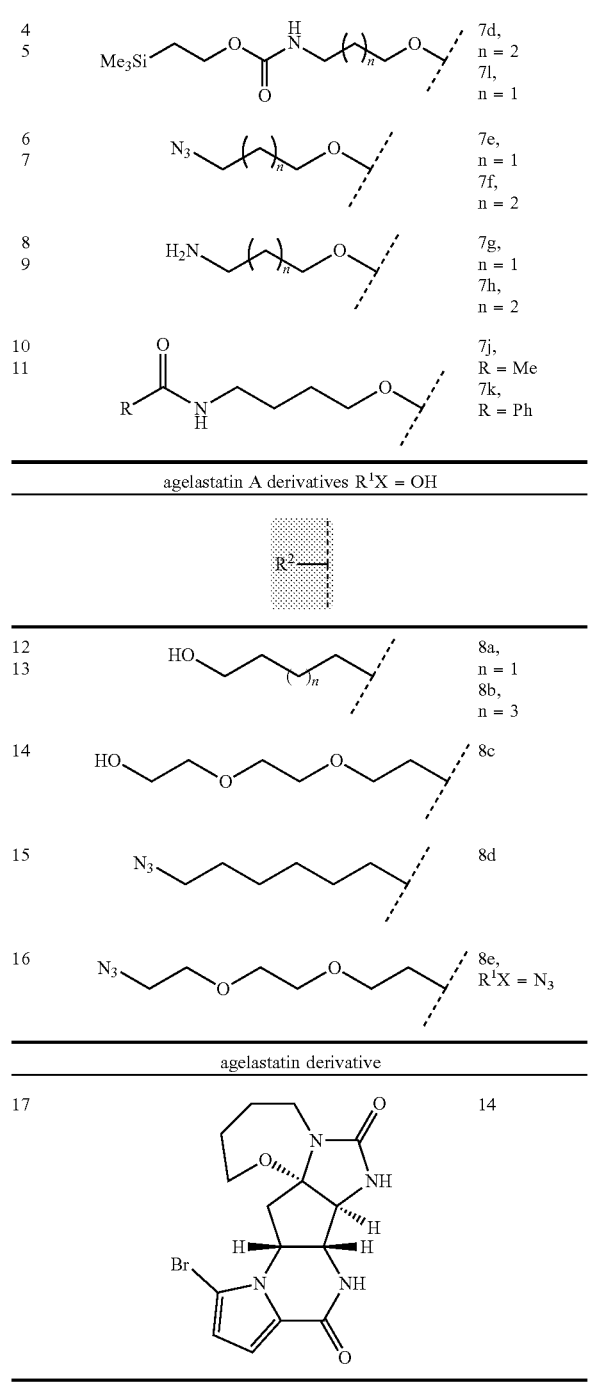

Studies of AgE in Breast Cancer Microenvironments. In the aforementioned 3D assay system, AgA (1) at low concentrations abrogates the effects of up-regulated fibroblast OPN on cancer cell adhesion, invasion, and cancer stem cell populations. Cancer cells exposed in co-culture to fibroblasts with up-regulated OPN demonstrated increased levels of lung metastasis in murine xenograft models, which were completely blocked by AgA (1) treatment of the co-cultures.[9] Given the interest in examining other agelastatins for activity in blocking vitamin D-induced OPN transcription in fibroblasts, the other natural members of the agelastatin alkaloid family, (−)-agelastatins B-F (2-6, FIG. 1) were first examined, prepared as described in earlier synthetic studies.[3] It was found that AgA (1) and AgE (5) had the desired activity, suggesting a possible negative influence by $N_1$-dealkylation (AgD and AgF), C4-hydroxylation (AgC), or C14-bromination (AgB and AgF) of the agelastatin core.[14] Interestingly, it was found that AgE (5) consistently blocked stimulated OPN transcription and demonstrated increased potency (FIG. 3) in comparison to AgA (1) in two dimensional (2D) cultures, prompting future examination of new C5-substituted agelastatins in blocking OPN transcription in fibroblasts.

Furthermore, the efficacy of AgE (5) was tested in blocking the effects of up-regulated fibroblast OPN in 3D co-cultures with the breast cancer cell line SUM1315. Cancer cells were co-cultured in 3D media mixture with reduction mammary fibroblasts (RMF) with either wild-type retroviral hairpin control vector (C-RMF) or Tiam1 silencing hairpin vector (shTiam-RMF). While both control and Tiam1-deficient fibroblasts secrete OPN to some degree, fibroblasts with Tiam1 silencing have up-regulated OPN.[9,11] Co-cultures were treated with dimethylsulfoxide (DMSO), AgA (1) at 75-nM concentration, or AgE (5) at 25-nM or 50-nM concentration.

Figure 4:
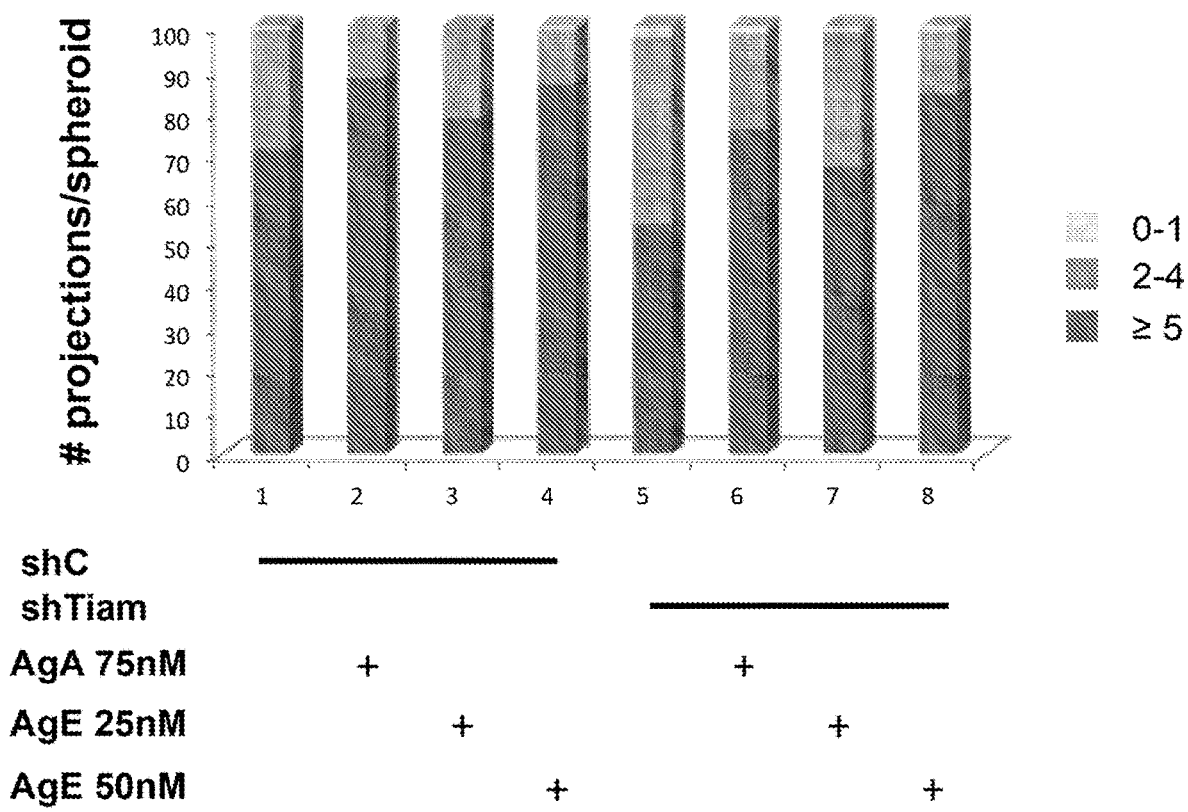
FIG. 4 shows the effect of AgE (5) on breast cancer cell invasion in co-cultures with mammary fibroblasts. Number of projections/spheroid for SUM1315 breast cancer cells and indicated mammary fibroblasts in 3D mixed cell spheroid co-culture, shown as percent of total spheroids. shC=control silencing retroviral hairpin vector. shTiam=Tiam-1 silencing hairpin vector.

In the co-cultures, fibroblasts and breast cancer cells aggregate together to form spheres, with the fibroblasts forming the interior core and the cancer cells on the exterior.[12] SUM1315 is an aggressive breast cancer cell line, and under these conditions the cancer cells form multicellular projections extending out into the 3D matrix, with the number and/or length of the projections indicating degree of invasiveness. Co-culture with Tiam1-deficient fibroblasts promotes increased invasiveness, increased cancer stem cell populations, and metastasis of breast cancer cells after isolation from co-culture and implantation into mice. This is consistent with increased OPN secretion, seen as increased numbers of projections per sphere (FIG. 4, column 5) as compared to control fibroblasts (FIG. 4, column 1). Incorporation of AgA (1) at 75-nM concentration with Tiam1-deficient fibroblasts (FIG. 4, column 6) decreases the number of projections to the baseline number seen with control fibroblast co-culture. Furthermore, including AgE (5) at 25-nM concentration (FIG. 4, column 7) partially restores the number of projections toward baseline, while AgE (5) at 50-nM concentration (FIG. 4, column 8) decreases the number of projections to below the baseline condition. Treatment of co-cultures of SUM1315/Tiam1-deficient human mammary fibroblasts with AgA prevents subsequent lung metastasis of breast cancer cells when implanted into immune deficient mice. Excitingly, these results suggest that AgE (5) is more potent than AgA (1) in decreasing the invasiveness induced by Tiam1-deficient fibroblasts.

Figure 5:
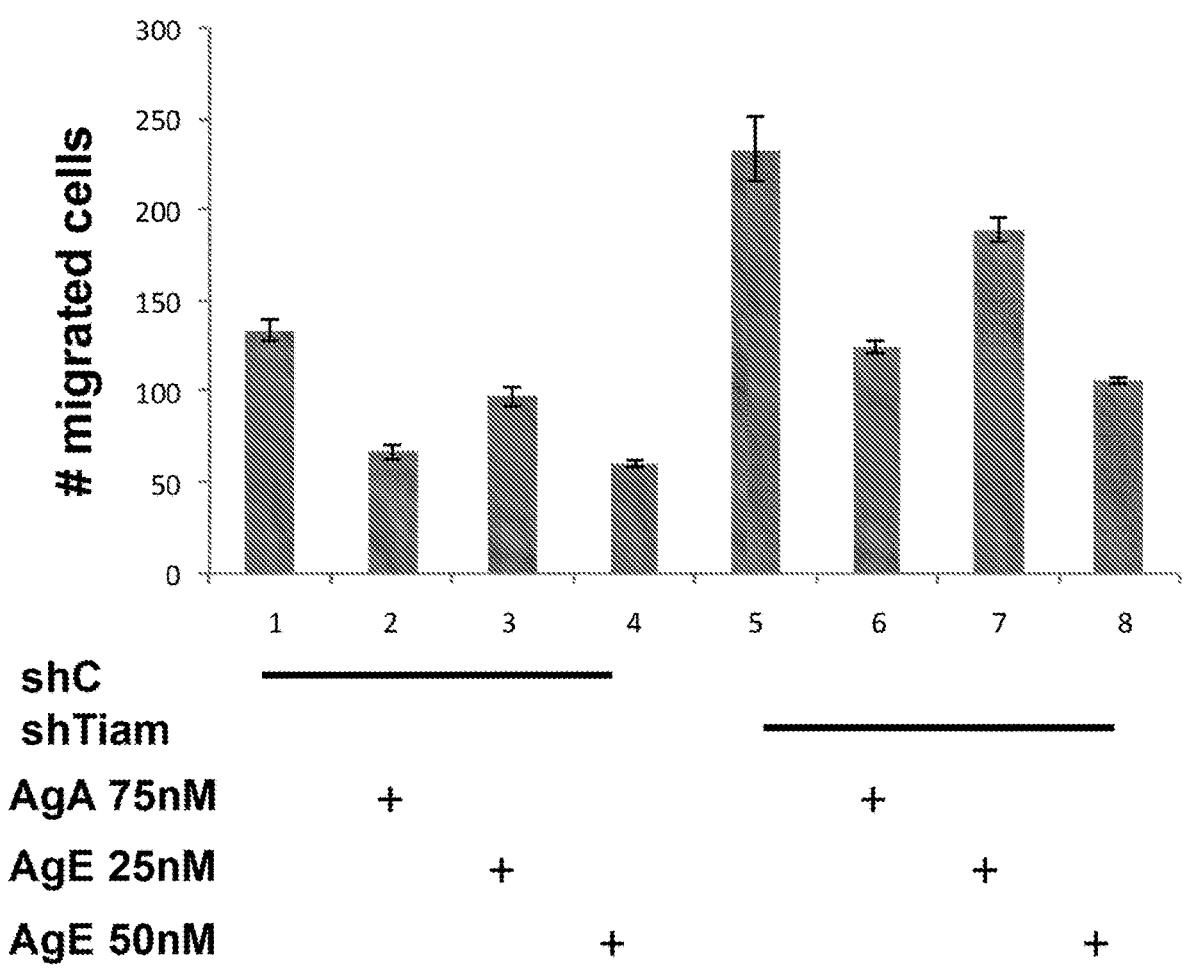
FIG. 5 shows the effect of AgE (5) on migration potential of breast cancer cells isolated from co-culture with mammary fibroblasts.

Breast cancer cells from the 3D co-cultures were isolated to greater than 99o/o purity as described previously[11,9] for further assessment. Adhesion of these post-co-culture (PCC) cells was assessed through transwell migration assay (FIG. 5). As with the invasion assay results, migration was notably increased in PCC cells exposed to Tiam1 I-deficient fibroblasts (FIG. 5, column 5) compared with PCC cells exposed to control fibroblasts (FIG. 5, column 1), and this was blocked by incorporation of AgA (1) at 75-nM concentration in the co-cultures (FIG. 5, column 6). Significantly, including AgE (5) at 25-nM and 50-nM concentrations (FIG. 5, columns 7-8) also decreased the migration, with the 50-nM treatment decreasing the number of migrating cells below the baseline condition.

Figure 6:
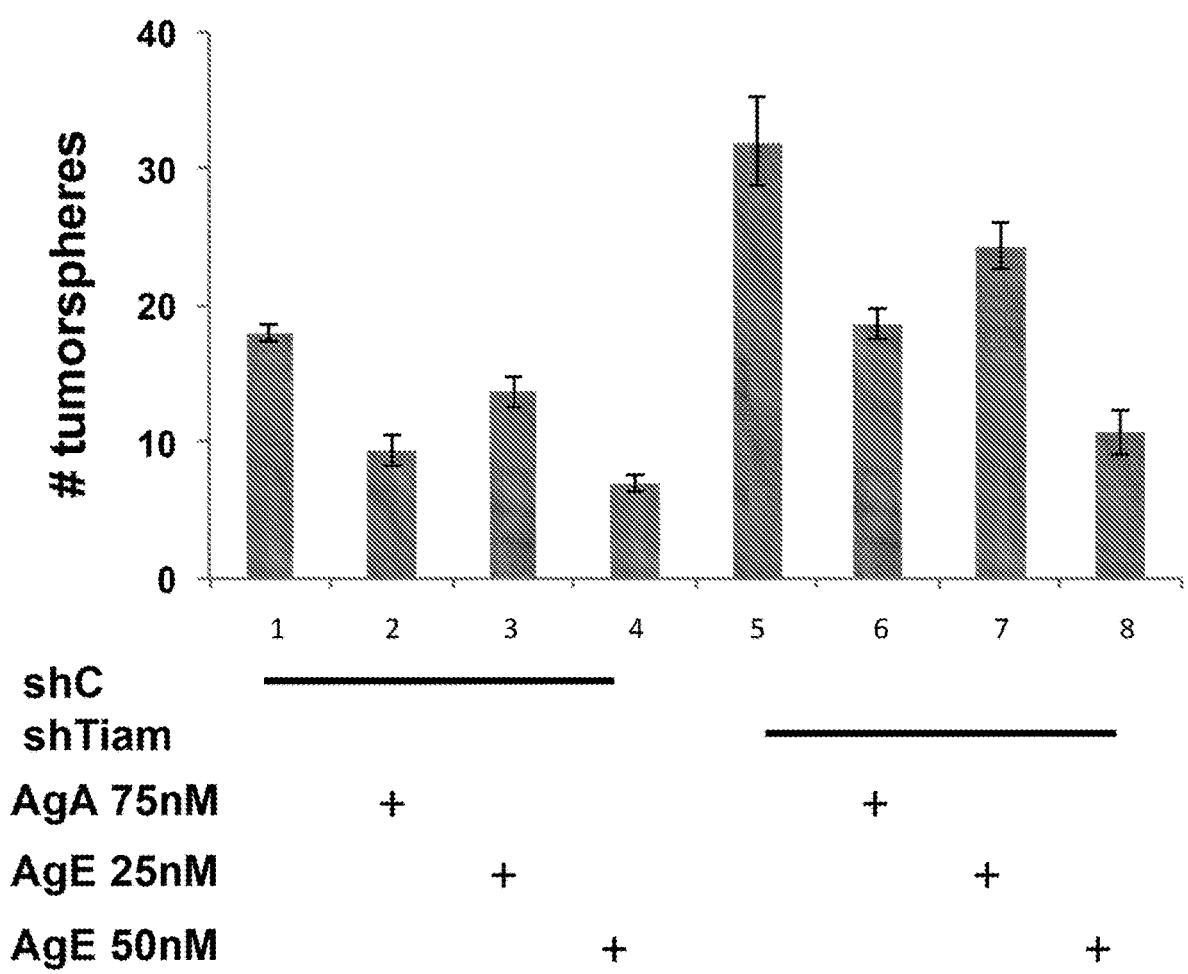
FIG. 6 shows the effect of AgE (5) on tumorsphere formation by breast cancer cells isolated from co-culture with mammary fibroblasts.
Figure 7:
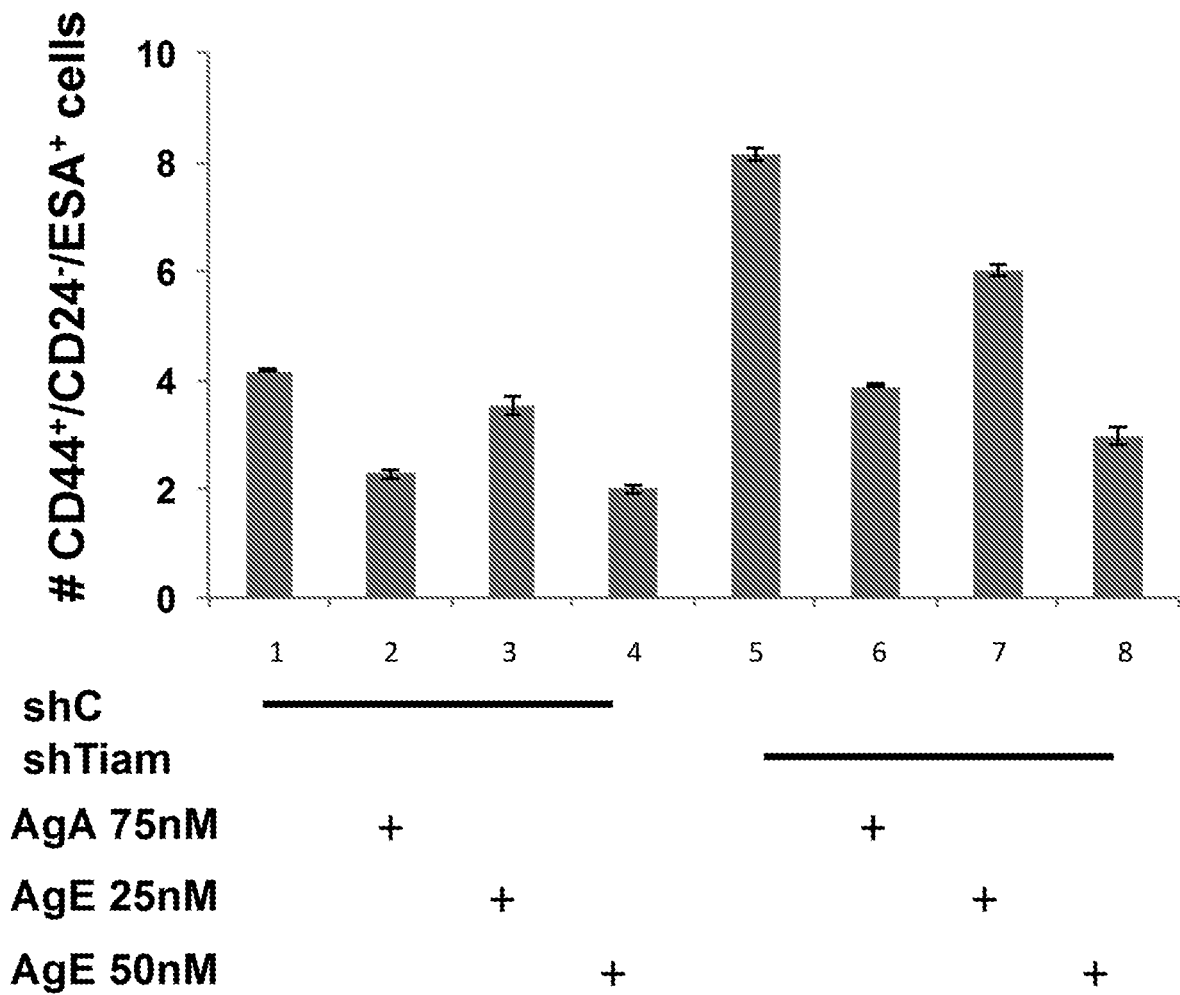
FIG. 7 shows the effect of AgE (5) on $CD44^+/CD24^-/ESA^+$ populations in breast cancer cells isolated from co-culture with mammary fibroblasts.

Two assays for breast cancer stem cell populations include tumorsphere formation in low adherence culture conditions and flow cytometry for specific cell surface markers ($CD44^+/CD24^-/ESA^+$). Results of both assays on the PCC cells showed analogous findings to the aforementioned invasion and migration assays Incorporation of AgA (1) at 75-nM concentration completely blocked the increased numbers of tumorspheres (FIG. 6, column 6) or cancer stem cells (FIG. 7, column 6) induced by Tiam1-deficient fibroblasts, compared with control fibroblasts (FIGS. 6-7, column 1). Incorporation of AgE (5) at 25-nM concentration had a partial effect (FIGS. 6-7, column 7), while AgE (5) at 50-nM concentration decreased tumorsphere (FIG. 6, column 8) and cancer stem cell (FIG. 7, column 8) numbers below baseline. Significantly, these results consistently suggest that AgE (5) is more potent than AgA (1) in blocking the effects of fibroblast OPN on the invasiveness, migration potential, and cancer stem cell populations in associated breast cancer cells.

The next tests were directed to whether direct treatment of mice with agelastatins could block the lung metastasis seen with the mixed cell xenograft model (co-implantation of breast cancer cell line SUM1315 and Tiam1-deficient human).

Figure 9:
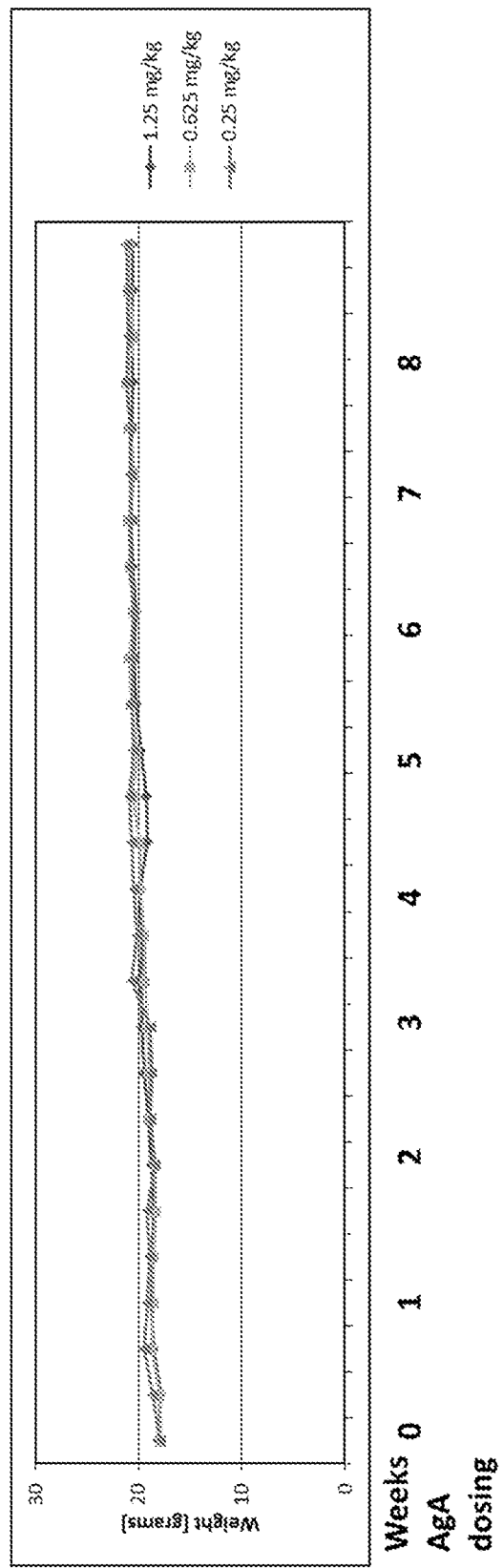
FIG. 9 shows a dose-toxicity experiment for AgA.
Figure 10:
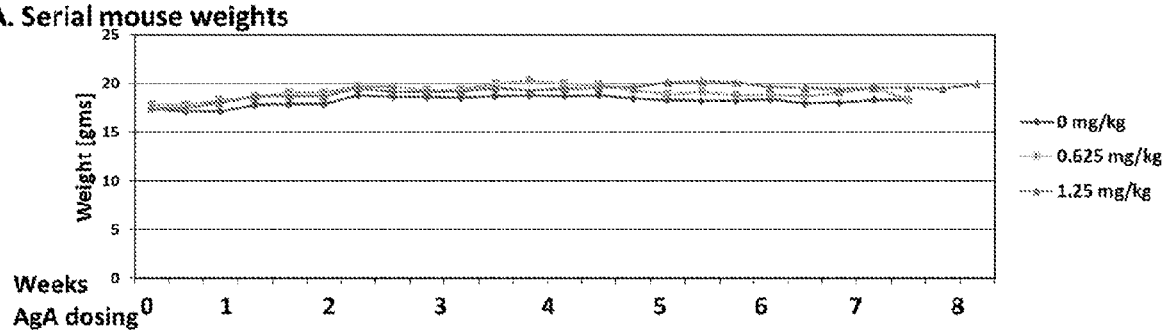
FIG. 10 shows the direct treatment of mixed cell xenograft-bearing mice with AgA. Mixed cell tumor-fibroblast xenografts were established in all mice.
Figure 10:
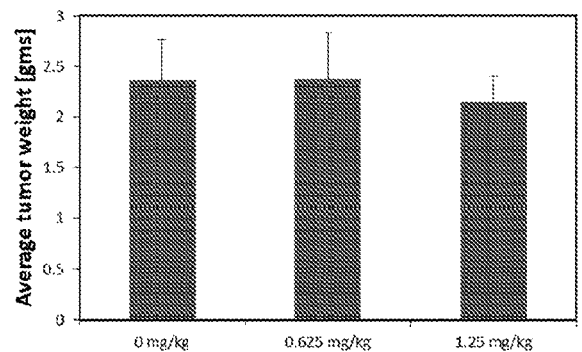
Figure 11:
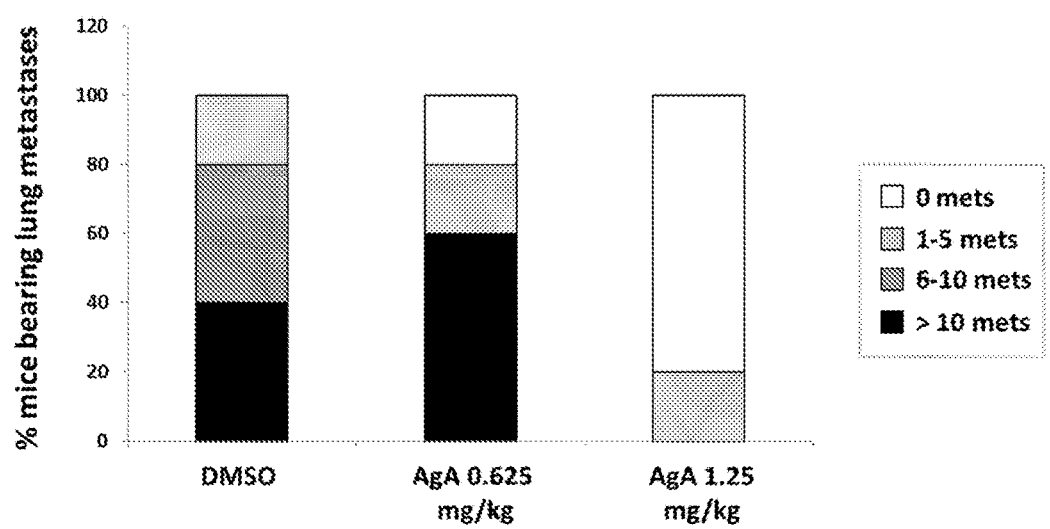
FIG. 11 shows AgA effects on lung metastasis in mixed cell xenograft-bearing mice.

The initial experiments with serial-treated mice bearing breast cancer xenografts with AgA at 2.5 mg/kg (the only published dose in the literature) induced toxicity in the mice within 2 weeks of treatment initiation. In the next studies, mice were treated with 3 lower doses of AgA (1.25 mg/kg, 0.625 mg/kg, and 0.25 mg/kg) in DMSO using 5×/week IP injection (5 mice/cohort) and observed for toxicity (FIG. 9). All mice gained weight as expected and none exhibited physical signs of toxicity, such as fur ruffling, hunching, decreased movement. Next, the direct treatment of mixed cell xenograft-bearing mice with AgA was examined. Mixed cell tumor-fibroblast xenografts were established in all mice and after healing from implantation surgery, treatment of 3 cohorts with AgA or DMSO vehicle was initiated (5 mice/cohort) (FIG. 10). All mice gained weight as expected (FIG. 10A) and final tumor weights at the implantation site were the same in all cohorts at necropsy, indicating no effect on primary tumorigenesis (FIG. 10B). The effects of AgA on lung metastasis in mixed cell xenograft-bearing mice was examined next (FIG. 11). Lung sections (FFPE) from mice shown in FIG. 10 were examined using hematoxylin & eosin and vimentin staining (SUM1315 exhibits strong vimentin expression) and clusters of metastatic cells counted. Two lung sections/mouse were examined; data represent numbers/individual lung section. As can be seen from FIG. 11, at 1.25 mg/kg, almost 800 of mice had 0 metastases and the remaining mice all had between 1 and 5 (compared to about 40 of mice having >10 metastases in the control group).

Figure 12:
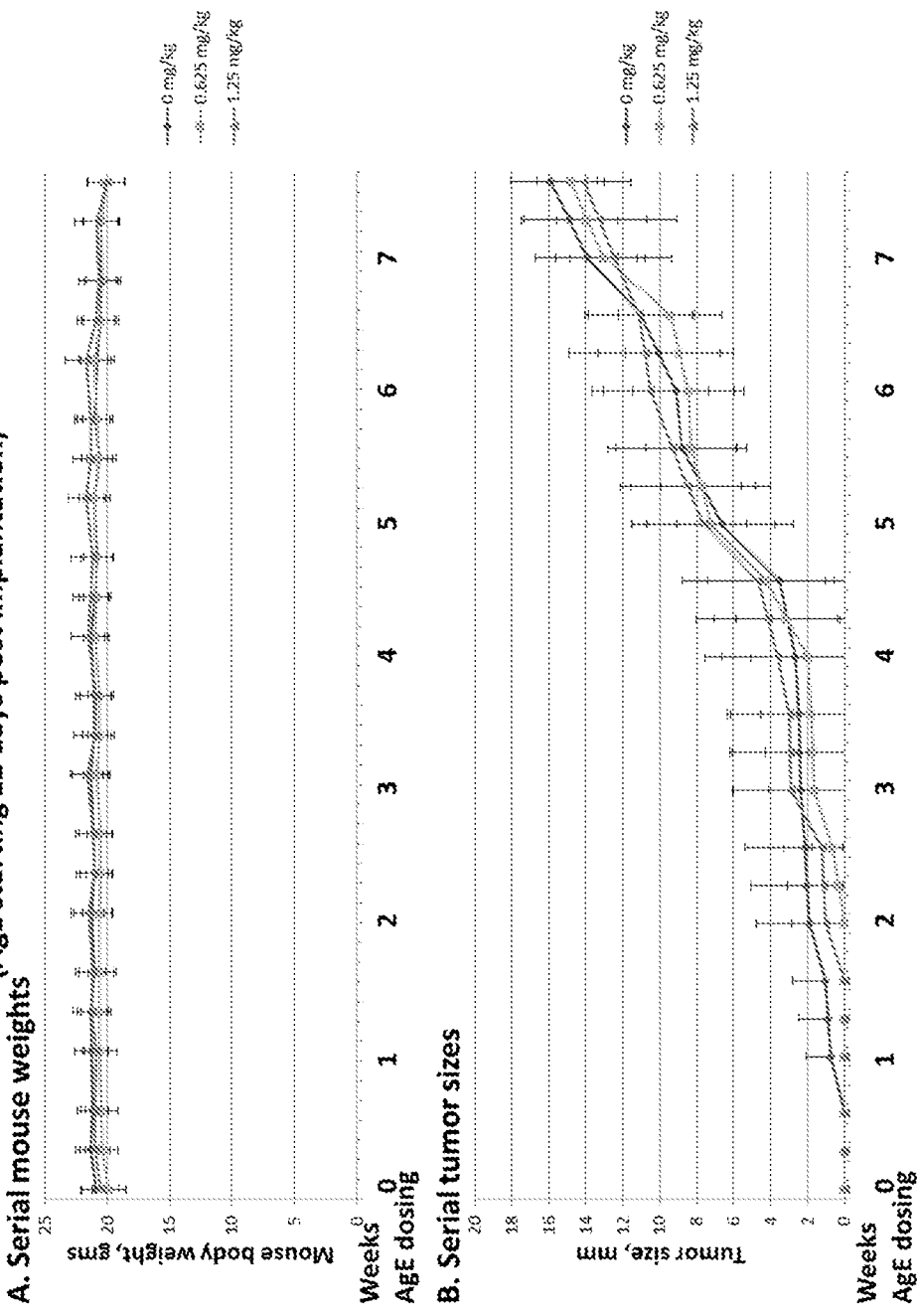
FIG. 12 shows the direct treatment of mixed cell xenograft-bearing mice with AgE.

The direct treatment of mixed cell xenograft-bearing mice with AgE was next tested (FIG. 12). Mixed cell tumor-fibroblast xenografts were established in all mice and after healing from implantation surgery, treatment of 3 cohorts with AgE or DMSO vehicle was initiated as indicated (8 mice per cohort). All mice gained weight as expected (FIG. 12A) and growth kinetics of tumor growth at the implantation site were the same in all cohorts, again indicating no effect on primary tumorigenesis (FIG. 12B).

Figure 13:
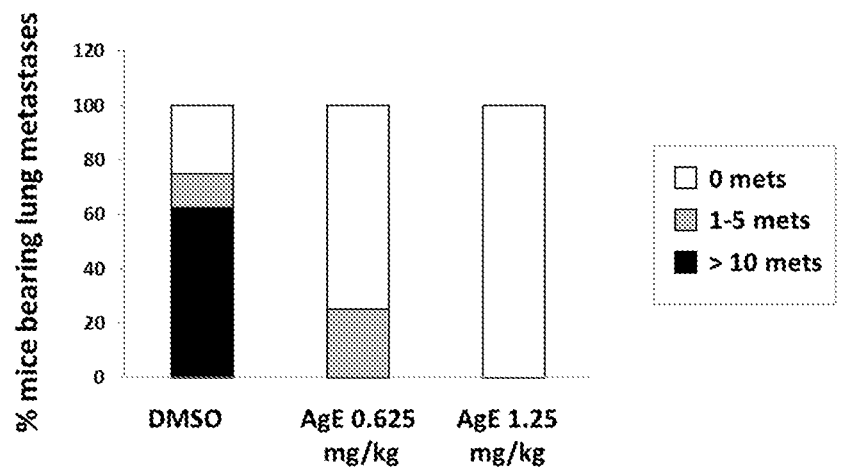
FIG. 13 shows AgE effects on lung metastasis in mixed cell xenograft-bearing mice.

The effects of AgE on lung metastasis in mixed cell xenograft-bearing mice was examined next (FIG. 13). Lung sections (FFPE) from mice shown in FIG. 10 were examined using hematoxylin & eosin and vimentin staining (SUM1315 exhibits strong vimentin expression) and clusters of metastatic cells counted. Two lung sections/mouse were examined; data represent numbers/individual lung section. As can be seen from FIG. 13, at 1.25 mg/kg, all mice had 0 metastases and about 80% of mice at 0.625 mg/kg had 0 metastases (compared to about 60% of mice having >10 metastases in the control group).

The above data indicate that both AgA and AgE are effective in suppressing/preventing lung metastasis at tolerable doses in the mixed cell xenograft model. At the doses used, AgA and AgE do not significantly impair primary tumorigenesis. Metastatic spread of cancer is primary cause of cancer death and there are no drugs currently available directed against cancer metastasis. This is a significant unmet clinical need. The data suggest that AgA, AgE, and derivatives may therefore have important uses in the adjuvant setting—i.e. prevention of metastatic spreading—in conjunction with other treatment(s) directed at the primary tumor.

Figure 14:
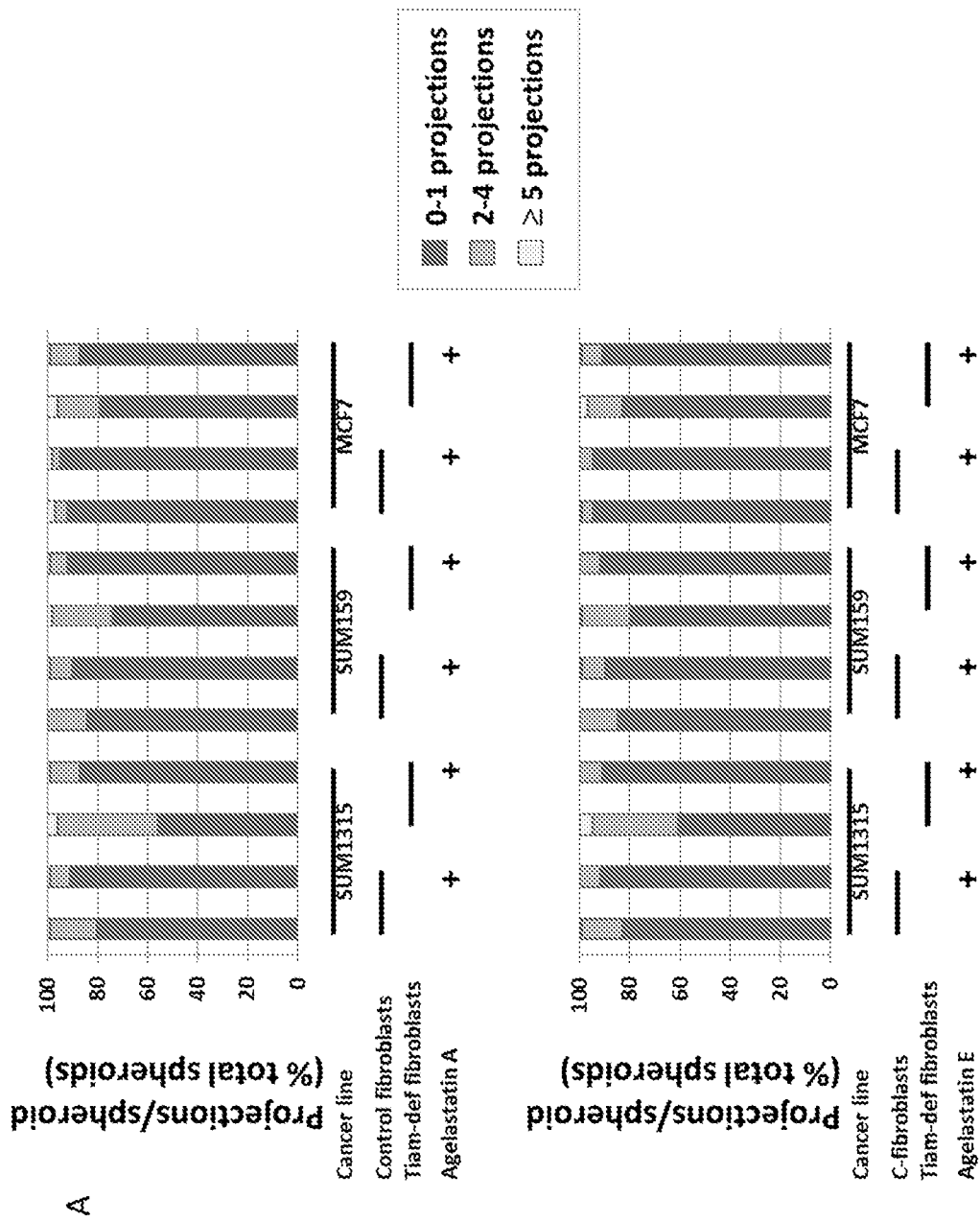
FIG. 14 shows the effect of Tiam1-deficient fibroblasts and agelastatin inhibition in breast cancer co-cultures. Human breast cancers consist of a group of sub-types that are distinguished clinically by cellular expression of estrogen receptor (ER), progesterone receptor (PR), and HER2.
Figure 14:
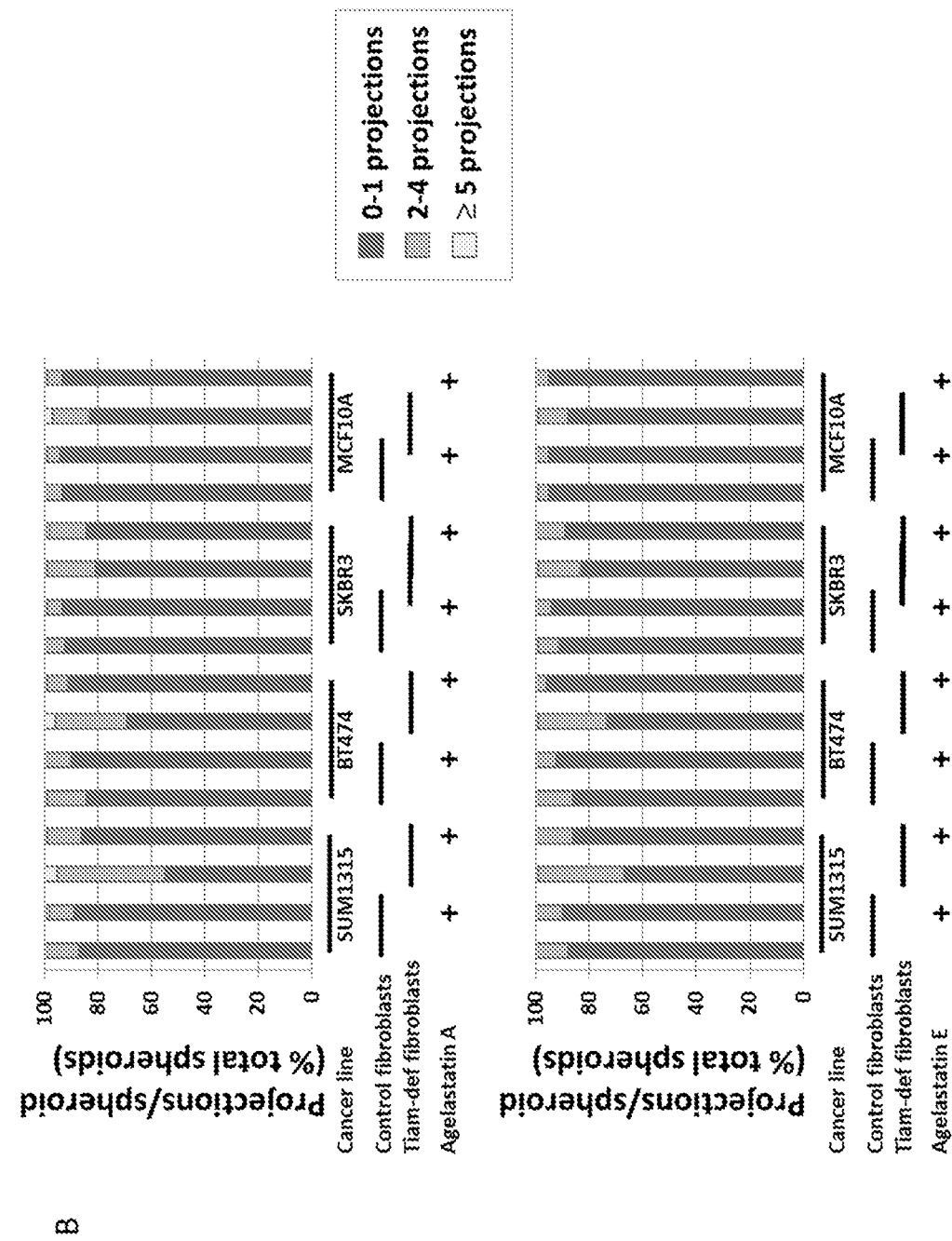
Figure 15:
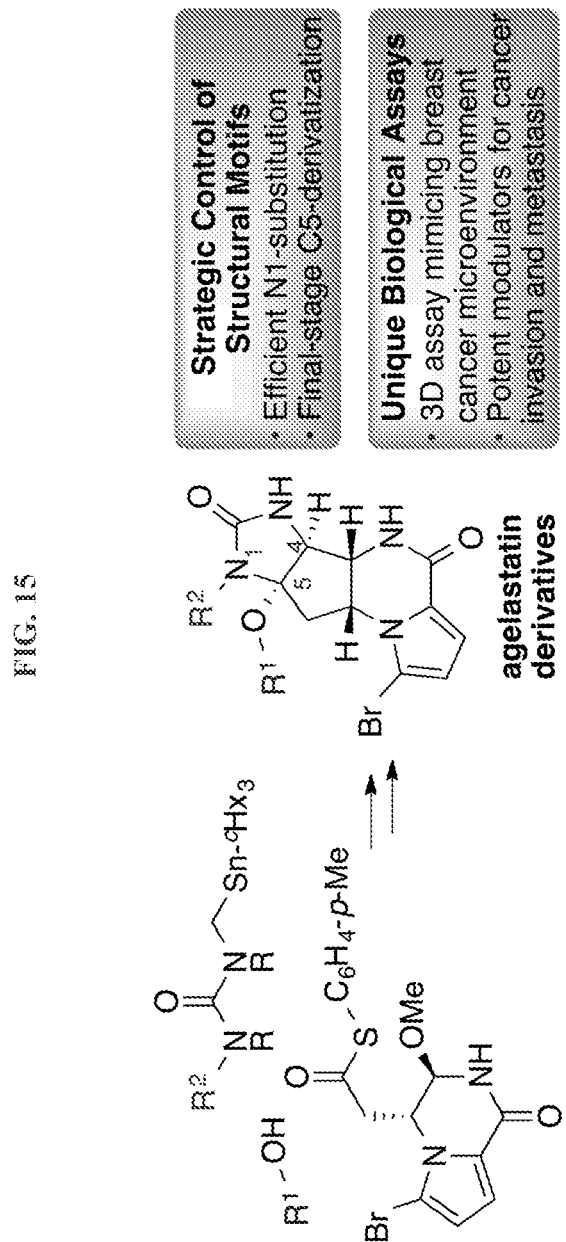
FIG. 15 shows an overview of the functionalization of the agelastatin core in accordance with certain embodiments of the present disclosure.

Lastly, the effect of Tiam1-deficient fibroblasts and agelastatin inhibition in breast cancer co-cultures was examined (FIG. 14). Human breast cancers consist of a group of sub-types that are distinguished clinically by cellular expression of estrogen receptor (ER), progesterone receptor (PR), and HER2. This is often recapitulated in experimental models with a panel of breast cancer cell lines expressing different immunophenotypes, and are often classified as luminal A or B sub-types (ER and/or PR+), HER2+, unclassified triple-negative (ER-PR– HER2–, EGFR or CK5/6–) and basal-like (ER-PR-HER2–, EGFR or CK5/6+). The 3D co-culture model has been used to test representative lines of each sub-type for responsiveness to the fibroblast Tiam1-osteopontin pathway and agelastatin inhibition:

| | |
|---|---|
| SUM 1315 | triple negative |
| SUM159 | triple negative |
| MCF7 | luminal A |
| BT474 | luminal B |
| SKBR3 | HER2 |
| MCF10A | basal |

Each cancer cell line was established in co-culture with either control or Tiam1-deficient fibroblasts to form the mixed cell spheroids, and treated with DMSO or agelastatin A or E as indicated. Invasiveness is assessed by the formation of multi-cellular projections emanating from the spheroid into the 3D media, and is scored by assessing proportions of spheroids exhibiting increasing numbers of projections. It was previously shown that changes in invasiveness correlate with changes in migration, cancer stem cells, and metastatic potential. For each cell line, co-culture with Tiam-deficient fibroblasts increases the invasiveness of the line, and treatment with agelastatin A or E blocks the increased invasiveness. The degree of the effects vary across the lines, with SUM1315 and BT474 being most sensitive, and MCF7 and MCF10A being least sensitive. This is not unexpected, as the co-culture conditions were optimized for SUM1315. It is likely that varying the co-culture conditions would affect the behavior of each cell line in the system and potentially augment degree of response. Nevertheless, all cell lines responded to the fibroblast co-culture in the same way, suggesting that treatment with agelastatins A, E, and their respective derivatives will be effective across the range of breast cancer sub-types.

With increased understanding of the effects of the agelastatin alkaloids in breast cancer microenvironments and on preventing and delaying the spread of metastasis, particularly the observation that AgE (5) showed increased potency as compared to AgA (1), a series of agelastatin derivatives was prepared (Table 1) and their biological effects on breast cancer invasiveness were studied.

Development of Agelastatin E Derivatives. By treatment of AgA (1) with methanesulfonic acid to promote the formation of C5-iminium ion 9 (FIG. 2), followed by in situ trapping with a series of nucleophiles, the agelastatin derivatives 7a-7f (Table 2) were synthesized. Condensation of commercially available 3-butyn-1-ol and 3-buten-1-ol with AgA (1) provided the desired derivatives 7a and 7b, respectively (Table 2, entries 1-2). The use of 3-mercaptopropiophenone[15] as the nucleophile afforded the C5-sulfide derivative 7c (Table 2, entry 3). The carbamate derivative 7d was prepared using the corresponding trimethylsilyl ethoxy carbamate-protected 4-aminobutan-1-ol as the nucleophile (Table 2, entry 4). Similarly, the condensation of 3-azidopropan-1-ol and 4-azidobutan-1-ol[16] with AgA (1) resulted in formation of azide derivatives 7e and 7f, respectively (Table 2, entries 5-6). These derivatives provided functional groups amenable to further diversification for use in concurrent biological evaluation.

Azide derivatives 7e and 7f were reduced to the corresponding amines 7g and 7h, respectively, under Staundinger reaction conditions (Scheme 1). The primary amine 7g was converted to carbamate 7i upon treatment with 4-nitrophenyl 2-(trimethylsilyl)ethyl carbonate in the presence of triethylamine. Likewise, primary amine 7h was converted to the acetamide 7j and benzamide 7k upon exposure to acetic anhydride and benzoyl chloride, respectively. This subset of AgE derivatives provided compounds with a range of linker length along with azide, amine, amide, and carbamate functional groups for the biological evaluation and comparison with AgA (1) and AgE (5) as modulators of breast cancer invasiveness (vide infra).

TABLE 2

Synthesis of AgE derivatives 7a-7f from AgA (1). Conditions: (a) MeSO$_3$H, CH$_3$CN. * CH$_2$Cl$_2$ used as solvent.

| entry | R¹X— | derivative | yield |
|---|---|---|---|
| 1 | (3-butynyloxy) | 7a | 87% |
| 2 | (3-butenyloxy) | 7b | 68% |
| 3 | Ph-C(O)-CH$_2$CH$_2$-S— | 7c | 93% |
| 4 | Me$_3$Si-CH$_2$CH$_2$-O-C(O)-NH-(CH$_2$)$_4$-O— | 7d | 63% |
| 5* | N$_3$-(CH$_2$)$_n$-CH$_2$CH$_2$-O— | 7e, n = 1 | 74% |
| 6* |  | 7f, n = 2 | 76% |

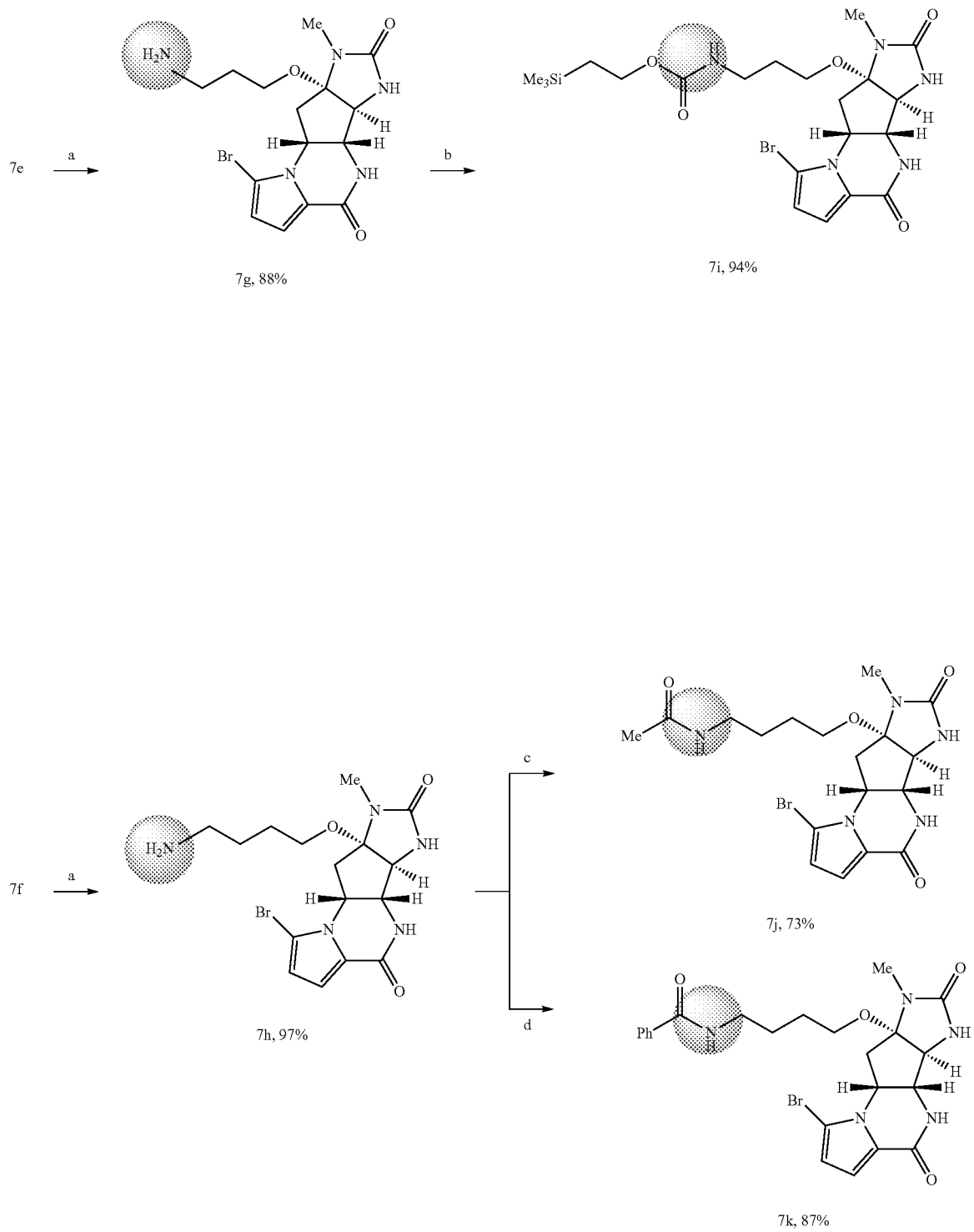

Scheme 1 Chemical diversification of AgE derivatives 7e-7h.

Conditions: (a) PPh₃, THF—H₂O (9:1). (b) 4-nitrophenyl 2-(trimethylsilyl)ethyl carbonate, NEt₃, CH₂Cl₂, (c) Ac₂O, NEt₃, DMAP, THF. (d) BzCl, NEt₃, THF.

Development of Agelastatin A Derivatives. The preparation of the urea-based organostannane reagent 13 (Table 3) was necessary for the introduction of substituents at the N1-position of agelastatin. The use of substituted urea 13 enabled access to the corresponding N1-substituted pre-agelastatins en route to the desired N1-substituted agelastatins. Through the use of 1,1'-carbonyldiimidazole[17] as a phosgene equivalent, the versatile intermediate 16 was accessed and converted to substituted ureas 13a-13c upon treatment with the desired primary amine (Table 3).[3,18]

TABLE 3

Synthesis of substituted ureas 13a-13c. Conditions: (a) 1,1'-carbonyldiimidazole, DMAP, CH$_2$Cl$_2$, 85%. (b) DMAP, CH$_2$Cl$_2$, 40° C.

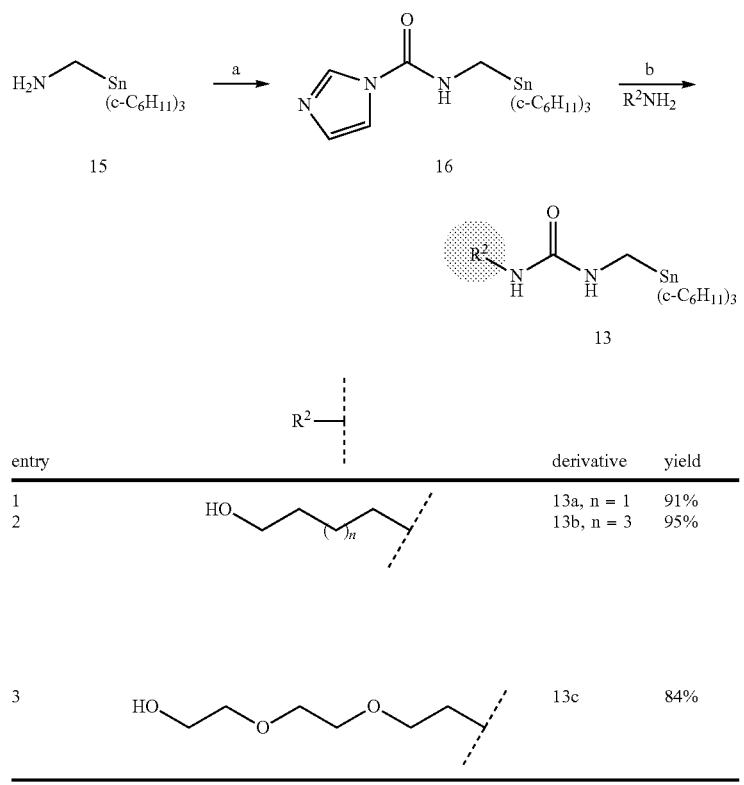

| entry | R$^2$— | derivative | yield |
|---|---|---|---|
| 1 | HO–(CH$_2$)$_n$– | 13a, n = 1 | 91% |
| 2 | | 13b, n = 3 | 95% |
| 3 | HO–CH$_2$CH$_2$–O–CH$_2$CH$_2$–O–CH$_2$CH$_2$– | 13c | 84% |

The copper-mediated coupling of substituted urea 13 with versatile thioester (+)-12 directly afforded the N1-substituted imidazolone 11 that served as the substrate for the C-ring cyclization chemistry to afford the N1-substituted AgA derivative series 8 (Table 4).[3] The use of N1-substituents with a primary alcohol functional group was envisioned to enable post-cyclization diversification of the agelastatin core in analogy with the C5-ether series. Pre-agelastatins 11b and 11c provided modest yield of the corresponding N1-substituted agelastatin derivatives 8b and 8c, respectively (Table 4, entries 2-3). Interestingly, the shorter 4-methylene spacer pre-agelastatin 11a provided the N1-substituted AgA derivative 8a (Table 4, entry 1) along with the pentacyclic agelastatin derivative 14 (Scheme 2). The inefficient formation of N1-substituted agelastatin derivative 8a is likely due to competitive intramolecular trapping of the C5-iminium ion 17 to afford the pentacyclic derivative 14 (Scheme 2). Notably, ether 14 serves as a link between AgE and AgA derivatives, including both N1- and C5-modifications. An anticipated slower rate of intramolecular cyclization using the longer N1-substituents in pre-agelastatins 11b and 11c is consistent with the observed greater, albeit modest, yield of the corresponding derivatives 8b and 8c, respectively (Table 4).

Scheme 2 Observed double cyclization of tricycle 11a to penacycle 14.

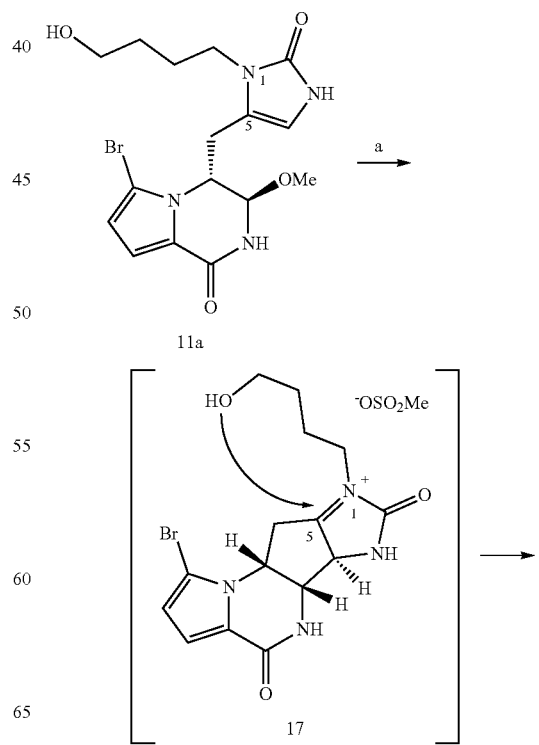

-continued

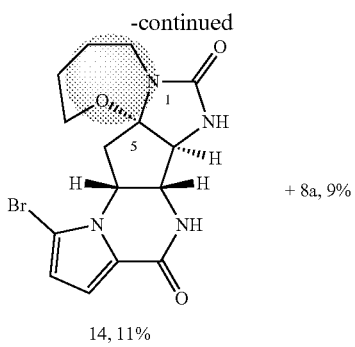

+ 8a, 9%

14, 11%

Conditions: (a) MeSO₃H, H₂O, 100° C.

The primary alcohol of the N1-substituent of AgA derivatives 8a-8c presents an opportunity for introduction of an azide functional group that may be used in the future for further modifications similar to those accomplished in the AgE derivative series 7. Indeed, using the more readily accessible agelastatin derivatives 8b and 8c the corresponding azide derivative was prepared in a single step (Scheme 3). The primary alcohol 8b was converted to the agelastatin azide 8d in 38% yield, along with 34% recovery of the starting material (72% BRSM). When using more forcing conditions required for complete conversion of the more recalcitrant triethyleneglycol derivative 8c to the corresponding azide, the formation of the bis-azide 8e consistent with an additional C5-azidation was observed. Interestingly, mass spectrometric analysis of bis-azide 8e shows consistency with other AgA derivatives in formation of its corresponding C5-iminium ion as a major observed molecular

TABLE 4

Synthesis of AgA derivatives 8a-8c using copper-mediated coupling. Conditions: (a) CuTC, THF, 50° C.; HCl, MeOH, 50° C. (b) MeSO₃H, H₂O, 100° C. CuTC = copper (I) thiophene-2-carboxylate. * 8a was isolated along with pentacyclic derivative 14 (11%).

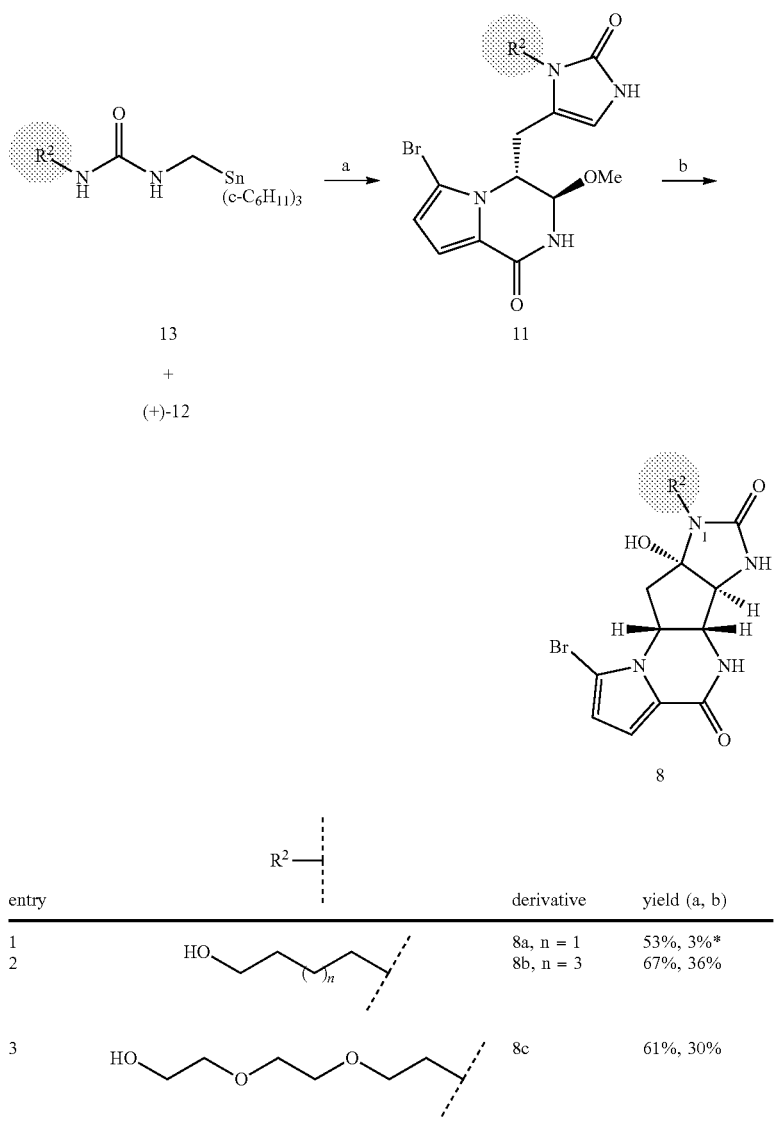

| entry | R² | derivative | yield (a, b) |
|---|---|---|---|
| 1 | HO~~~(  )ₙ~ | 8a, n = 1 | 53%, 3%* |
| 2 | | 8b, n = 3 | 67%, 36% |
| 3 | HO~~O~~O~ | 8c | 61%, 30% | ion. This was the first example of azide substitution at the C5-position of the agelastatin alkaloids. The covalent linkage of the alcohol and azide functional groups offered in the AgA derivatives 8a-8e was designed to be complementary to the ionizable linkage present in the AgE derivative series 7.

Scheme 3 Chemical diversification of AgA derivatives 8b and 8c to the corresponding azides.

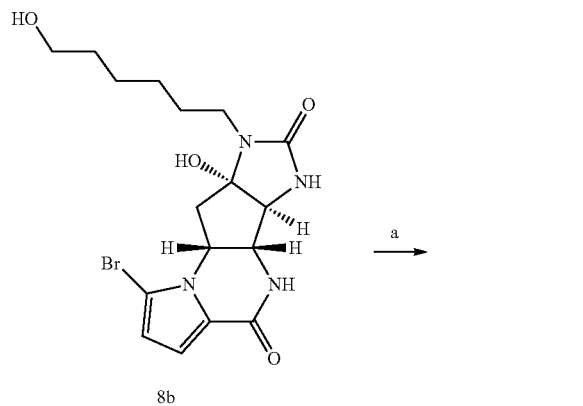

8b

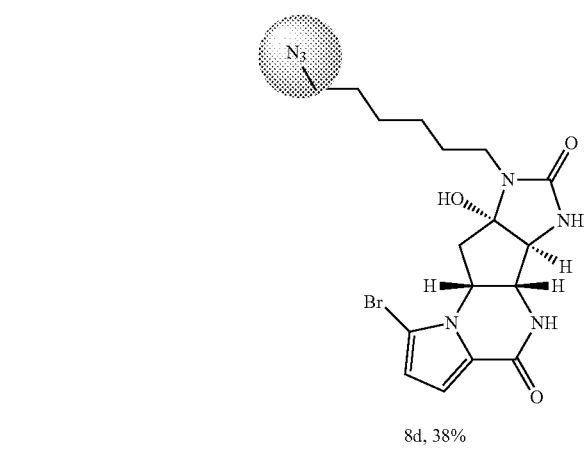

8d, 38%

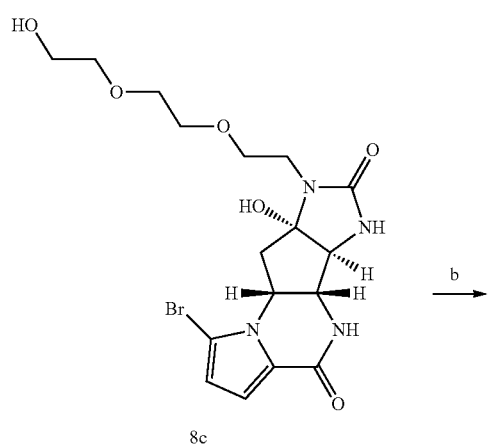

8c

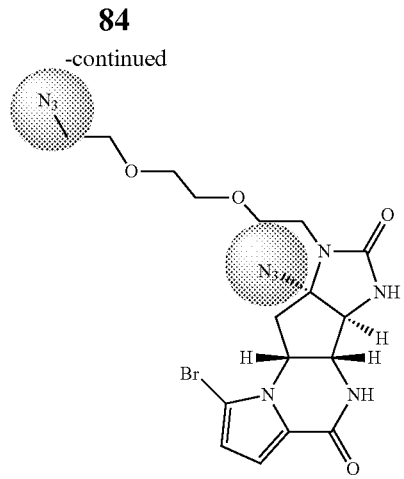

8e, 54%

Conditions: PPh$_3$, (X equiv), diisopropylazodicarboxylate (X equiv), diphenyl phosphoryl azide (X equiv), THF. (a) X = 2, 38% (isolated along with 34% recovered starting material). (b) X = 10, 54%.

Biological Study of Agelastatin Alkaloid Derivatives. The synthesized Agelastatin derivatives were compared to AgA (1) and AgE (5) for efficacy in blocking vitamin D-induced OPN transcription. The results of these investigations with selected and most informative derivatives are summarized in FIG. 8. Of particular interest in these screens were the AgE derivative carbamate 7d and the AgA derivative azide 8d. In further studies of AgA derivatives the triethyleneglycol linked bis-azide 8e showed improved efficacy in the assays. Indeed, bis-azide 8e at 94-nM concentration demonstrates statistical equivalence to AgE (5) at 50-nM concentration in blocking vitamin D-induced OPN transcription. The AgE derivatives 7i-7k (Scheme 1) were designed in an effort to better understand the promising potency of carbamate 7d in preliminary assays. The aim was to differentiate between the different aspects of the linker that led to increased potency, such as the electronic properties, steric bulk, and linker length. Interestingly, the 4-methylene linked carbamate 7d maintained slightly improved potency compared to the related 3-methylene linked carbamate 7i, consistent with the notion that the linker length is important to maintaining the desired inhibitory activity in such AgE derivatives. While the acetamide derivative 7j maintains the substituent chain length of carbamate 7d, its comparatively decreased activity suggests that the acetamide group is not as effective as the larger trimethylsilylethoxy substituent of carbamate 7d. Simple benzamide derivative 7k excitingly shows the desired potency comparable to carbamate 7d by preserving the substituent chain length of carbamate 7d while offering a larger amide group as compared to acetamide 7j. Notably, these results highlight the notion that agelastatin derivitization (such as N1- and C5-substitution) are not only tolerated in agelastatins with potency in modulation of breast cancer invasiveness, but also have already offered ample opportunities to access compounds that begin to approach the newly discovered potency of AgE (5) in this context. Importantly, the chemistry described herein can easily be modified (for example by using different nucleophile classes) to enable access to a wide range of new synthetic agelastatin derivatives (e.g., AgA and AgE derivatives) as potential modulators of breast cancer invasion and metastasis.

CONCLUSIONS

It was demonstrated that (−)-AgE (5) is more potent than (−)-AgA (1) in blocking fibroblast-mediated effects on cancer cell invasion, migration, and cancer stem cell populations. Importantly, non-cytotoxic doses were established for delivery of agelastatin alkaloids to breast cancer microenvironments in order to study their activity in blocking the induced OPN transcription in fibroblasts that can modulate these cancer cell behaviors. Based on the exciting recognition of the potent activity of AgE (5) and AgA (1) in this context, the synthesis of a variety of C5- and N1-substituted agelastatin derivatives were prepared, culminating in the AgE and AgA derivative series 7 and 8, respectively (Table 1). Highlights of the synthetic strategy include: 1) efficient C5-derivatization of AgA (1) using functional nucleophiles based on the conversion of AgA (1) to AgE (5),[3] 2) selective N1-functionalization using imidazolone synthesis methodology,[3] 3) diversification of complex agelastatin derivatives and establishment of precedence for access to more complex synthetic derivatives. Furthermore, it is demonstrated that new synthetic derivatives 7d and 7k (100-nM concentration) as well as derivative 8e (94-nM concentration) are statistically equivalent to AgE (5) at 50-nM concentration. The chemistry described here provides a foundation for rapid access to agelastatin derivatives with high potency (50-100 nM) as modulators for cancer invasion and metastasis. These findings highlight the outstanding potential for development of potent agelastatin derivatives with functional handles for further chemical derivatization and biological applications.

Example 2. Experimental

General Methods. All reactions were performed in oven-dried or flame-dried round-bottom flasks. The flasks were fitted with rubber septa, and reactions were conducted under a positive pressure of argon. Cannulae or gas-tight syringes with stainless steel needles were used to transfer air- or moisture-sensitive liquids. Where necessary (so noted) solutions were deoxygenated by argon purging for a minimum of 10 min. Flash column chromatography was performed as described by Still et al.[19] using granular silica gel (60-Å pore size, 40-63 μm, 4-6% $H_2O$ content). Analytical thin layer chromatography (TLC) was performed using glass plates pre-coated with 0.25 mm 230-400 mesh silica gel impregnated with a fluorescent indicator (254 nm). Thin layer chromatography plates were visualized by exposure to short wave ultraviolet light (254 nm) and irreversibly stained by treatment with an aqueous solution of ceric ammonium molybdate (CAM) or an aqueous solution of potassium permanganate ($KMnO_4$) or an alcoholic solution of ninhydrin, followed by heating (~1 min) on a hot plate (~250° C.). Organic solutions were concentrated at 29-30° C. on rotary evaporators capable of achieving a minimum pressure of ~2 Torr, then at ~0.5 Torr (vacuum pump) unless otherwise indicated. Proton ($^1H$) and carbon ($^{13}C$) nuclear magnetic resonance spectra were recorded with 600 MHz, 500 MHz and 400 MHz spectrometers. Proton nuclear magnetic resonance ($^1H$ NMR) spectra are reported in parts per million on the δ scale and are referenced from the residual protium in the NMR solvent [$CDCl_3$: δ 7.26 ($CDCl_3$), $CD_3OD$: δ 3.31 ($CD_2HOD$), DMSO-$d_6$: δ 2.50 (DMSO-$d_5$)]. Data are reported as follows: chemical shift [multiplicity (s=singlet, d=doublet, t=triplet, q=quartet, m=multiplet), coupling constant(s) in Hertz, integration]. Carbon-13 nuclear magnetic resonance ($^{13}C$ NMR) spectra are recorded in parts per million on the δ scale and are referenced from the carbon signals of the solvent ($CDCl_3$: δ 77.16, $CD_3OD$: δ 49.15, DMSO-$d_6$: δ 39 52). Data are reported as follows: chemical shift. Infrared data (IR) were obtained with a FTIR and are reported as follows: [frequency of absorption (cm$^{-1}$), intensity of absorption (s=strong, m=medium, w=weak, br=broad)]. High-resolution mass spectrometric data (HRMS) were recorded on a FT-ICR-MS spectrometer using electrospray ionization (ESI) source or direct analysis in real time (DART) ionization source.

General Procedure for Synthesis of AgE Derivatives 7a-7f. Methanesulfonic acid (10 equiv) was added slowly to a solution of (−)-agelastatin A (1 equiv) and nucleophile in acetonitrile or dichloromethane. Upon consumption of starting material as shown by thin layer chromatography, the reaction mixture was diluted with ethyl acetate or dichloromethane as indicated (10 mL). Reactions conducted over molecular sieves were filtered through a plug of cotton and further diluted with the indicated solvent (10 mL). The crude organic mixture was washed sequentially with saturated aqueous sodium bicarbonate (2×15 mL) and saturated aqueous sodium chloride (1×10 mL). The combined aqueous layers were extracted with organic solvent (2×10 mL). The combined organic layers were dried over anhydrous sodium sulfate, were filtered, and were concentrated under reduced pressure. The resulting residue was purified by flash column chromatography on silica gel to afford agelastatin derivatives 7a-7f.

Alkyne Derivative 7a was synthesized according to the general procedure for synthesis of AgE derivatives using 3-butyn-1-ol (0.5 mL) and acetonitrile (2.5 mL) over 4 Å molecular sieves (30 mg). After 17.5 h, the crude residue after work-up using ethyl acetate was purified by flash column chromatography on silica gel (eluent: 10% acetone in dichloromethane, then 5%→10% methanol in dichloromethane) to afford alkyne 7a (10.0 mg, 87%0) as a white solid. $^1H$ NMR (500 MHz, $CD_3OD$, 23° C.): δ 6.92 (d, J=4.1 Hz, 1H), 6.34 (d, J=4.1 Hz, 1H), 4.62 (dt, J=12.1, 6.0 Hz, 1H), 4.15-4.07 (m, 2H), 3.53-3.44 (m, 1H), 3.38-3.31 (m, 1H), 2.82 (s, 3H), 2.73-2.65 (m, 1H), 2.47 (ddt, J=6.8, 4.3, 2.4 Hz, 2H), 2.32 (t, J=2.7 Hz, 1H), 2.23-2.14 (m, 1H). $^{13}C$ NMR (126 MHz, ($CD_3OD$, 23° C.): δ 161.8, 161.1, 124.2, 116.2, 114.0, 107.5, 99.9, 82.0, 71.0, 62.8, 62.3, 61.8, 53.8, 39.2, 24.9, 20.5. FTIR (thin film) cm$^{-1}$: 2930 (w), 1667 (s), 1551 (w), 1425 (m), 1098 (w), 747 (w) HRMS (ESI) (m/z): calc'd for $C_{16}H_{18}BrN_4O_3$, [M+H]$^+$: 393.0557, found: 393.0552. TLC (10% methanol in dichloromethane), Rf: 0.69 (UV, CAM).

Alkene Derivative 7b was synthesized according to the general procedure for synthesis of AgE derivatives using 3-buten-1-ol (0.5 mL) and acetonitrile (2.5 mL) over 4 Å molecular sieves (30 mg). After 18 h, the crude residue after work-up using ethyl acetate was purified by flash column chromatography on silica gel (eluent: 10% acetone in dichloromethane, then 5%→10% methanol in dichloromethane) to afford alkene 7b (8.1 mg, 68%) as a white solid. $^1H$ NMR (500 MHz, $CD_3OD$, 23° C.): δ 6.91 (d, J=4.1 Hz, 1H), 6.33 (d, J=4.2 Hz, 1H), 5.84 (td, J=15.4, 14.5, 6.5 Hz, 1H), 5.17-5.00 (m, 2H), 4.61 (dt, J=12.2, 5.9 Hz, 1H), 4.18-4.02 (m, 2H), 3.42 (q, J=7.6 Hz, 1H), 3.31-3.21 (m, 1H), 2.78 (s, 3H), 2.66 (dd, J=13.4, 6.5 Hz, 1H), 2.35 (q, J=6.8 Hz, 2H), 2.16 (t, J=12.8 Hz, 1H). $^{13}C$ NMR (125 MHz, $CD_3OD$, 23° C.): δ 161.9, 161.1, 136.3, 124.2, 117.5, 116.2, 114.0, 107.5, 99.8, 63.8, 62.3, 61.7, 53.8, 39.3, 35.1, 24.9. FTIR (thin film) cm$^{-1}$: 2926 (w), 1668 (s), 1551 (w), 1425 (m), 1091 (w), 747 (w). HRMS (ESI) (m/z): calc'd for $C_{16}H_{20}BrN_4O_3$, [M+H]$^+$: 395.0713, found: 395.0692. TLC (10% methanol in dichloromethane), Rf: 0.43 (UV, CAM).

Sulfide Derivative 7c was synthesized according to the general procedure for synthesis of AgE derivatives using 3-mercaptopropiophenone[15] (99.7 mg, 6.00×10$^2$ μmol, 20.5 equiv) in acetonitrile (3.0 mL) over 4 Å molecular sieves (20 mg). After 1 h, the crude residue after work-up using ethyl acetate was purified by flash column chromatography on silica gel (eluent: 0%→10% methanol in dichloromethane) to afford sulfide 7c (13.6 mg, 93%) as a white solid $^1$H NMR (400 MHz, CD$_3$OD, 23° C.): δ 8.04-7.94 (m, 2H), 7.61 (d, J=7.4 Hz, 1H), 7.51 (dd, J=8.3, 7.0 Hz, 2H), 6.91 (d, J=4.1 Hz, 1H), 6.32 (d, J=4.1 Hz, 1H), 4.78 (dt, J=11.8, 6.1 Hz, 1H), 4.47 (s, 1H), 4.19 (d, J=5.4 Hz, 1H), 3.35 (t, J=6.9 Hz, 2H), 2.91 (dd, J=12.5, 6.9 Hz, 1H), 2.87 (s, 3H), 2.81-2.67 (m, 2H), 1.95 (dd, J=13.5, 11.7 Hz, 1H), $^{13}$C NMR (101 MHz, CD$_3$OD, 23° C.): δ 199.7, 161.6, 161.0, 138.0, 134.7, 130.0, 129.3, 124.3, 116.3, 114.1, 107.5, 77.9, 67.5, 63.4, 54.8, 41.0, 38.8, 25.2, 24.1. FTIR (thin film) cm$^{-1}$: 2920 (w), 2361 (w), 1667 (s), 1551 (w), 1423 (m), 1195 (w). HRMS (ESI) (m/z): calc'd for C$_{21}$H$_{22}$BrN$_4$O$_3$S, [M+H]$^+$: 489.0591, found: 489.0595. TLC (5% methanol in dichloromethane), Rf: 0.46 (UV, CAM).

4-Methylene Carbamate Derivative 7d was synthesized according to the general procedure for synthesis of AgE derivatives using 2-(trimethylsilyl)ethyl (4-hydroxybutyl) carbamate[20] (1.40×10$^2$ mg, 6.00×10$^2$ μmol, 20.5 equiv) in acetonitrile (3.0 mL) over 4 Å molecular sieves (25 mg). After 3 h, the crude residue after work-up using ethyl acetate was purified by flash column chromatography on silica gel (eluent: 20%→30% acetone in dichloromethane, then 5%→10% methanol in dichloromethane) to afford 4-methylene carbamate 7d (10.5 mg, 63%) as a white solid. $^1$H NMR (400 MHz, CD$_3$OD, 23° C.): δ 6.89 (d, J=4.1 Hz, 1H), 6.31 (d, J=4.1 Hz, 1H), 4.59 (dt, J=12.1, 6.0 Hz, 1H), 4.17-4.05 (m, 4H) 3.36 (dt, J=9.0, 5.8 Hz, 1H), 3.24 (dt, J=9.1, 5.8 Hz, 1H), 3.08 (td, J=6.8, 4.3 Hz, 2H), 2.76 (s, 3H), 2.68-2.60 (m, 1H), 2.20-2.10 (m, 1H), 1.65-1.49 (m, 4H), 0.99-0.92 (m, 2H), 0.02 (s, 9H). $^{13}$C NMR (101 MHz, CD$_3$OD, 23° C.): δ 161.9, 161.1, 159.5, 124.2, 116.2, 114.0, 107.5, 99.9, 63.9, 63.7, 62.3, 61.7, 53.8, 41.4, 39.4, 27.9, 27.8, 24.9, 18.8, -1.3. FTIR (thin film) cm$^{-1}$: 2949 (w), 1669 (s), 1489 (w), 1423 (m), 1249 (m), 1106 (w), 835 (m), 747 (m). HRMS (ESI) (m/z): calc'd for C$_{22}$H$_{35}$BrN$_5$O$_5$Si, [M+H]$^+$: 556.1585, found: 556.1567. TLC (10% methanol in dichloromethane), Rf: 0.59 (UV, CAM).

3-Methylene Azide Derivative 7e was synthesized according to the general procedure for synthesis of AgE derivatives using 3-azidopropan-1-ol[16] (415 mg, 4.10 mmol, 20.0 equiv) in dichloromethane (13 mL). The reaction mixture became homogeneous upon addition of methanesulfonic acid. After 14 h, the reaction mixture was diluted with dichloromethane and quenched with aqueous sodium hydroxide (0.5 N, 20 mL) before general work-up procedure. The crude residue was purified by flash column chromatography on silica gel (eluent: 20% acetone in dichloromethane, then 5%→109, methanol in dichloromethane) to afford 3-methylene azide 7e (64.4 mg, 74%) as a white solid. $^1$H NMR (500 MHz, DMSO-d$_6$, 23° C.): δ 7.96 (s, 1H), 7.34 (s, 1H), 6.74 (d, J=4.0 Hz, 1H), 6.35 (d, J=4.0 Hz, 1H), 4.41 (dt, J=12.0, 5.9 Hz, 1H), 4.02 (d, J=5.4 Hz, 1H), 3.97 (d, J=1.8 Hz, 1H), 3.41 (td, J=6.6, 2.6 Hz, 2H), 3.28 (dt, J=9.3, 6.2 Hz, 1H), 3.24-3.17 (m, 1H), 2.65 (s, 3H), 2.56-2.51 (m, 1H), 1.99 (t, J=12.6 Hz, 1H), 1.79 (p, J=6.5 Hz, 2H). $^{13}$C NMR (126 MHz, DMSO-d$_6$, 23° C.): δ 158.7, 157.6, 123.6, 113.5, 112.0, 104.7, 97.5, 60.1, 59.5, 59.3, 51.9, 47.8, 37.7, 28.3, 23.9. FTIR (thin film) cm$^{-1}$: 2928 (w), 2097 (w), 1666 (s), 1549 (w), 1423 (m), 1348 (w), 1107 (w), 746 (m). HRMS (DART) (m/z): calc'd for C$_{15}$H$_{19}$BrN$_7$O$_3$, [M+H]$^+$: 424.0727, found: 424.0717. TLC (10% methanol in dichloromethane), Rf: 0.53 (UV, CAM).

4-Methylene Azide Derivative 7f was synthesized according to the general procedure for synthesis of AgE derivatives using 4-azidobutan-1-ol[16] (276 mg, 2.40 mmol, 20.0 equiv) in dichloromethane (8.0 mL). The reaction mixture became homogeneous upon addition of methanesulfonic acid. After 26 h, the reaction mixture was diluted with dichloromethane and quenched with aqueous sodium hydroxide (0.5 N, 20 mL) before general work-up procedure. The crude residue was purified by flash column chromatography on silica gel (eluent: 20% acetone in dichloromethane, then 5%→10% methanol in dichloromethane) to afford 4-methylene azide 7f (39.8 mg, 76%) as a white solid. $^1$H NMR (500 MHz, DMSO-d$_6$, 23° C.): δ 7.97 (s, 1H), 7.31 (d, J=2.0 Hz, 1H), 6.74 (d, J=3.9 Hz, 1H), 6.35 (d, J=4.0 Hz, 1H), 4.41 (dt, J=11.9, 6.0 Hz, 1H), 4.01 (d, J=5.4 Hz, 1H), 3.97 (d, J=2.2 Hz, 1H), 3.37-3.34 (m, 2H), 3.28-3.19 (m, 1H), 3.19-3.11 (m, 1H), 2.64 (s, 3H), 2.58-2.51 (m, 1H), 1.98 (t, J=12.5 Hz, 1H), 1.58 (s, 4H). $^{13}$C NMR (126 MHz. DMSO-d$_6$, 23° C.): δ 158.7, 157.6, 123.6, 113.5, 112.0, 104.7, 97.5, 61.6, 60.1, 59.4, 51.9, 50.5, 37.8, 26.3, 25.4, 24.0. FTIR (thin film) cm$^{-1}$: 2925 (w), 2097 (w), 1668 (s), 1549 (w), 1424 (m), 1107 (w), 745 (w). HRMS (DART) (m/z): calc'd for C$_{16}$H$_{21}$BrN$_7$O$_3$, [M+H]$^+$: 438.0884, found: 438.0875. TLC (18% methanol, 2% ammonium hydroxide in chloroform), Rf: 0.43 (UV, CAM).

General Procedure for Staudinger Reduction. Triphenylphosphine (2.40 equiv) was added to a suspension of azide derivative (1 equiv) in tetrahydrofuran-water (9:1, 0.1 M). Upon consumption of starting material as shown by thin layer chromatography, reaction mixture was diluted with dichloromethane and concentrated under reduced pressure. Crude residue was purified by flash column chromatography on silica gel (eluent: 0→10% methanol in dichloromethane, then 18% methanol and 2% ammonium hydroxide in chloroform) to afford amines 7g-7h.

3-Methylene Amine Derivative 7g was synthesized according to the general procedure for Staudinger reduction of azide derivatives using 3-methylene azide 7e (26.5 mg, 62.5 μmol, 1 equiv). After 3.5 days, the crude residue was purified by flash column chromatography on silica gel to afford amine 7g (21.9 mg, 88%) as a white solid $^1$H NMR (400 MHz, CD$_3$OD, 23° C.): δ 6.91 (d, J=4.1 Hz, 1H), 6.33 (d, J=4.1 Hz, 1H), 4.62 (dt, J=12.0, 6.0 Hz, 1H), 4.16-4.04 (m, 2H), 3.50-3.37 (m, 1H), 3.30-3.27 (m, 1H), 2.79 (s, 3H) 2.74 (t, J=7.0 Hz, 2H), 2.71-2.63 (m, 1H), 2.16 (t, J=12.7 Hz, 1H), 1.76 (p, J=6.5 Hz, 2H). $^{13}$C NMR (101 MHz, CD$_3$OD, 23° C.): δ 161.9, 161.1, 124.2, 116.2, 114.0, 107.5, 99.9, 62.2 (2C), 61.7, 53.8, 39.9, 39.4, 33.3, 24.9. FTIR (thin film) cm$^{-1}$: 2925 (w), 2359 (w), 1695 (m), 1652 (s), 1550 (m), 1424 (m), 1096 (w), 745 (w). HRMS (DART) (m/z): calc'd for C$_{16}$H$_{21}$BrN$_5$O$_3$, [M+H]$^+$: 398.0822, found: 398.0823. TLC (18% methanol, 2% ammonium hydroxide in chloroform), Rf: 0.07 (UV, CAM, ninhydrin).

4-Methylene Amine Derivative 7h was synthesized according to the general procedure for Staudinger reduction of azide derivatives using 4-methylene azide 7f (29.0 mg, 66.2 μmol, 1 equiv). After 3 days, the crude residue was purified by flash column chromatography on silica gel to afford 4-methylene amine 7h (26.6 mg, 97%) as a white solid. $^1$H NMR (500 MHz, CD$_3$OD, 23° C.): δ 6.91 (d, J=4.1 Hz, 1H), 6.33 (d, J=3.9 Hz, 1H), 4.61 (dt, J=12.1, 6.0 Hz, 1H), 4.12 (d, J=5.4 Hz, 1H), 4.08 (s, 1H), 3.38 (dt, J=9.1, 5.9 Hz, 1H), 3.26 (dt, J=9.1, 6.1 Hz, 1H), 2.78 (s, 3H), 2.71-2.63 (m, 3H), 2.15 (t, J=12.7 Hz, 1H), 1.69-1.50 (m, 4H). $^{13}$C NMR (126 MHz, CD$_3$OD, 23° C.): δ 161.8, 161.1, 124.2, 116.2, 114.0, 107.5, 99.8, 63.9, 62.2, 61.7, 53.8, 42.3, 39.4, 30.3, 28.1, 24.9. FTIR (thin film) cm$^{-1}$: 2926 (w), 2359 (w), 1652 (m), 1550 (m), 1423 (s), 1303 (w), 1096 (w), 745 (m). HRMS (ESI) (m/z): calc'd for C$_{16}$H$_{23}$BrN$_5$O$_3$, [M+H]$^+$:

412.0979, found: 412.0994. TLC (18% methanol, 2% ammonium hydroxide in chloroform), Rf: 0.08 (UV, CAM, ninhydrin).

3-Methylene Carbamate Derivative 7i. A solution of 4-nitrophenyl 2-(trimethylsilyl)ethyl carbonate[21] (5.8 mg, 21 µmol, 1.2 equiv) in dichloromethane (20 µL) was added to a solution of 3-methylene amine 7g (6.8 mg, 17 µmol, 1 equiv), triethylamine (3.6 µL, 26 µmol, 1.5 equiv), and 4-dimethylaminopyridine (0.4 mg, 3 µmol, 0.2 equiv) in dichloromethane (170 µL). After 26 h. reaction mixture was diluted with dichloromethane (1 mL) and purified by flash column chromatography on silica gel (eluent: 20% acetone in dichloromethane, then 0→18% methanol and 2% ammonium hydroxide in chloroform) to afford 3-methylene carbamate 7i (8.7 mg, 94%) as a white solid. $^1$H NMR (500 MHz, CD$_3$OD, 23° C.): δ 6.92 (d, J=4.2 Hz, 1H), 6.34 (d, J=3.9 Hz, 1H), 4.61 (dt, J=12.1, 6.0 Hz, 1H), 4.15-4.10 (m, 3H), 4.08 (s, 1H), 3.43-3.34 (m, 1H), 3.30-3.11 (m, 3H), 2.78 (s, 3H), 2.71-2.63 (m, 1H), 2.17 (t, J=12.7 Hz, 1H), 1.77 (p, J=6.3 Hz, 2H), 1.03-0.93 (m, 2H), 0.05 (s, 9H). $^{13}$C NMR (126 MHz, CD$_3$OD, 23° C.): δ 161.8, 161.1, 159.5, 124.2, 116.2, 114.0, 107.5, 99.9, 64.0, 62.2, 61.6 (2C), 53.8, 39.4, 39.0, 31.0, 24.9, 18.8, −1.3. FTIR (thin film) cm$^{-1}$: 2950 (w), 1698 (s), 1661 (s), 1552 (w), 1424 (m), 1250 (w), 838 (w). HRMS (DART) (m/z): calc'd for C$_{21}$H$_{33}$BrN$_5$O$_5$Si, [M+H]$^+$: 542.1429, found: 542.1429. TLC (18% methanol, 2% ammonium hydroxide in chloroform), Rf: 0.63 (UV, CAM).

General Procedure for Acylation of Amines Acylating reagent (2.0 equiv) was added to a solution of amine derivative (1 equiv) and triethylamine (2.0 equiv) in tetrahydrofuran (400 µL). Upon complete conversion of starting material as shown by thin layer chromatography, reaction was diluted with dichloromethane (3 mL) and quenched with saturated aqueous sodium bicarbonate (3 mL). Layers were separated and aqueous was extracted with dichloromethane (3×5 mL). Combined organic layers were dried over anhydrous sodium sulfate and concentrated under reduced pressure. Crude residue was purified by flash column chromatography on silica gel (eluent: 0→7% methanol in dichloromethane, then 9% methanol and 1% ammonium hydroxide in chloroform→18% methanol and 2% ammonium hydroxide in chloroform) to afford amides 7j-7k.

Acetamide Derivative 7j was synthesized according to the general procedure for acylation of amine derivatives using acetic anhydride and amine 7h (6.8 mg, 17 µmol, 1 equiv) with 4-dimethylaminopyridine (0.4 mg, 3 µmol, 0.2 equiv) additive. After 2.5 hours, the crude residue after work-up was purified by flash column chromatography on silica gel to afford acetamide 7j (5.5 mg, 73%) as a white solid. $^1$H NMR (500 MHz, CD$_3$OD, 23° C.): δ 6.91 (d, J=4.1 Hz, 1H), 6.33 (d, J=4.0 Hz, 1H), 4.61 (dt, J=12.1, 6.1 Hz, 1H), 4.12 (d, J=5.5 Hz, 1H), 4.10 (s, 1H), 3.42-3.36 (m, 1H), 3.29-3.12 (m, 3H), 2.79 (s, 3H), 2.70-2.63 (m, 1H), 2.15 (t, J=12.7 Hz, 1H), 1.93 (s, 3H), 1.66-1.53 (m, 4H). $^{13}$C NMR (126 MHz, CD$_3$OD, 23° C.): δ 173.4, 161.9, 161.1, 124.2, 116.2, 114.0, 107.5, 99.9, 63.7, 62.2, 61.7, 53.8, 40.2, 39.4, 27.9, 27.4, 24.9, 22.7. FTIR (thin film) cm$^{-1}$: 2929 (w), 2359 (w), 1652 (s), 1550 (m), 1423 (m), 1373 (w), 1096 (w), 747 (w). HRMS (ESI) (m/z): calc'd for C$_{18}$H$_{25}$BrN$_5$O$_4$, [M+H]$^+$: 454.1084, found: 454.1082. TLC (18% methanol, 2% ammonium hydroxide in chloroform), Rf: 0.34 (UV, CAM).

Benzamide Derivative 7k was synthesized according to the general procedure for acylation of amine derivatives using benzoyl chloride and amine 7h (7.1 mg, 17 µmol, 1 equiv). After 3.5 hours, the crude residue after work-up was purified by flash column chromatography on silica gel to afford benzamide 7k (7.7 mg, 87%) as a white solid. $^1$H NMR (500 MHz, CD$_3$OD, 23° C.): δ 7.85-7.78 (m, 2H), 7.56-7.49 (m, 1H), 7.4-7.40 (m, 2H), 6.91 (d, J=4.1 Hz, 1H), 6.33 (d, J=3.9 Hz, 1H), 4.61 (dt, J=12.0, 6.0 Hz, 1H), 4.14 (s, 1H), 4.12 (d, J=5.4 Hz, 1H), 3.47-3.32 (m, 4H), 2.79 (s, 3H), 2.70-2.63 (m, 1H), 2.16 (t, J=12.7 Hz, 1H), 1.77-1.65 (m, 4H). $^{13}$C NMR (126 MHz, CD$_3$OD, 23° C.): δ 170.5, 161.9, 161.1, 135.9, 132.7, 129.7, 128.4, 124.2, 116.2, 114.0, 107.5, 99.9, 63.7, 62.3, 61.7, 53.8, 40.8, 39.4, 28.0, 27.5, 24.9 FTIR (thin film) cm$^{-1}$: 2933 (w), 2359 (w), 1700 (s), 1652 (s), 1550 (m), 1424 (m), 1096 (w), 712 (w). HRMS (ESI) (m/z): calc'd for C$_{23}$H$_{27}$BrN$_5$O$_4$, [M+H]$^+$: 516.1241, found: 516.1225 TLC (18% methanol, 2% ammonium hydroxide in chloroform), Rf: 0.50 (UV, CAM).

Urea Intermediate 16. 1,1'-Carbonyldiimidazole (362 mg, 2.23 mmol, 1.10 equiv) and 4-dimethylaminopyridine (37.3 mg, 305 µmol, 0.150 equiv) were added sequentially to a solution of 1-(tricyclohexylstannyl)-methanamine (15) (theoretical: 808 mg, 2.03 mmol, 1 equiv)[22] in dichloromethane (34 mL). After 45 min, the reaction mixture was concentrated and the crude residue was purified by flash column chromatography on silica gel (eluent: 30→75% ethyl acetate in hexanes) to afford urea intermediate 16 (847 mg, 85% over two steps) as a white crystalline solid. $^1$H NMR (600 MHz, CDCl$_3$, 23° C.): δ 8.07 (s, 1H), 7.31 (s, 1H), 7.07 (s, 1H), 6.32 (t, J=5.5 Hz, 1H), 3.18-3.04 (m, 2H), 1.95-1.81 (m, 6H), 1.72-1.50 (m, 18H), 1.37-1.19 (m, 9H). $^{13}$C NMR (101 MHz, CDCl$_3$, 23° C.): δ 149.2, 135.7, 129.9, 116.3, 32.4, 29.3, 27.6, 27.2, 23.7. FTIR (thin film) cm$^{-1}$: 3223 (w), 3036 (w), 2913 (s), 2843 (m), 1710 (s), 1288 (m), 1075 (m), 842 (m). HRMS (ESI) (m/z): calc'd for C$_{23}$H$_{40}$N$_3$OSn, [M+H]$^+$: 494.2188, found: 494.2223. TLC (509% ethyl acetate in hexanes), Rf: 0.27 (UV, CAM).

General Procedure for the Synthesis of Substituted Ureas. Amine (1.00 equiv) and 4-dimethylaminopyridine (0.150 equiv) were added to a solution of urea intermediate 16 (1 equiv) in dichloromethane (0.2 M). The reaction flask was sealed with a Teflon wrapped glass stopper and heated to 40° C. Upon consumption of the starting materials as determined by thin layer chromatography, the reaction mixture was cooled to 23° C. and concentrated under reduced pressure. The crude residue was purified by flash column chromatography on silica gel to afford substituted ureas 13a-13c.

4-Methylene Alcohol Urea 13a was prepared according to the general procedure for synthesis of substituted ureas using 4-aminobutanol (156 µL, 1.69 mmol, 1.00 equiv). After 24 h, the crude residue was purified by flash column chromatography on silica gel (eluent: 30→100% ethyl acetate in hexanes) to afford 4-methylene alcohol urea 13a (790 mg, 91%) as a white solid $^1$H NMR (600 MHz, CDCl$_3$, 23° C.): δ 4.66 (s, 1H), 4.23 (t, J=4.8 Hz, 1H), 3.69 (q, J=5.6 Hz, 2H), 3.26 (q, J=6.3 Hz, 2H), 2.85-2.64 (m, 2H), 1.94-1.77 (m, 6H), 1.72-1.46 (m, 20H), 1.38-1.21 (m, 9H). $^{13}$C NMR (126 MHz, CDCl$_3$, 23° C.): δ 160.2, 62 3, 40.3, 32.4, 29 7, 29.2, 27.2, 27.1, 26.9, 22.1. FTIR (thin film) cm$^{-1}$: 3307 (m), 2911 (s), 2841 (m), 1616 (m), 1569 (s), 1443 (m), 990 (m). HRMS (ESI) (m/z): calc'd for C$_{24}$H$_{46}$N$_2$NaO$_2$Sn [M+Na]$^+$: 537.2473, found: 537.2488. TLC (75% ethyl acetate in hexanes), Rf: 0.28 (UV, CAM).

6-Methylene Alcohol Urea 13b was prepared according to the general procedure for synthesis of substituted ureas using 6-aminohexanol (357 mg, 3.05 mmol, 1.00 equiv). After 25 h, The crude residue was purified by flash column chromatography on silica gel (eluent: 40→80% ethyl acetate in hexanes) to afford 6-methylene alcohol urea 13b (1.56 g, 95%) as a white solid. $^1$H NMR (500 MHz, CDCl$_3$, 23° C.): δ 4.97 (t, J=5.7 Hz, 1H), 4.62 (s, 1H), 3.56 (q, J=6.1 Hz, 2H), 3.12 (q, J=6.7 Hz, 2H), 2.96 (d, J=5.1 Hz, 1H), 2.78-2.68 (m, 2H), 1.88-1.75 (m, 6H), 1.66-1.44 (m, 22H), 1.38-1.16 (m, 13H). $^{13}$C NMR (126 MHz, CDCl$_3$, 23° C.): δ 160.0, 62.6, 40.5, 32.7, 32.4, 30.5, 29.3, 27.2, 26.9, 26.6, 25.4, 22.2. FTIR (thin film) cm$^{-1}$: 3336 (w), 2915 (s), 2845 (s), 1729 (w), 1585 (m), 1444 (m), 991 (m). HRMS (DART) (m/z): calc'd for $C_{26}H_{51}BrN_2O_2Sn$, [M+H]$^+$: 543.2967, found: 543.2966 TLC (75% ethyl acetate in hexanes), Rf: 0.57 (UV, CAM).

Triethyleneglycol Urea 13c was prepared according to the general procedure for synthesis of substituted ureas using 2-(2-(2-aminoethoxy)ethoxy)ethan-1-ol$^{23}$ (455 mg, 3.05 mmol, 1.00 equiv). After 24 h, the crude residue was purified by flash column chromatography on silica gel (eluent: 40→100% ethyl acetate in hexanes) to afford triethyleneglycol urea 13c (1.47 g, 84%) as a white solid. $^1$H NMR (400 MHz, CDCl$_3$, 23° C.): δ 5.13 (t, J=4.9 Hz, 1H), 4.47 (s, 1H), 3.81-3.75 (m, 2H), 3.73-3.59 (m, 8H), 3.43 (q, J=5.3 Hz, 2H), 2.88-2.77 (m, 2H), 2.72 (t, J=6.1 Hz, 1H), 1.96-1.81 (m, 6H), 1.73-1.54 (m, 18H), 1.42-1.21 (m, 9H) $^{13}$C NMR (126 MHz, CDCl$_3$, 23° C.): δ 159.9, 72.6, 70 9, 70.5 (2C), 61.9, 40.5, 32.4, 29.3, 27.2, 26.9, 22.2. FTIR (thin film) cm$^{-1}$: 3339 (w), 2914 (s), 2845 (s), 1729 (w), 1553 (m), 1445 (m), 1070 (s), 991 (m). HRMS (ESI) (m/z): calc'd for $C_{26}H_{50}N_2NaO_4Sn$, [M+Na]$^+$: 597.2685, found: 597.2714. TLC (75% ethyl acetate in hexanes), Rf: 0.18 (UV, CAM).

4-Methylene Alcohol Pre-Agelastatin 11a was prepared according to the published procedure for synthesis of pre-agelastatins$^{3a}$ using urea 13a (659 mg, 1.28 mmol, 3.00 equiv). The crude residue adsorbed onto silica gel was purified by flash column chromatography on silica gel (eluent: 9% methanol and 1% ammonium hydroxide in chloroform→18% methanol and 2% ammonium hydroxide in chloroform) to afford 4-methylene alcohol pre-agelastatin 11a (94 mg, 53% over two steps) as an off-white solid. $^1$H NMR (600 MHz, CD$_3$OD, 23° C.): δ 6.91 (d, J=4.0 Hz, 1H), 6.28 (d, J=4.0 Hz, 1H), 6.00 (s, 1H), 4.77 (s, 1H), 4.55 (t, J=7.3 Hz, 1H), 3.68-3.60 (m, 1H), 3.58-3.55 (m, 2H), 3.52-3.46 (m, 1H), 3.34 (s, 3H), 2.93 (dd, J=15.5, 6.8 Hz, 1H), 2.78 (dd, J=15.5, 7.9 Hz, 1H), 1.71-1.64 (m, 2H), 1.54-1.51 (m, 2H). $^{13}$C NMR (126 MHz, CD$_3$OD, 23° C.): δ 161.1, 155.9, 124.5, 119.7, 116.1, 113.5, 108.8, 108.7, 84.7, 62.5, 58.2, 55.2, 41.9, 30.8, 29.5, 27.5. δ FTIR (thin film) cm$^{-1}$: 3207 (br-m), 2932 (w), 2871 (w), 1652 (s), 1550 (m), 1418 (m), 1076 (s). HRMS (DART) (m/z): calc'd for $C_{16}H_{22}BrN_4O_4$, [M+H]$^+$: 413.0819, found: 413.0816. TLC (18% methanol, 2% ammonium hydroxide in chloroform), Rf: 0.31 (UV, CAM).

6-Methylene Alcohol Pre-Agelastatin 11 b was prepared according to the published procedure for synthesis of pre-agelastatins$^{3a}$ using urea 13b (975 mg, 1.80 mmol, 3.00 equiv). The crude residue adsorbed onto silica gel was purified by flash column chromatography on silica gel (eluent: 6% methanol and 0.6% ammonium hydroxide in chloroform→14% methanol and 1.6% ammonium hydroxide in chloroform) to afford 6-methylene alcohol pre-agelastatin 11b (178 mg, 67% over two steps) as an off-white solid. $^1$H NMR (500 MHz, CD$_3$OD, 23° C.): δ 6.91 (d, J=4.1 Hz, 1H), 6.28 (d, J=4.1 Hz, 1H), 6.02 (s, 1H), 4.76 (d, J=1.4 Hz, 1H), 4.55 (ddd, J=7.7, 6.5, 1.3 Hz, 1H), 3.63-3.51 (m, 3H), 3.44-3.38 (m, 1H), 3.34 (s, 3H), 2.92 (dd, J=15.4, 6.7 Hz, 1H), 2.77 (ddd, J=15.4, 7.9, 0.9 Hz, H), 1.65-1.49 (m, 4H), 1.42-1.30 (m, 4H). $^{13}$C NMR (126 MHz, CD$_3$OD, 23° C.): δ 161.1, 155.9, 124.5, 119.8, 116.1, 113.6, 108.7 (2C), 84.7, 62.9, 58.3, 55.2, 42.0, 33.6, 30.9, 29.6, 27.7, 26.7. FTIR (thin film) cm$^{-1}$: 3212 (br-m), 2931 (m), 2857 (w), 1658 (s), 1551 (w), 1419 (m), 1084 (m). HRMS (DART) (m/z): calc'd for $C_{18}H_{26}BrN_4O_4$, [M+H]$^+$: 441.1132, found: 441.1132. TLC (18% methanol, 2% ammonium hydroxide in chloroform), Rf: 0.56 (UV, CAM).

Triethyleneglycol Pre-Agelastatin 11c was prepared according to the published procedure for synthesis of pre-agelastatins$^{3a}$ using urea 13c (1.29 g, 2.25 mmol, 3.00 equiv). The crude residue adsorbed onto silica gel was purified by flash column chromatography on silica gel (eluent: 9% methanol and 1% ammonium hydroxide in chloroform→18% methanol and 2% ammonium hydroxide in chloroform) to afford triethyleneglycol pre-agelastatin 11c (218 mg, 61% over two steps) as an off-white solid. $^1$H NMR (400 MHz, CD$_3$OD, 23° C.): δ 6.91 (d, J=4.1 Hz, 1H), 6.27 (d, J=4.0 Hz, H), 5.97 (s, 1H), 4.76 (d, J=1.5 Hz, 1H), 4.69 (td, J=7.4, 1.5 Hz, 1H), 3.70-3.65 (m, 2H), 3.65-3.61 (m, 4H), 3.60-3.55 (m, 4H), 3.54-3.47 (m, 2H), 3.34 (s, 3H), 2.99 (dd, J=15.5, 6.9 Hz, 1H), 2.83 (dd, J=15.5, 7.8 Hz, 1H). $^{13}$C NMR (101 MHz, CD$_3$OD, 23° C.): δ 161.2, 155.9, 124.5, 120.9, 116.0, 113.4, 108.8, 108.2, 84.7, 73.8, 71.8, 71.5, 70.6, 62 3, 57.9, 55.2, 42 7, 29.7. FTIR (thin film) cm$^{-1}$: 3226 (br-m), 2921 (m), 2870 (m), 1652 (s), 1419 (m), 1086 (m). HRMS (DART) (m/z): calc'd for $C_{18}H_{26}BrN_4O_6$, [M+H]$^+$: 473.1030, found: 473.1021. TLC (18% methanol, 2% ammonium hydroxide in chloroform). Rf: 0.47 (UV. CAM).

4-Methylene Alcohol Derivative 8a and Pentacyclic Derivative 14 were prepared according to the published procedure for synthesis of (−)-agelastatin A$^{3a}$ using 4-methylene alcohol pre-agelastatin 11a (26.0 mg, 63.0 μmol, 1 equiv). The crude residue adsorbed onto silica gel was purified by flash column chromatography on silica gel (chloroform→18% methanol and 2% ammonium hydroxide in chloroform) to afford 4-methylene alcohol derivative 8a (0.8 mg, 3%) as an off-white solid along with the pentacyclic derivative 14 (2.6 mg, 11%) as an off-white solid. 4-Methylene Alcohol Derivative 8a: $^1$H NMR (600 MHz, CD$_3$OD, 23° C.): δ 6.91 (d, J=4.1 Hz, 1H), 6.33 (d, J=4.1 Hz, 1H), 4.65 (dt, J=12.0, 5.9 Hz, 1H), 4.09 (d, J=5.5 Hz, 1H), 3.86 (s, 1H), 3.61 (td, J=6.6, 2.8 Hz, 2H), 3.30-3.18 (m, 2H), 2.65 (dd, J=13.1, 6.3 Hz, 1H), 2.17 (t, J=12.7 Hz, 1H), 1.84-1.75 (m, 2H), 1.62 (p, J=6.8 Hz, 2H). $^{13}$C NMR (101 MHz, CD$_3$OD, 23° C.): δ 161.9, 161.2, 124.3, 116.2, 113.9, 107.4, 96.1, 67.7, 62.8, 62.4, 54.5, 41.3, 40.3, 31.4, 28.0. FTIR (thin film) cm$^{-1}$: 3276 (br-m), 2933 (w), 1653 (s), 1552 (w), 1424 (m), 1375 (w). HRMS (DART) (m/z): calc'd for $C_{15}H_{20}BrN_4O_4$, [M+H]$^+$: 399.0662, found: 399.0655. TLC (18% methanol, 2% ammonium hydroxide in chloroform), Rf: 0.19 (U V, CAM). Pentacyclic Derivative 14: $^1$H NMR (500 MHz, CD$_3$OD, 23° C.): δ 6.91 (d, J=4.1 Hz, 1H), 6.33 (d, J=4.1 Hz, 1H), 4.64 (dt, J=12.0, 6.0 Hz, 1H), 4.14 (d, J=5.3 Hz, 1H), 3.95 (s, 1H), 3.87 (d, J=12.9 Hz, 1H), 3.79 (d, J=14.4 Hz, 1H), 3.41-3.32 (m, 2H), 2.97-2.89 (m, 1H), 2.50 (dd, J=13.1, 6.7 Hz, 1H), 2.14 (t, J=12.6 Hz, 1H), 1.77-1.59 (m, 4H). $^{13}$C NMR (101 MHz, CD$_3$OD, 23° C.): δ 161.9, 161.2, 124.3, 116.3, 114.0, 107.5, 100.7, 66.2, 64.8, 62.0, 54.2, 41.9, 41.2, 31.3, 27.4. FTIR (thin film) cm$^{-1}$: 3247 (br-m), 2940 (m), 1696 (s), 1659 (s), 1552 (m), 1422 (s), 1091 (m). HRMS (DART) (m/z): calc'd for $C_{15}H_{18}BrN_4O_3$, [M+H]$^+$: 381.0557, found: 381.0552. TLC (18% methanol, 2% ammonium hydroxide in chloroform), Rf: 0.59 (UV, CAM).

6-Methylene Alcohol Derivative 8b was prepared according to the published procedure for synthesis of (−)-agelastatin A$^{3a}$ using 6-methylene pre-agelastatin 11 b (1.00×10$^2$ mg, 227 μmol, 1 equiv). The crude residue adsorbed onto silica gel was purified by flash column chromatography on silica gel (6% methanol and 0.6% ammonium hydroxide in chloroform→18% methanol and 2% ammonium hydroxide in chloroform) to afford 6-methylene alcohol derivative 8b (35 mg, 36%) as an off-white solid. $^1$H NMR (400 MHz, CD$_3$OD, 23° C.): δ 6.91 (d, J=4.0 Hz, 1H), 6.33 (d, J=4.1 Hz, 1H), 4.63 (dt, J=12.0, 5.9 Hz, 1H), 4.09 (d, J=5.5 Hz, 1H), 3.85 (s, 1H), 3.56 (t, J=6.5 Hz, 2H), 3.23 (dq, J=14.5, 8.4 Hz, 2H), 2.63 (dd, J=13.0, 6.3 Hz, 1H), 2.17 (t, J=12.6 Hz, 1H), 1.84-1.67 (nm, 2H), 1.56 (dd, J=8.8, 5.2 Hz, 2H), 1.47-1.39 (m, 4H). $^{13}$C NMR (101 MHz, CD$_3$OD, 23° C.): δ 161.9, 161.2, 124.3, 116.2, 114.0, 107.3, 96.1, 67.7, 63.0, 62.4, 54.5, 41.4, 40.4, 33.8, 31.5, 28.3, 26.9. FTIR (thin film) cm$^{-1}$: 3254 (br-s), 2929 (m), 2856 (m), 1652 (s), 1551 (m), 1422 (s), 1027 (w). HRMS (DART) (m/z): calc'd for C$_{17}$H$_{24}$BrN$_4$O$_4$, [M+H]$^+$: 427.0975, found: 427.0970. TLC (18% methanol, 2% ammonium hydroxide in chloroform), Rf: 0.27 (UV, CAM).

Triethyleneglycol Derivative Sc was prepared according to the published procedure for synthesis of (−)-agelastatin A$^{3a}$ using triethylene glycol pre-agelastatin 11c (1.80×10$^2$ mg, 3.80×10$^2$ μmol, 1 equiv). The crude residue adsorbed onto silica gel was purified by flash column chromatography on silica gel (6% methanol and 0.6% ammonium hydroxide in chloroform→18% methanol and 2% ammonium hydroxide in chloroform) to afford triethyleneglycol derivative 8c (52 mg, 30%) as an off-white solid. $^1$H NMR (600 MHz, CD$_3$OD, 23° C.): δ 6.92 (d, J=3.9 Hz, 1H), 6.33 (d, J=3.9 Hz, 1H), 4.68-4.59 (m, 1H), 4.09 (d, J=5.7 Hz, 1H), 3.89 (s, 1H), 3.73-3.62 (m, 9H), 3.55 (h, J=7.3, 6.5 Hz, 2H), 3.42-3.33 (m, 1H), 2.79 (dd, J=12.9, 6.4 Hz, 1H), 2.19-2.09 (m, 1H) $^{13}$C NMR (126 MHz, CD$_3$OD, 23° C.): δ 161.7, 161.2, 124.3, 116.2, 113.9, 107.4, 95.9, 73.8, 71.6, 71.5, 70.6, 67.8, 62.3, 62.2, 54.6, 41.5, 40.1. FTIR (thin film) cm$^{-1}$: 3264 (br-s), 2921 (w), 1645 (s), 1551 (m), 1093 (m), 1024 (m). HRMS (DART) (m/z): calc'd for C$_{17}$H$_{24}$BrN$_4$O$_6$, [M+H]$^+$: 459.0874, found: 459.0895. TLC (18% methanol, 2% ammonium hydroxide in chloroform), Rf: 0.35 (UV, CAM).

General Procedure for the Synthesis of Azide Derivatives. Alcohol derivative (1 equiv) and triphenylphosphine were dissolved in tetrahydrofuran. After 5 min, diisopropylazodicarboxylate and diphenylphosphorylazide were added sequentially. Upon consumption of the alcohol derivative by thin layer chromatography, the reaction mixture was concentrated under reduced pressure. The crude residue was purified by flash column chromatography to afford azide derivatives 8d-e.

6-Methylene Azide Derivative 8d was synthesized from 6-methylene alcohol derivative 8b according to the general procedure for the synthesis of azide derivatives using triphenylphosphine (12.6 mg, 48.0 μmol, 2.00 equiv), diisopropylazodicarboxylate (9.4 μL, 48 μmol, 2.0 equiv), and diphenylphosphorylazide (10.6 μL, 48.0 μmol, 2.00 equiv) in tetrahydrofuran (350 μL). After 21 h, the crude residue was purified by flash column chromatography on silica gel (chloroform→18% methanol and 2% ammonium hydroxide in chloroform) to afford 6-methylene azide derivative 8d (4.2 mg, 38%) as a white solid along with recovered 6-methylene alcohol derivative 8b (3.5 mg, 34%). Reaction yield was 72% based on recovered starting material. $^1$H NMR (600 MHz, CD$_3$OD, 23° C.): δ 6.91 (d, J=4.1 Hz, 1H), 6.34 (d, J=4.1 Hz, 1H), 4.64 (dt, J=12.1, 5.9 Hz, 1H), 4.09 (d, J=5.5 Hz, 1H), 3.86 (s, 1H), 3.28-3.16 (m, 2H), 2.63 (dd, J=13.1, 6.3 Hz, 1H), 2.17 (t, J=12.6 Hz, 1H), 1.83-1.67 (m, 2H), 1.66-1.37 (m, 6H), 1.32-1.22 (m, 2H). $^{13}$C NMR (126 MHz, CD$_3$OD, 23° C.): 161.9, 161.2, 124.3, 116.2, 114.0, 107.2, 96.1, 67.7, 62.4, 54.5, 52.5, 41.4, 40.3, 31.4, 30.0, 27.9, 27.8. δ FTIR (thin film) cm$^{-1}$: 3222 (br-m), 2930 (m), 2856 (s), 2095 (s), 1669 (s), 1118 (m). HRMS (DART) (m/z) calc'd for C$_{17}$H$_{23}$BrN$_7$O$_3$, [M+H]$^+$: 452.1040, found: 452.1058 TLC (9% methanol, 10/% ammonium hydroxide in chloroform), Rf: 0.28 (UV, CAM).

Triethyleneglycol Bis-Azide Derivative Se was synthesized from triethyleneglycol derivative 8c according to the general procedure for the synthesis of azide derivatives using triphenylphosphine (36.0 mg, 137 μmol, 10.0 equiv), diisopropylazodicarboxylate (27.0 μL, 137 μmol, 10.0 equiv), and diphenylphosphorylazide (31.0 μL, 137 μmol, 10.0 equiv) in tetrahydrofuran (274 μL). After 6 h, the crude residue was purified by flash column chromatography on silica gel (chloroform→18% methanol and 2% ammonium hydroxide in chloroform) to afford triethyleneglycol bis-azide derivative 8e (3.7 mg, 54%) as a white solid. $^1$H NMR (500 MHz, CD$_3$OD, 23° C.): δ 6.93 (d, J=4.1 Hz, 1H), 6.35 (d, J=4.0 Hz, 1H), 4.79 (dt, J=12.1, 6.2 Hz, 1H), 4.23 (s, 1H), 4.18 (d, J=5.5 Hz, 1H), 3.82-3.56 (m, 6H), 3.53 (t, J=5.7 Hz, 2H), 3.33 (dd, J=5.2, 1.8 Hz, 2H), 2.98 (dd, J=13.5, 6.5 Hz, 1H), 2.13-2.06 (m, 1H), 1.35-1.26 (m, 2H). $^{13}$C NMR (126 MHz, CD$_3$OD, 23° C.): S 161.3, 161.0, 124.2, 116.4, 114.1, 107.7, 88.5, 71.7 (2C), 71.3, 70.4, 66.1, 62.1, 54.6, 51.9, 41.5, 39.9. FTIR (thin film) cm$^{-1}$. 3255 (br-w), 2920 (m), 2852 (w), 2105 (s), 1700 (m), 1662 (s), 1424 (m), 1102 (br-m). HRMS (DART) (m/z): calc'd for C$_{17}$H$_{21}$BrN$_7$O$_4$, [M−N$_3$]$^+$: 466.0833, found: 466.0922 TOF MS (ESI) (m/z): calc'd for C$_{17}$H$_{21}$BrN$_{10}$NaO$_4$, [M+Na]$^+$: 531.0823, found: 531.12. TLC (18% methanol, 2% ammonium hydroxide in chloroform), Rf: 0.50 (UV, CAM).

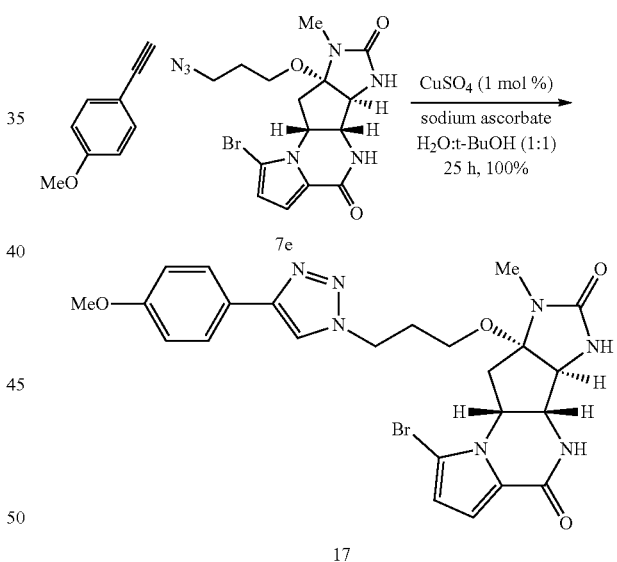

17

Figure 16:
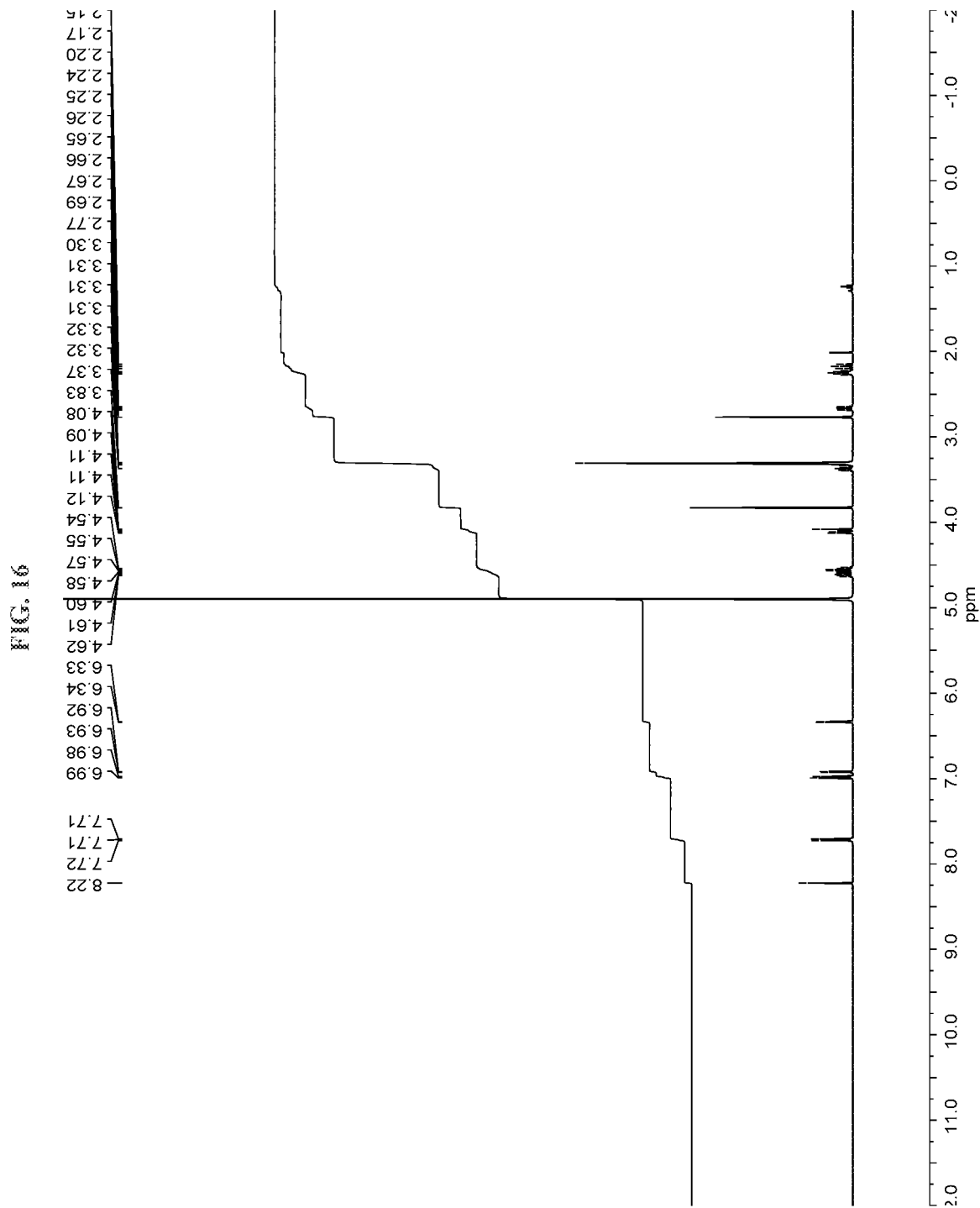
FIG. 16 is a $^1$H NMR spectrum confirming the structure of triazole 17.
Figure 17:
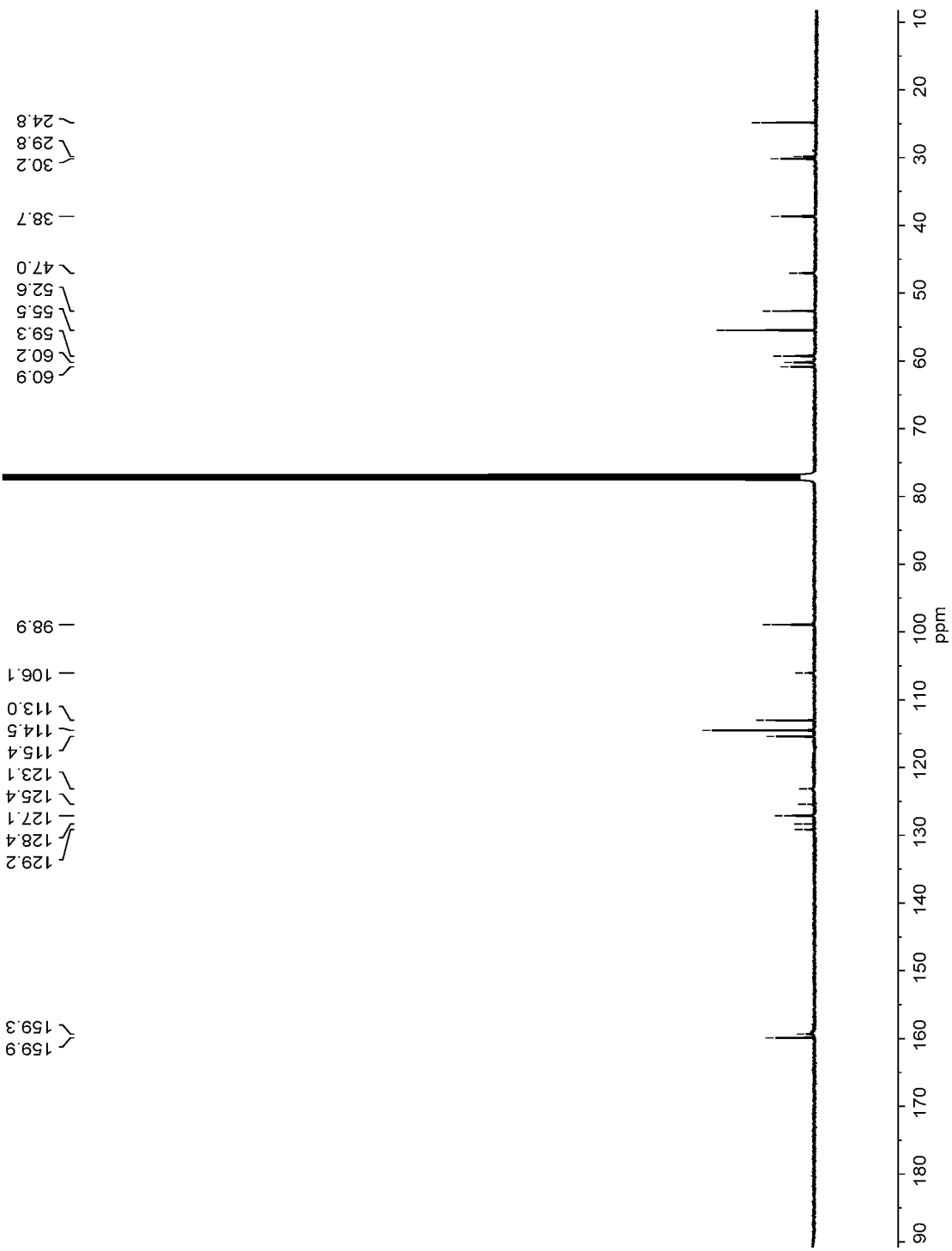
FIG. 17 is a $^{13}$C NMR spectrum confirming the structure of triazole 17.

Procedure for the Synthesis of Triazole 17 from Azide 7e. Azide 7e (10.6 mg, 25.0 μmol, 1 equiv) and 4-ethynylanisole (3.3 μL, 25.0 μmol, 1.0 equiv) were suspended in t-BuOH (75 μL) and H$_2$O (75 μL). A freshly prepared solution of sodium ascorbate (1.0 M in H$_2$O, 2.5 μL, 0.1 equiv) was added, followed by a freshly prepared solution of copper (II) sulfate pentahydrate (0.3 M in H$_2$O, 0.8 μL, 0.01 equiv). The reaction mixture was sealed under an atmosphere of argon and stirred vigorously. After 25 h, thin layer chromatography indicated full consumption of starting material. The reaction solution was diluted with dichloromethane (2 mL) and methanol (2 mL) and concentrated under reduced pressure. The crude residue was purified flash column chromatography on silica gel (eluent: 5→10% methanol in dichloromethane with 2% toluene) to afford 1,2,3-triazole 17 (13.9 mg, 100%) as a white solid. Spectral data is shown in FIGS. 16 and 17. $^1$H NMR (500 MHz, CD$_3$OD, 25° C.): δ 8.22 (s, 1H), 7.72 (d, J=8.8 Hz, 1H), 6.98 (d, J=8.8 Hz, 2H), 6.92 (d, J=4.1 Hz, 1H), 6.34 (d, J=4.1 Hz, 1H), 4.64-4.50 (m, 3H), 4.12 (d, J=5.5 Hz, 1H), 4.08 (s, 1H), 3.83 (s, 3H), 3.41-3.35 (m, 1H), 3.36-3.30 (m, 1H), 2.77 (s, 3H), 2.67 (dd, J=13.3, 6.4 Hz, 1H), 2.25 (p, J=6.3 Hz, 2H), 2.17 (t, J=12.8 Hz, 1H). $^{13}$C NMR (100 MHz, CDCl$_3$, 25° C.): δ 159.9, 159.3, 129.2, 128.4, 127.1, 125.4, 123.1, 115.4, 114.5, 113.0, 106.1, 98.9, 60.9, 60.2, 59.3, 55.5, 52.6, 47.0, 38.7, 30.2, 29.8, 24.8. TLC (7% methanol in dichloromethane with 2% toluene). Rf: 0.28 (UV, CAM).

3.31-3.26 (m, 2H), 2.58-2.53 (m, 1H), 2.15 (t, J=12.2 Hz, 1H), 1.94-1.91 (m, 2H), 1.62-1.55 (m, 2H), 1.48-1.38 (m, 6H), 1.28-1.24 (m, 2H), $^{19}$F NMR (376 MHz, CD$_3$OD, 25° C.): δ −134.7 (m, 2F), −140.0 (m, 2F), −140.4 (m, 2F), −153.2 (m, 1F), −163.7 (m, 2F). TLC (8% methanol in dichloromethane), Rf: 0.08 (UV, CAM).

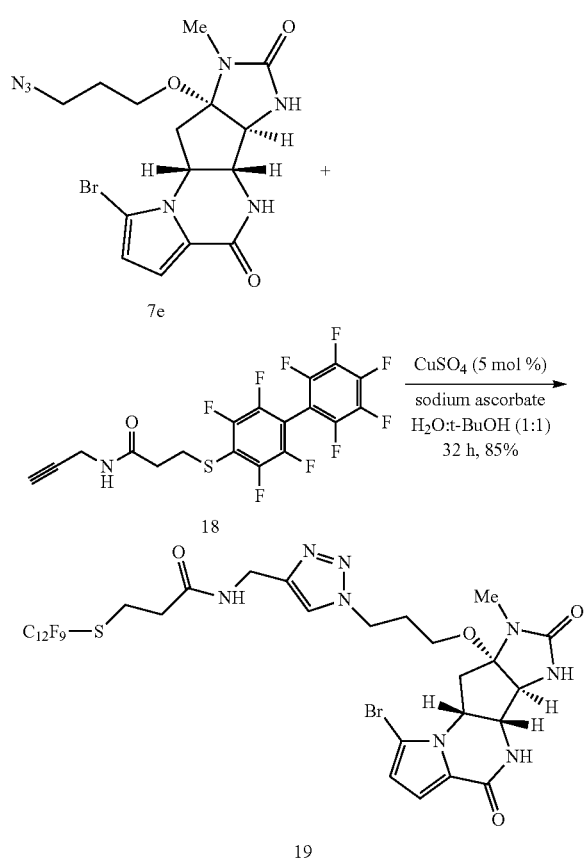

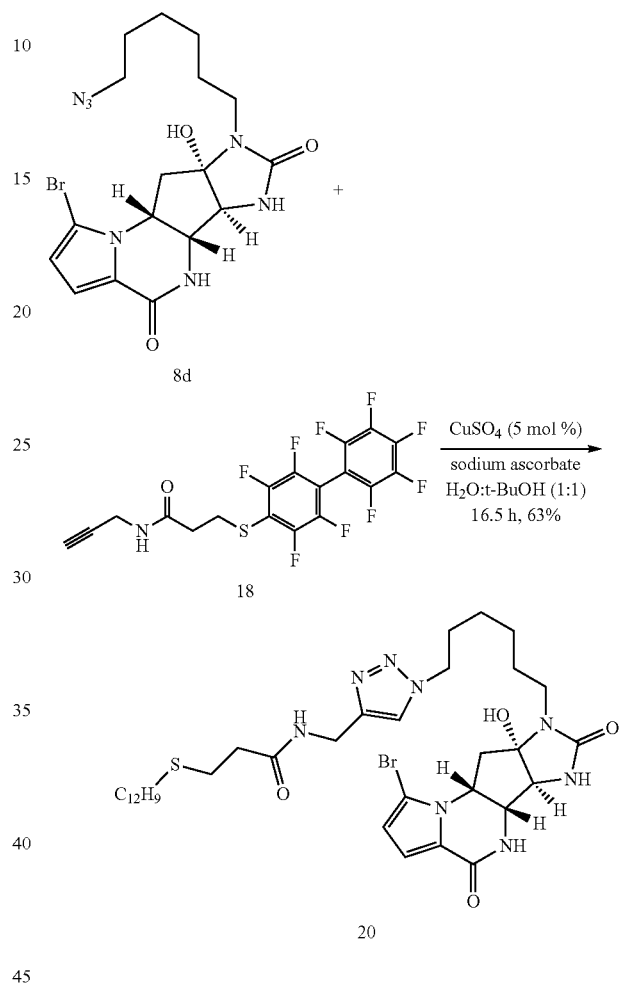

Figure 18:
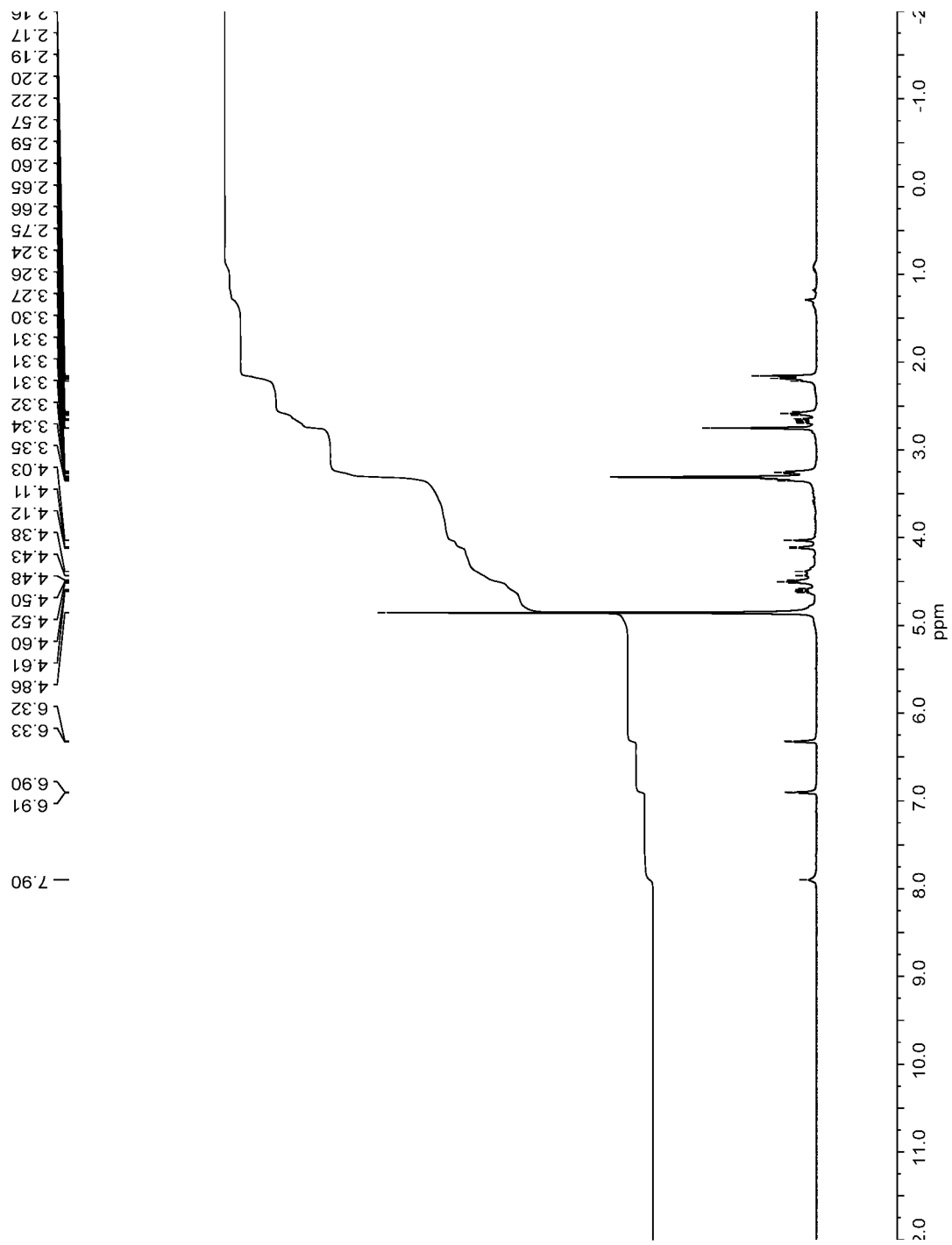
FIG. 18 is $^1$H NMR spectrum confirming the structure of triazole 19.
Figure 19:
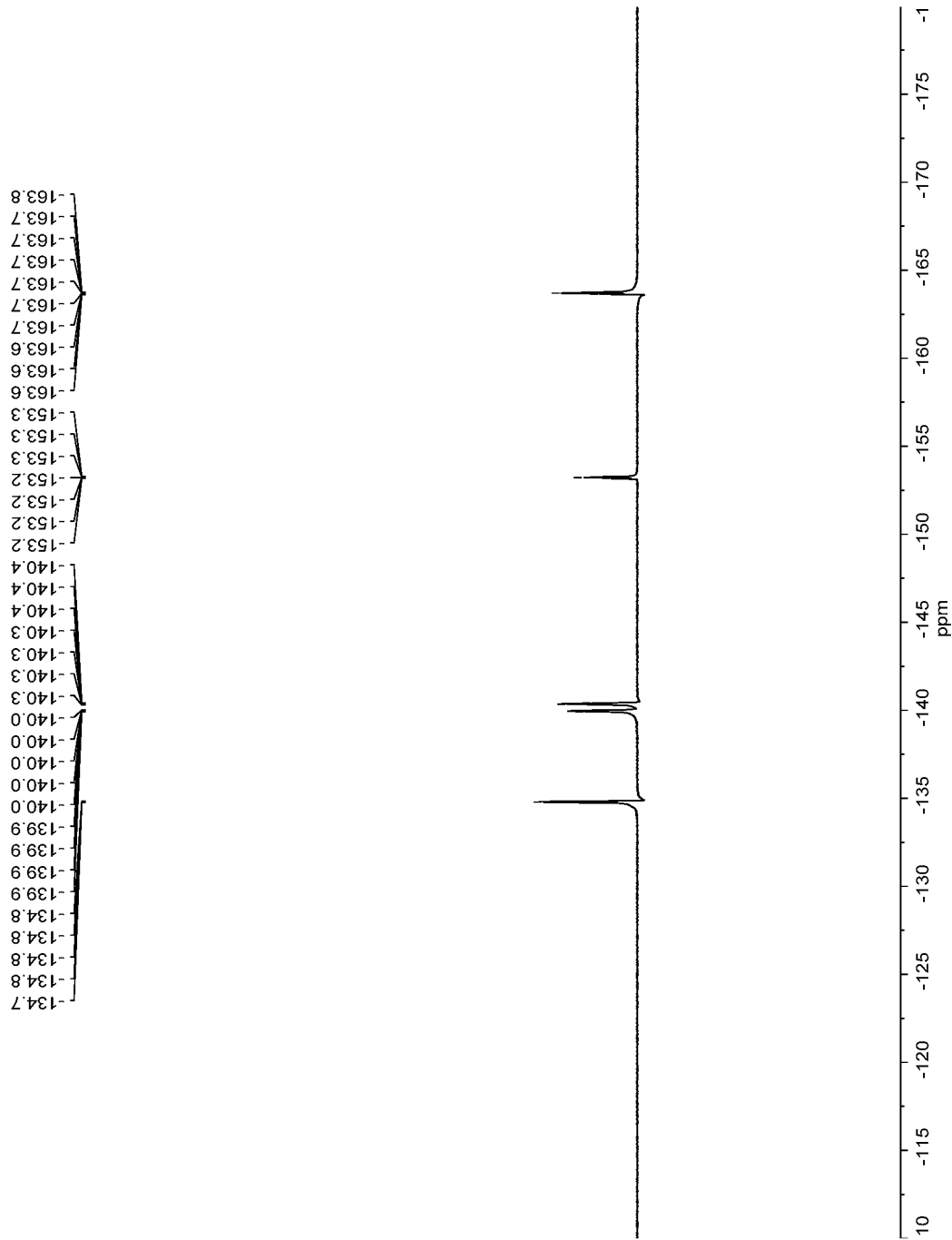
FIG. 19 is $^{19}$F NMR spectrum confirming the structure of triazole 19.

Procedure for the Synthesis of Triazole 19 from Azide 7e. Azide 7e (10.6 mg, 25.0 μmol, 1 equiv) and compound 18 (11.4 mg, 25.0 μmol, 1.0 equiv) were suspended in t-BuOH (125 μL) and H$_2$O (125 μL). Sodium ascorbate (2.5 mg, 12.5 μmol, 0.5 equiv) was added, followed by copper (II) sulfate pentahydrate (0.3 mg, 1.25 μmol, 0.05 equiv). The reaction mixture was sealed under an atmosphere of argon and stirred vigorously. After 32 h. thin layer chromatography indicated full consumption of starting material. The reaction solution was diluted with dichloromethane (2 mL) and methanol (2 mL) and concentrated under reduced pressure. The crude residue was purified flash column chromatography on silica gel (eluent: 0→10% methanol in dichloromethane) to afford 1,2,3-triazole 19 (18.7 mg, 85%) as a white solid. Spectral data is shown in FIGS. 18 and 19. $^1$H NMR (600 MHz, CD$_3$OD, 25° C.): δ 7.86 (s, 1H), 6.90 (d, J=4.2 Hz, 1H), 6.32 (d, J=4.3 Hz, 1H), 4.63-4.59 (m, 1H), 4.40-4.38 (m, 2H), 4.24-4.20 (m, 1H), 4.12-4.04 (m, 1H), 3.35-3.32 (m, 2H), Procedure for the Synthesis of Triazole 20 from Azide 8d. Azide 8d (2.0 mg, 4.4 μmol, 1 equiv) and compound 18 (2.0 mg, 4.4 μmol, 1.0 equiv) were suspended in t-BuOH (40 μL) and H$_2$O (40 μL). Sodium ascorbate (0.44 mg, 2.2 μmol, 0.50 equiv) was added, followed by copper (II) sulfate pentahydrate (0.05 mg, 0.2 μmol, 0.05 equiv). The reaction mixture was sealed under an atmosphere of argon and stirred vigorously. After 16.5 h, thin layer chromatography indicated full consumption of starting material. The reaction solution was diluted with dichloromethane (2 mL) and methanol (2 mL) and concentrated under reduced pressure. The crude residue was purified flash column chromatography on silica gel (eluent: 0→10% methanol in dichloromethane) to afford 1,2,3-triazole 20 (18.7 mg, 85%) as a white solid. $^1$H NMR (600 MHz, CD$_3$OD, 25° C.): δ 7.86 (s, 1H), 6.90 (d, J=4.2 Hz, 1H), 6.32 (d, J=4.3 Hz, 1H), 4.63-4.59 (m, 1H), 4.40-4.38 (m, 2H), 4.24-4.20 (m, 1H), 4.12-4.04 (m, 1H), 3.35-3.32 (m, 2H), 3.31-3.26 (m, 2H), 2.58-2.53 (m, 1H), 2.15 (t, J=12.2 Hz, 1H), 1.94-1.91 (m, 2H), 1.62-1.55 (m, 2H), 1.48-1.38 (m, 6H), 1.28-1.24 (m, 2H). $^{19}$F NMR (376 MHz, CD$_3$OD, 25° C.): δ −134.7 (m, 2F), −140.0 (m, 2F), −140.4 (m, 2F), −153.2 (m, 1F), −163.7 (m, 2F). TLC (8% methanol in dichloromethane), Rf: 0.08 (UV, CAM).

Cell Culture Methods. All RMF cell lines were grown in Dulbecco's modified Eagle's medium (DMEM) supplemented with 10% bovine calf serum. The human breast cancer line, SUM1315, was grown in Ham's F12 nutrient mixture with 5% fetal bovine serum, 10 ng/mL epidermal growth factor (EGF), and 5 µg/mL insulin. All culture media contained 100 Units/mL penicillin and 100 µg/mL, streptomycin and 0.1% fungizone. The parental RMF cell line expressing green fluorescent protein (GFP) and the human breast cancer cell line SUM1315 were kind gifts from Dr. Charlotte Kuperwasser, Tufts University.[24] Derivation of the stable fibroblast sub-lines shTiam-RMF and C-RMF has been described previously.[12]

Figure 3:
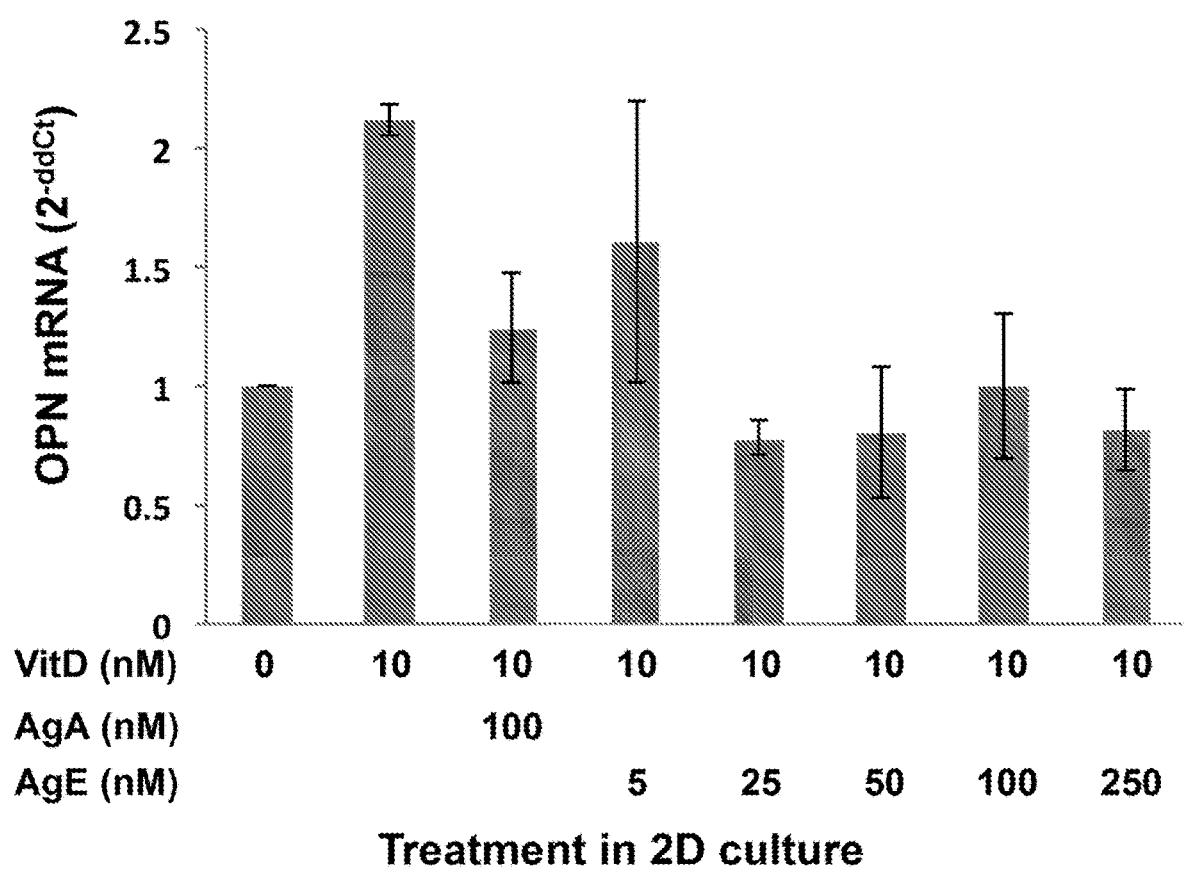
FIG. 3 shows that AgE (5) blocks stimulated transcription of osteopontin in fibroblasts.
Figure 8:
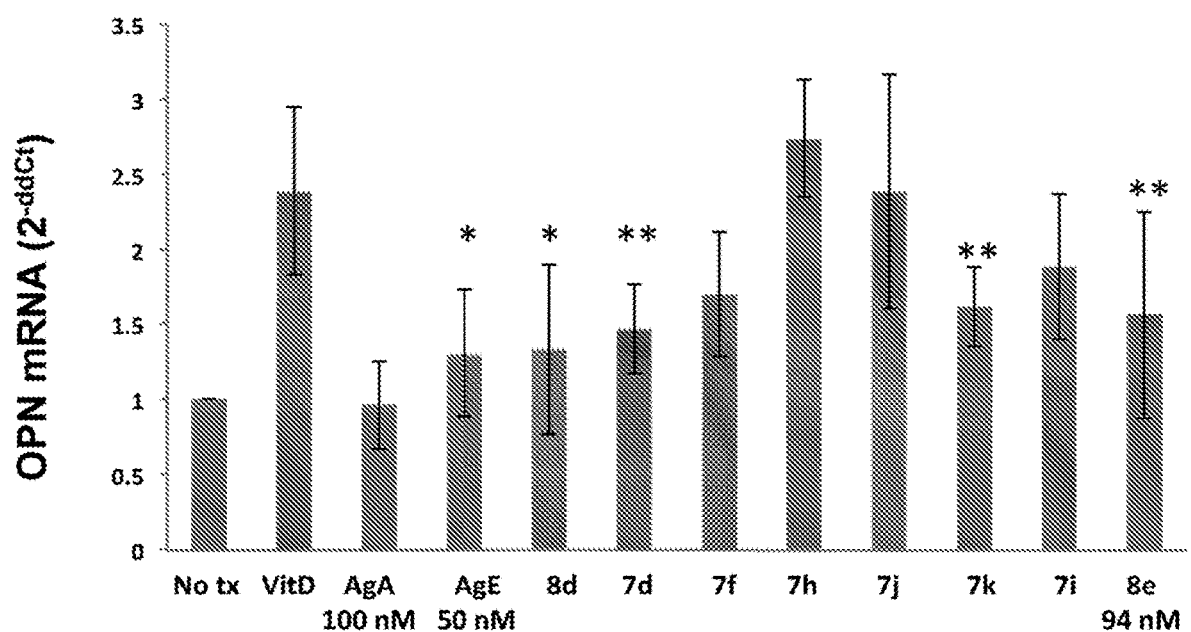
FIG. 8 shows the varying effects of agelastatin derivatives in blocking stimulated fibroblast expression of osteopontin. All agelastatin derivatives were tested at 100-nM concentration unless noted otherwise. * indicates statistical equivalence with AgA (1) at 100-nM concentration; ** indicates equivalence with AgE (5) at 50-nM concentration, but not AgA (1) at 100-nM concentration by T-test.

Quantitative Reverse Transcription Polymerase Chain Reaction (RT-PCR) for OPN (FIGS. 3 and 8). Total RNA synthesis was carried out using the acid guanidinium thiocyanate-phenol-chloroform extraction method[25] per manufacturer protocol. First strand cDNA synthesis was performed using a version of Moloney murine leukemia virus reverse transcriptase per manufacturer protocol. Some mammary fibroblasts were treated with 48 hours of 10 nM vitamin D and AgA, AgE, or agelastatin derivative as indicated prior to assay. Quantitative PCR was performed in triplicate reactions in 20-µl volumes containing cDNA with cyanine dye and DNA polymerase master mix, using the following primer sets: glyceraldehyde 3-phosphate dehydrogenase (GAPDH), 5'-CTGCACCACCAACTGCTTAG-3' (sense)(SEQ ID NO. 1), 5'-TTCAGCTCAGG-GATGACCTT-3' (antisense)(SEQ ID NO. 2); OPN, 5'-GC-CATACCAGTTAAACAGGC-3' (sense)(SEQ ID NO. 5), 5'-GACCTCAGAAGATGCACTAT-3' (antisense)(SEQ ID NO. 4). Real-time PCR parameters: 95° C. for 10 min; 95° C. for 30 s, 60° C. for 60 s, 72° C. for 60s for 40 cycles. Data analysis was done using a continuous fluorescence detector. The comparative threshold cycle ($2^{-\Delta\Delta CT}$) value[26] was calculated following GAPDH normalization. Results indicate mean+/−SD and represent a composite of at least duplicate experiments, each with triplicate conditions.

Spheroid Co-Culture Methods (FIG. 4). Three-dimensional co-cultures with SUM1315 cells and fibroblast lines were established in phenol-red free basement membrane matrix from the Engelbreth-Holm-Swarm mouse sarcoma (medium mixture as previously described)[9] Cultures had equal volumes of DMSO, AgA, or AgE incorporated into the matrix and culture medium at the indicated concentrations. Stock solutions (1 mM) were stored in DMSO at −20° C. and diluted in culture medium to indicated final concentrations.

Number of projections per spheroid was quantified using an Eclipse TS100 inverted tissue culture microscope and depicted as number of spheroids with indicated number of projections as percent of total spheroids. At least 100 spheroids were counted for each experimental condition. Results are representative of duplicate experiments. Cells were isolated from 3D co-cultures and cancer cells were separated from fibroblasts as described previously. Flow cytometry was used to demonstrate purity of cells isolated post-coculture to greater than 99% cancer cells using GFP markers to identify RMFs.

Transwell Migration Assays (FIG. 5). Transwell migration of SUM1315 after isolation from mixed cell spheroid co-cultures with indicated mammary fibroblasts, with or without indicated agelastatin compound. Cultured cells were deprived of serum overnight, trypsinized, and plated at a density of 1×10⁵/mL. (2×(10⁴ cells/basket) in the upper basket of transwell chambers with a filter pore size of 8 µm. Cells were allowed to migrate for 5 h at 37° C. toward lower chambers containing either DMEM alone or supplemented with 25% filter-sterilized conditioned medium harvested from NIH3T3 cells. Non-migrated cells were then removed from the upper side of the filter using a cotton swab. Filters were fixed and stained with a three-step hematology stain protocol comparable to the Wright-Giemsa method. Filters were cut out and mounted on glass slides under coverslips using microscope immersion oil. Migrated cells were counted in nine random fields for each replicate of biologic triplicates using an Eclipse TS100 microscope and 20× objective. Results are representative of duplicate experiments.

Tumorsphere Assays (FIG. 6). The SUM1315 breast cancer cells isolated from 3D co-cultures with indicated mammary fibroblasts and indicated concentrations of AgA or AgE were trypsinized and cell clumps were broken up by gentle pipetting several times. After low-speed centrifugation (1200 rpm), cell pellets were re-suspended in corresponding culture medium, and passed through a 40-µm filter to obtain single cell suspensions. Five thousand cells in 4 mL culture medium were plated per well in ultra-low attachment 6-well plates. Tumorspheres were quantitated within 10 to 14 days in culture and sphere images were obtained on an Eclipse TS100 inverted microscope. Results are representative of duplicate experiments, each with biologic triplicates.

Flow Cytometry Assays (FIG. 7). Populations of SUM1315 breast cancer cells were quantified by flow cytometry for expression of indicated cell surface markers using fluorophore-conjugated antibodies after isolation from 3D co-cultures with indicated fibroblasts. Aliquots of 0.5× 10⁶ cells in 100 µL of fluorescence-activated cell sorting buffer (phosphate-buffered saline with 2% bovine serum albumin) were stained with epithelial cell adhesion molecule epithelial specific antigen (ESA) fluorescein isothiocyanate (FITC) [clone VU-ID9, 1:10]. CD24-phycoerythrin (PE) [clone ML5, 1:400], and CD44-allophycocyanin (APC) [clone G44-26, 1:50] antibodies in the dark at room temperature for 30 min. At the end of incubation, 900☐µL of fluorescence-activated cell sorting buffer was added to the cell/antibody mixture, and cells were then analyzed using an advanced digital processing analyzer. To set background gating, other cell aliquots were stained with isotype control antibodies conjugated with corresponding fluorophore (APC mouse immunoglobulin G (IgG) subclass 2b kappa (κ); PE mouse IgG2a κ; FITC mouse IgG) so that the nonspecific $CD44^+/CD24^-/ESA^+$ staining represented less than 0.5% of the cell population. Cells were first gated using APC and PE to identify the $CD44^+/CD24^-$ population, followed by secondary gating on FITC to identify the $CD44^+/CD24^-/ESA^+$ cells. Results are representative of duplicate experiments, each with biologic triplicates.

Effects of Agelastatin Derivatives (FIG. 8). Quantitative RT-PCR for OPN mRNA relative to GAPDH control from mammary fibroblasts treated with 48 hours of vitamin D, and AgA, AgE, or agelastatin derivatives as indicated. Results indicate mean+/−SD and represent a composite of at least duplicate experiments, each with triplicate conditions. Detailed experimental methods are described above for FIG. 3.

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

REFERENCES

The following publications are hereby incorporated herein by reference in their entireties for all purposes:
1. (a) D'Ambrosio, M.; Guerriero, A.; Debitus, C.; Ribes, O.; Pusset, J.; Leroy, S.; Pietra, F. *J. Chem. Soc., Chem. Commun.* 1993, 1305-1306. (b) D'Ambrosio. M.; Guerriero, A.; Chiasera, G.; Pietra. F. *Helv. Chim. Acta* 1994, 77, 1895-1902. (c) D'Ambrosio, M.; Guerriero, A.; Ripamonti, M.; Debitus, C.; Waikedre, J.; Pietra, F. *Helv Chim.* Acta 1996, 79, 727-735. (d) Pettit, G. R; Ducki, S.; Herald, D. L.; Doubek, D. L.; Schmidt, J. M.; Chapuis, J.-C. *Oncol. Res.* 2005, 15, 11-20. (e) Hong, T. W.; Jímenez, D. R.; Molinski, T. F. *J. Nat. Prod.* 1998, 61, 158-161. (f) Tilvi, S.; Moriou, C.; Martin, M.-T.; Gallard, J.-F.; Sorres, J.; Patel, K.; Petek, S.; Debitus, C.; Ermolenko, L.; Al-Mourabit, A. *J. Nat. Prod.* 2010, 73, 720-723.
2. (a) Meijer, L.; Thunnissen, A.; White, A. W.; Garnier, M.; Nikolic, M.; Tsai, L.; Walter, J.; Cleverley, K. E.; Salinas, P. C.; Wu, Y.; Biernat, J.; Mandelkow, E.; Kim, S.; Pettit, G. R. *Chem. Biol.* 2000, 7, 51-63. (b) Hale, K. J.; Domostoj, M. M; El-Tanani, M.; Campbell, F. C.; Mason, C. K. In *Strategies and Tactics in Organic Synthesis*; Harmata, M., Ed.; Elsevier Academic Press: London, 2005; Vol. 6, Chapter 11, pp 352-394. (c) Mason, C. K.; McFarlane, S.; Johnston, P. G.; Crowe, P.; Erwin, P. J.; Domostoj, M. M; Campbell, F. C.; Manaviazar, S.; Hale, K. J.; El-Tanani, M. *Mol. Cancer Ther.* 2008, 7, 548-558. (d) Li, Z.; Kamon, T.; Personett, D. A.; Caulfield, T.; Copland, J. A.; Yoshimitsu, T.; Tun, H. W. *Med. Chem. Commun.* 2012, 3, 233-237. (e) Li, Z.; Shigeoka, D.; Caulfield, T. R; Kawachi, T.; Qiu, Y.; Kamon, T.; Arai, M.; Tun, H. W.; Yoshimitsu, T. *Med. Chem. Commun.* 2013, 4, 1093-1098.
3. (a) Movassaghi, M.; Siegel, D. S.; Han, S. *Chem. Sci.* 2010, 1, 561-566. (b) Han, S.; Siegel, D. S.; Morrison, K. C.; Hergenrother, P. J.; Movassaghi, M. *J. Org. Chem.* 2013, 78, 11970. (c) Movassaghi, M; Hergenrother, P. J. Compounds, Compositions and Methods of Agelastatin Alkaloids. U.S. Pat. No. 9,434,736, Sep. 6, 2016.
4. For a review on total synthesis of agelastatin alkaloids, see: (a) Dong, G. *Pure Appl. Chem.* 2010, 82, 2231-2246. For the total synthesis of agelastatin alkaloids, see: (b) Stien, D.; Anderson, G. T.; Chase, C. E.; Koh, Y.; Weinreb, S. M. *J. Am. Chem. Soc.* 1999, 121, 9574-9579. (c) Feldman, K. S.; Saunders, J. C. *J. Am. Chem. Soc.* 2002, 124, 9060-9061. (d) Feldman, K. S.; Saunders, J. C.; Wrobleski, M. L. *J. Org. Chem.* 2002, 67, 7096-7109. (e) Domostoj, M. M.; Irving, E.; Scheinmann, F.; Hale, K. *J. Org. Lett.* 2004, 6, 2615-2618. (f) Davis, F. A.; Deng, *J. Org. Lett.* 2005, 7, 621-623. (g) Trost, B. M; Dong, G. *J. Am. Chem. Soc.* 2006, 128, 6054-6055. (h) Ichikawa, Y.; Yamaoka, T.; Nakano, K.; Kotsuki, H. *Org. Lett.* 2007, 9, 2989-2992. (i) Yoshimitsu, T.; Ino, T.; Tanaka, T. *Org. Lett.* 2008, 10, 5457-5460. (j) Dickson, P. D.; Wardrop, D. J. *Org. Lett.* 2009, 11, 1341-1344. (k) Hama, N.; Matsuda, T.; Sato, T.; Chida, N. *Org. Lett.* 2009, 11, 2687-2690. (l) Wehn, P. M.; Du Bois, J. *Angew. Chem. Int. Ed.* 2009, 48, 3802-3805. (m) Davis, F. A.; Zhang, Y.; Qiu, H. *Synth. Commun.* 2009, 39, 1914-1919. (n) Trost, B. M.; Dong, G. *Chem. Eur. J.* 2009, 15, 6910-6919.
5. For the formal total synthesis of agelastatin alkaloids, see: (a) Hale, K. J.; Domostoj, M. M.; Tocher, D. A.; Irving, E.; Scheinmann, F. *Org. Lett.* 2003, 5, 2927-2930. (b) Yoshimitsu, T.; Ino, T.; Futamura, N.; Kamon, T.; Tanaka, T. *Org. Lett.* 2009, 11, 3402-3405. (c) Menjo, Y.; Hamajima, A.; Sasaki, N.; Hamada, Y. *Org. Lett.* 2011, 13, 5744-5747. (d) Kano, T.; Sakamoto, R.; Akakura, M.; Maruoka, K. *J. Am. Chem. Soc.* 2012, 134, 7516-7520. (e) Shigeoka, D.; Kamon T.; Yoshimitsu, T. Beilstein *J. Org. Chem.* 2013, 9, 860-865. For synthetic studies towards agelastatin alkaloids, see: (f) Anderson, G. T.; Chase, C. E.; Koh, Y.; Stien, D.; Weinreb, S. M. *J. Org. Chem.* 1998, 63, 7594-7595. (g) Baron, E.; O'Brien, P.; Towers, T. D. *Tetrahedron Lett.* 2002, 43, 723-726. (h) Porter, M. J.; White, N. J.; Howells, G. E.; Laffan, D. D. P. *Tetrahedron Lett.* 2004, 45, 6541-6543.
6. (a) Reyes, J. C. P.; Romo, D. *Angew. Chem. Int. Ed.* 2012, 51, 6870-6873. (b) Yamaoka, T.; Ichikawa, Y.; Kotsuki, H. *J. Syn. Org. Chem. Jpn* 2012, 70, 615-628. (c) Duspara, P. A.; Batey, R A. *Angew. Chem. Int. Ed.* 2013, 52, 10862-10866.
7. (a) Stout, P. E.; Choi, M. Y.; Castro, J. E.; Molinski, T. F. *J. Med. Chem.* 2014, 57, 5085-5093. (b) Jouanneau, M.; McClary, B.; Reyes, J. C. P.; Chen, R.; Chen, Y.; Plunkett, W.; Cheng, X.; Milinichik, A. Z.; Albone, E. F.; Liu, J. O.; Romo, D. *Bioorg. Med.* Chem. Lett. 2016, 26, 2092-2097.
8. Han, S.; Siegel, D. S.; Movassaghi, M. *Tetrahedron Lett.* 2012, 53, 3722-3723
9. Xu, K.; Buchsbaum, R. J. *J. Vis. Exp.* 2012, 62, e3760.
10. Xu, K.; Tian, X.; Oh, S. Y.; Movassaghi, M.; Naber, S. P.; Kuperwasser, C.; Buchsbaum, R. *J. Breast Cancer Res.* 2016, 18, 14.
11. Liu, J.; Xu, K.; Chase, M; Ji, Y.; Logan, J. K.; Buchsbaum, R. J. *J. Cell Sci.* 2012, 125, 376-386.
12. Xu, K.; Rajagopal, S.; Klebba, I.; Dong, S.; Ji, Y.; Liu, J.; Kuperwasser, C.; Garlick, J. A.; Naber, S. P.; Buchsbaum, R. J. *Oncogene* 2010, 29, 6533-6542.
13. Mice developed hunched posture, decreased mobility, fur ruffling, and lack of weight gain, leading to termination of experiment per established animal protocol guidelines.
14. In preliminary experiments testing effects on cell proliferation, it was confirmed that none of the natural agelastatin alkaloids induced cytotoxicity over a range of concentrations up to at least 250 nM.
15. Coste, A.; Kim, J.; Adams, T. C.; Movassaghi, M. *Chem. Sci.* 2013, 4, 3191-3197.

16. Mantovani, G.; Ladmiral, V.; Tao, L.; Haddleton, D. M. *Chem. Commun.* 2005, 2089-2091.
17. For discussion of the use of 1,1'-carbonyldiimidazole in urea synthesis, see: Duspara, P. A.; Islam, Md. S.; Lough, A. J.; Batey, R. A. *J. Org. Chem.* 2012, 77, 10362-10368 and references therein.
18. For a review on synthetic methodologies for unsymmetrical ureas, see: Gallou, I. *Org. Prep. Proc. Int.* 2007, 39, 355-383.
19. Still, W. C.; Kahn, M; Mitra, A. *J. Org. Chem.* 1978, 43, 2923-2925.
20. Kromann, H.; Krikstolaiyte, S.; Andersen, A. J.; Andersen, K.; Krogsgaard-Larsen, P.; Jaroszewski, J. W.; Egebjerg, J.; Strømgaard, K. *J. Med. Chem.* 2002, 45, 5745-5754.
21. Okoth, R.; Basu, A. *Beilstein J. Org. Chem.* 2013, 9, 608-612.
22. Synthesized from tricyclohexyltin chloride and diiodomethane according to the protocol described in reference 3a. Due to high sensitivity of (tricyclohexylstannyl)methanamine to purification procedures, it is used crude immediately after work-up.
23. Moreau, J.; Marchand-Brynaert, J. *Eur. J. Org. Chem.* 2011, 9, 1641-1644.
24. Fillmore, C. M.; Kuperwasser, C. *Breast Cancer Res.* 2008, 10, R25.
25. Chomczynski, P.; Sacchi, N. *Anal. Biochem.* 1987, 162, 156-159.
26. Schmittgen, T. D.; Livak, K. J. *Nature Protocols* 2008, 3, 1101-1108.
27. Antropow, A. H.; Xu, K.; Buchsbaum, R. J.; Movassaghi, M. *J. Org. Chem.* 2017, 82, 7720.

The invention claimed is:

1. A compound of Formula (I):

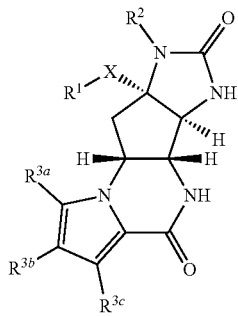

(I)

or a pharmaceutically acceptable salt, tautomer, or stereoisomer thereof, wherein:

X is —O—, —S—, or —N(R$^6$)—;

R$^{3a}$, R$^{3b}$, and R$^{3c}$ are each independently H or halogen;

(i) R$^1$ is H, C$_{1-10}$ alkyl, C$_{2-10}$ alkenyl, or C$_{2-8}$ alkynyl, each of which is optionally substituted with one or more R$^4$, or alternatively, X and R$^1$ combine to form —N$_3$, R$^2$ is C$_{1-10}$ alkyl, C$_{2-10}$ alkenyl, or C$_{2-8}$ alkynyl, each of which is substituted with one or more R$^5$, wherein up to 3 —CH$_2$— units of R$^2$ are each optionally replaced by an —O—, —S—, or —NR$^6$—, provided that no adjacent —CH$_2$— groups are replaced, or alternatively, R$^1$ and R$^2$ taken together with the atoms to which they are attached form a C$_{5-10}$ heterocycloalkyl, C$_{5-10}$ heterocycloalkenyl, or C$_{5-10}$ heterocycloalkynyl ring, each of which is optionally substituted with one or more R$^4$, and each instance of R$^4$ is independently halogen, C$_{1-5}$ alkyl, oxo, —OH, —OR$^6$, —N$_3$, —N(R$^6$)$_2$, —NH(C=O)R$^6$, —NH(C=O)OR$^6$, —NH(C=O)N(R$^6$)$_2$, —(C=O)R$^6$, monocyclic heteroaryl of 5 or 6 ring atoms,

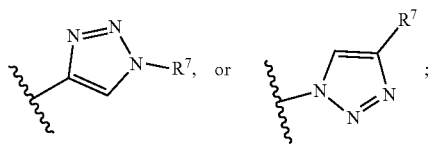

or (ii): R$^1$ is C$_{1-10}$ alkyl, C$_{2-10}$ alkenyl, or C$_{2-8}$ alkynyl, each of which is optionally substituted with one or more R$^4$, or alternatively, X and R$^1$ combine to form —N$_3$, R$^2$ is C$_{1-10}$ alkyl, C$_{2-10}$ alkenyl, or C$_{2-8}$ alkynyl, each of which is optionally substituted with one or more R$^5$, wherein up to 3 —CH$_2$-units of R$^2$ are each optionally replaced by an —O—, —S—, or —NR$^6$—, provided that no adjacent —CH$_2$— groups are replaced, and each instance of R$^4$ is independently halogen, C$_{1-5}$ alkyl, —OH, —OR$^6$, —N$_3$, —N(R$^6$)$_2$, —NH(C=O)R$^6$, —NH(C=O)OR$^6$, —NH(C=O)N(R$^6$)$_2$, —(C=O)R$^6$, monocyclic heteroaryl of 5 or 6 ring atoms,

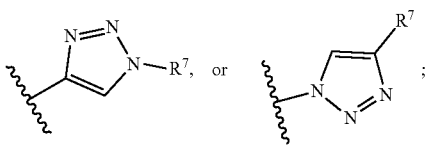

each instance of R$^5$ is independently halogen, oxo, —OH, —OR$^6$, —N$_3$, —N(R$^6$)$_2$,

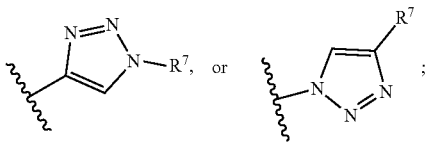

each instance of R$^6$ is independently H, C$_{1-5}$ alkyl, C$_{2-5}$ alkenyl, C$_{2-5}$ alkynyl, —C$_{1-5}$ alkyl-SiMe$_3$, phenyl, or monocyclic heteroaryl of 5 or 6 ring atoms;

R$^7$ is selected from the group consisting of hydrogen, optionally substituted aliphatic, optionally substituted heteroaliphatic, optionally substituted phenyl, optionally substituted monocyclic heteroaryl of 5 or 6 ring atoms, and optionally substituted acyl;

each of the substituents of the substituted aliphatic, substituted heteroaliphatic, substituted phenyl, substituted monocyclic heteroaryl of 5 or 6 ring atoms, and substituted acyl is independently selected from the group consisting of oxo, -halogen, C$_1$-C$_6$ alkyl, C$_1$-C$_6$ alkoxy, C$_1$-C$_6$ haloalkyl, C$_1$-C$_6$haloalkoxy, —OC$_1$-C$_6$ alkenyl, —OC$_1$-C$_6$ alkynyl, —C$_1$-C$_6$ alkenyl, —C$_1$-C$_6$ alkynyl, —OH, —CN, —CH$_2$CN, —OP(O)(OH)$_2$, —C(O)OH, —OC(O)C$_1$-C$_6$ alkyl, —C(O)C$_1$-C$_6$ alkyl, —OC(O)OC$_1$-C$_6$ alkyl, —NH$_2$, —NH(C$_1$-C$_6$ alkyl), —N(C$_1$-C$_6$ alkyl)$_2$, —C(O)NH$_2$, —C(O)NH(C$_1$-C$_6$ alkyl), —C(O)N(C$_1$-C$_6$ alkyl)$_2$, —S(O)$_2$—C$_1$-C$_6$ alkyl, —S(O)$_2$—C$_1$-C$_6$ haloalkyl, —C$_0$-C$_6$ alkylenyl-S(O)$_2$NH$_2$, —S(O)$_2$NHC$_1$-C$_6$ alkyl, —S(O)$_2$N(C$_1$-C$_6$ alkyl)$_2$, —NHS(O)$_2$C$_1$-C$_6$ alkyl, and —N(C$_1$-C$_6$ alkyl)S(O)$_2$(C$_1$-C$_6$ alkyl), wherein each of the alkyl, alkoxy, haloalkyl, haloalkoxy, alkenyl, alkynyl, and alkylenyl is unsubstituted; and with the proviso that the compound is not agelastatin E,

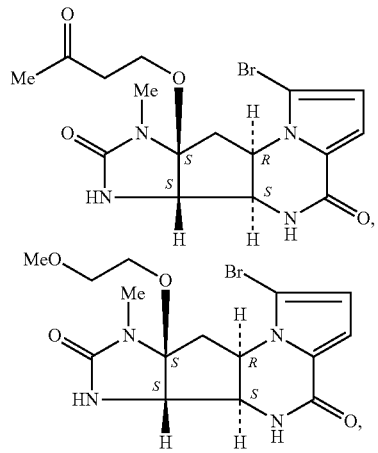

-continued

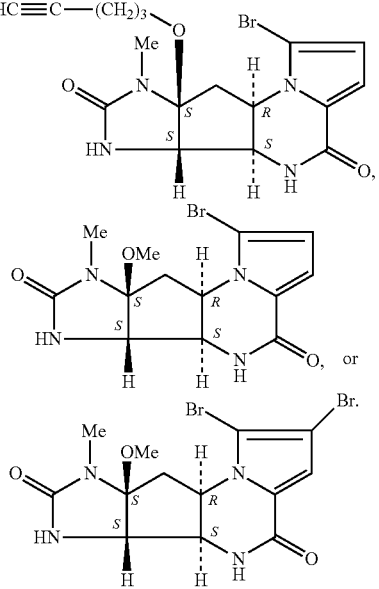

2. The compound of claim 1, wherein the compound is a compound of Formula (Ia):

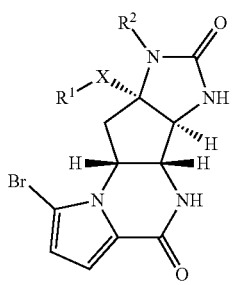
(Ia)

or a pharmaceutically acceptable salt, tautomer, or stereoisomer thereof.

3. The compound of claim 1, wherein the compound is a compound of Formula (Ib):

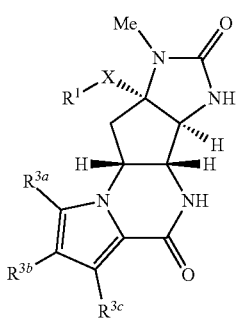
(Ib)

or a pharmaceutically acceptable salt, tautomer, or stereoisomer thereof.

4. The compound of claim 3, wherein the compound is a compound of Formula (Ic):

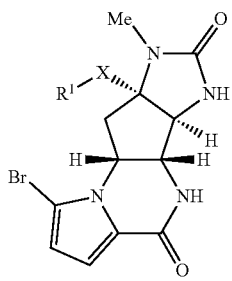
(Ic)

or a pharmaceutically acceptable salt, tautomer, or stereoisomer thereof.

5. The compound of claim 1, wherein the compound is a compound of Formula (Id):

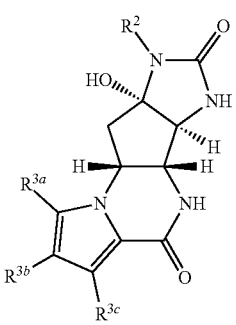
(Id)

or a pharmaceutically acceptable salt, tautomer, or stereoisomer thereof.

6. The compound of claim 5, wherein the compound is a compound of Formula (Ie):

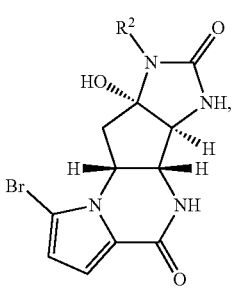
(Ie)

or a pharmaceutically acceptable salt, tautomer, or stereoisomer thereof.

7. The compound of claim 1, or a pharmaceutically acceptable salt, tautomer, or stereoisomer thereof, wherein $R^{3a}$ is Br or Cl, $R^{3b}$ is H, and $R^{3c}$ is H.

8. The compound of claim 1, or a pharmaceutically acceptable salt, tautomer, or stereoisomer thereof, wherein $R^{3a}$ is Br or Cl, $R^{3b}$ is Br or Cl, and $R^3{}_c$ is H.

9. The compound of claim 1, wherein the compound is of the formula:

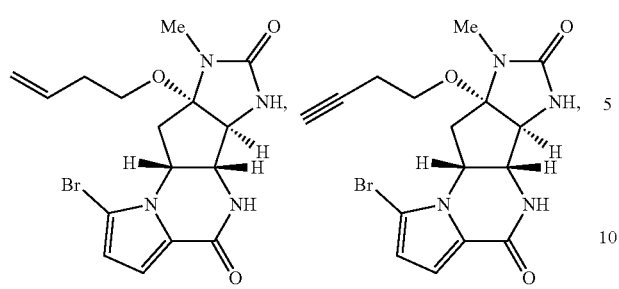
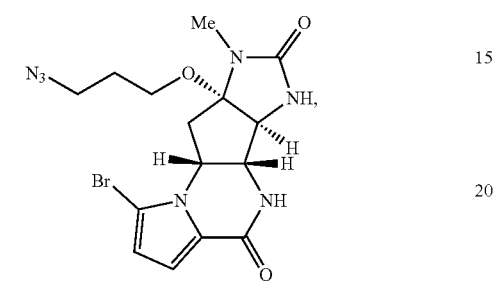
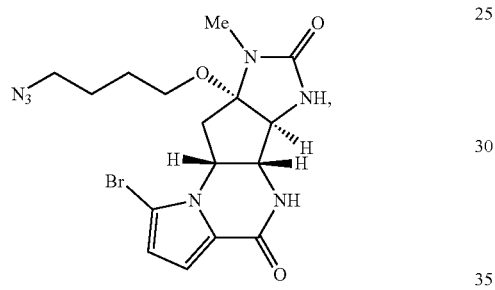
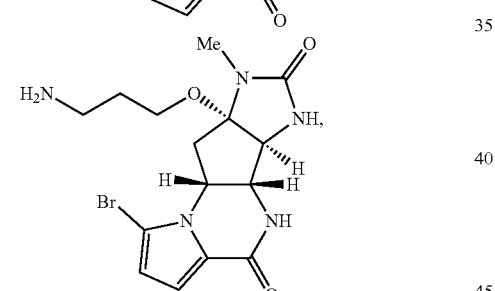
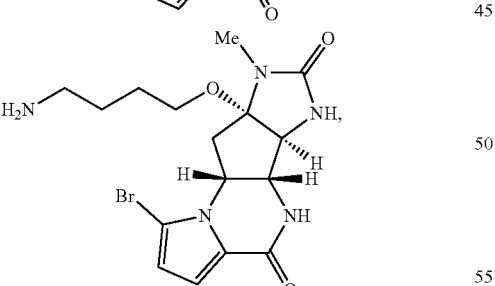
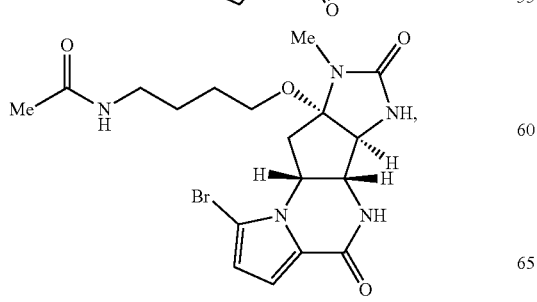
-continued
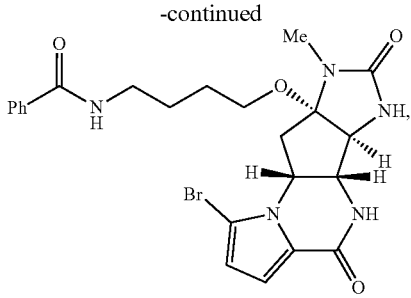
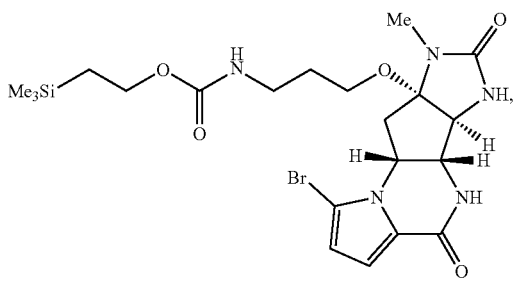
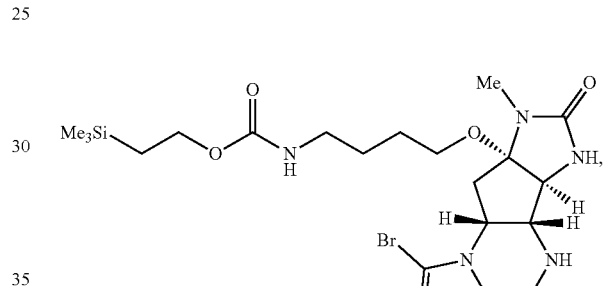
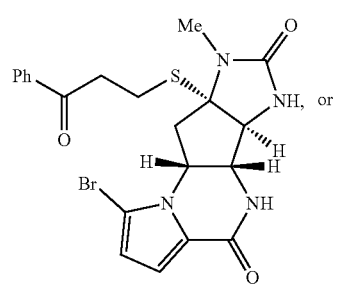
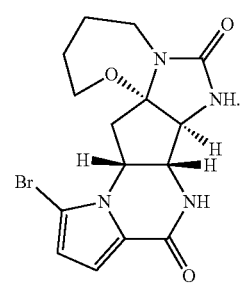

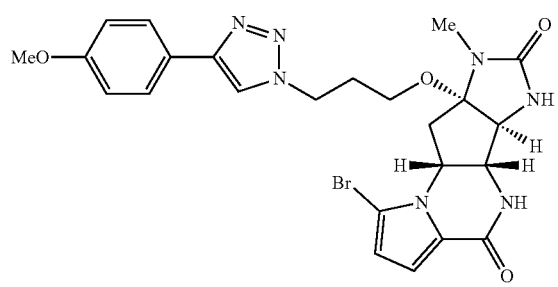 [SMILES: COc1ccc(-c2cn(CCCO[C@@]34C[C@@H]5[C@@H](NC(=O)c6ccc(Br)n65)[C@@H]3NC(=O)N4C)nn2)cc1]

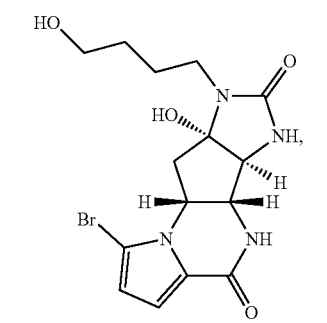

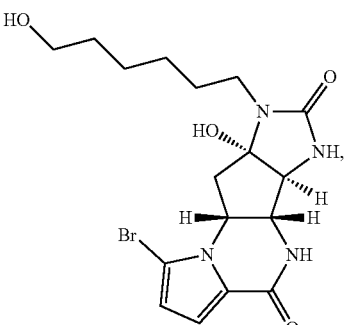

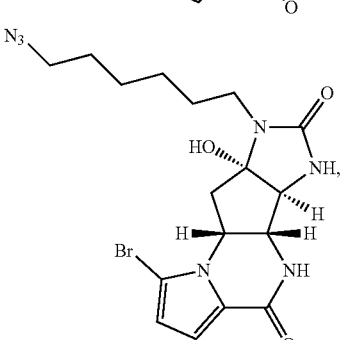

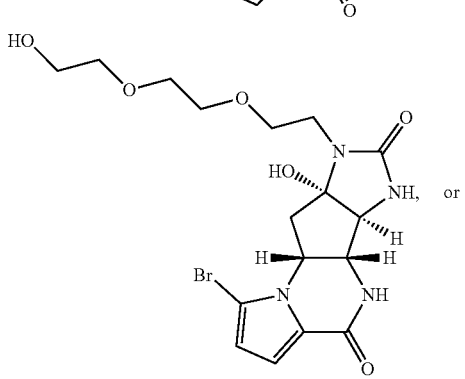

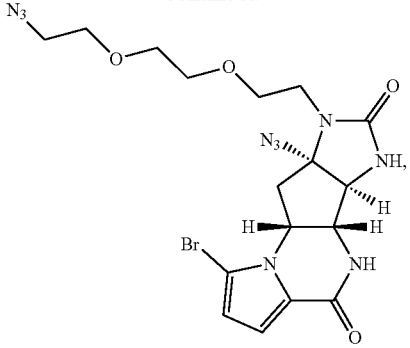

or a pharmaceutically acceptable salt, tautomer, or stereoisomer thereof.

10. The compound of claim 1, wherein the compound is of the formula:

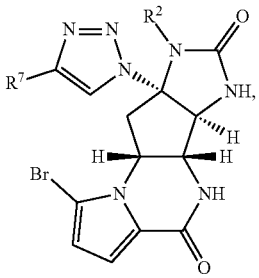

or a pharmaceutically acceptable salt, tautomer, or stereoisomer thereof, wherein $R^2$ is H or Me.

11. The compound of claim 1, or a pharmaceutically acceptable salt, tautomer, or stereoisomer thereof, wherein X is —O—.

12. The compound of claim 1, or a pharmaceutically acceptable salt, tautomer, or stereoisomer thereof, wherein $R^1$, $R^2$, and $R^4$ are as defined in (i).

13. The compound of claim 12, or a pharmaceutically acceptable salt, tautomer, or stereoisomer thereof, wherein $R^2$ is $C_{1-10}$ alkyl substituted with one or more $R^5$, wherein up to 3 —CH$_2$— units of $R^2$ are each optionally replaced by an —O—, —S—, or —NR$^6$—, provided that no adjacent —CH$_2$— groups are replaced.

14. The compound of claim 13, or a pharmaceutically acceptable salt, tautomer, or stereoisomer thereof, wherein up to 3 —CH$_2$— units of $R^2$ are each optionally replaced by an O.

15. The compound of claim 12, or a pharmaceutically acceptable salt, tautomer, or stereoisomer thereof, wherein $R^2$ is $C_{1-10}$ alkyl substituted with one or more $R^5$, wherein no —CH$_2$— units of $R^2$ are replaced by an —O—, —S—, or —NR$^6$.

16. The compound of claim 12, or a pharmaceutically acceptable salt, tautomer, or stereoisomer thereof, wherein at least one instance of $R^5$ is —OH or —N$_3$.

17. The compound of claim 1, or a pharmaceutically acceptable salt, tautomer, or stereoisomer thereof, wherein $R^1$, $R^2$, and $R^4$ are as defined in (ii).

18. The compound of claim 17, or a pharmaceutically acceptable salt, tautomer, or stereoisomer thereof, wherein $R^2$ is unsubstituted methyl.

19. The compound of claim 17, or a pharmaceutically acceptable salt, tautomer, or stereoisomer thereof, wherein $R^1$ is $C_{1-10}$ alkyl, $C_{2-10}$ alkenyl, or $C_{2-8}$ alkynyl, each of which is optionally substituted with one or more $R^4$.

20. The compound of claim 17, or a pharmaceutically acceptable salt, tautomer, or stereoisomer thereof, wherein $R^1$ is $C_{1-10}$ alkyl substituted with one or more $R^4$.

21. The compound of claim 17, or a pharmaceutically acceptable salt, tautomer, or stereoisomer thereof, wherein $R^1$ is $C_{2-10}$ alkenyl or $C_{2-8}$ alkynyl, each of which is optionally substituted with one or more $R^4$.

22. The compound of claim 1, or a pharmaceutically acceptable salt, tautomer, or stereoisomer thereof, wherein X and $R^1$ are combined to form $—N_3$.

23. The compound of claim 1, or a pharmaceutically acceptable salt thereof.

24. The compound of claim 9, or a pharmaceutically acceptable salt thereof.

25. A pharmaceutical composition comprising a compound of claim 1, or a pharmaceutically acceptable salt, tautomer, or stereoisomer thereof, and a pharmaceutically acceptable excipient.

26. A method for the treatment, prevention, or delay of cancer, comprising administering to a subject in need thereof an effective amount of a compound of claim 1, or a pharmaceutically acceptable salt, tautomer, or stereoisomer thereof.

27. A method of making a compound of claim 1, or a pharmaceutically acceptable salt, tautomer, or stereoisomer thereof, comprising addition of a nucleophile to an iminium intermediate of Formula (II), or a salt thereof:

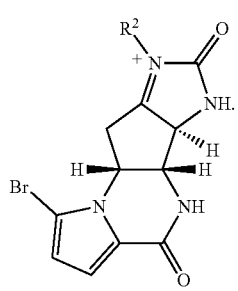
(II)

28. A method of making a compound of claim 1, or a pharmaceutically acceptable salt, tautomer, or stereoisomer thereof, comprising acid-promoted cyclization of a compound of Formula (III), or a salt thereof, to afford a compound of Formula (Id), or a salt thereof:

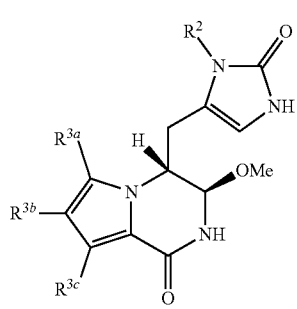
(III)

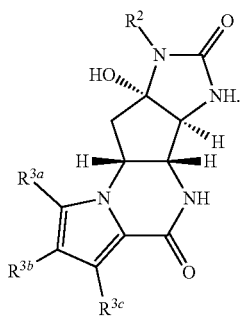
(Id)

29. The method of claim 26 for the treatment of cancer.

30. The method of claim 29, wherein the cancer is breast cancer, lung cancer, colorectal cancer, stomach cancer, ovarian cancer, papillary thyroid carcinoma, melanoma, prostate cancer, esophageal cancer, liver cancer, bladder cancer, renal cancer, head or neck cancer, salivary gland cancer, endometrial cancer, cervical cancer, pancreatic cancer, sarcoma, glioblastoma, glioma, or pleural mesothelioma.

31. The method of claim 29, wherein the cancer is breast cancer.

32. The method of claim 29, wherein the cancer is ductal carcinoma in situ, invasive ductal carcinoma, tubular carcinoma, medullary carcinoma, mucinous carcinoma, papillary carcinoma, cribriform carcinoma, invasive lobular carcinoma, inflammatory breast cancer, lobular carcinoma in situ, luminal A breast cancer, luminal B breast cancer, triple-negative breast cancer, basal-like breast cancer, HER2-enriched breast cancer, or normal-like breast cancer.

33. The method of claim 29, wherein the cancer is metastatic breast cancer or recurrent metastatic breast cancer.

34. The method of claim 29, wherein the cancer is characterized by a tumor microenvironment exhibiting down regulation of fibroblast Tiam1 and upregulation of fibroblast osteopontin.

35. The method of claim 29, wherein the cancer is characterized by a tumor microenvironment exhibiting upregulation of fibroblast osteopontin.

36. The method of claim 29 further comprising coadministration to the subject an additional therapeutic agent selected from the group consisting of antitumor agents, anti-metabolites, anti-estrogens, aromatase inhibitors, estrogen receptor antagonists, targeted therapies, tyrosine kinase inhibitors, and immune checkpoint inhibitors.

37. The method of claim 29, wherein the subject is a human.

38. The method of claim 27, wherein the nucleophile is $R^1$—XH, and X is —O—, —S—, or —N($R^4$)—.

39. The method of claim 28, wherein the acid is methanesulfonic acid, p-toluenesulfonic acid, sulfuric acid, hydrochloric acid, trifluoroacetic acid, trifluoromethanesulfonic acid, or nitric acid.

40. The method of claim 28 further comprising copper-mediated coupling between a compound of Formula (IV), or a salt thereof, and a compound of Formula (V), or a salt thereof:

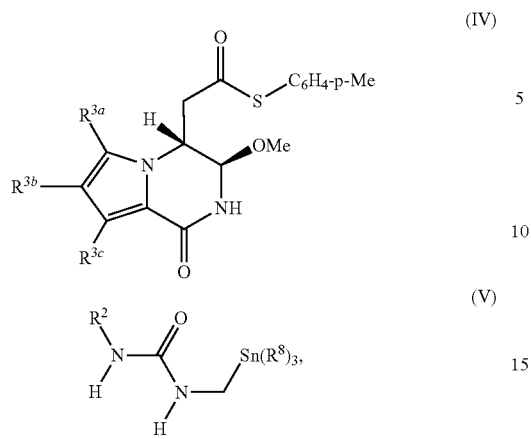
to make the compound of Formula (III), wherein $R^8$ is alkyl or cycloalkyl.
41. The method of claim 40, wherein the copper-mediated coupling is carried out with copper(I)-thiophene-2-carboxylate or copper(I) diphenylphosphinate.
42. The method of claim 40 further comprising treatment with an acid.
* * * * *